(12) United States Patent
Burgey et al.

(10) Patent No.: US 8,039,460 B2
(45) Date of Patent: Oct. 18, 2011

(54) CGRP RECEPTOR ANTAGONISTS

(75) Inventors: Christopher S. Burgey, Philadelphia, PA (US); Daniel V. Paone, Lansdale, PA (US); Anthony W. Shaw, Harleysville, PA (US); Diem N. Nguyen, Harleysville, PA (US); Zhengwu J. Deng, Eagleville, PA (US); Theresa M. Williams, Harleysville, PA (US); Joseph P. Vacca, Telford, PA (US); Craig M. Potteiger, Reading, PA (US); Harold G. Selnick, Ambler, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1222 days.

(21) Appl. No.: 11/665,523

(22) PCT Filed: Oct. 12, 2005

(86) PCT No.: PCT/US2005/036763
§ 371 (c)(1),
(2), (4) Date: Apr. 12, 2007

(87) PCT Pub. No.: WO2006/044504
PCT Pub. Date: Apr. 27, 2006

(65) Prior Publication Data
US 2008/0113966 A1 May 15, 2008

Related U.S. Application Data

(60) Provisional application No. 60/618,451, filed on Oct. 13, 2004, provisional application No. 60/683,837, filed on May 24, 2005.

(51) Int. Cl.
*A61P 1/08* (2006.01)
*A61P 35/00* (2006.01)
*A61K 31/55* (2006.01)
*C07D 487/04* (2006.01)
*C07D 519/00* (2006.01)

(52) U.S. Cl. .............. 514/214.01; 514/214.02; 514/221; 540/500; 540/578; 540/579; 540/593

(58) Field of Classification Search ............. 514/214.01, 514/214.02, 221; 540/500, 578, 579, 593
See application file for complete search history.

(56) References Cited

U.S. PATENT DOCUMENTS
6,552,043 B1  4/2003  Patchett et al.

FOREIGN PATENT DOCUMENTS
WO  WO 00/18764  4/2000
WO  WO 03/104236  12/2003

*Primary Examiner* — Brenda Coleman
(74) *Attorney, Agent, or Firm* — Gerard M. Devlin; Raynard Yuro

(57) ABSTRACT

Compounds of Formula (I): and Formula (II): (where variables $R^2$, $R^4$, A, B, D, W, X, Y and Z are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

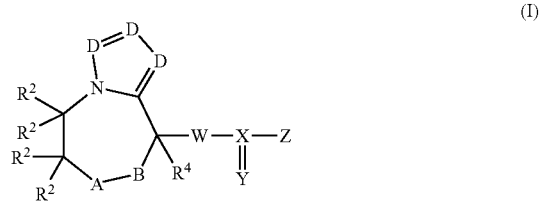

(I)

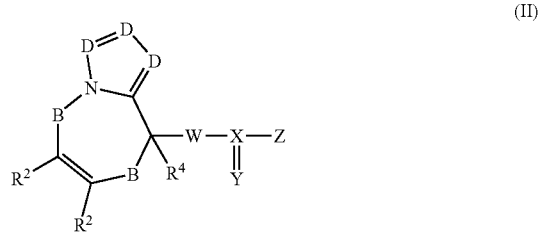

(II)

11 Claims, No Drawings

CGRP RECEPTOR ANTAGONISTS

RELATED APPLICATION DATA

This is a National filing under 35 USC 371 of PCT/US2005/036763, filed Oct. 12, 2005, which claims priority from U.S. Ser. No. 60/618,451, filed Oct. 13, 2004 and U.S. Ser. No. 60/683,837, filed May 24, 2005.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache. Compelling evidence of the efficacy of CGRP antagonists for the treatment of migraine has been provided by clinical studies using intravenously administered BIBN4096BS. This CGRP antagonist was found to be a safe and effective acute treatment for migraine (Olesen et al., N. Engl. J. Med., 2004, 350(11), 1104-1110).

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of Formula I:

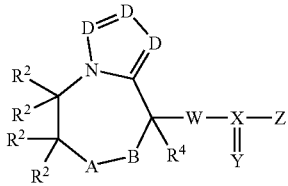

and Formula II:

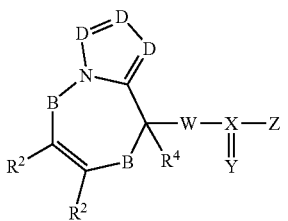

(where variables $R^2$, $R^4$, A, B, D, W, X, Y and Z are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to CGRP antagonists which include compounds of Formula I:

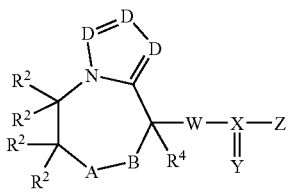

wherein:
Z is selected from:

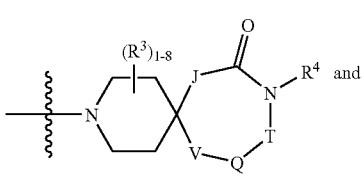

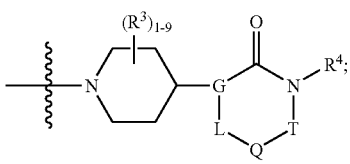

A is a bond, $C(R^2)_2$, O, $S(O)_m$ or $NR^2$;
B is $(C(R^2)_2)_n$;
D is independently selected from N and $C(R^1)$;
$R^1$ is independently selected from:
1) H, $C_1$-$C_6$ alkyl, $C_2$-$C_6$ alkenyl, $C_2$-$C_6$ alkynyl, $C_{3-6}$ cycloalkyl, and heterocycle, unsubstituted or substituted with one or more substituents each independently selected from:
    a) $C_{1-6}$ alkyl,
    b) $C_{3-6}$ cycloalkyl,
    c) aryl, unsubstituted or substituted with 1-5 substituents each independently selected from $R^4$,
    d) heteroaryl, unsubstituted or substituted with 1-5 substituents each independently selected from $R^4$,
    e) heterocycle, unsubstituted or substituted with 1-5 substituents each independently selected from $R^4$,
    f) $(F)_p C_{1-3}$ alkyl,
    g) halogen,
    h) $OR^4$,
    i) $O(CH_2)_s OR^4$,
    j) $CO_2 R^4$,
    k) $(CO)NR^{10}R^{11}$,
    l) $O(CO)NR^{10}R^{11}$,
    m) $N(R^4)(CO)NR^{10}R^{11}$,
    n) $N(R^{10})(CO)R^{11}$,
    o) $N(R^{10})(CO)OR^{11}$,
    p) $SO_2 NR^{10}R^{11}$,
    q) $N(R^{10}) SO_2 R^{11}$,
    r) $S(O)_m R^{10}$,
    s) CN,
    t) $NR^{10}R^{11}$,
    u) $N(R^{10})(CO)NR^4 R^{11}$, and,
    v) $O(CO)R^4$;
2) aryl or heteroaryl, unsubstituted or substituted with one or more substituents each independently selected from:
    a) $C_{1-6}$ alkyl,
    b) $C_{3-6}$ cycloalkyl,
    c) aryl, unsubstituted or substituted with 1-5 substituents each independently selected from $R^4$,
    d) heteroaryl, unsubstituted or substituted with 1-5 substituents each independently selected from $R^4$,
    e) heterocycle, unsubstituted or substituted with 1-5 substituents each independently selected from $R^4$,
    f) $(F)_p C_{1-3}$ alkyl,
    g) halogen,
    h) $OR^4$,
    i) $O(CH_2)_s OR^4$,
    j) $CO_2 R^4$,
    k) $(CO)NR^{10}R^{11}$,
    l) $O(CO)NR^{10}R^{11}$,
    m) $N(R^4)(CO)NR^{10}R^{11}$,
    n) $N(R^{10})(CO)R^{11}$,
    o) $N(R^{10})(CO)OR^{11}$,
    p) $SO_2 NR^{10}R^{11}$,
    q) $N(R^{10}) SO_2 R^{11}$,
    r) $S(O)_m R^{10}$,
    s) CN,
    t) $NR^{10}R^{11}$,
    u) $N(R^{10})(CO)NR^4 R^{11}$, and
    v) $O(CO)R^4$;
    where any two independent $R^1$ and the atom or atoms to which they are attached optionally join to form a ring selected from $C_{3-6}$ cycloalkyl, aryl, heterocycle, and heteroaryl;

$R^2$ is independently selected from:
1) H, $C_0$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10}) SO_2 R^{11}$,
   r) $S(O)_m R^{10}$,
   s) CN,
   t) $NR^{10}R^{11}$,
   u) $N(R^{10})(CO)NR^4 R^{11}$, and,
   v) $O(CO)R^4$;
2) aryl or heteroaryl, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10}) SO_2 R^{11}$,
   r) $S(O)_m R^{10}$,
   s) CN,
   t) $NR^{10}R^{11}$,
   u) $N(R^{10})(CO)NR^4 R^{11}$, and
   v) $O(CO)R^4$,
   where any two independent $R^2$ on the same or adjacent atoms optionally join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl;

$R^{10}$ and $R^{11}$ are independently selected from: H, $C_{1-6}$ alkyl, $(F)_p C_{1-6}$ alkyl, $C_{3-6}$ cycloalkyl, aryl, heteroaryl, and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl, or morpholinyl, which is ring is unsubstituted or substituted with 1-5 substituents each independently selected from $R^4$;

$R^4$ is independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;

X is C or S;

Y is O, $(R^4)_2$, NCN, $NSO_2 CH_3$ or $NCONH_2$, or Y is $O_2$ when X is S;

$R^6$ is independently selected from H and:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10}) SO_2 R^{11}$,
   r) $S(O)_m R^{10}$,
   s) CN,
   t) $NR^{10}R^{11}$,
   u) $N(R^{10})(CO)NR^4 R^{11}$, and
   v) $O(CO)R^4$;

J is a bond, $C(R^6)_2$, O or $NR^6$;

V is selected from a bond, $C(R^6)_2$, O, $S(O)_m$, $NR^6$, $C(R^6)_2$—$C(R^6)_2$, $C(R^6)$=$C(R^6)$, $C(R^6)_2$—$N(R^6)$, $C(R^6)$=N,N$(R^6)$—$C(R^6)_2$, N=$C(R^6)$, and $N(R^6)$—$N(R^6)$);

G-L is selected from: N,N—$C(R^6)_2$, C=$C(R^6)$, C=N, $C(R^6)$, $C(R^6)$—$C(R^6)_2$, $C(R^6)$—$C(R^6)_2$—$C(R^6)_2$, C=C$(R^6)$—$C(R^6)_2$, $C(R^6)$—$C(R^6)$=$C(R^6)$, $C(R^6)$—$C(R^6)_2$—$N(R^6)$, C=$C(R^6)$—$N(R^6)$, $C(R^6)$—$C(R^6)$=N, $C(R^6)$—N$(R^6)$—$C(R^6)_2$, C=N—$C(R^6)_2$, $C(R^6)$—N=$C(R^6)$, $C(R^6)$—N$(R^6)$—$N(R^6)$, C=N—$N(R^6)$, N—$C(R^6)_2$—C$(R^6)_2$, N—$C(R^6)$=$C(R^6)$, N—$C(R^6)_2$—$N(R^6)$, N—$C(R^6)$=N,N—$N(R^6)$—$C(R^6)_2$ and N—N=$C(R^6)$;

Q is independently selected from:
(1) =$C(R^{7a})$—,
(2) —$C(R^{7a})_2$—,
(3) —C(=O)—,
(4) —$S(O)_m$—,
(5) =N—, and
(6) —$N(R^{7a})$—;

T is independently selected from:
(1) =C(R$^{7b}$)—,
(2) —C(R$^{7b}$)$_2$—,
(3) —C(=O)—,
(4) —S(O)$_m$—,
(5) =N—, and
(6) —N(R$^{7b}$)—;

R$^3$ is independently selected from H, substituted or unsubstituted C$_1$-C$_3$ alkyl, F, CN and CO$_2$R$^4$;

R$^{7a}$ and R$^{7b}$ are each independently selected from R$^2$, where R$^{7a}$ and R$^{7b}$ and the atom or atoms to which they are attached optionally join to form a ring selected from C$_{3-6}$ cycloalkyl, aryl, heterocycle, and heteroaryl, which ring is unsubstituted or substituted with 1-10 substituents each each independently selected from R$^6$;

p is 0 to 2q+1, for a substituent with q carbons;
m is 0, 1 or 2;
n is 0 or 1;
s is 1, 2 or 3;
and pharmaceutically acceptable salts and individual diastereomers thereof.

Further embodiments of the invention are CGRP antagonists of Formula I which include compounds of the Formula Ia:

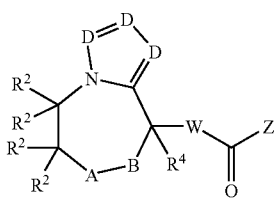

Ia wherein:
A is a bond, C(R$^2$)$_2$, O, S(O)$_m$ or NR$^2$;
B is (C(R$^2$)$_2$)$_n$;
n is 0 or 1; and
D, R$^2$, R$^4$, W, Z, and m are as defined in Formula I;
and pharmaceutically acceptable salts and individual stereoisomers thereof.

Additional embodiments of the invention are CGRP antagonists of Formula I which include compounds of the Formula Ib:

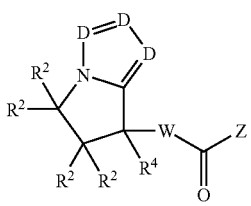

Ib wherein:
D, R$^2$, R$^4$, W, Z, and m are as defined in Formula I;
and pharmaceutically acceptable salts and individual stereoisomers thereof.

Additional embodiments of the invention are CGRP antagonists of Formula I which also include compounds of the Formula Ic:

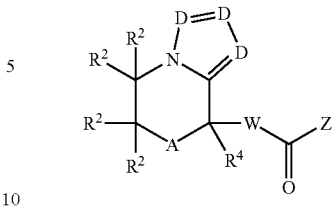

Ic wherein:
A is C(R$^2$)$_2$, O, S(O)$_m$ or NR$^2$;
D, R$^2$, R$^4$, W, Z, and m are as defined in Formula I;
and pharmaceutically acceptable salts and individual stereoisomers thereof.

Additional embodiments of the invention are CGRP antagonists of Formula I which include compounds of the Formula Id:

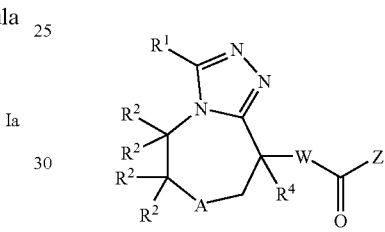

Id wherein:
A is C(R$^2$)$_2$, O, S(O)$_m$ or NR$^2$;
R$^1$, R$^2$, R$^4$, W, Z, and m are defined in Formula I;
and pharmaceutically acceptable salts and individual stereoisomers thereof.

Additional embodiments of the invention are CGRP antagonists of Formula I which include compounds of the Formula Ie:

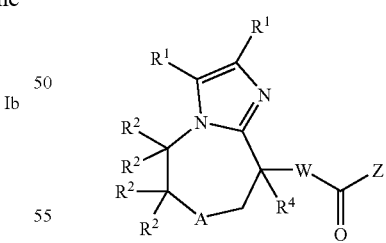

Ie wherein:
A is C(R$^2$)$_2$, O, S(O)$_m$ or NR$^2$;
R$^1$, R$^2$, R$^4$, W, Z, and m are defined in Formula I;
and pharmaceutically acceptable salts and individual stereoisomers thereof.

Additional embodiments of the invention are CGRP antagonists of Formula I which include compounds of the Formula If:

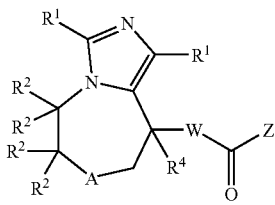

wherein:
A is $C(R^2)_2$, O, $S(O)_m$ or $NR^2$;
$R^1$, $R^2$, $R^4$, W, Z, and m are defined in Formula I;
and pharmaceutically acceptable salts and individual stereoisomers thereof.

Further embodiments of the invention are CGRP antagonists of Formulae Ia-Ie,
wherein:
$R^1$ is selected from:
1) H, $C_1$-$C_6$ alkyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) CN,
   l) $NR^{10}R^{11}$, and
   m) $O(CO)R^4$; and
2) aryl or heteroaryl, unsubstituted or substituted with one or more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10}) SO_2 R^{11}$,
   j) $S(O)_m R^4$,
   k) CN,
   l) $NR^{10}R^{11}$, and,
   m) $O(CO)R^4$;
$R^2$ is selected from:
1) H, $C_0$-$C_6$ alkyl, $C_2$-$C_6$ alkynyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $S(O)_m R^4$,
   l) CN,
   m) $NR^{10}R^{11}$, and
   n) $O(CO)R^4$; and
2) aryl or heteroaryl, unsubstituted or substituted with one more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10}) SO_2 R^{11}$,
   j) $S(O)_m R^4$,
   k) CN,
   l) $NR^{10}R^{11}$, and
   m) $O(CO)R^4$,
where any two independent $R^2$ on the same or adjacent atoms optionally join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl;
$R^{10}$ and $R^{11}$ are independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl and morpholinyl, which ring is unsubstituted or substituted with 1-5 substituents each independently selected from $R^4$;
$R^4$ is independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy;
W is O, $NR^4$ or $C(R^4)_2$;
$R^6$ is independently selected from H and:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10}) SO_2 R^{11}$,
   j) $S(O)_m R^4$,
   k) CN,
   l) $NR^{10}R^{11}$ and
   m) $O(CO)R^4$; and J is a bond, $C(R^5)_2$, O, or $NR^5$, and V is a bond, $C(R^6)_2$, O, $S(O)_m$, $NR^6$, $C(R^6)_2—C(R^6)_2$, $C(R^6)=C(R^6)$, $C(R^6)_2—N(R^6)$, $C(R^6)=N,N(R^6)—C(R^6)_2$, $N=C(R^6)$ or $N(R^6)—N(R^6)$, such that when:

J is a bond, V is a bond and Z is Z1 the following structure forms:

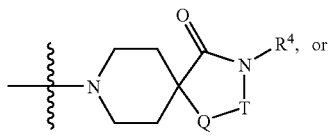

J is a bond, V is a bond, Z is Z1 and T is —C(=O)—, the following structure forms:

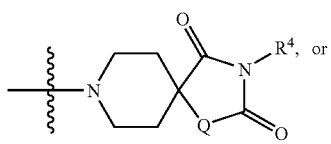

J is a bond and Z is Z1 the following structure forms:

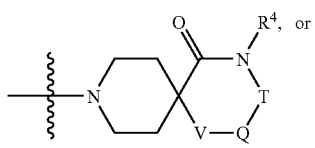

V is a bond and Z is Z1 the following structure forms:

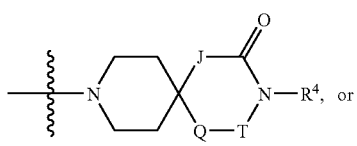

G-L is N, and Z is Z2 the following structure forms:

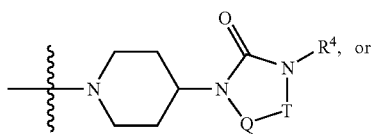

G-L is N—$C(R^6)_2$, and Z is Z2 the following structure forms:

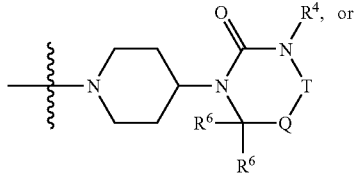

G-L is C=$C(R^6)$, and Z is Z2 the following structure forms:

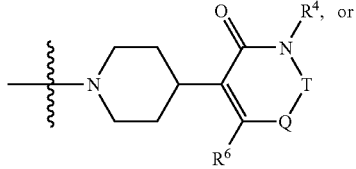

G-L is C=N, and Z is Z2 the following structure forms:

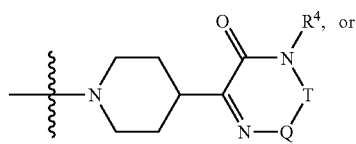

G-L is N—$C(R^6)_2$—$C(R^6)_2$, and Z is Z2 the following structure forms:

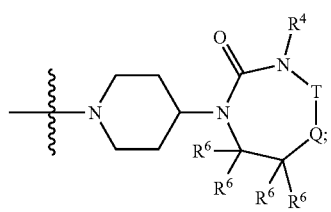

Q is independently selected from:
(1) =$C(R^{7a})$—,
(2) —$C(R^{7a})_2$—,
(3) —C(=O)—,
(4) —$S(O)_m$—,
(5) =N—, and
(6) —$N(R^{7a})$—;

T is independently selected from:
(1) =$C(R^{7b})$—,
(2) —$C(R^{7b})_2$—,
(3) —C(=O)—,
(4) —$S(O)_m$—,
(5) =N—, and
(6) —$N(R^{7b})$—;

$R^3$ is independently selected from H, substituted or unsubstituted $C_1$-$C_3$ alkyl, F, CN and $CO_2R^4$;
$R^{7a}$ and $R^{7b}$ are each independently selected from $R^2$, where $R^{7a}$ and $R^{7b}$ and the atom or atoms to which they are attached optionally join to form a ring selected from $C_{3-6}$cycloalkyl, aryl, heterocycle, and heteroaryl, which ring is unsubstituted or substituted with 1-10 substituents each each independently selected from $R^6$;
p is 0 to 2q+1, for a substituent with q carbons
m is 0 to 2;
s is 1 to 3;
and pharmaceutically acceptable salts and individual stereoisomers thereof.

Still further embodiments of the invention are CGRP antagonists of Formulae Ia-Ie, wherein:
$R^1$ is selected from:
1) H, $C_1$-$C_6$ alkyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) phenyl, unsubstituted or substituted with 1-5 substituents each independently selected from $R^4$,
   d) heteroaryl, unsubstituted or substituted with 1-5 substituents each independently selected from $R^4$,
      and where heteroaryl is selected from:
      imidazole, isoxazole, oxazole, pyrazine, pyrazole, pyridazine, pyridine, pyrimidine, and thiazole;
   e) heterocycle, unsubstituted or substituted with 1-5 substituents each independently selected from $R^4$, and where heterocycle is selected from: azetidine, dioxane, dioxolane, morpholine, oxetane, piperazine, piperidine, pyrrolidine, tetrahydrofuran, and tetrahydropyran;
f) $(F)_pC_{1-3}$ alkyl,
g) halogen,
h) $OR^4$,
i) $O(CH_2)_sOR^4$,
j) $CO_2R^4$,
k) CN,
l) $NR^{10}R^{11}$,
m) $O(CO)R^4$;

2) aryl or heteroaryl, selected from: phenyl, imidazole, isoxazole, oxazole, pyrazine, pyrazole, pyridazine, pyridine, pyrimidine, and thiazole,
unsubstituted or substituted with one or more substituents each independently selected from:
a) $C_{1-6}$ alkyl,
b) $C_{3-6}$ cycloalkyl,
c) $(F)_pC_{1-3}$ alkyl,
d) halogen,
e) $OR^4$,
f) $CO_2R^4$,
g) $(CO)NR^{10}R^{11}$,
h) $SO_2NR^{10}R^{11}$,
i) $N(R^{10})SO_2R^{11}$,
j) $S(O)_mR^4$,
k) CN,
l) $NR^{10}R^{11}$, and
m) $O(CO)R^4$;

$R^2$ is selected from:
1) H, $C_0$-$C_6$ alkyl, $C_{3-6}$ cycloalkyl and heterocycle, unsubstituted or substituted with one or more substituents each independently selected from:
a) $C_{1-6}$ alkyl,
b) $C_{3-6}$ cycloalkyl,
c) phenyl, unsubstituted or substituted with 1-5 substituents each independently selected from $R^4$,
d) heteroaryl, unsubstituted or substituted with 1-5 substituents each independently selected from $R^4$,
and where heteroaryl is selected from: benzimidazole, benzothiophene, furan, imidazole, indole, isoxazole, oxazole, pyrazine, pyrazole, pyridazine, pyridine, pyrimidine, pyrrole, thiazole, thiophene, and triazole;
e) heterocycle, unsubstituted or substituted with 1-5 substituents where the substituents are independently selected from $R^4$, and where heterocycle is selected from: azetidine, imidazolidine, imidazoline, isoxazoline, isoxazolidine, morpholine, oxazoline, oxazolidine, oxetane, pyrazolidine, pyrazoline, pyrroline, tetrahydrofuran, tetrahydropyran, thiazoline, and thiazolidine;
f) $(F)_pC_{1-3}$ alkyl,
g) halogen,
h) $OR^4$,
i) $O(CH_2)_sOR^4$,
j) $CO_2R^4$,
k) CN,
l) $NR^{10}R^{11}$, and
m) $O(CO)R^4$; and 2) aryl or heteroaryl, selected from:
phenyl, benzimidazole, benzothiophene, furan, imidazole, indole, isoxazole, oxazole, pyrazine, pyrazole, pyridazine, pyridine, pyrimidine, pyrrole, thiazole, thiophene, and triazole, unsubstituted or substituted with one or more substituents each independently selected from:
a) $C_{1-6}$ alkyl,
b) $C_{3-6}$ cycloalkyl,
c) $(F)_pC_{1-3}$ alkyl,
d) halogen,
e) $OR^4$,
f) $CO_2R^4$,
g) $(CO)NR\ OR^{11}$,
h) $SO_2NR^{10}R^{11}$,
i) $N(R^{10})SO_2R^{11}$,
j) $S(O)_mR^4$,
k) CN,
l) $NR^{10}R^{11}$, and
m) $O(CO)R^4$,
where any two independent $R^2$ on the same or adjacent atoms optionally join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, $R^{10}$ and $R^{11}$ are independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl and morpholinyl, which ring is unsubstituted or substituted with 1-5 substituents each independently selected from $R^4$;

$R^4$ is independently selected from: H, $C_{1-6}$ alkyl, $(F)_pC_{1-6}$ alkyl, $C_{3-6}$ cycloalkyl, aryl, heteroaryl and phenyl, unsubstituted or substituted with hydroxy or $C_1$-$C_6$ alkoxy;

W is $NR^4$ or $C(R^4)_2$;

$R^6$ is independently selected from H and:
a) $C_{1-6}$ alkyl,
b) $C_{3-6}$ cycloalkyl,
c) $(F)_pC_{1-3}$ alkyl,
d) halogen,
e) $OR^4$,
f) $CO_2R^4$,
g) $(CO)NR^{10}R^{11}$,
h) $SO_2NR^{10}R^{11}$,
i) $N(R^{10})SO_2R^{11}$,
j) $S(O)_mR^4$,
k) CN,
l) $NR^{10}R^{11}$, and
m) $O(CO)R^4$;

J is a bond, V is a bond, Z is Z1, Q is —$N(R^{7a})$—, and T is —C(=O)—, such that the following structure forms:

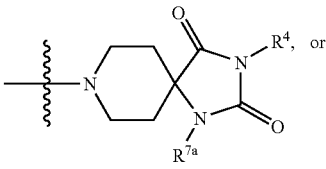

J is a bond, V is a bond, Z is Z1, Q is —$C(R^{7a})_2$—, and T is —C(=O)—, such that the following structure forms:

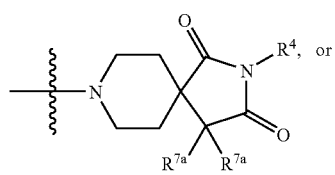

J is a bond, V is a bond, Z is Z1, Q is —N═, and T is ═C(R$^{7b}$)—, such that the following structure forms:

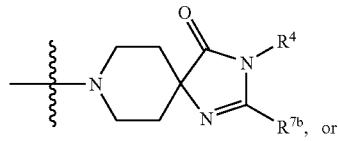

J is a bond, V is a bond, Z is Z1, Q is —C(R$^{7a}$)$_2$—, and T is —C(R$^{7b}$)$_2$—, such that the following structure forms:

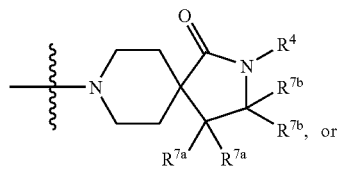

J is a bond, V is a bond, Z is Z1, Q is —C(R$^{7a}$)═, T is ═C(R$^{7b}$)—, and the atoms to which R$^{7a}$ and R$^{7b}$ are attached are joined together to form a benzene, pyridine, or diazine ring such that one of the following structures form:

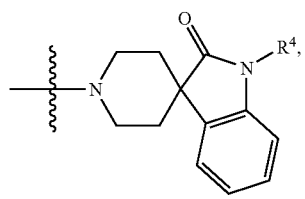

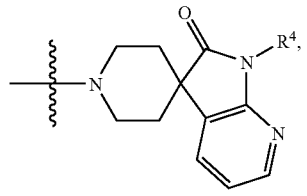

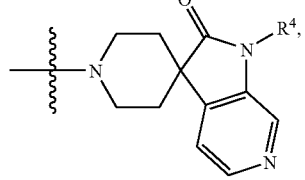

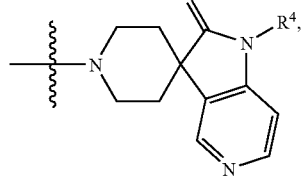

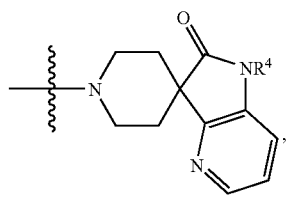

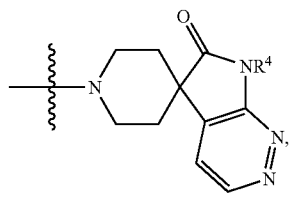

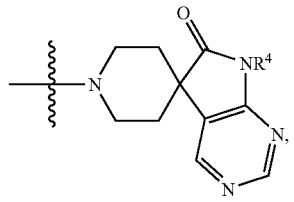

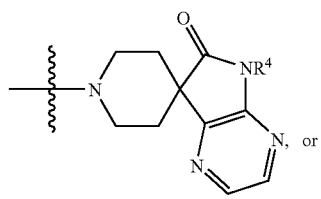

J is a bond, V is C(R$^6$)$_2$, Z is Z1, Q is —C(R$^{7a}$)═, T is ═C(R$^{7b}$)—, and the atoms to which R$^{7a}$ and R$^{7b}$ are attached are joined together to form a benzene, or pyridine ring such that one the following structures form:

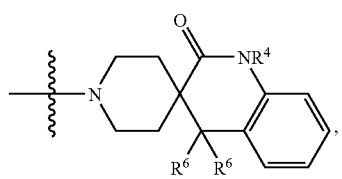

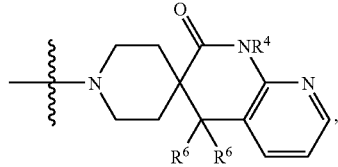

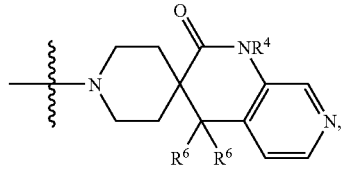

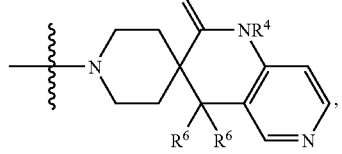

-continued

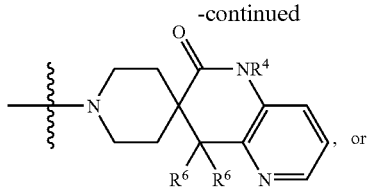, or

J is O, V is a bond, Z is Z1, Q is —C(R$^{7a}$)═, T is ═C(R$^{7b}$)—, and the atoms to which R$^{7a}$ and R$^{7b}$ are attached are joined together to form a benzene, or pyridine ring such that one of the following structures form:

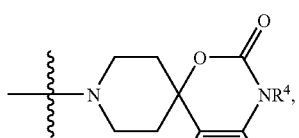,

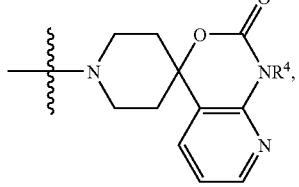,

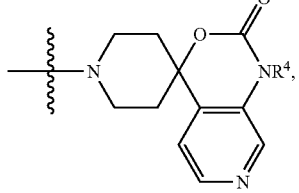,

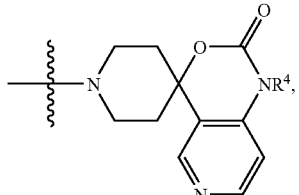,

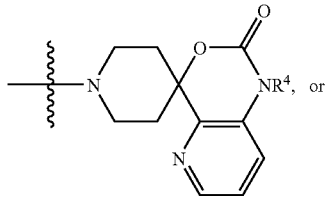, or

G-L is N, Z is Z2, Q is —C(R$^{7a}$)$_2$—, and T is —C(R$^{7b}$)$_2$—, such that the following structure forms:

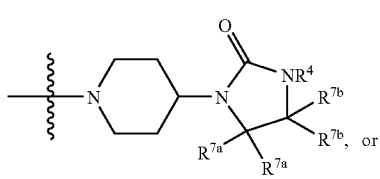,

G-L is N, Z is Z2, Q is —C(R$^{7a}$)═ and T is ═C(R$^{7b}$)— such that the following structure forms:

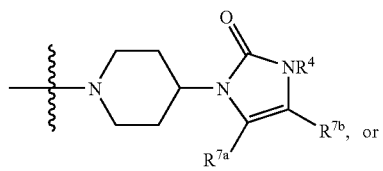, or

G-L is N, Z is Z2, Q is —N═, and T is ═C(R$^{7b}$)—, such that the following structure forms:

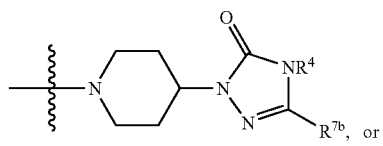, or

G-L is N, Z is Z2, Q is —C(R$^{7a}$)$_2$—, and T is —C(O)—, such that the following structure forms:

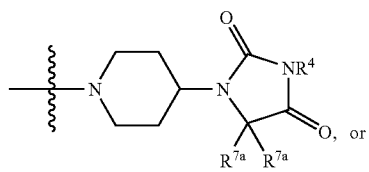, or

G-L is C═C(R$^6$), Z is Z2, Q is —C(R$^{7a}$)═ and T is ═C(R$^{7b}$)—, such that the following structure forms:

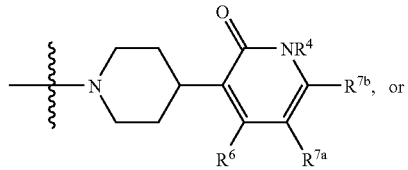, or

G-L is C═C(R$^6$), Z is Z2, Q is —C(R$^{7a}$)═ and T is ═N—, such that the following structure forms:

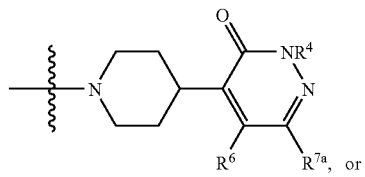, or

G-L is C═C(R$^6$), Z is Z2, Q is —N═ and T is ═C(R$^{7b}$)—, such that the following structure forms:

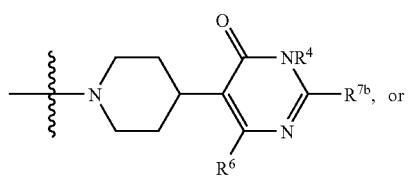, or

G-L is C=N, Z is Z2, Q is —C(R$^{7a}$)= and T is =C(R$^{7b}$)—, such that the following structure forms:

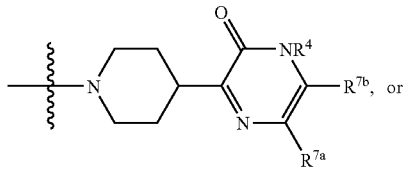, or

G-L is N, Z is Z2, Q is —C(R$^{7a}$)=, and T is =C(R$^{7b}$)—, and the atoms to which R$^{7a}$ and R$^{7b}$ are attached are joined together to form a benzene, pyridine, or diazine ring such that one of the following structures form:

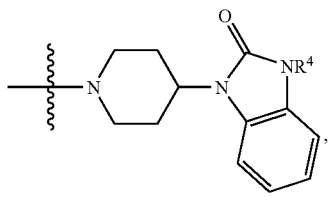

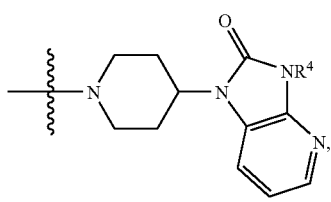

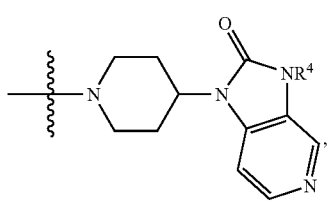

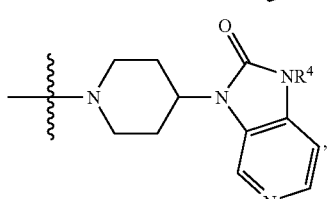

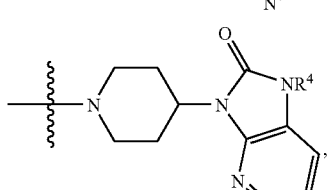

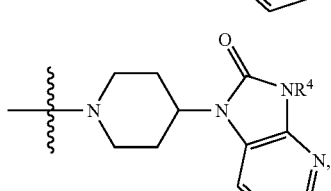

-continued

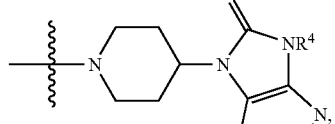

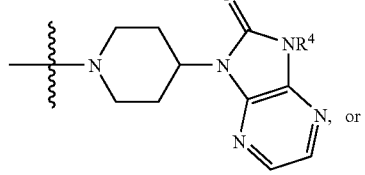, or

G-L is N—C(R$^6$)$_2$, Z is Z2, Q is —C(R$^{7a}$)=, and T is =C(R$^{7b}$)—, and the atoms to which R$^{7a}$ and R$^{7b}$ are attached are joined together to form a benzene, or pyridine ring such that one of the following structures form:

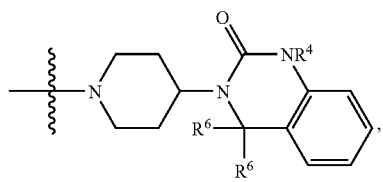

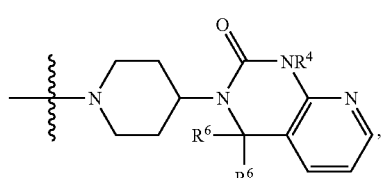

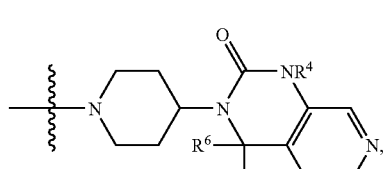

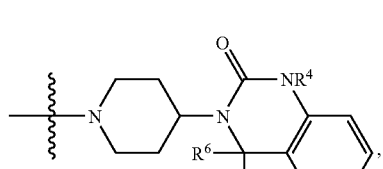

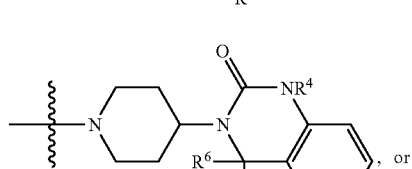, or

G-J is C=N, Z is Z2, Q is —C(R$^{7a}$)=, and T is =C(R$^{7b}$)—, and the atoms to which R$^{7a}$ and R$^{7b}$ are attached are joined together to form a benzene ring such that the following structure forms:

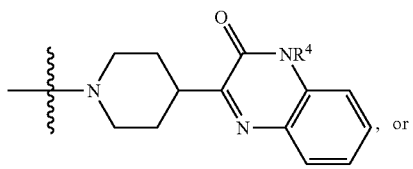

G-L is C=C(R$^6$), Z is Z2, Q is —C(R$^{7a}$)=, and T is =C(R$^{7b}$)—, and the atoms to which R$^{7a}$ and R$^{7b}$ are attached are joined together to form a benzene ring such that the following structure forms:

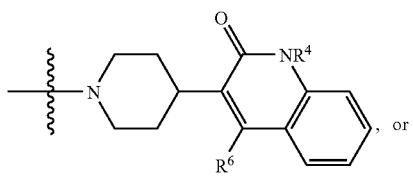

G-L is N—C(R$^6$)$_2$—C(R$^6$)$_2$, Z is Z2, Q is —C(R$^{7a}$)=, and T is =C(R$^{7b}$)—, and the atoms to which R$^{7a}$ and R$^{7b}$ are attached are joined together to form a benzene ring such that the following structure forms:

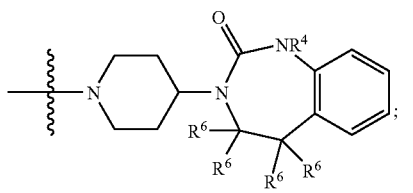

R$^3$ is independently selected from H, substituted or unsubstituted C$_1$-C$_3$ alkyl, F, CN and CO$_2$R$^4$;
R$^{7a}$ and R$^{7b}$ are each independently selected from R$^2$, where R$^{7a}$ and R$^{7b}$ and the atom or atoms to which they are attached optionally join to form a ring selected from C$_{3-6}$cycloalkyl, aryl, heterocycle, and heteroaryl which is unsubstituted or substituted with 1-10 substituents each each independently selected from R$^6$;
p is 0 to 2q+1, for a substituent with q carbons
m is 0 to 2;
s is 1 to 3;
and pharmaceutically acceptable salts and individual stereoisomers thereof.

Another embodiment of the invention includes CGRP antagonists which include compounds of Formula II:

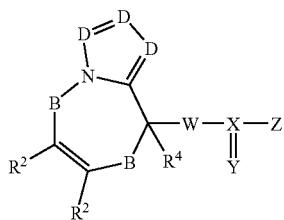

II wherein:
B, J, Q, T, V, W, X, Y, R$^1$, R$^2$, R3 and R4 are as defined in Formula I, and pharmaceutically acceptable salts and individual diastereomers thereof.

It is to be understood that where one or more of the above recited structures or substructures recite multiple substituents having the same designation each such variable may be the same or different from each similarly designated variable. For example, R$^2$ is recited four times in Formula I, and each R$^2$ in Formula I may independently be any of the substructures defined under R$^2$. The invention is not limited to structures and substructures wherein each R$^2$ must be the same for a given structure. The same is true with respect to any variable appearing multiple time in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not every substituent or combination of substituents which are said to form rings are capable of forming a ring structure in every circumstance or situation. Moreover, even those substituents capable of ring formation may or may not form a ring structure in every circumstance or situation.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus C$_{1-6}$alkyl is defined to identify the group as having 1, 2, 3, 4, 5 or 6 carbons in a linear or branched arrangement, such that C$_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which which forms a ring of three or more atoms. $C_0$ or $C_0$alkyl is defined to identify the presence of a direct covalent bond.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronaphthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The number of certain variables present in certain instances is defined in terms of the number of carbons present. For example, variable "p" is occasionally defined as follows: "p is 0 to 2q+1, for a substituent with q carbons". Where the substituent is "$(F)_p C_{1-3}$ alkyl" this means that when there is one carbon, there are 2(1)+1=3 fluorines. When there are two carbons, there are 2(2)+1=5 fluorines, and when there are three carbons there are 2(3)=1=7 fluorines.

When variables G and L are presented or depicted as "G-L" this indicates that G and L together represent a particular moiety. G-L may represent a single ring atom or various arrangements of multiple ring atoms. For instance, G-L is at times herein defined as the single ring atom N, and is at other times defined as multiple ring atoms $N-C(R^6)_2$, $C=C(R^6)$, and so forth.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 μg) were incubated in 1 ml of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 μl) was added and the radioactivity was counted on a Topcount (Packard Instrument). Data analysis was carried out by using Prism and the K$_i$ was determined by using the Cheng-Prusoff equation (Cheng & Prusoff (1973) *Biochem. Pharmacol.* 22, 3099-3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 μg/ml streptomycin at 37° C., 95% humidity, and 5% CO$_2$. For cAMP assays, cells were plated at 5×10$^5$ cells/well in 96-well poly-D-lysine-coated plates (Becton-Dickinson) and cultured for ~18 h before assay. Cells were washed with phosphate-buffered saline (PBS, Sigma) then pre-incubated with 300 μM isobutylmethylxanthine in serum-free MEM for 30 min at 37° C. Antagonist was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct fall Schild plots (Arunlakshana & Schild (1959) *Br. J. Pharmacol.* 14, 48-58).

RECOMBINANT RECEPTOR: Human CRLR (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 ug/ml streptomycin, and maintained at 37° C. and 95% humidity. Cells were subcultured by treatment with 0.25% trypsin with 0.1% EDTA in HBSS. Stable cell line generation was accomplished by co-transfecting 10 ug of DNA with 30 ug Lipofectamine 2000 (Invitrogen) in 75 cm$^2$ flasks. CRLR and RAMP1 expression constructs were co-transfected in equal amounts. Twenty-four hours after transfection the cells were diluted and selective medium (growth medium+300 ug/ml hygromycin and 1 ug/ml puromycin) was added the following day. A clonal cell line was generated by single cell deposition utilizing a FACS Vantage SE (Becton Dickinson). Growth medium was adjusted to 150 ug/ml hygromycin and 0.5 ug/ml puromycin for cell propagation.

RECOMBINANT RECEPTOR BINDING ASSAY: Cells expressing recombinant human CRLR/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 ug of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (Amersham Biosciences) and antagonist. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was carried out with the apparent dissociation constant (K$_i$) determined by using a non-linear least squares fitting the bound CPM data to the equation below:

$$Y_{obsd} = \frac{Y_{min} + (Y_{max} - Y_{min})(100 - \% I_{min}/100)}{1 + ([\text{Drug}]/K_i(1 + [\textit{Radiolabel}]/K_d)^{nH}}$$

Where Y is observed CPM bound, Y$_{max}$ is total bound counts, Y min is non specific bound counts, (Y max−Y min) is specific bound counts, % I max is the maximum percent inhibition, % I min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and $IC_{50}$ values determined from a 4-parameter logistic fit as defined by the equation $y=((a-d)/(1+(x/c)^b)+d$, where y=response, x=dose, a=max response, d=min response, c=inflection point and b=slope.

In particular, the compounds of the following examples had activity as antagonists of the CGRP receptor in the aforementioned assays, generally with a $K_i$ or $IC_{50}$ value of less than about 50 µM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an an anti-migraine agent, such as ergotamine and dihydroergotamine, or other serotonin agonists, especially a $5-HT_{1B/1D}$ agonist, for example sumatriptan, naratriptan, zolmitriptan, eletriptan, almotriptan, frovatriptan, donitriptan, and rizatriptan, a $5-HT_{1D}$ agonist such as PNU-142633 and a $5-HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sulfentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a brakykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrine precursor; antianxiety agents such as diazepam, alprazolam, chlordiazepoxide and chlorazepate; serotonin $5HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocomiine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapene; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-$HT_1$ agonist, especially a 5-$HT_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes. The synthesis of intermediates and final compounds may be conducted as described in Schemes 1-17.

REACTION SCHEMES

The preparation of final compounds proceeds through intermediates such as those of formula I and formula II, and the synthesis of each intermediate is described herein.

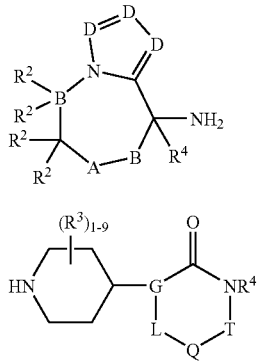

In general, intermediates of the formulas III and IV can be coupled through a urea linkage as shown in Scheme 1. The resulting amine after deprotection of intermediate 1 can be converted to a reactive carbamate, for example p-nitrophenylcarbamate 2, which is subsequently reacted with an amine like that of intermediate 3 to produce urea 4. Other activated intermediates known to those skilled in the art can be used to prepare compounds like 4. For example, the resultant primary amine after deprotection of 1 can be directly acylated with the appropriate carbamoyl chloride.

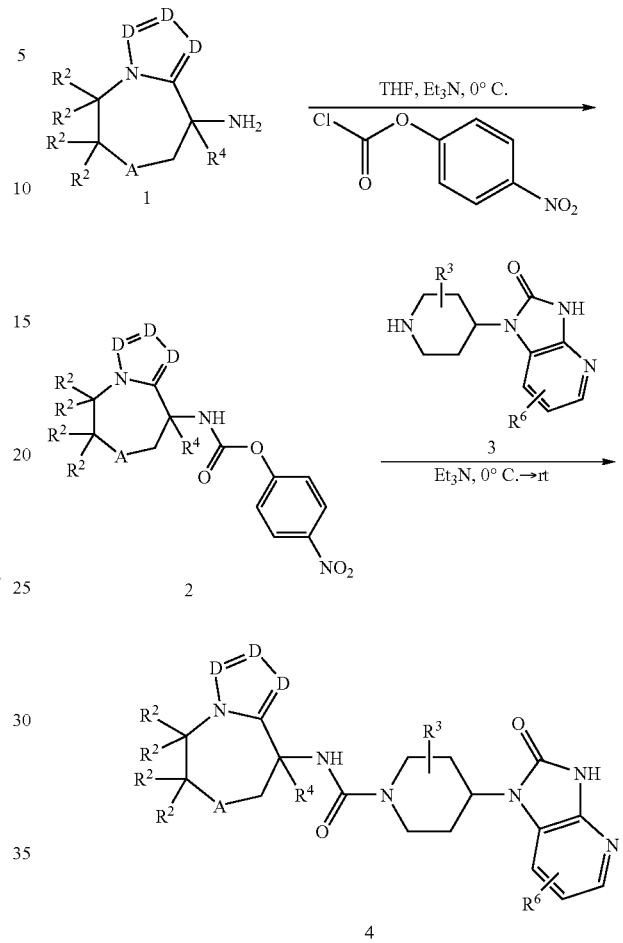

The synthesis of compounds represented by Intermediate IV can be accomplished by procedures similar to those described in Henning et al., J. Med. Chem., 1987, 30, 814-819; Carpino et al., WO 96/35713; Brown et al., J. Chem. Soc. 1957, 682-686; Barlin et al., Aust. J. Chem. 1982, 35 (11), 2299-2306; and references cited therein.

Additionally, the synthesis of compounds represented by Intermediate IV can be accomplished according to Schemes 2-10. For example, a diamino heterocycle, such as 2,3-diaminopyridine 5, can be reductively alkylated with ketones such as 6 to give the monoalkylated product 7 (Scheme 2). Ring closure with carbonyldiimidazole furnishes imidazolone 8. Final deprotection under standard conditions gives the intermediate 3.

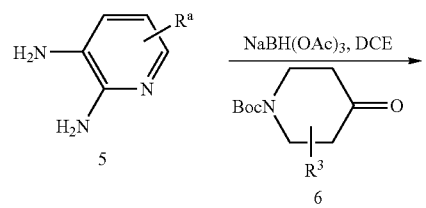

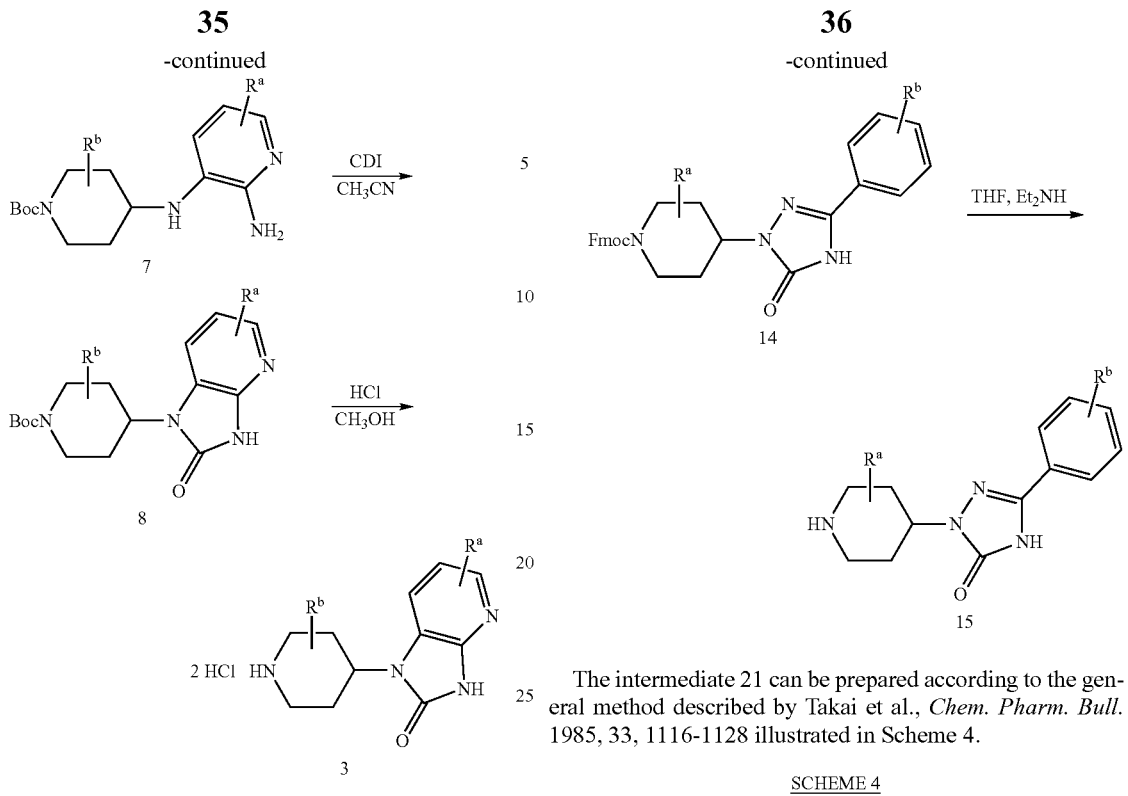

Triazolinones can be prepared according to Scheme 3. For example, a 4-piperidinone 9 can be reductively aminated with a carbazate which, after reduction of hydrazone 10, gives the monoalkylated product 11. Deprotection to afford hydrazine 12 and condensation/ring closure with a benzothioyl carbamate such as 13 furnishes triazolinone 14. Final deprotection under standard conditions gives the product 15.

The intermediate 21 can be prepared according to the general method described by Takai et al., *Chem. Pharm. Bull.* 1985, 33, 1116-1128 illustrated in Scheme 4.

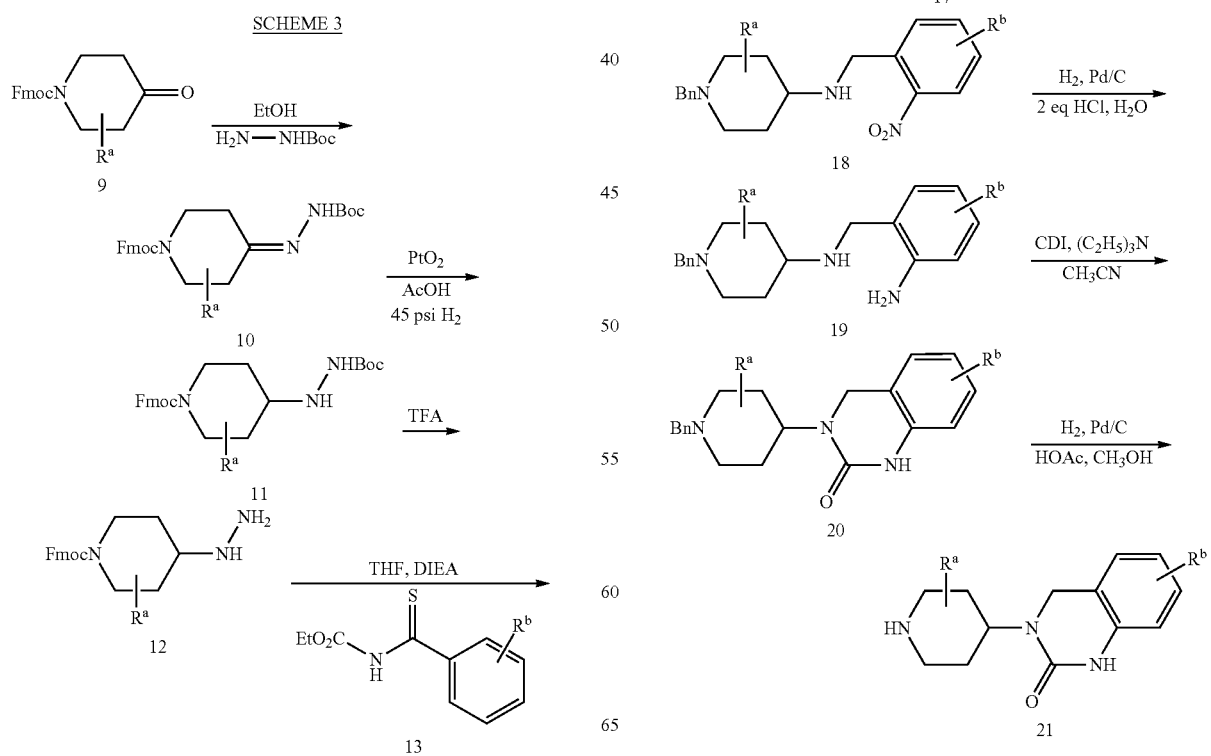

A similar synthetic strategy can be used to construct the related benzodiazepinone of formula 29 shown in Scheme 5. The starting alcohols 22 are commercially available, or prepared according to procedures known to those skilled in the art. Alcohol 22 can be converted to a halide using standard conditions, such as triphenylphosphine and bromine to prepare the bromide 23. The halide is displaced with azide nucleophile, and the azide 24 reduced under standard conditions to give the primary amine 25. This amine can be reductively alkylated with a suitably protected 4-piperidinone to give compound 26. Reduction of the nitro group is easily accomplished using a variety of conditions, and subsequent cyclization can be achieved with carbonyldiimidazole to afford cyclic urea 28. Deprotection then liberates amine 29.

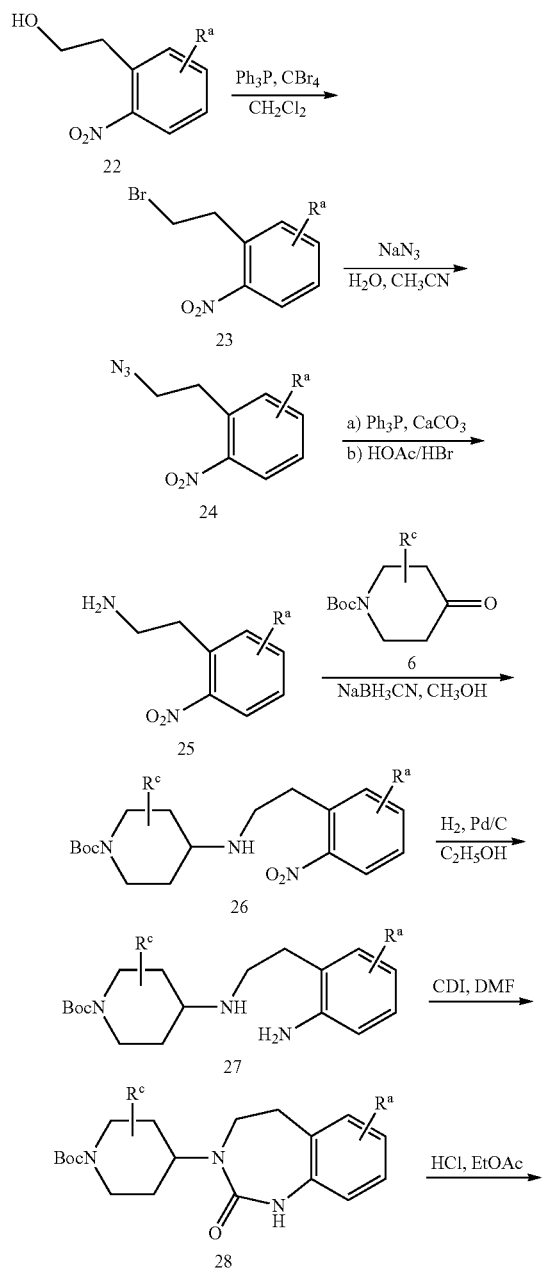

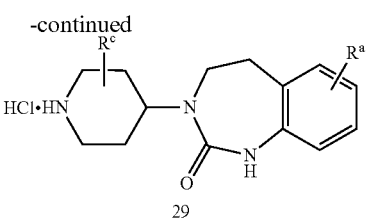

Quinolone 34 can be prepared by reaction of the anion derived from 2-chloroquinoline and lithium diisopropylamide, with piperidone 31 (Scheme 6). Concomitant elimination of the tertiary alcohol and hydrolysis of the chloroquinoline is accomplished with aqueous hydrochloric acid. Removal of the piperidine N-benzyl protective group by catalytic hydrogenation also reduces the olefin formed in the previous step and results in amine 34.

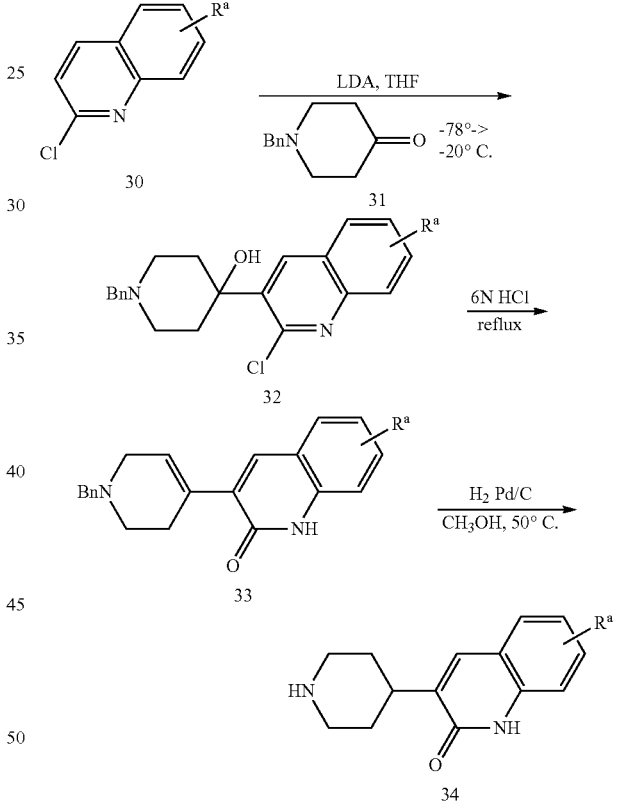

7-Azaindole (35) may be protected with a variety of protecting groups, such as the (trimethylsilyl)ethoxymethyl group shown in Scheme 7. Following the method of Marfat and Carter (*Tetrahedron Lett.*, 1987, 28, 4027-4030), treatment of 36 with pyridine hydrobromide perbromide provides the dibromoazaoxindole 37, which may be reduced to the corresponding azaoxindole 38 by reaction with zinc. The key alkylation of 38 with methyl 1,2-bis(bromomethyl)-4-benzoate (39) is carried out using cesium carbonate in DMF to afford the spiroazaoxindole 40. A variety of other bases and solvents may be employed in this alkylation reaction, and use of an alternative alkylating agent to the dibromide shown here can lead to different products. Removal of the SEM protecting group under standard conditions followed by saponification provides the acid intermediate 42. The methodology shown in Scheme 7 is not limited to azaoxindoles such as 38, but may be applied to a variety of suitably protected heterocyclic systems to give the corresponding spiro compounds.

26, 4205-4208) affords the spiropiperidine 46. The methodology shown in Scheme 8 is not limited to azaoxindoles such as 38, but may be applied to a variety of suitably protected heterocyclic systems to give the corresponding spiro compounds.

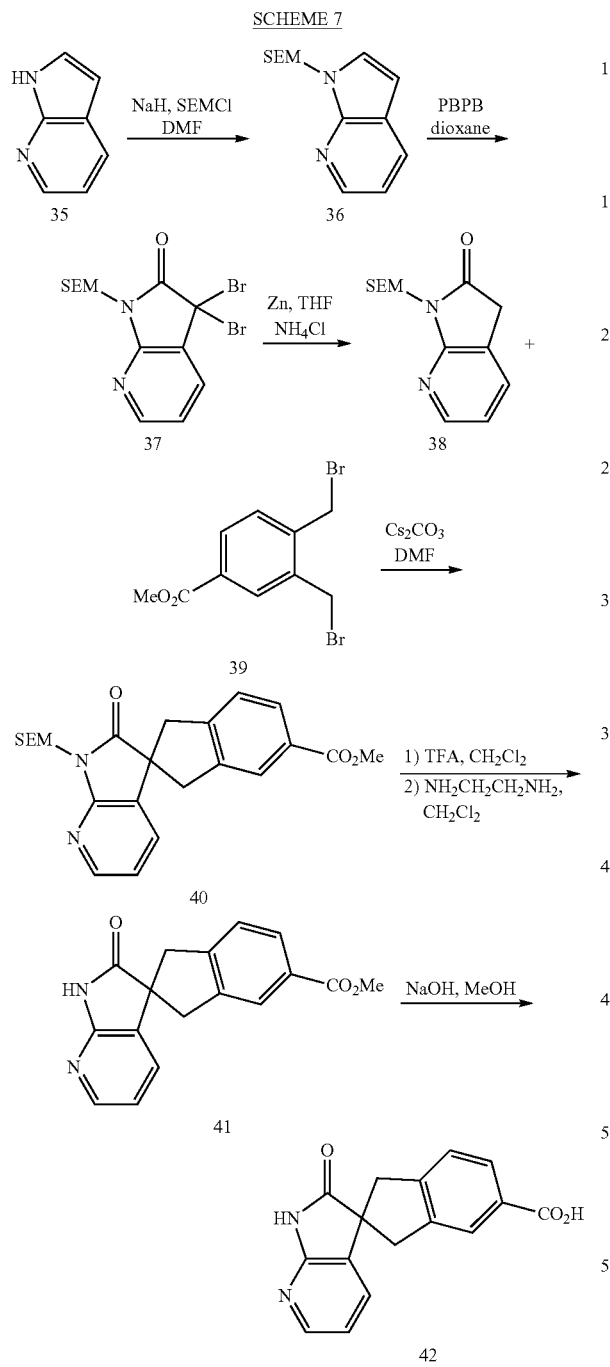

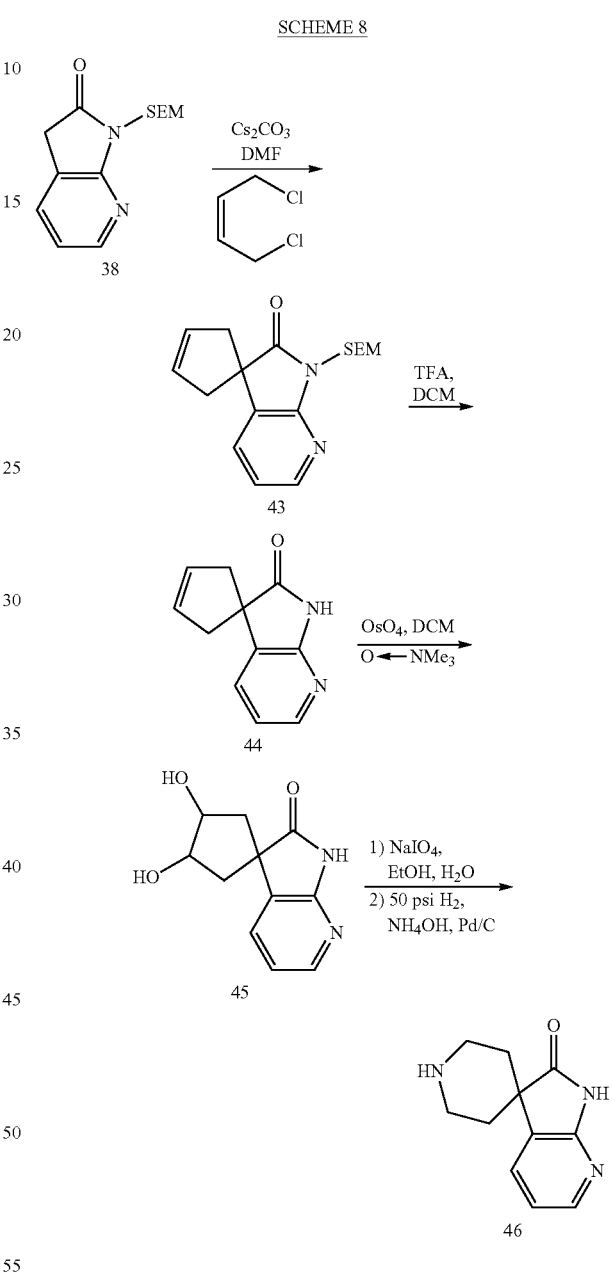

Alkylation of azaoxindole 38 with cis-1,4-dichloro-2-butene is carried out using cesium carbonate in DMF to afford the spiroazaoxindole 43 (Scheme 8). Removal of the SEM protecting group under standard conditions followed by osmium tetroxide catalyzed dihydroxylation provides the diol intermediate 45. Periodate oxidative cleavage of the diol, followed by a double reductive amination (*Org. Lett.*, 2000, The synthesis of the related spiropyridobenzoxazinone can be accomplished according to Scheme 9. 2-Amino-6-chloropyridine 47 can be protected as its Boc derivative under the action of sodium hexamethyldisilazide and di-tert-butyl dicarbonate. Ortho metalation under the conditions of Davies (*Tetrahedron Lett.*, 2004, 45, 1721-1724) and addition of the resultant anion to N-benzyloxycarbonyl-4-piperidinone, gives after in situ cyclization product 50. Final deprotection and dechlorination under standard hydrogenolysis conditions gives the intermediate 51.

SCHEME 9

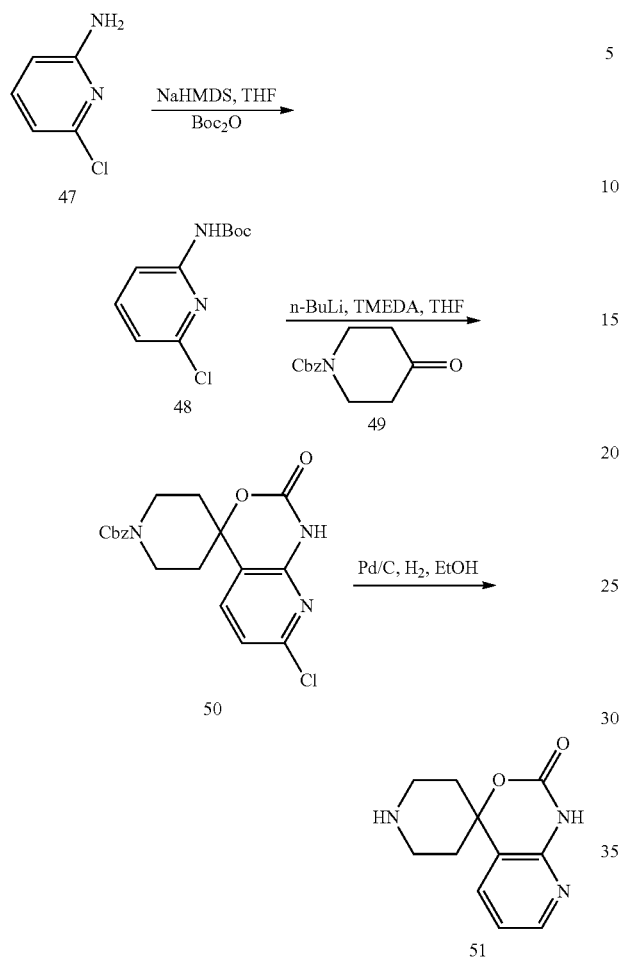

SCHEME 10

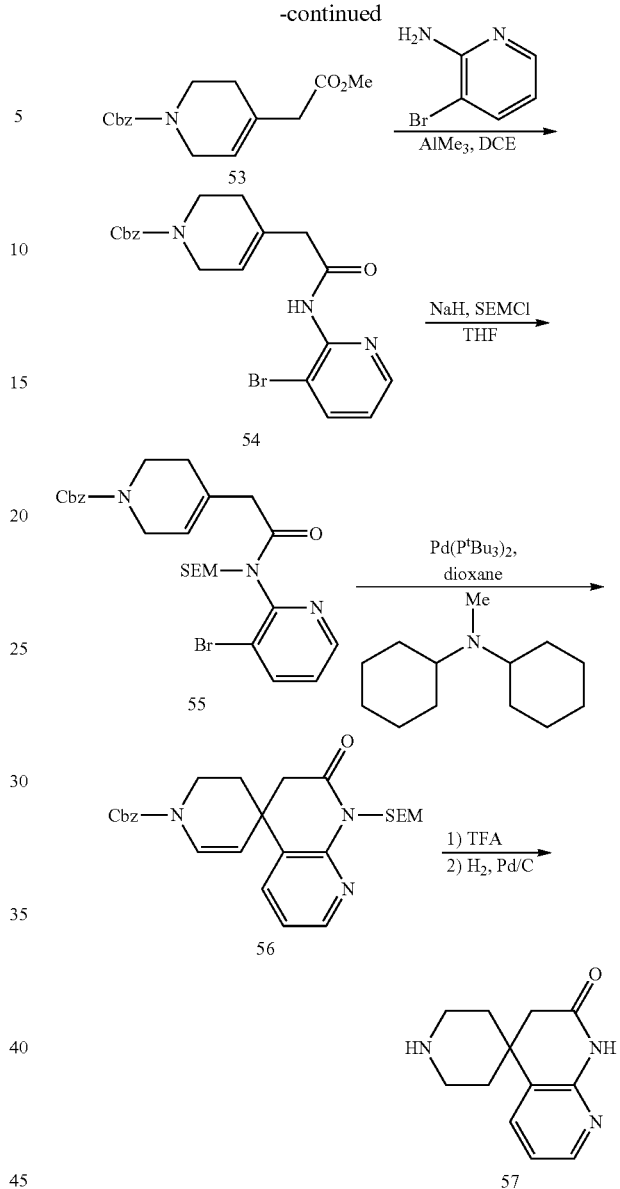

In Scheme 10, Wittig reaction of the 4-ketopiperidine 49 gives the α,β-unsaturated ester 52. The resulting product can be isomerized to the β,γ-unsaturated ester 53 under basic conditions (*Tetrahedron Lett,* 2004, 4401-4404). Trimethyla- luminum mediated amidation with 2-amino-3-bromopyridine followed by amide alkylation with 2-(trimethylsilyl) ethoxymethyl chloride affords the product 55. The key palladium-mediated spirocyclization can be affected through the Fu modification (*J. Amer. Chem. Soc.,* 2001, 6989-7000) of the Heck reaction. A two-stage deprotection with concomitant double bond reduction under standard conditions gives the desired spironaphthyridinone 57.

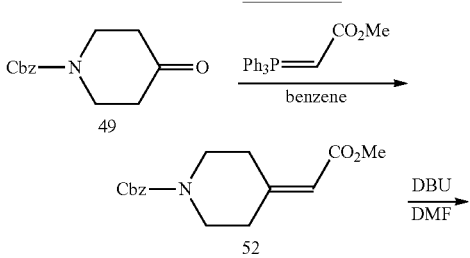

Caprolactams can be assembled following an olefin metathesis strategy as outlined in Scheme 11. 2,4-Dimethoxybenzylamine hydrochloride is alkylated with 2,3-dibromopropane under mild basic conditions to give amine 59. (2R)-2-{[(benzyloxy)carbonyl]amino}pent-4-enoic acid (60), prepared in one step from commercially available D-allyl glycine according to known procedures (*J. Chem. Soc.,* 1962, 3963-3968), can be coupled to amine 59 under a variety of conditions to give amide 61. A variety of transition metal catalyzed cross couplings can be performed on the vinyl bromide, for example palladium-mediated arylations with phenylboronic acid and sodium carbonate, yielding styrene derivative 62. Ring-closing metathesis occurs in the presence of the Grubbs second generation ruthenium catalyst in dichloromethane with mild heating to afford lactam 63. Removal of the dimethoxybenzyl group and hydrogenation with in situ protection of the primary amine gives the corresponding saturated lactam 65. Treatment with Lawesson's reagent yields thioamide compounds of the general formula 66.

SCHEME 11

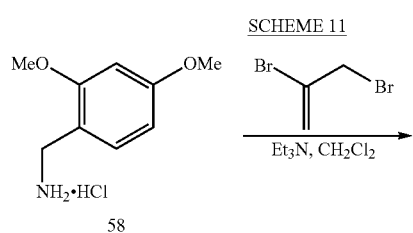

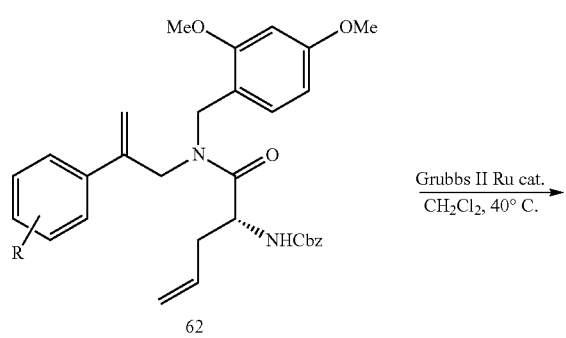

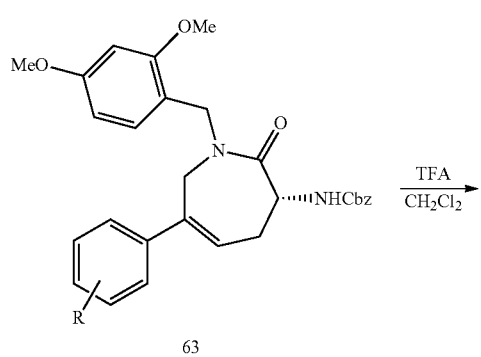

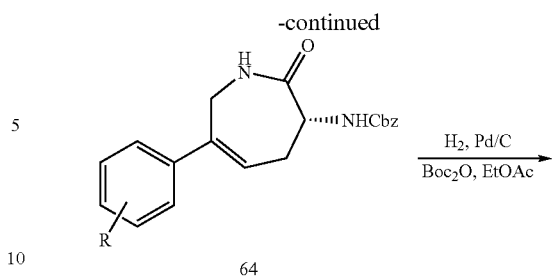

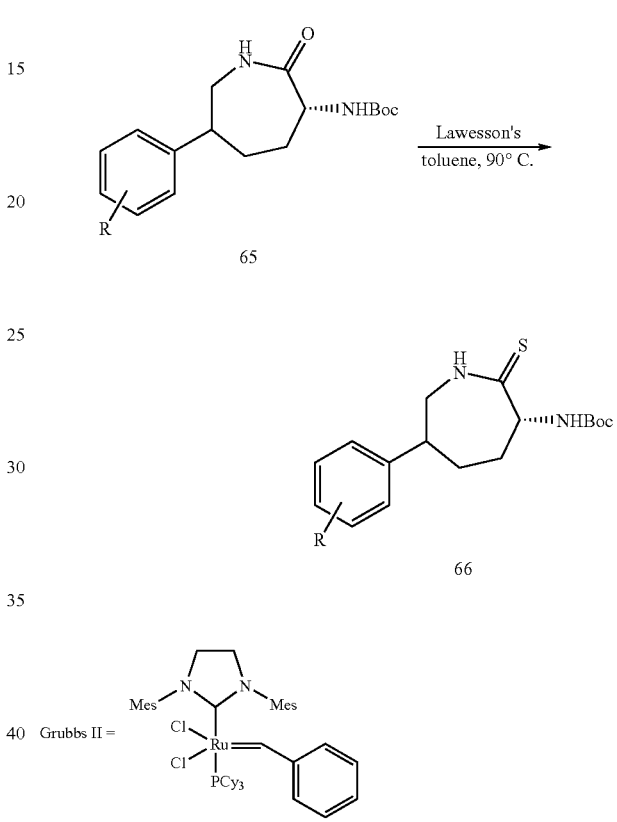

Alternatively, a C6-aryl group can be introduced as outlined in Scheme 12. Addition of nitromethane to the known glutamic acid derived aldehyde 67 (*Tetrahedron Asymmetry*, 1998, 3381-94), followed by in situ elimination affords nitro olefin 68. Addition of the aryl group via a boronic acid derivative, or similar equivalent, can be accomplished in a stereoselective manner through chiral ligand-Rh catalysis. Concomitant nitro reduction and benzyl ester hydrogenolysis affords the amino acid 70. Ring closure under standard conditions, followed by removal of a single tert-butoxycarbonyl group furnishes the lactam 72. Treatment with Lawesson's reagent yields thioamide compounds of the general formula 73.

SCHEME 12

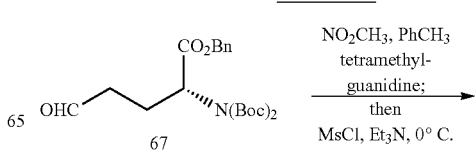

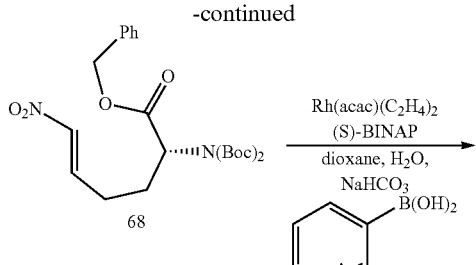

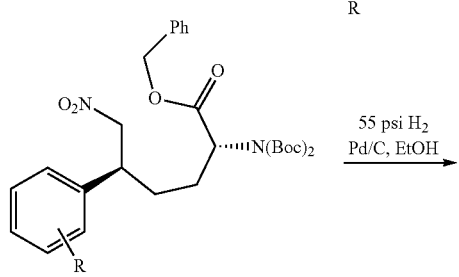

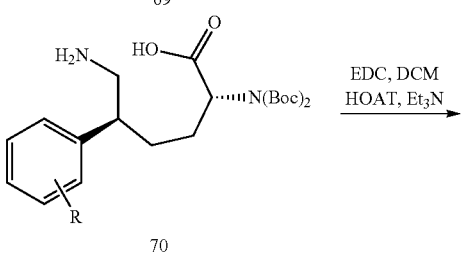

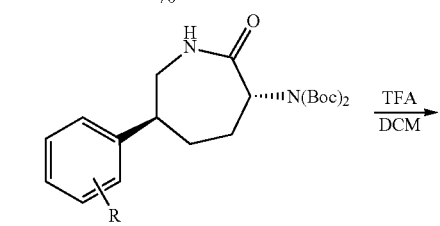

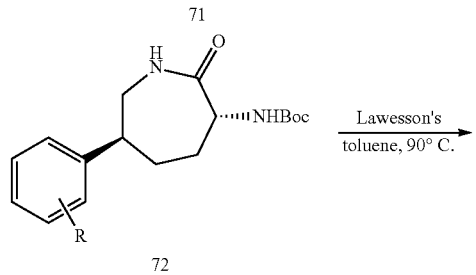

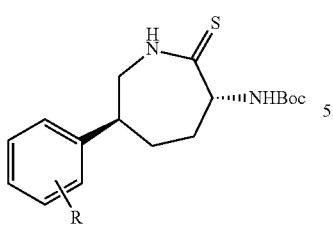

Variation at the 6-position of the caprolactams can be introduced by employing a similar strategy (Scheme 13). Ring-closing metathesis can be performed directly on vinyl bromide 61 using the Grubbs second generation ruthenium catalyst to give cyclic vinyl bromide 74. Removal of the dimethoxybenzyl group and palladium-mediated cross coupling, in this case with a boronic acid, furnishes compounds of the general formula 76. The transformation of 75 to 76 is not limited to boronic acid derivatives. After standard hydrogenation, treatment with Lawesson's reagent yields thioamide compounds of the general formula 78.

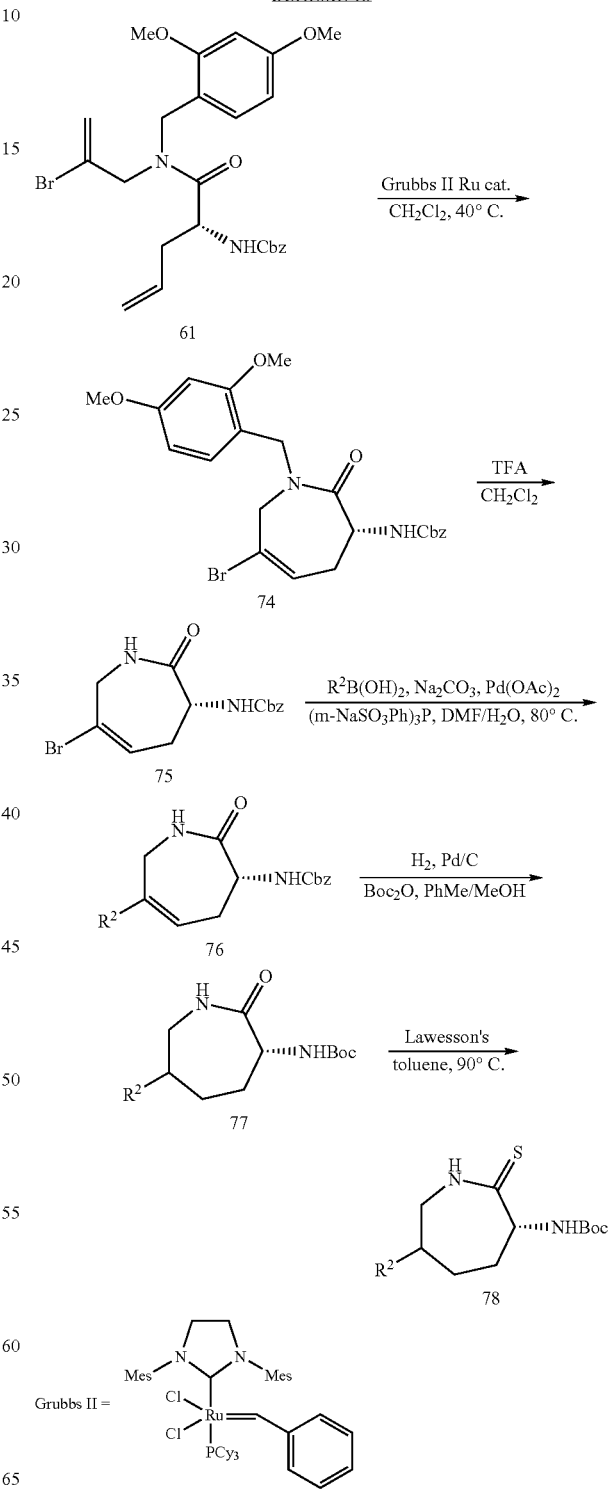

Alternatively, addition of a Grignard or similar reagent to the nitro olefin 68 followed by nitro reduction and benzyl ester hydrogenolysis affords various amino acids such as 80 (Scheme 14). Ring closure under standard conditions, followed by removal of a single tert-butoxycarbonyl group furnishes the lactam 77. Treatment with Lawesson's reagent yields thioamide compounds of the general formula 78.

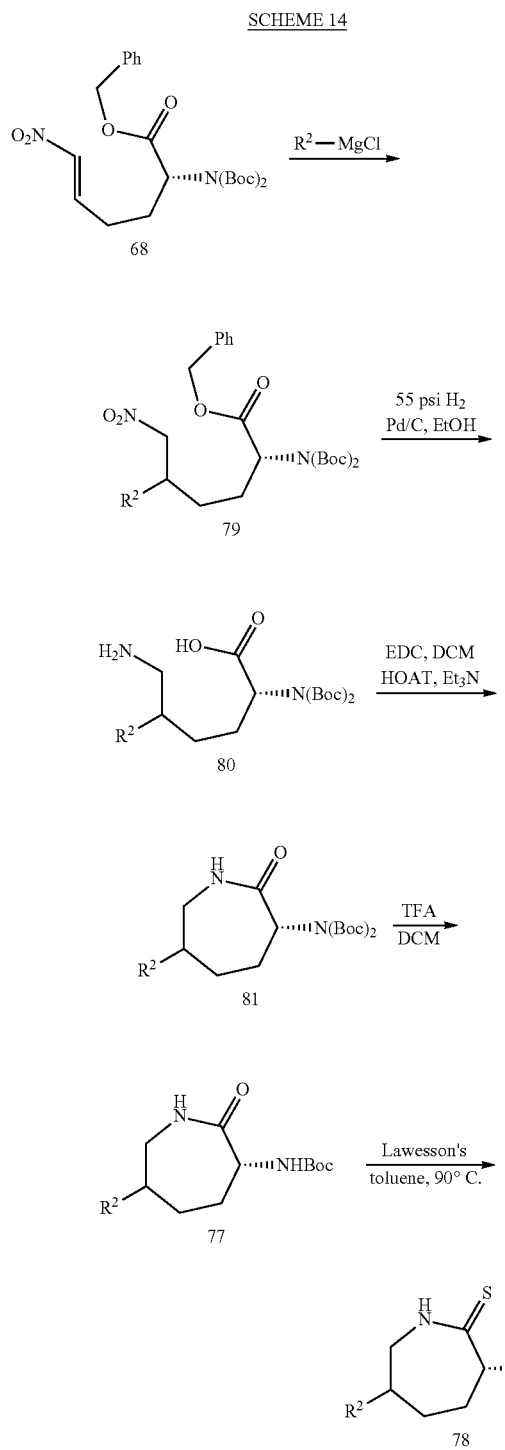

The required amino alcohols for imidazole synthesis were either commercially available or prepared as shown in Scheme 15. Treatment of aldehydes with trimethylsilyl cyanide gives cyanohydrins 83 which can be reduced to the appropriate amino alcohols 84 with lithium aluminum hydride.

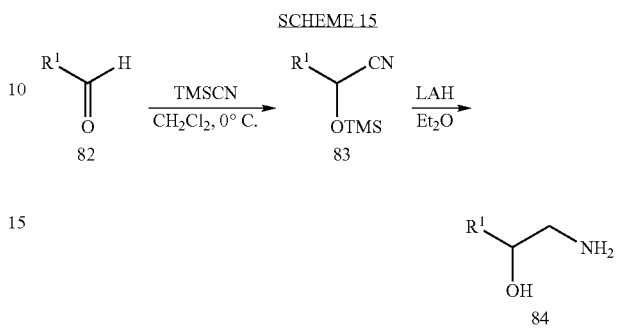

Fused imidazoles are prepared as shown in Scheme 16. Thioamide 78 is reacted with a variety of amino alcohols 84 in the presence of mercury (II) chloride to give amidines 85. Oxidation of the alcohol with concomitant ring closure using either the Dess-Martin periodinane or pyridinium dichromate finally yields imidazoles of the general formula 1.

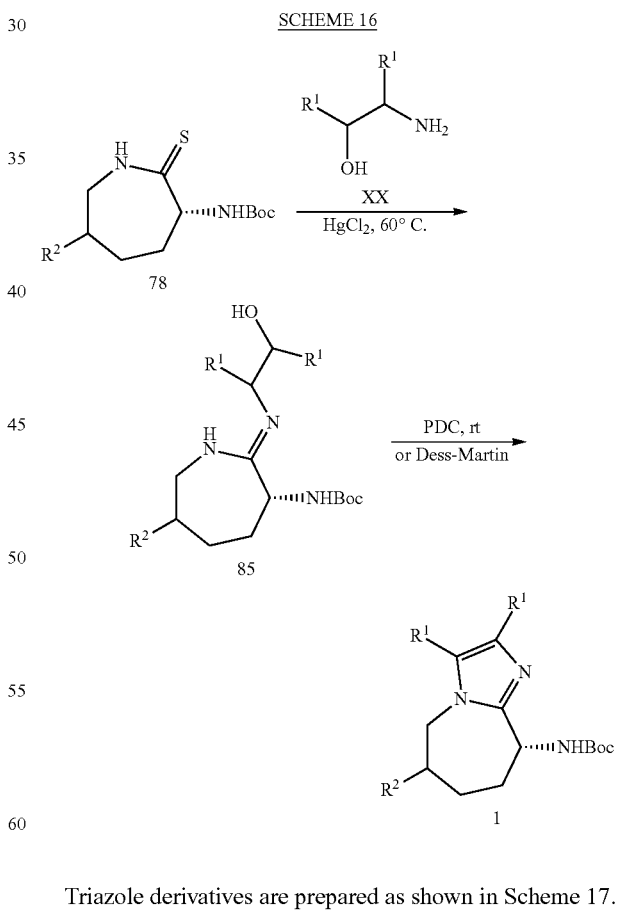

Triazole derivatives are prepared as shown in Scheme 17. Addition of hydrazine to thioamide 78 gives the corresponding hydrazide 86. Various carboxylic acids or acid chlorides can undergo couplings under standard conditions affording after ring closure the desired fused triazoles 87.

SCHEME 17

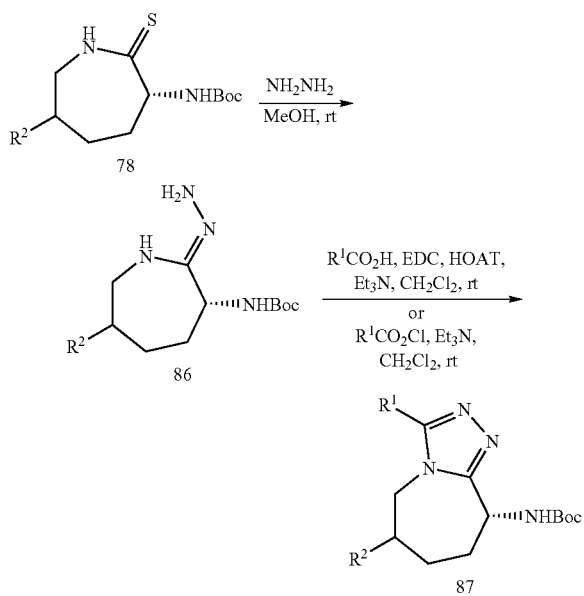

In some cases the final product may be further modified, for example, by manipulation of substituents. These manipulations may include, but are not limited to, reduction, oxidation, alkylation, acylation, and hydrolysis reactions which are commonly known to those skilled in the art. Moreover, in some cases the order of carrying out the foregoing reaction schemes may be varied to facilitate the reaction or to avoid unwanted reaction products.

INTERMEDIATES AND EXAMPLES

The following examples are provided so that the invention might be more fully understood. These examples are illustrative only and should not be construed as limiting the invention in any way.

INTERMEDIATE 1

2-Oxo-1-(4-piperidinyl)-2,3-dihydro-1H-imidazo[4,5-b]pyridine dihydrochloride

Step A. 2-Amino-3-[(1-tert-butoxycarbonylpiperidin-4-yl)amino)pyridine

Sodium triacetoxyborohydride (14.5 g, 68.7 mmol) was added to a solution of 2,3-diaminopyridine (5.00 g, 45.8 mmol) and N-(tert-butoxycarbonyl)-4-piperidone (9.58 g, 48.1 mmol) in dichloroethane (75 mL) at room temperature. After 5 h, additional sodium triacetoxyborohydride was added (1.8 g) and again after another 2.5 h. The reaction was stirred overnight, and quenched with 5% aqueous sodium hydroxide. This was extracted with methylene chloride, and washed with 5% aqueous sodium hydroxide, water and saturated sodium chloride solution. After drying over sodium sulfate, the solution was filtered and evaporated to give the crude product. This was purified by chromatography (silica gel, 3 to 5% methanol in methylene chloride gradient elution), which gave the title compound (4.44 g). MS 293 (M+1)
$^1$H NMR (500 MHz, CD$_3$OD) δ 7.32 (dd, J=5, 1 Hz, 1H), 6.85 (dd, J=8, 1 Hz, 1H), 6.59 (dd, J=8, 5 Hz, 1H), 4.04 (d, J=13 Hz, 2H), 3.46 (m, 1H), 2.98 (br s, 2H), 2.01 (dd, J=12, 2 Hz, 2H), 1.46 (s, 9H), 1.37 (qd, J=12, 4 Hz, 2H).

Step B. 2-Oxo-1-(1-tert-butoxycarbonylpiperidin-4-yl)-2,3-dihydro-1H-imidazo[4,5-b]pyridine Carbonyldiimidazole (0.70 g, 4.33 mmol) was added to a solution of 2-amino-3-[(1-tert-butoxycarbonylpiperidin-4-yl)amino]pyridine (1.15 g, 3.93 mmol) in acetonitrile (150 mL) at room temperature. After several hours, an additional amount of carbonyldiimidazole was added (0.81 g), and the reaction stirred overnight. The acetonitrile was evaporated in vacuo, the residue partitioned between water and chloroform, and the organic phase washed with saturated brine and dried over magnesium sulfate. The crude product was purified by chromatography (silica gel, 1.2 to 2.5% methanol in methylene chloride gradient elution), which gave the title compound (1.09 g). $^1$H NMR (500 MHz, CDCl$_3$) δ 9.39 (br s, 1H), 8.04 (dd, J=5, 1 Hz, 1H), 7.33 (dd, J=8, 1 Hz, 1H), 6.99 (dd, J=8, 5 Hz, 1H), 4.50 (m, 1H), 4.32 (br s, 2H), 2.86 (br s, 2H), 2.20 (m, 2H), 1.86 (d, J=12 Hz, 2H), 1.50 (s, 9H).

Step C. 2-Oxo-1-(4-piperidinyl)-2,3-dihydro-1H-imidazo[4,5-b]pyridine dihydrochloride 2-Oxo-1-(1-tert-butoxycarbonylpiperidin-4-yl)-2,3-dihydro-1H-imidazo[4,5-b]pyridine (1.03 g, 3.23 mmol) was dissolved in methanol (25 mL) and a solution of 2 N hydrochloric acid in ether (8 mL) was added at room temperature. After 2 h, the volatiles were removed in vacuo, to give the title compound (0.92 g). MS 219 (M+1). $^1$H NMR (500 MHz, CD$_3$OD) δ 8.01 (dd, J=6, 1 Hz, 1H), 7.83 (d, J=8 Hz, 1H), 7.28 (dd, J=8, 6 Hz, 1H), 4.60 (m, 1H), 3.59 (d, J=12 Hz, 2H), 3.21 (t, J=12 Hz, 2H), 2.70 (dq, J=13, 4 Hz, 2H), 2.12 (d, J=13 Hz, 2H).

INTERMEDIATE 2

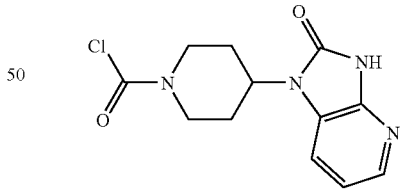

4-(2-Oxo-2,3-dihydro-1H-imidazo[4,5-b]pyridin-1-yl)piperidine-1-carbonyl chloride Phosgene (20% wt. in toluene; 1.8 mL, 3.43 mmol) was added to a suspension of 2-oxo-1-piperidinium-4-yl-2,3-dihydro-1H-imidazo[4,5-b]pyridin-4-ium dichloride (100 mg, 0.343 mmol) and 2,6-lutidine (0.50 mL, 4.293 mmol) in dichloromethane (5 mL) at 0° C. After 2 h, the solution was added to saturated aqueous sodium bicarbonate and extracted with ethyl acetate. The organic layer was washed with water (2×), saturated brine, dried over magnesium sulfate, filtered and concentrated. Dichloromethane (10 mL) was added, and the mixture was filtered to give the title compound as a solid (48 mg). MS 281 (M+1). ¹H NMR (500 MHz, (CD₃)₂SO) δ 11.58 (s, 1H), 7.90 (d, J=5.1 Hz, 1H), 7.67 (d, J=7.6 Hz, 1H), 7.01-6.99 (m, 1H), 4.52-4.46 (m, 1H), 4.31-4.23 (m, 2H), 3.38-3.33 (m, 1H), 3.19-3.14 (m, 1H), 2.32-2.24 (m, 2H), 1.84-1.81 (m, 2H).

INTERMEDIATE 3

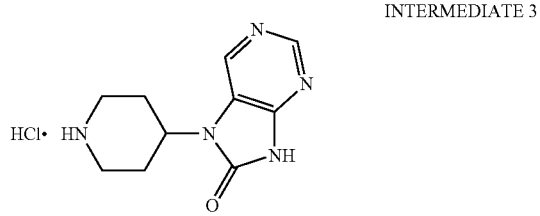

7-Piperidin-4-yl-7,9-dihydro-8H-purin-8-one hydrochloride

Step A. 4-Amino-5-[(1-tert-butoxycarbonylpiperidin-4-yl)amino)pyrimidine

A mixture of 4,5-diaminopyrimidine (1.0 g, 9.1 mmol), N-(tert-butoxycarbonyl)-4-piperidone (3.0 g, 15 mmol) and sodium triacetoxyborohydride (1.2 g, 5.6 mmol) in dichloroethane (60 mL) was stirred at room temperature for 3 d. The reaction was partitioned between chloroform (200 mL) and 3 N sodium hydroxide (30 mL). After drying over magnesium sulfate, the organic phase was concentrated to give the title compound as a tan gum. MS 294 (M+1)

Step B. 7-(1-Benzylpiperidin-4-yl)-7,9-dihydro-8H-purin-8-one

The crude product from Step A, 4-amino-5-[(1-tert-butoxycarbonylpiperidin-4-yl)amino)pyrimidine, was refluxed with carbonyldiimidazole (3.0 g, 18 mmol) in tetrahydrofuran (250 mL) for 2 d, cooled and concentrated. The crude product was dissolved in ethyl acetate (25-50 mL), which in four crops gave the title compound as a white crystalline solid (1.3 g). MS 320 (M+1)

Step C. 7-Piperidin-4-yl-7,9-dihydro-8H-purin-8-one hydrochloride

A mixture of 7-(1-benzylpiperidin-4-yl)-7,9-dihydro-8H-purin-8-one (1.2 g, 3.7 mmol) in 4 N hydrogen chloride in dioxane (50 mL), was stirred vigorously at room temperature for 3 h. The reaction was concentrated in vacuo to give the title compound as a white solid. MS 220 (M+1)

INTERMEDIATE 4

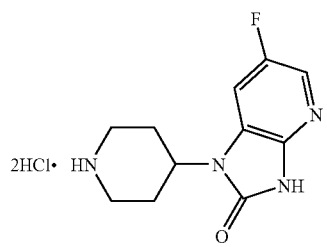

4-Fluoro-2-oxo-1-(4-piperidinyl-2,3-dihydro-1H-imidazo[4,5-b]pyridine

Step A.
N-(5-Fluoropyridin-2-yl)-2,2-dimethylpropanamide

To a 0° C. solution of 2-amino-5-fluoropyridine (1.00 g, 8.92 mmol) and triethylamine (1.35 g, 13.4 mmol) in dichloromethane (30 mL) was added trimethylacetyl chloride (1.29 g, 10.7 mmol) and DMAP (0.11 g, 0.89 mmol). The solution was allowed to warm to room temperature. After 4 h, saturated aqueous NaHCO₃ was added, the layers separated and the aqueous phase backwashed with DCM. The combined organics were dried over magnesium sulfate, filtered and concentrated and the residue purified by silica gel chromatography (5%→40% EtOAc/hexanes) to give the title compound (1.34 g). MS 197.3 (M+1).

Step B. N-(3-Azido-5-fluoropyridin-2-yl)-2,2-dimethylpropanamide

To a −78° C. solution of N-(5-fluoropyridin-2-yl)-2,2-dimethylpropanamide (1.34 g, 6.83 mmol) in tetrahydrofuran (25 mL) was added tert-butyllithium (1.31 mL of a 1.7 M solution, 20.5 mmol) dropwise. After 3 h at −78° C., 4-dodecylbenzenesulfonyl azide (3.60 g, 10.2 mmol) was added at the reaction was allowed to warm to room temperature. After 1 h, saturated aqueous NH₄Cl was added, and the tetrahydrofuran was removed via rotary evaporator. Dichloromethane was added, the layers separated and the aqueous phase backwashed with DCM. The combined organics were dried over magnesium sulfate, filtered and concentrated and the residue purified by two successive silica gel chromatographies (10%→80% EtOAc/hexanes, then 5%→42% EtOAc/hexanes) to give the title compound (0.275 g). MS 234.0 (M+1).

Step C. 3-Azido-5-fluoropyridin-2-amine

N-(3-Azido-5-fluoropyridin-2-yl)-2,2-dimethylpropanamide (275 mg, 1.16 mmol) in 3 N HCl (5 mL) was heated to 100° C. After 2 h, the volatiles were removed in vacuo, to give the title compound as its HCl salt (180 mg). MS 154.2 (M+1).

Step D. 5-Fluoropyridine-2,3-diamine

The HCl salt of 3-azido-5-fluoropyridin-2-amine (1.90 g, 10.0 mmol) was dissolved in tetrahydrofuran (100 mL) and treated with MP-Carbonate (Argonaut, 11.5 g). After 1 h, the mixture was filtered, rinsed with more tetrahydrofuran, and concentrated. This residue was dissolved in ethanol (50 mL), purged with argon, and 10% palladium on carbon was added (0.15 g). Hydrogen was introduced (1 atm) and the reaction stirred until complete. The catalyst was filtered and the solvent evaporated from the filtrate to give the title compound (1.18 g). MS 128.0 (M+1)

Step E. tert-Butyl 4-[(2-amino-5-fluoropyridin-3-yl)amino]piperidine-1-carboxylate Sodium triacetoxyborohydride (2.95 g, 13.9 mmol) was added to a solution of 5-fluoropyridine-2,3-diamine (1.18 g, 9.28 mmol), acetic acid (0.56 g, 9.28 mmol) and I-(t-butoxycarbonyl)-4-piperidone (1.85 g, 9.28 mmol) in 1,2-dichloroethane (20 mL) at room temperature. After 1 h, the reaction was quenched with water (20 mL) and extracted with dichloromethane. After drying over sodium sulfate, the solution was filtered and evaporated to give the crude product. This was purified by chromatography, (silica gel, 5%→15% MeOH/DCM; then C-18, 95% water/acetonitrile→5% water/acetonitrile with 0.1% trifluoroacetic acid) to give the title compound (0.73 g). MS 311.2 (M+1).

Step F. tert-Butyl 4-(6-fluoro-2-oxo-2,3-dihydro-1H-imidazo[4,5-b]pyridin-1-yl)piperidine-1-carboxylate Carbonyldiimidazole (1.53 g, 9.41 mmol) was added to a solution of tert-butyl 4-[(2-amino-5-fluoropyridin-3-yl)amino]piperidine-1-carboxylate (0.73 g, 2.35 mmol) in acetonitrile (10 mL) at room temperature. The reaction was stirred until all the starting material was consumed (approximately 2 h) and then the solvent was evaporated in vacuo. The residue was diluted with water, extracted with dichloromethane (3×), dried over magnesium sulfate and then concentrated. The crude product was purified by chromatography (silica gel, 1% to 10% methanol in methylene chloride gradient elution), which gave the title compound (0.309 g). MS 337.2 (M+1)

Step G. 4-Fluoro-2-oxo-1-(4-piperidinyl)-2,3-dihydro-1H-imidazo[4,5-b]pyridine tert-Butyl 4-(6-fluoro-2-oxo-2,3-dihydro-1H-imidazo[4,5-b]pyridin-1-yl)piperidine-1-carboxylate (340 mg, 1.01 mmol) was dissolved in dichloromethane (5 mL) and trifluoroacetic acid (5 mL) was added. After 2 h, the reaction was concentrated, diluted with dichlormethane (5 mL) and a solution of 1 N hydrochloric acid in 1,4-dioxane (2 mL) was added at room temperature. Concentration afforded the title compound (302 mg). MS 237.2 (M+1) $^1$H NMR (500 MHz, CD$_3$OD) δ 7.92 (br s, 1H), 7.70 (dd, 1H), 4.60 (m, 1H), 3.60 (s, 2H), 3.25 (dd, 2H), 2.70 (m, 2H), 2.10 (d, 2H).

INTERMEDIATE 5

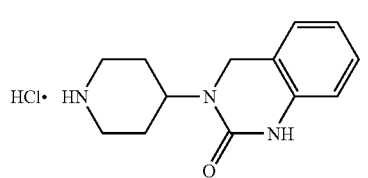

3-(4-Piperidinyl)-3,4-dihydroquinazolin-2(1H)-one hydrochloride

The title compound was prepared according to the procedure described by H. Takai et al., in Chem. Pharm. Bulletin 1985, 33(3) 1116-1128. $^1$H NMR (500 MHz, DMSO-d$_6$) δ 9.31 (s, 1H), 8.79 (br s, 1H), 8.58 (br s, 1H), 7.13 (t, J=8 Hz, 2H), 6.88 (t, J=8 Hz, 1H), 6.77 (d, J=8 Hz, 1H), 4.37 (tt, J=12, 4 Hz, 1H), 4.29 (s, 2H), 3.00 (q, J=11 Hz, 2H), 2.06 (dq, J=4, 12 Hz, 2H), 1.73 (d, J=12 Hz, 2H).

INTERMEDIATE 6

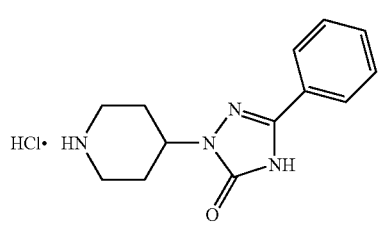

5-Phenyl-1-piperidin-4-yl-2,4-dihydro-3H-1,2,4-triazol-3-one hydrochloride

Step A: 9H-Fluoren-9-ylmethyl 4-[(t-butoxycarbonyl)hydrazono]piperidine-1-carboxylate A solution of 1-[(9H-fluoren-9-yl)methyloxycarbonyl]-4-piperidone (16.0 g, 50.0 mmol) and tert-butyl carbazate 7.25 g, 55.5 mmol) in ethanol (250 mL) was refluxed for 1 h. The solution was cooled and concentrated. Addition of ether (100 mL) produced the title compound as a white precipitate (21.0 g). $^1$H NMR (500 MHz, CDCl$_3$) δ 7.77 (d, J=7 Hz, 2H), 7.57 (d, J=7 Hz, 2H), 7.40 (t, J=7 Hz, 2H), 7.32 (t, J=7 Hz, 2H), 4.50 (br s, 2H), 4.24 (t, J=6 Hz, 1H), 3.4-3.7 (br m, 4H), 2.47 (br s, 2H), 2.2-2.1 (br m, 2H), 1.56 (s, 9H).

Step B: 9H-Fluoren-9-ylmethyl 4-[(t-butoxycarbonyl)hydrazino]piperidine-1-carboxylate A solution of 9H-fluoren-9-ylmethyl 4-[(t-butoxycarbonyl)hydrazono]piperidine-1-carboxylate (10.0 g, 22.9 mmol) in acetic acid (150 mL) was shaken with platinum oxide (1.0 g) under 45 psi hydrogen on a Parr apparatus for 2 h. The solution was filtered and concentrated to give the title compound.

Step C: 9H-Fluoren-9-ylmethyl 4-hydrazinopiperidine-1-carboxylate

A solution of 9H-fluoren-9-ylmethyl 4-[(tert-butoxycarbonyl)hydrazino]piperidine-1-carboxylate (20 g, 45.7 mmol) was dissolved in trifluoroacetic acid (100 mL) and stirred at room temperature for 1.5 h. The reaction was concentrated and the residue dissolved in methanol and purified by reverse phase HPLC. Pure fractions were isolated and combined to give the trifluoroacetic acid salt of the title compound (3.01 g). $^1$H NMR (500 MHz, DMSO-d$_6$) δ 7.89 (d, J=8 Hz, 2H), 7.61 (d, J=8 Hz, 2H), 7.40 (t, J=8 Hz, 2H), 7.32 (t, J=8 Hz, 2H), 4.33 (d, J=6 Hz, 2H), 4.25 (t, J=6 Hz, 1H), 4.0-3.5 (br s, 6H), 3.05 (br s, 1H), 2.80 (br s, 2H), 1.89 (br s, 2H), 1.2 (br s, 2H).

Step D: 9H-Fluoren-9-ylmethyl 4-(5-oxo-3-phenyl-4,5-dihydro-1H-1,2,4-triazol-1-yl)piperidine-1-carboxylate A solution of 9H-fluoren-9-ylmethyl 4-hydrazinopiperidine-1-carboxylate trifluoroacetic acid salt (2.95 g, 6.54 mmol) was refluxed for 2 h with ethyl N-benzothioyl carbamate (1.50 g, 7.1 mmol) (prepared by the procedure of E. P. Papadopoulus, J. Org. Chem., 1976, 41(6) 962-965) in tetrahydrofuran (30 mL) with diisopropylethyl amine (1.25 mL, 7.1 mmol). The reaction was cooled and concentrated, then dissolved with heating in acetonitrile. A white solid crystallized upon cooling, giving the title compound (2.06 g). $^1$H NMR (500 MHz, CDCl$_3$) δ 7.80 (d, J=7 Hz, 2H), 7.77 (d, J=7 Hz, 2H), 7.61 (d, J=7 Hz, 2H), 7.48 (m, 3H), 7.40 (t, J=7 Hz, 2H), 7.33 (t, J=7 Hz, 2H), 4.46 (d, J=6 Hz, 2H), 4.36 (m, 2H), 4.27 (t, J=6 Hz, 1H), 4.26 (br s, 1H), 3.02 (br s, 2H), 2.04 (br s, 2H), 1.94 (br m, 2H).

Step E: 5-Phenyl-1-piperidin-4-yl-2,4-dihydro-3H-1,2,4-triazol-3-one hydrochloride A solution of 9H-fluoren-9-ylmethyl 4-(5-oxo-3-phenyl-4,5-dihydro-1H-1,2,4-triazol-1-yl)piperidine-1-carboxylate (2.06 g, 4.41 mmol) and diethylamine (15 mL) in tetrahydrofuran (15 mL) was stirred at room temperature for 2 h. The reaction was concentrated and the crude product purified by column chromatography (silica gel, 0 to 10% {5% ammonium hydroxide/methanol} in dichloromethane gradient elution), giving the title compound as a white solid (0.95 g). $^1$H NMR (500 MHz, CDCl$_3$) δ 7.84 (d, J=7 Hz, 2H), 7.47 (m, 3H), 4.30 (m, 1H), 3.25 (d, J=13 Hz, 2H), 2.79 (t, J=13 Hz, 2H), 2.04 (d, J=4, 12 Hz, 2H), 1.93 (br d, J=10 Hz, 2H).

INTERMEDIATE 7

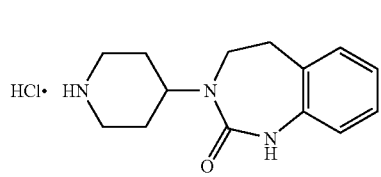

3-(4-Piperidinyl)-1,3,4,5-tetrahydro-2H-1,3-benzodiazepin-2-one hydrochloride

Step A. 2-(2-Bromoethyl)nitrobenzene

Triphenylphosphine (39.2 g, 0.150 mol) and carbon tetrabromide (49.5 g, 0.150 mol) were added sequentially to a solution of 2-(2-hydroxyethyl)-nitrobenzene (25.0 g, 0.150 mol) in methylene chloride (400 mL) at 0° C. The reaction was stirred overnight and quenched with saturated sodium bicarbonate solution. The methylene chloride phase was washed with saturated brine and dried over magnesium sulfate. The crude product was treated with ethyl acetate, and the precipitated triphenylphosphine oxide removed by filtration. Further purification by flash chromatography by (silica gel, 0-10% ethyl acetate in hexane gradient elution) produced the title compound (27.9 g).

Step B. 2-(2-Azidoethyl)nitrobenzene

Sodium azide (22.8, 0.351 mol) in water (60 mL) was added to a solution of 2-(2-bromoethyl)-nitrobenzene (27.9 g, 0.121 mol) in acetonitrile (120 mL). The reaction was refluxed for 4 h, cooled, and partitioned between methylene chloride and water. The organic phase was washed with saturated brine, and dried over magnesium sulfate. The title compound was obtained as an oil (22.8 g).

Step C. 2-(2-Aminoethyl)nitrobenzene

Triphenylphosphine (31.1 g, 0.118 mol) and calcium carbonate (50 mg, 0.5 mmol) were added to a solution of 2-(2-azidoethyl)nitrobenzene (22.8 g, 0.118 mol) in benzene (500 mL). The reaction was stirred at room temperature until complete. The solvent was removed in vacuo, and the residue treated with acetic acid (100 mL) and 48% hydrogen bromide (100 mL) at 100° C. for 1 h. The reaction was cooled and concentrated. Water was added and the solution extracted with methylene chloride. The aqueous layer was made basic by the addition of 5% aqueous sodium hydroxide solution, then extracted with ethyl acetate. The organic phase was washed with saturated brine and dried over sodium sulfate. The title compound was obtained as an oil (8.0 g). MS 167 (M+1).

Step D. t-Butyl 4-{[2-(2-nitrophenyl)ethyl]amino}piperidine-1-carboxylate

A solution of 2-(2-aminoethyl)nitrobenzene (8.00 g, 48.1 mmol) and 1-t-butoxycarbonyl-4-piperidinone (9.59 g, 48.1 mmol) in methanol (100 mL) was brought to pH 5 by the addition of acetic acid. Sodium cyanoborohydride (4.53 g, 72.2 mmol) was added and the reaction stirred for 3 h. Methanol was removed in vacuo, and the residue partitioned between ethyl acetate and saturated sodium bicarbonate solution. The organic phase was washed with saturated brine and dried over sodium sulfate. The title compound was obtained as an oil (19.27 g). MS 350 (M+1).

Step E. t-Butyl 4-{[2-(2-aminophenyl)ethyl]amino}piperidine-1-carboxylate tert-Butyl 4-{[2-(2-nitrophenyl)ethyl]amino}piperidine-1-carboxylate and 10% palladium on carbon (1.9 g) were stirred in ethanol (250 mL) overnight under one atmosphere hydrogen. Catalyst was filtered from the solution and solvent removed in vacuo to provide the title compound (17.2 g). MS 320 (M+1)

Step F. 3-(1-t-Butoxycarbonyl-4-piperidinyl)-1,3,4,5-tetrahydro-2H-1,3-benzodiazepin-2-one Carbonyldiimidazole (8.73 g, 53.8 mmol) was added to a solution of tert-butyl 4-{[2-(2-aminophenyl)ethyl]amino}piperidine-1-carboxylate (17.2 g, 53.8 mmol) in dimethylformamide (200 mL), and stirred at room temperature for 2 h. The reaction was diluted with ethyl acetate and extracted with water, then saturated brine. The crude product was purified by chromatography (silica gel, 0-30% ethyl acetate in methylene chloride gradient elution). The title compound was obtained as a dark solid (4.8 g).

Step G. 3-(4-Piperidinyl)-1,3,4,5-tetrahydro-2H-1,3-benzodiazepin-2-one hydrochloride A solution of 3-(1-t-butoxycarbonyl-4-piperidinyl)-1,3,4,5-tetrahydro-2H-1,3-benzodiazepin-2-one (4.80 g, 13.9 mmol) in ethyl acetate (300 mL) was saturated with hydrogen chloride gas at 0° C. The reaction was allowed to warm to room temperature and stirred overnight. The solid was filtered and washed with ethyl acetate. The ethyl acetate filtrate was concentrated for a second crop. The title compound was obtained as a solid (2.94 g). MS 246 (M+1). $^1$H NMR (500 MHz, CD$_3$OD) δ 7.10 (m, 2H), 6.94 (d, J=8 Hz, 1H), 6.91 (t, J=8 Hz, 1H), 4.35 (tt, J=10, 1 Hz, 1H), 3.52 (m, 4H), 3.12 (t, J=12 Hz, 2H), 3.05 (m, 2H), 2.07 (qd, J=12, 4 Hz, 2H), 1.99 (m, 2H).

INTERMEDIATE 8

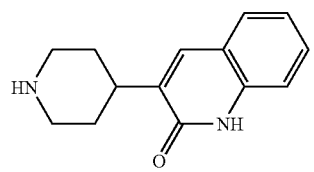

3-(4-Piperidinyl)quinolin-2-(1H)-one

Step A. 3-(1-Benzyl-4-hydroxypiperidin-4-yl)-2-chloroquinoline

A solution of n-butyllithium in hexane (1.6 M, 38.2 mL, 61.1 mmol) was added to a solution of diisopropylamine (8.6 mL, 61.1 mmol) in tetrahydrofuran (140 mL) at −78° C. under argon. After 1 h, a solution of 2-chloroquinoline (10.00 g, 61.1 mol) in tetrahydrofuran (30 mL) was added via syringe. After 1 h, a solution of 1-benzyl-4-piperidinone (11.3 mL, 61.1 mmol) was added, and the reaction stirred for an additional 40 min at −78° C., then allowed to warm to room temperature. The reaction was cooled to −20° C. and quenched with water. The reaction solution was extracted with ethyl acetate, and the organic phase washed with saturated brine and dried over magnesium sulfate. Chromatographic purification (silica gel, 0 to 10% {5% ammonium hydroxide/methanol} in methylene chloride gradient elution) gave the title compound, 11.3 g. MS 353 (M+1). $^1$H NMR (500 MHz, CDCl$_3$) δ 8.33 (s, 1H), 8.00 (d, J=8 Hz, 1H), 7.82 (d, J=8 Hz, 1H), 7.72 (dt, J=1, 10 Hz, 1H), 7.57 (dt, J=1, 8 Hz, 1H), 7.39-7.26 (m, 5H), 3.61 (s, 2H), 2.85 (d, J=11 Hz, 2H), 2.59 (t, J=12 Hz, 2H), 2.48 (dt, J=4, 13 Hz, 2H), 2.13 (d, J=12 Hz, 2H).

Step B. 3-(1-Benzyl-1,2,3,6-tetrahydropyridin-4-yl)quinolin-2-(1H)-one 3-(1-Benzyl-4-hydroxypiperidin-4-yl)-2-chloroquinoline (11.0 g, 31.1 mmol) was refluxed in 6 N hydrochloric acid for 8 h. The solution was cooled and water (100 mL) added. The precipitated solid was collected and dried to give the title compound, 7.9 g. MS 317 (M+1).
$^1$H NMR (500 MHz, CD$_3$OD) δ 7.97 (s, 1H), 7.70 (d, J=7 Hz, 1H), 7.60 (m, 2H), 7.55 (m, 4H), 7.35 (d, J=9 Hz, 1H), 7.27 (t, J=8 Hz, 1H), 6.50 (m, 1H), 4.49 (ABq, J=13 Hz, Δv=16 Hz, 2H), 3.92 (m, 2H), 3.76 (dt, J=12, 4 Hz, 1H), 3.40 (m, 1H), 2.96 (m, 2H).

Step C. 3-(4-Piperidinyl)quinolin-2-(1)-one

A solution of 3-(1-benzyl-1,2,3,6-tetrahydropyridin-4-yl)quinolin-2-(1H)-one (4.00 g, 12.6 mmol) in methanol (500 mL) was degassed with argon, and 10% palladium on carbon (1.2 g) added. The reaction was placed under 1 atm hydrogen and heated to 50° C. for 5.5 h. The reaction was cooled and filtered through celite. Concentration provided the title compound, 2.7 g. MS 229 (M+1). $^1$H NMR (500 MHz, CD$_3$OD) δ 7.80 (s, 1H), 7.67 (d, J=8 Hz, 1H), 7.51 (t, J=8 Hz, 1H), 7.33 (d, J=8 Hz, 1H), 7.25 (t, J=8 Hz, 1H), 3.52 (t, J=12 Hz, 2H), 3.17 (dt, J=3, 13 Hz, 2H), 3.15 (m, overlaps with δ 3.17 peak, 1H), 2.18 (d, J=14 Hz, 2H), 1.91 (dq, J=3, 12 Hz, 2H).

INTERMEDIATE 9

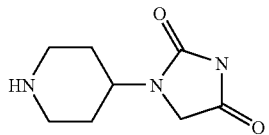

1-Piperidin-4-ylimidazolidine-2,4-dione

Step A: tert-Butyl 4-[(2-ethoxy-2-oxoethyl)amino]piperidine-1-carboxylate

Sodium cyanoborohydride (189 mg, 3.01 mmol) was added to a solution of 1-boc-4-piperidone (500 mg, 2.51 mmol) and glycine ethyl ester hydrochloride (350 mg, 2.51 mmol) in methanol (12.5 mL). After 16 h, the mixture was quenched with saturated ammonium chloride solution, concentrated, and partitioned between dichloromethane and saturated sodium bicarbonate solution. The organic layer was washed with brine, dried over magnesium sulfate, filtered, and concentrated. Purification by silica gel chromatography [100% dichloromethane→95% dichloromethane/5% (10% ammonium hydroxide/methanol)] gave the title compound (600 mg).

Step B: tert-Butyl 4-(2,4-dioxoimidazolidin-1-yl)piperidine-1-carboxylate

Potassium cyanate (31 mg, 0.384 mmol) was added to a solution of tert-butyl 4-[(2-ethoxy-2-oxoethyl)amino]piperidine-1-carboxylate (100 mg, 0.384 mmol) in water (2 mL). Acetic acid was then added to adjust pH of reaction to 4-5 and the mixture was heated at 40° C. After 16 h, the reaction was cooled to ambient temperature and purified by reverse phase HPLC (C-18, 95% water/acetonitrile→5% water/acetonitrile with 0.1% trifluoroacetic acid) to give the title compound (33 mg).

Step C: 1-Piperidin-4-ylimidazolidine-2,4-dione

Trifluoroacetic acid (0.300 mL) was added to a solution of tert-butyl 4-(2,4-dioxoimidazolidin-1-yl)piperidine-1-carboxylate (32 mg, 0.113 mmol) in dichloromethane (1 mL). After 4 h, the reaction was concentrated to give the title compound. MS 184.04 (M+1).

INTERMEDIATE 10

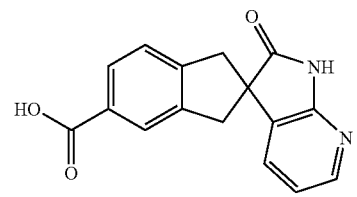

(±)-2'-Oxo-1,1',2',3-tetrahydrospiro[indene-2,3'-pyrrolo[2,3-b]pyridine]-5-carboxylic acid Step A. 1-{[2-Trimethylsilyl)ethoxy]methyl}-1H-pyrrolo[2,3-b]pyridine Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with H$_2$O (500 mL) and the mixture was extracted with CH$_2$Cl$_2$ (5×300 mL). The combined organic layers were washed with brine, dried over MgSO$_4$, filtered, concentrated and dried under high vacuum to give the title compound. MS: m/z=249(M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine (43.1 g, 0.174 mol) in dioxane (300 mL) was added dropwise over 30 min to a suspension of pyridine hydrobromide perbromide (277 g, 0.868 mol) in dioxane (300 mL). The reaction was stirred at ambient temperature using an overhead mechanical stirrer. After 60 min, the biphasic reaction mixture was quenched with H$_2$O (300 mL) and extracted with EtOAc. The aqueous layer was washed with EtOAc (2×300 mL) and the combined organic layers were washed with H₂O (4×300 mL; the final wash was pH 5-6), then brine (300 mL), then dried over MgSO₄, filtered and concentrated under reduced pressure. The crude product was immediately dissolved in CH₂Cl₂ and the solution filtered through a plug of silica, eluting with CH₂Cl₂ until the dark red color had completely eluted from the plug. The filtrate was washed with saturated aqueous NaHCO₃ (400 mL), then brine (400 mL), dried over MgSO₄ and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one (65 g, 0.154 mol) in THF (880 mL) and saturated aqueous ammonium chloride (220 mL). After 3 h, the reaction was filtered and concentrated in vacuo. The residue was partitioned between EtOAc and H₂O which resulted in the formation of a white precipitate. Both layers were filtered through a Celite pad and the layers were separated. The aqueous layer was washed with EtOAc (2×) and the combined organic layers were washed with H₂O, dried over MgSO₄, filtered, and concentrated. The crude product was filtered through a plug of silica gel eluting with CH₂Cl₂:EtOAc—90:10 and the eluant was concentrated under reduced pressure to provide the title compound. MS: m/z=265(M+1).

Step D. (±)-Methyl 2'-oxo-1'-{[2-(trimethylsilyl)ethoxy]methyl}-1,1',2',3-tetrahydrospiro[indene-2,3'-pyrrolo[2,3-b]pyridine]-5-carboxylate To a solution of methyl 1,2-bis(bromomethyl)-4-benzoate (9.20 g, 28.6 mmol) and 1-{[2-(trimethylsilyl)ethoxy]methyl}-1,3-dihydro-2H-pyrrolo[2,3-b]pyridin-2-one (7.55 g, 28.6 mmol) in DMF (70 mL) was added cesium carbonate (9.78 g, 30.0 mmol). After 4 h the reaction mixture was partitioned between Et₂O (100 mL) and H₂O (100 mL). The aqueous layer was extracted further with Et₂O (2×100 mL). The combined organic layers were washed with H₂O (2×100 mL), then brine (100 mL), then dried over MgSO₄, filtered, and concentrated under reduced pressure. The crude product was purified by silica gel chromatography, eluting with a gradient of hexane:EtOAc—85:15 to 70:30, to give the title compound. MS: m/z=425 (M+1).

Step E. (±)-2'-Oxo-1,1',2',3-tetrahydrospiro[indene-2,3'-pyrrolo[2,3-b]pyridine]-5-carboxylic acid To a solution of (±)-methyl 2'-oxo-1'-{[2-(trimethylsilyl)ethoxy]methyl}-1,1',2',3-tetrahydrospiro[indene-2,3'-pyrrolo[2,3-b]pyridine]-5-carboxylate (3.65 g, 8.60 mmol) in CH₂Cl₂ (80 mL) was added CF₃CO₂H (40 mL, 52 mmol) and the resulting mixture was stirred at ambient temperature for 18 h, then concentrated in vacuo. The residue was dissolved in CH₂Cl₂ (100 mL) and treated with ethylene diamine (2.3 mL, 34.4 mmol). The reaction mixture was stirred at ambient temperature for 18 h, then diluted with saturated aqueous NaHCO₃ (50 mL). The organic layer was removed and the aqueous layer was extracted further with CH₂Cl₂ (2×100 mL). The combined organic layers were washed with brine (50 mL), then dried over MgSO₄, filtered, and concentrated in vacuo. The crude product was purified by silica gel chromatography, eluting with CH₂Cl₂:MeOH—97:3, to give methyl 2'-oxo-1,1',2',3-tetrahydrospiro[indene-2,3'-pyrrolo[2,3-b]pyridine]-5-carboxylate as a tan solid. This solid was dissolved in MeOH (22 mL) and 1 N sodium hydroxide (25.4 mL, 25.4 mmol) was added. The reaction mixture was heated at 60° C. for 18 h then allowed to cool. The mixture was acidified by addition of 6 N HCl, and the resulting precipitate was isolated by filtration, washed with H₂O, and dried in vacuo to give the title compound as an off-white solid. MS: m/z=281 (M+1).

INTERMEDIATE 11

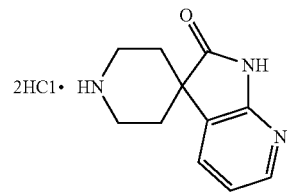

Spiro[piperidine-4,3'-pyrrolo[2,3-b]pyridin]-2'(1'H)-one dihydrochloride

Step A. 1-{[2-Trimethylsilyl)ethoxy]methyl}-1H-pyrrolo[2,3-b]pyridine

Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with H₂O (500 mL) and the mixture was extracted with CH₂Cl₂ (5×300 mL). The combined organic layers were washed with brine, dried over MgSO₄, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.174 mol) in dioxane (300 mL) was added dropwise over 30 min to a suspension of pyridine hydrobromide perbromide (277 g, 0.868 mol) in dioxane (300 mL). The reaction was stirred at ambient temperature using an overhead mechanical stirrer. After 60 min, the biphasic reaction mixture was quenched with H₂O (300 mL) and extracted with EtOAc. The aqueous layer was washed with EtOAc (2×300 mL) and the combined organic layers were washed with H₂O (4×300 mL; the final wash was pH 5-6), then brine (300 mL), then dried over MgSO₄, filtered and concentrated under reduced pressure. The crude product was immediately dissolved in CH₂Cl₂ and the solution filtered through a plug of silica, eluting with CH₂Cl₂ until the dark red color had completely eluted from the plug. The filtrate was washed with saturated aqueous NaHCO₃ (400 mL), then brine (400 mL), dried over MgSO₄ and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro- 2H-pyrrolo[2,3-b]pyridin-2-one from Step B (65 g, 0.154 mol) in THF (880 mL) and saturated aqueous ammonium chloride (220 mL). After 3 h, the reaction was filtered and concentrated in vacuo. The residue was partitioned between EtOAc and H$_2$O which resulted in the formation of a white precipitate. Both layers were filtered through a Celite pad and the layers were separated. The aqueous layer was washed with EtOAc (2×) and the combined organic layers were washed with H$_2$O, dried over MgSO$_4$, filtered, and concentrated. The crude product was filtered through a plug of silica gel eluting with CH$_2$Cl$_2$:EtOAc—90:10 and the eluant was concentrated under reduced pressure to provide the title compound. MS: m/z=265 (M+1).

Step D. spiro[cyclopent-3-ene-1,3'-pyrrolo[2,3-b]pyridin]-2'(1'H)-one

To a solution of cis-1,4-dichloro-2-butene (1.98 g, 15.8 mmol) and 1-{[2-(trimethylsilyl)ethoxy]methyl}-1,3-dihydro-2H-pyrrolo[2,3-b]pyridin-2-one (3.49 g, 13.2 mmol) in DMF (175 mL) was added cesium carbonate (10.7 g, 32.9 mmol). After 24 h the reaction mixture was partitioned between Et$_2$O (200 mL) and H$_2$O (200 mL). The aqueous layer was extracted further with Et$_2$O (2×200 mL). The combined organic layers were washed with H$_2$O (2×100 mL), then brine (100 mL), dried over MgSO$_4$, filtered, and concentrated under reduced pressure. To a solution of this material in dichloromethane (150 mL) was added trifluoroacetic acid (150 mL). After 1 h, the reaction was concentrated, dissolved in EtOH (150 mL) and 2N HCl (150 mL) was added. This mixture was heated at 45° C. for 48 h. The mixture was concentrated, diluted with saturated aqueous NaHCO$_3$, and extracted with dichloromethane (2×). The combined organic layers were dried and concentrated. The crude product was purified by silica gel chromatography, eluting with a gradient of 0 to 5% methanol:dichloromethane to give the title compound (0.62 g). MS: m/z=187.1 (M+1).

Step E. 3,4-dihydroxyspiro[cyclopentane-1,3'-pyrrolo[2,3-b]pyridin]-2'(1'H)-one To a mixture of trimethylamine-N-oxide dihydrate (408 mg, 3.67 mmol) and spiro[cyclopent-3-ene-1,3'-pyrrolo[2,3-b]pyridin]-2'(1'H)-one (622 mg, 3.34 mmol) in dichloromethane (115 mL) was added osmium tetroxide (25 uL of 2.5% solution in 2-methyl-2-propanol). After 24 h the reaction mixture was concentrated. The crude product was loaded onto a silica gel chromatography column with a minimal amount of methanol and eluted with a gradient of 5 to 20% methanol:dichloromethane to give the title compound (0.63 g). MS: m/z 221.0 (M+1).

Step F. tert-butyl 2'-oxo-1',2'-dihydro-1H-spiro[piperidine-4,3'-pyrrolo[2,3-b]pyridine]-1-carboxylate To a mixture of 3,4-dihydroxyspiro[cyclopentane-1,3'-pyrrolo[2,3-b]pyridin]-2'(1'H)-one (640 mg, 2.91 mmol) in 3:1 ethanol:water (160 mL) was added sodium periodate (622 mg, 2.91 mmol). Upon consumption of the starting material, ammonium hydroxide (50 mL) was slowly added to the reaction mixture. Palladium hydroxide (200 mg, 20%) was added and the reaction was hydrogenated at 50 psi. After 24 h, 200 mg of palladium hydroxide was added and the hydrogenation continued for an additional 24 h. The reaction mixture was filtered through celite and concentrated. This material was dissolved in DMF (10 mL) and di-tert-butyl dicarbonate (635 mg, 2.91 mmol) was added followed by triethylamine (0.811 mL, 5.82 mmol). After 24 h, the reaction was diluted with saturated aqueous NaHCO$_3$ and extracted with ether (3×). The combined organic layers were washed with water (3×), dried and concentrated. The crude product was purified by silica gel chromatography, eluting with a gradient of 0 to 10% methanol:dichloromethane to give the title compound (489 mg). MS: m/z=304.1 (M+1).

Step G. Spiro[piperidine-4,3'-pyrrolo[2,3-b]pyridin]-2'(1'H)-one dihydrochloride tert-Butyl 2'-oxo-1',2'-dihydro-1H-spiro[piperidine-4,3'-pyrrolo[2,3-b]pyridine]-1-carboxylate (451 mg, 1.49 mmol) was dissolved in ethyl acetate (3 mL) and a solution of 4N hydrochloric acid in dioxane (7.5 mmol) was added at room temperature. After 24 h, the volatiles were removed in vacuo, to give the title compound (404 mg). MS 204.1 (M+1). $^1$H NMR (500 MHz, CD$_3$OD) δ 8.31 (d, J=7.1 Hz, 1H), 8.20 (d, J=6.1 Hz, 1H), 7.45 (dd, J=6.8, 6.8 Hz, 1H), 3.74 (brdd, 2H), 3.47 (brdd, 2H), 2.35 (brddd, 2H), 2.21 (brd, 2H).

INTERMEDIATE 12

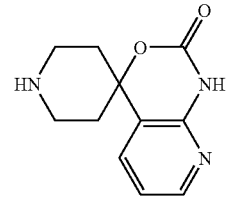

Spiro[piperidine-4,4'-pyrido[2,3-d][1,3]oxazin]-2'(1'H)-one

Step A. tert-Butyl (6-chloropyridin-2-yl)carbamate

To a solution of 2-amino-6-chloropyridine (25.0 g, 194.5 mmol) and sodium hexamethyldisilazide (1.0 M; 427.8 mL, 427.8 mmol) in tetrahydrofuran (175 mL) was added a solution of di-tert-butyl dicarbonate (46.69 g, 213.9 mmol) in tetrahydrofuran (175 mL). After 48 h, the reaction mixture was concentrated and the residue was partitioned between ethyl acetate (150 mL) and 1N HCl (500 mL). The aqueous layer was extracted further with ethyl acetate (2×). The combined organic layers were washed with saturated aqueous sodium bicarbonate, dried over magnesium sulfate, filtered, and concentrated. Recrystallization was accomplished by dissolving the crude residue in a minimal amount of ethanol at 60° C. The solution was allowed to cool to ambient temperature and water was added. Precipitated solid was filtered and dried to give the title compound (33.45 g). MS: m/z=173.0 (M−$^t$Bu).

Step B. Benzyl 7'-chloro-2'-oxo-1',2'-dihydro-1H-spiro[piperidine-4,4'-pyrido[2,3-d][1,3]oxazine]-1-carboxylate To a −20° C. solution of N,N,N',N'-tetramethylethylenediamine (22.3 mL, 147.6 mmol) in tetrahydrofuran (180 mL) was added n-butyllithium (2.5 M; 59.0 mL, 147.6 mmol) over 10 min. After 30 min, the mixture was cooled to −78° C. and tert-butyl (6-chloropyridin-2-yl)carbamate (15.0 g, 65.6 mmol) in tetrahydrofuran (60 mL) was added over 15 min. After 2.5 h, a solution of N-benzyloxycarbonyl-4-piperidinone (23.0 g, 98.4 mmol) in tetrahydrofuran (60 mL) was added over 10 min. The reaction was allowed to warm to ambient temperature. After 1 h, the reaction was heated to 40° C. After 18 h, the mixture was quenched with saturated aqueous sodium bicarbonate and the mixture extracted with dichloromethane (3×). The combined organic extracts were washed with water, saturated brine, dried over magnesium sulfate, filtered, and concentrated. Recrystallization was accomplished by dissolving the crude residue in ethanol (450 mL) at 65° C. The solution flask was placed in the freezer at −20° C. After 18 h, the precipitated solid was filtered, washed with ether, dried to give the title compound (11.9 g). MS: m/z=388.0 (M+1)

Step C. Spiro[piperidine-4,4'-pyrido[2,3-d][1,3]oxazin]-2'(1'H)-one

Palladium (10% on carbon; 1.5 g) was added to a solution of benzyl 7'-chloro-2'-oxo-1',2'-dihydro-1H-spiro[piperidine-4,4'-pyrido[2,3-d][1,3]oxazine]-1-carboxylate (3.01 g, 7.76 mmol) in ethanol (150 mL). The reaction vessel was evacuated and back-filled with nitrogen (3×), then back-filled with hydrogen (1 atm). After 24 h, additional palladium (10% on carbon; 0.5 g) was added. After 4 h, the mixture was filtered through celite and concentrated to give the title compound (1.62 g). MS 220.1 (M+1). $^1$H NMR (500 MHz, CD$_3$OD) δ 8.26 (dd, J=1.7, 5.0 Hz, 1H), 7.69 (dd, J=1.6, 7.7 Hz, 1H), 7.16 (dd, J=5.0, 7.7 Hz, 1H), 3.49-3.42 (m, 4H), 2.38-2.25 (m, 4H).

INTERMEDIATE 13

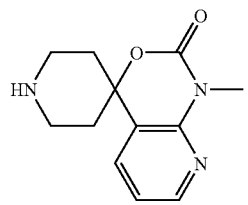

1'-Methylspiro[piperidine-4,4'-pyrido[2,3-d][1,3]oxazin]-2'(1'H)-one

Step A. Benzyl 7'-chloro-1'-methyl-2'-oxo-1',2'-dihydro-1H-spiro[piperidine-4,4'-pyrido[2,3-d][1,3]oxazine]-1-carboxylate To a 0° C. solution of benzyl 7'-chloro-2'-oxo-1',2'-dihydro-1H-spiro[piperidine-4,4'-pyrido[2,3-d][1,3]oxazine]-1-carboxylate (0.56 g, 1.43 mmol) in DMF (14 mL) was added lithium bis(trimethylsilyl)amide (2.86 mL of 1M solution, 2.86 mmol) followed by methyl iodide (0.11 mL, 2.28 mmol). After 1 h, more methyl iodide was added (0.55 mL, 1.14 mmol). After a further 1 h, the reaction was diluted with EtOAc, extracted with water (3×) and brine, dried over MgSO$_4$, filtered, and concentrated under reduced pressure. The crude product was purified by silica gel chromatography, eluting with a gradient of 0 to 4% methanol:dichloromethane to give the title compound (0.47 g). MS 402.0 (M+1).

Step B. 1'-Methylspiro[piperidine-4,4'-pyrido[2,3-d][1,3]oxazin]-2'(1'H)-one

10% Palladium on carbon (230 mg) was added to a solution of benzyl 7'-chloro-1'-methyl-2'-oxo-1',2'-dihydro-1H-spiro[piperidine-4,4'-pyrido[2,3-d][1,3]oxazine]-1-carboxylate (0.47 g, 1.17 mmol) in MeOH (40 mL). The reaction vessel was evacuated and back-filled with nitrogen (3×), then back-filled with hydrogen (1 atm). After 4 h, the mixture was filtered though celite and concentrated to give the title compound (0.35 g). MS 234 (M+1).

INTERMEDIATE 14

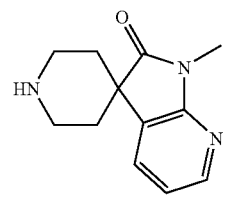

1'-Methylspiro[piperidine-4,3'-pyrrolo[2,3-b]pyridin]-2'(1'H)-one

Prepared essentially following the procedure outlined for the preparation of Intermediate 13.

INTERMEDIATE 15

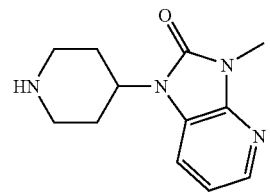

3-Methyl-1-piperidin-4-yl-1,3-dihydro-2H-imidazo[4,5-b]pyridin-2-one

Prepared essentially following the procedure outlined for the preparation of Intermediate 13.

INTERMEDIATE 16

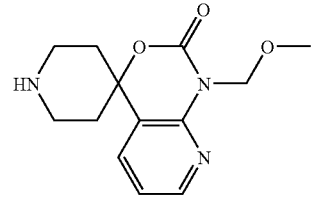

1'-(Methoxymethyl)spiro[piperidine-4,4'-pyrido[2,3-d][1,3]oxazin]-2'(1'H)-one

Step A. Benzyl 7'-chloro-1'-(methoxymethyl)-2'-oxo-1',2'-dihydro-1H-spiro[piperidine-4,4'-pyrido[2,3-d][1,3]oxazine]-1-carboxylate To a 0° C. solution of benzyl 7'-chloro-2'-oxo-1',2'-dihydro-1H-spiro[piperidine-4,4'-pyrido[2,3-d][1,3]oxazine]-1-carboxylate (0.20 g, 0.51 mmol) in DMF (4 mL) was added lithium bis(trimethylsilyl)amide (2.86 mL of 1M solution, 2.86 mmol) followed by chloromethyl methyl ether (0.094 mL, 1.01 mmol). After 0.5 h, the reaction was diluted with EtOAc, extracted with water (3×) and brine, dried over MgSO$_4$, filtered, and concentrated under reduced pressure.

The crude product was purified by silica gel chromatography, eluting with a gradient of 0 to 20% ethyl acetate:dichloromethane to give the title compound (0.21 g). MS 432.1 (M+1).

Step B. 1'-(Methoxymethyl)spiro[piperidine-4,4'-pyrido[2,3-d][1,3]oxazin]-2'(1'H)-one 10% Palladium on carbon (103 mg) was added to a solution of benzyl 7'-chloro-1'-(methoxymethyl)-2'-oxo-1',2'-dihydro-1H-spiro[piperidine-4,4'-pyrido[2,3-d][1,3]oxazine]-1-carboxylate (0.21 g, 0.48 mmol) in MeOH (10 mL). The reaction vessel was evacuated and back-filled with nitrogen (3×), then back-filled with hydrogen (1 atm). After 4 h, the mixture was filtered though celite and concentrated to give the title compound (0.14 g). MS 264 (M+1).

INTERMEDIATE 17

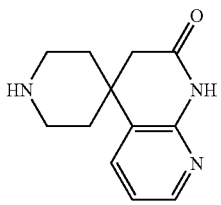

1H-Spiro[1,8-naphthyridine-4,4'-piperidin]-2(3H)-one

Step A. Benzyl 4-(2-methoxy-2-oxoethylidene)piperidine-1-carboxylate

A solution of N-benzyloxycarbonyl-4-piperidinone (5.0 g, 21.4 mol) and methyl (triphenylphosphoranylidene)acetate (10.0 g, 30.0 mmol) in benzene (100 mL) was heated at 75° C. for 48 h. The reaction was concentrated, diluted with ether, the precipitate filtered off, and the rinsate concentrated. The crude product was purified by silica gel chromatography, eluting with a gradient of 20 to 60% ethyl acetate:hexanes to give the title compound (5.25 g). MS: m/z=290.1 (M+1).

Step B. Benzyl 4-(2-methoxy-2-oxoethyl)-3,6-dihydropyridine-1(2H)-carboxylate

A solution of benzyl 4-(2-methoxy-2-oxoethylidene)piperidine-1-carboxylate (5.25 g, 18.1 mol) and 1,8-diazabicyclo[5.4.0]undec-7-ene (2.71 mL, 18.1 mol) in DMF (120 mL) was stirred at room temperature. After 3 d the reaction was diluted with water and extracted with ether (4×). The organic washes were combined, dried over MgSO₄, filtered and concentrated under reduced pressure. The crude product was purified by silica gel chromatography, eluting with a gradient of 5 to 30% ethyl acetate:hexanes to give the title compound (2.44 g). MS: m/z=290.1 (M+1). $^1$H NMR (500 MHz, CDCl₃) δ 7.30-7.25 (m, 5H), 5.5 (brs, 1H), 5.2 (s, 2H), 4.0 (brs, 2H), 3.7 (s, 3H), 3.6 (brs, 2H), 3.0 (s, 2H), 2.2 (brs, 2H).

Step C. Benzyl 4-{2-[(3-bromopyridin-2-yl)amino]-2-oxoethyl}-3,6-dihydropyridine-1(2H)-carboxylate Trimethylaluminum (2.0 M, 2.05 mL, 4.10 mol) was added slowly to a 0° C. solution of benzyl 4-(2-methoxy-2-oxoethyl)-3,6-dihydropyridine-1(2H)-carboxylate (0.79 g, 2.73 mol) and 2-amino-3-bromopyridine (0.520 g, 3.00 mmol) in 1,2-dichloroethane (15 mL). After 30 min, the reaction was heated to 55° C. for 48 h. The reaction was quenched by the careful addition of saturated aqueous sodium bicarbonate and the mixture extracted with dichlormethane (4×). The combined organic layers were washed with 1N sodium potassium tartrate, brine, dried over MgSO₄, filtered, and concentrated. The crude product was purified by silica gel chromatography, eluting with a gradient of 50 to 100% ethyl acetate:hexanes to give the title compound (2.44 g). MS: m/z=430.0 (M+1).

Step D. Benzyl 4-[2-((3-bromopyridin-2-yl){[2-(trimethylsilyl)ethoxy]methyl}amino)-2-oxoethyl]-3,6-dihydropyridine-1(2H-carboxylate Sodium hydride (60% dispersion in mineral oil; 117 mg, 4.88 mol) was added in portions over 10 min to a solution of benzyl 4-{2-[(3-bromopyridin-2-yl)amino]-2-oxoethyl}-3,6-dihydropyridine-1(2H)-carboxylate (1.91 g, 4.43 mol) in THF (15 mL) at 0° C. After 0.5 h, 2-(trimethylsilyl)ethoxymethyl chloride (0.861 mL, 4.88 mol) was then added slowly, keeping the temperature of the reaction mixture below 10° C. After 4 h, sodium hydride (60 mg) and 2-(trimethylsilyl)ethoxymethyl chloride (0.45 ml) were added and the reaction allowed to warm to room temperature overnight. The reaction was quenched with saturated aqueous ammonium chloride and the mixture was extracted with CH₂Cl₂ (3×). The combined organic layers were dried over MgSO₄, filtered, and concentrated. The crude product was purified by silica gel chromatography, eluting with a gradient of 40 to 70% ethyl acetate:hexanes to give the title compound (1.51 g). MS: m/z=560.2 (M+1).

Step E. Benzyl 2-oxo-1-{[2-(trimethylsilyl)ethoxy]methyl}-2,2',3,3'-tetrahydro-1H,1'H-spiro[1,8-naphthyridine-4,4'-pyridine]-1'-carboxylate To a mixture of N-methyldicyclohexylamine (0.042 mg, 0.20 mmol) and benzyl 4-[2-((3-bromopyridin-2-yl){[2-(trimethylsilyl)ethoxy]methyl}amino)-2-oxoethyl]-3,6-dihydropyridine-1(2H)-carboxylate (100 mg, 0.178 mmol) in dioxane (2 mL) was added bis(tri-tert-butylphosphine) palladium(0) (9 mg, 0.018 mmol). After 5 min, the reaction was heated to 50° C. After 90 min, bis(tri-tert-butylphosphine) palladium(0) (9 mg) was added. After an additional 30 min at 50° C., the reaction mixture was diluted with water and extracted with ether (3×). The combined organic layers were dried over MgSO₄, filtered, and concentrated. The crude product was purified by silica gel chromatography, eluting with a gradient of 5 to 60% ethyl acetate:hexanes to give the title compound (68 mg). MS: m/z=480.2 (M+1).

Step F. 1H-Spiro[1,8-naphthyridine-4,4'-piperidin]-2(3H)-one

To a mixture of benzyl 2-oxo-1-{[2-(trimethylsilyl)ethoxy]methyl}-2,2',3,3'-tetrahydro-1H,1'H-spiro[1,8-naphthyridine-4,4'-pyridine]-1'-carboxylate (384 mg, 0.800 mmol) in dichloromethane (10 mL) was added trifluoroacetic acid (10 mL). After 3 h, the reaction was concentrated, diluted with dichloromethane (10 mL) and ethylenediamine (720 mg, 12.0 mmol) was added. After 18 h, the reaction was concentrated, the residue partitioned between saturated aqueous NaHCO₃ and dichloromethane, and the layers separated. The aqueous phase was extracted with further portions of dichloromethane (2×), the organic layers combined, dried, and concentrated. 10% Palladium on carbon (300 mg) was added to a solution of this material in EtOH (10 mL). The reaction vessel was evacuated and back-filled with nitrogen (3×), then back-filled with hydrogen (1 atm). After 24 h, the mixture was filtered though celite and concentrated to give the title compound (130 mg). MS 218.1 (M+1). $^1$H NMR (500 MHz, CD$_3$OD) δ 8.14 (dd, J=1.6, 5.0 Hz, 1H), 7.80 (dd, J=1.6, 7.7 Hz, 1H), 7.10 (dd, J=5.0, 7.7 Hz, 1H), 2.98-2.95 (m, 4H), 2.78 (s, 2H), 1.96-1.90 (m, 2H), 1.69 (brd, J=11.5 Hz, 2H).

INTERMEDIATE 18

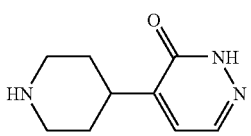

4-Piperidin-4-ylpyridazin-3(2H)-one

Step A: Benzyl 4-[1-(ethoxycarbonyl)but-3-en-1-yl]piperidine-1-carboxylate

To a −78° C. solution of benzyl 4-(2-ethoxy-2-oxoethyl)piperidine-1-carboxylate (5.02 g, 16.4 mmol) in tetrahydrofuran (90 mL) was added lithium hexamethyldisilazide (1.0 M in THF, 18.1 mL, 18.1 mmol). After 1 h, allyl bromide (2.19 g, 18.1 mmol) was added, the reaction stirred at this temperature for 0.5 h, then warmed to 25° C. After 3 h, the reaction was quenched with saturated aqueous ammonium chloride and extracted with ethyl acetate (2×). The combined organic extracts were dried over magnesium sulfate, filtered, and concentrated. Purification by silica gel chromatography (100% hexanes→40% hexanes/ethyl acetate) to give the title compound (4.08 g). MS 346.1 (M+1).

Step B: Benzyl 4-[1-(ethoxycarbonyl)-3-oxopropyl]piperidine-1-carboxylate

Benzyl 4-[1-(ethoxycarbonyl)but-3-en-1-yl]piperidine-1-carboxylate (4.08 g, 11.8 mmol) was dissolved in tetrahydrofuran (45 mL), and osmium tetroxide (0.45 mL, 2.5% solution in t-butanol) was added followed by a solution of sodium periodate (7.57 g, 35.4 mmol) in water (37 mL). After 24 h, the reaction was diluted with saturated aqueous sodium sulfite and saturated aqueous sodium bicarbonate and extracted with ethyl acetate (4×). The combined organic extracts were dried over sodium sulfate, filtered and concentrated. Purification by silica gel chromatography (50% hexanes/ethyl acetate→100% ethyl acetate) to give the title compound (2.39 g). MS 348.1 (M+1).

Step C: Benzyl 4-(3-oxo-2,3-dihydropyridazin-4-yl)piperidine-1-carboxylate

Benzyl 4-[1-(ethoxycarbonyl)-3-oxopropyl]piperidine-1-carboxylate (2.39 g, 6.89 mmol) was dissolved in acetic acid (100 mL) and hydrazine (4.42 g, 137 mmol) was added. This mixture was heated at 50° C. for 24 h, and then concentrated to dryness. The residue was diluted with saturated aqueous sodium bicarbonate and extracted with dichloromethane (3×), the combined organics dried, and concentrated to give a white solid (1.90 g). This material was dissolved in acetonitrile (20 mL), copper(II) chloride (1.62 g, 12.0 mmol) added and the reaction heated to 50° C. After 2 h, the reaction was filtered through celite with dichloromethane. The rinsate was washed with water (75 mL) and the aqueous phase was back-washed with dichloromethane (3×). The combined organic washes were washed with 1N HCl, dried and concentrated. Purification by silica gel chromatography (100% dichloromethane→88% dichloromethane/methanol) to give the title compound (0.90 g). MS 314.1 (M+1).

Step D: 4-Piperidin-4-ylpyridazin-3(2H)-one

A solution of benzyl 4-(3-oxo-2,3-dihydropyridazin-4-yl)piperidine-1-carboxylate (0.90 mg, 2.88 mmol) and 10% Pd/C (500 mg) in ethanol (25 mL), was hydrogenated under a balloon for 4 h. The reaction was filtered through celite, washed with ethanol and concentrated to give the title compound (465 mg). MS 180.1 (M+1).

INTERMEDIATE 19

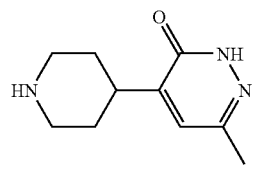

6-Methyl-4-piperidin-4-ylpyridazin-3 (2H)-one

Step A: Benzyl 4-(2-ethoxy-2-oxoethyl)piperidine-1-carboxylate

Benzyl chloridocarbonate (10.5 g, 61.3 mmol) was added to a solution of ethyl piperidin-4-ylacetate (10.0 g, 58.4 mmol) and sodium carbonate (46.2 g, 438 mmol) in dichloromethane (320 mL). After 18 h, the reaction mixture was filtered and concentrated. Purification by silica gel chromatography [75% hexanes/ethyl acetate→50% hexanes/ethyl acetate)] gave the title compound (17.6 g). MS 306.1 (M+1).

Step B: Benzyl 4-[1-(ethoxycarbonyl)-3-methylbut-3-en-1-yl]piperidine-1-carboxylate Lithium hexamethyldisilylazide (1.0 M in THF; 18.0 mL, 18.0 mmol) was added to a solution of benzyl 4-(2-ethoxy-2-oxoethyl)piperidine-1-carboxylate (5.0 g, 16.4 mmol) in tetrahydrofuran (90 mL) at −78° C. After 40 min, 3-bromo-2-methylprop-1-ene (1.81 mL, 18.0 mmol) was added and the reaction mixture was allowed to warm to ambient temperature. After 16 h, the reaction was quenched by the addition of saturated aqueous ammonium chloride and extracted with ethyl acetate (2×). The combined organic layers were dried over magnesium sulfate, filtered, and concentrated. Purified by silica gel chromatography (100% hexanes→40% hexanes/ethyl acetate) to give the title compound (2.88 g). MS 360.2 (M+1).

Step C: Benzyl 4-[1-(ethoxycarbonyl)-3-oxobutyl]piperidine-1-carboxylate

Osmium tetroxide (2.5 wt. % in t-BuOH; 0.3 mL, 0.001 mmol) was added to a solution of benzyl 4-[1-(ethoxycarbonyl)-3-methylbut-3-en-1-yl]piperidine-1-carboxylate (2.88 g, 8.01 mmol) in tetrahydrofuran (30 mL). Sodium periodate (5.14 g, 24.0 mmol) in water (26 mL) was added to the reaction mixture. After 5 days, the reaction was diluted with saturated aqueous sodium sulfite and saturated sodium bicarbonate and extracted with ethyl acetate (3×). The combined organic washes were dried over sodium sulfate, filtered and concentrated to give the title compound. MS 362.2 (M+1).

Step D: Benzyl 4-(6-methyl-3-oxo-2,3,4,5-tetrahydropyridazine-4-yl)piperidine-1-carboxylate Hydrazine (4.72 mL, 148.7 mmol) was added to a solution of benzyl 4-[1-(ethoxycarbonyl)-3-oxobutyl]piperidine-1-carboxylate (2.69 g, 7.44 mmol) in acetic acid (110 mL). The reaction mixture was heated at 50° C. After 1 h, the reaction mixture was concentrated. The residue was diluted with dichloromethane, neutralized by saturated aqueous sodium bicarbonate. The mixture was extracted with dichloromethane (3×), and the combined organic extracts were dried over magnesium sulfate and concentrated to give the title compound. MS 330.2 (M+1).

Step E: Benzyl 4-(6-methyl-3-oxo-2,3-dihydropyridazin-4-yl)piperidine-1-carboxylate Copper(II) chloride (anhydrous; 2.02 g, 15.05 mmol) was added to a solution of benzyl 4-(6-methyl-3-oxo-2,3,4,5-tetrahydropyridazine-4-yl)piperidine-1-carboxylate (2.48 g, 7.53 mmol) in acetonitrile (26 mL). The reaction mixture was heated at 90° C. After 18 h, the mixture was cooled to ambient temperature and concentrated. The residue was diluted with dichloromethane and 1 N HCl. The mixture was extracted with dichloromethane (3×), and the combined organic extracts were dried over magnesium sulfate and concentrated. Purification by silica gel chromatography (100% dichloromethane→90% dichloromethane/methanol) to give the title compound (1.45 g). MS 328.2 (M+1).

Step F: 6-Methyl-4-piperidin-4-ylpyridazin-3(2H)-one

Palladium (10% on carbon; 0.70 g) was added to a solution of benzyl 4-(6-methyl-3-oxo-2,3-dihydropyridazin-4-yl)piperidine-1-carboxylate (1.45 g, 4.43 mmol) in ethanol (100 mL). The reaction vessel was evacuated and back-filled with nitrogen (3×), then back-filled with hydrogen (1 atm). After 24 h, the mixture was filtered through celite and concentrated to give the title compound (0.86 g). MS 194.1 (M+1).

INTERMEDIATE 20

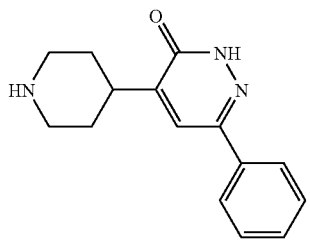

6-Phenyl-4-piperidin-4-ylpyridazin-3(2H)-one

Step A: [1-(Bromomethyl)vinyl]benzene

N-Bromosuccinimide (52.0 g, 292 mmol) and benzoylperoxide (2.0 g, 8.0 mmol) were added to a solution of isopropenylbenzene (82.0 g, 694 mmol) in carbon tetrachloride (200 mL). The reaction mixture was heated to reflux. After 18 h, additional N-bromosuccinimide (30.0 g, 168 mmol) was added. After 18 h, the mixture was allowed to cool to ambient temperature and the solid in the mixture was filtered off. The filtrate was concentrated and purified by vacuum distillation (95-120° C., 10 torr). The isolated mixture was purified by silica gel chromatography (100% hexanes) to give the title compound.

Step B: Benzyl 4-[1-(methoxycarbonyl)-3-phenyl-but-3-en-1-yl]piperidine-1-carboxylate Lithium hexamethyldisilylazide (1.0 M in THF; 7.31 mL, 7.31 mmol) was added to solution of benzyl 4-(2-methoxy-2-oxoethyl)piperidine-1-carboxylate (1.94 g, 6.65 mmol) in tetrahydrofuran (35 mL) at −78° C. After 40 min, [1-(bromomethyl)vinyl]benzene (1.08 mL, 7.31 mmol) was added and the reaction mixture was warmed to ambient temperature. After 18 h, the mixture was quenched with saturated aqueous ammonium chloride and extracted with ethyl acetate (2×). The combined organic extracts were dried over magnesium sulfate, filtered and concentrated. Purification by silica gel chromatography (100% hexanes→40% hexanes/ethyl acetate) gave the title compound (2.11 g). MS 408.2 (M+1).

Step C: Benzyl 4-[1-(methoxycarbonyl)-3-oxo-3-phenylpropyl]piperidine-1-carboxylate Osmium tetroxide (2.5 wt. % in t-BuOH; 0.2 mL, 0.001 mmol) was added to a solution of benzyl 4-[1-(methoxycarbonyl)-3-phenylbut-3-en-1-yl]piperidine-1-carboxylate (2.11 g, 5.19 mmol) in tetrahydrofuran (20 mL). Sodium periodate (3.33 g, 15.6 mmol) in water (17 mL) was added to the reaction mixture. After 18 h, saturated aqueous sodium sulfite and saturated aqueous sodium bicarbonate were added and the mixture was extracted with ethyl acetate (4×). The combined organic extracts were dried over magnesium sulfate, filtered and concentrated to give the title compound. MS 410.1 (M+1).

Step D: Benzyl 4-(3-oxo-6-phenyl-2,3,4,5-tetrahydropyridazine-4-yl)piperidine-1-carboxylate Hydrazine (3.31 mL, 104 mmol) was added to a solution of benzyl 4-[1-(methoxycarbonyl)-3-oxo-3-phenylpropyl]piperidine-1-carboxylate (2.14 g, 5.22 mmol) in acetic acid (70 mL). The reaction mixture was heated at 50° C. After 1 h, the reaction mixture was concentrated. The residue was diluted with dichloromethane, neutralized by saturated aqueous sodium bicarbonate. The mixture was extracted with dichloromethane (3×), and the combined organic extracts were dried over magnesium sulfate and concentrated to give the title compound. MS 392.1 (M+1).

Step E: Benzyl 4-(3-oxo-6-phenyl-2,3-dihydropyridazin-4-yl)piperidine-1-carboxylate Copper(II) chloride (anhydrous; 1.27 g, 9.45 mmol) was added to a solution of benzyl 4-(3-oxo-6-phenyl-2,3,4,5-tetrahydropyridazine-4-yl)piperidine-1-carboxylate (1.85 g, 4.73 mmol) in acetonitrile (16 mL). The reaction mixture was heated to 90° C. After 2 h, the mixture was allowed to cool to ambient temperature and concentrated. Dichloromethane was added to the concentrated mixture, followed by hydrochloric acid (1 N in water). The mixture was extracted with dichloromethane (3×) and the combined organic extracts were dried over magnesium sulfate and concentrated. Purification by silica gel chromatography (100% dichloromethane→90% dichloromethane/methanol) gave the title compound (1.1 g). MS 390.1 (M+1).

Step F: 6-Phenyl-4-piperidin-4-ylpyridazin-3(2H)-one

Palladium (10% on carbon; 0.50 g) was added to a solution of benzyl 4-(3-oxo-6-phenyl-2,3-dihydropyridazin-4-yl)piperidine-1-carboxylate (1.10 g, 2.82 mmol) in ethanol (50 mL). The reaction vessel was evacuated and back-filled with nitrogen (3×), then back-filled with hydrogen (1 atm). After 24 h, the mixture was filtered through celite and concentrated to give the title compound (709 mg). MS 256.2 (M+1).

INTERMEDIATE 21 and INTERMEDIATE 22

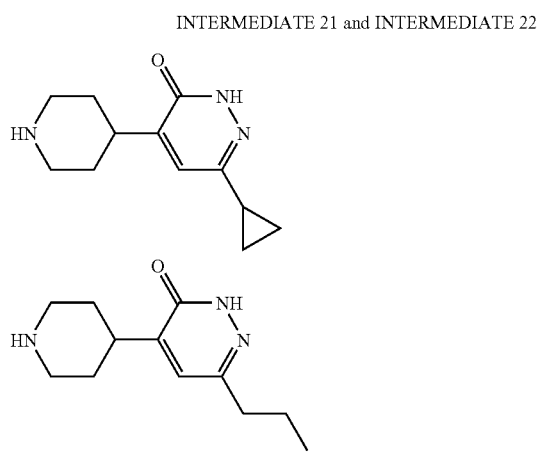

6-Cyclopropyl-4-piperidin-4-ylpyridazin-3(2H)-one and 4-piperidin-4-yl-6-propylpyridazin-3(2H)-one

Step A: Benzyl 4-[3-bromo-1-(ethoxycarbonyl)but-3-en-1-yl]piperidine-1-carboxylate Lithium hexamethyldisilylazide (1.0 M in THF; 7.20 mL, 7.20 mmol) was added to solution of benzyl 4-(2-ethoxy-2-oxoethyl)piperidine-1-carboxylate (2.0 g, 6.55 mmol) in tetrahydrofuran (30 mL) at −78° C. After 40 min, 2,3-dibromoprop-1-ene (0.70 mL, 7.20 mmol) was added. After 2 h, the reaction mixture was warmed to ambient temperature. After 18 h, the mixture was quenched with saturated ammonium chloride and extracted with ethyl acetate (2×). The combined organic extracts were dried over magnesium sulfate, filtered and concentrated. Purification by silica gel chromatography (80% hexanes/ethyl acetate→40% hexanes/ethyl acetate) gave the title compound (603 mg). MS 424.0 (M).

Step B: Benzyl 4-[3-cyclopropyl-1-(ethoxycarbonyl)but-3-en-1-yl]piperidine-1-carboxylate Dichloro [1,1'-bis(diphenylphosphino)ferrocene]palladium (II) dichloromethane adduct (137 mg, 0.187 mmol) was added to a solution of benzyl 4-[3-bromo-1-(ethoxycarbonyl)but-3-en-1-yl]piperidine-1-carboxylate (795 mg, 1.87 mmol) in ether (6 mL). The reaction mixture was cooled to 0° C. and cyclopropylmagnesium bromide (0.544 g, 3.75 mmol) was added. After 1 h, the mixture was warmed to ambient temperature. After 1 h, the mixture was cooled back to 0° C. and two additional portions of dichloro [1,1'-bis(diphenylphosphino)ferrocene]palladium(II) dichloromethane adduct (137 mg, 0.187 mmol) and cyclopropylmagnesium bromide (544 mg, 3.75 mmol) were added. The mixture was warmed to ambient temperature. After 18 h, hydrochloric acid (10% in water) was added and the mixture was extracted with ether (2×). The combined organic extracts were washed with saturated aqueous sodium bicarbonate, water, dried over magnesium sulfate, filtered and concentrated. Purification by silica gel chromatography (100% hexanes→50% hexanes/ethyl acetate) gave the title compound (173 mg). MS 386.2 (M+1).

Step C: Benzyl 4-[3-cyclopropyl-1-(ethoxycarbonyl)-3-oxopropyl]piperidine-1-carboxylate Osmium tetroxide (2.5 wt. % in t-BuOH; 17 uL, 0.001 mmol) was added to a solution of benzyl 4-[3-cyclopropyl-1-(ethoxycarbonyl)but-3-en-1-yl]piperidine-1-carboxylate (173 mg, 0.45 mmol) in tetrahydrofuran (2 mL). Sodium periodate (290 mg, 1.35 mmol) in water (1.5 mL) was added to the reaction mixture. After 18 h, saturated aqueous sodium sulfite and saturated aqueous sodium bicarbonate were added and the mixture was extracted with ethyl acetate (4×). The combined organic extracts were dried over magnesium sulfate, filtered and concentrated to give the title compound. MS 388.1 (M+1).

Step D: Benzyl 4-(6-cyclopropyl-3-oxo-2,3,4,5-tetrahydropyridazine-4-yl)piperidine-1-carboxylate Hydrazine (0.3 mL, 9.6 mmol) was added to a solution of benzyl 4-[3-cyclopropyl-1-(ethoxycarbonyl)-3-oxopropyl]piperidine-1-carboxylate (186 mg, 0.48 mmol) in acetic acid (7 mL). The reaction mixture was heated at 50° C. After 1 h, the reaction mixture was concentrated. The residue was diluted with dichloromethane and neutralized by saturated aqueous sodium bicarbonate. The mixture was extracted with dichloromethane (3×), and the combined organic extracts were dried over magnesium sulfate and concentrated to give the title compound. MS 356.2 (M+1).

Step E: Benzyl 4-(6-cyclopropyl-3-oxo-2,3-dihydropyridazin-4-yl)piperidine-1-carboxylate Copper(II) chloride (anhydrous; 101 mg, 0.75 mmol) was added to a solution of benzyl 4-(6-cyclopropyl-3-oxo-2,3,4,5-tetrahydropyridazine-4-yl)piperidine-1-carboxylate (134 mg, 0.38 mmol) in acetonitrile (16 mL). The reaction mixture was heated to 90° C. After 18 h, the mixture was cooled to ambient temperature and concentrated. Dichloromethane was added to the concentrated mixture, followed by hydrochloric acid (1 N in water). The mixture was extracted with dichloromethane (3×) and the combined organic extracts were dried over magnesium sulfate and concentrated. Purification by silica gel chromatography (100% dichloromethane→90% dichloromethane/methanol) gave the title compound (54 mg). MS 354.1 (M+1).

Step F: 6-Cyclopropyl-4-piperidin-4-ylpyridazin-3 (2H)-one and 4-piperidin-4-yl-6-propylpyridazin-3 (2H)-one Palladium (10% on carbon; 50 mg) was added to a solution of benzyl 4-(6-cyclopropyl-3-oxo-2,3-dihydropyridazin-4-yl)piperidine-1-carboxylate (54 mg, 0.15 mmol) in ethanol (20 mL). The reaction vessel was evacuated and back-filled with nitrogen (3×), then back-filled with hydrogen (1 atm). After 1 h, the mixture was filtered through celite and concentrated to give 1:1 mixture of the two title compounds (33 mg). MS 220.2 (M+1) and MS 222.2 (M+1).

INTERMEDIATE 23

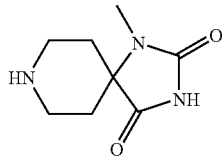

1-Methyl-1,3,8-triazaspiro[4.5]decane-2,4-dione

Step A: Benzyl 4-cyano-4-(methylamino)piperidine-1-carboxylate

A solution of potassium cyanide (2.79 g, 42.9 mmol) in water (5 mL) was added to a solution of benzyl 4-oxopiperidine-1-carboxylate (10.0 g, 42.9 mmol) and methylamine hydrochloride (2.90 g, 42.9 mmol) in water/methanol (1:1; 10 mL) at 0° C. The reaction mixture was allowed to warm to ambient temperature. After 48 h, additional methylamine hydrochloride (1.45 g, 21.4 mmol) was added. After 18 h, the mixture was diluted with ether, and extracted with ethyl acetate (3×). The combined organic extracts were dried over magnesium sulfate and concentrated down to 50 mL volume. HCl gas was bubbled to this solution for 5 min. The solid precipitated out of the solution was filtered and washed with ether (3×), ethyl acetate (3×) and dried under reduced pressure to give the hydrochloride salt of the title compound. MS 274.1 (M+1).

Step B: Benzyl 1-methyl-2,4-dioxo-1,3,8-triazaspiro [4.5]decane-8-carboxylate

A solution of potassium cyanate (5.74 g, 70.8 mmol) in water (9 mL) was added dropwise to a solution of the hydrochloride salt of benzyl 4-cyano-4-(methylamino)piperidine-1-carboxylate (9.68 g, 35.4 mmol) in acetic acid (27 mL). The reaction mixture was heated at 50° C. After 1 h, the mixture was poured into cold water (200 mL). The mixture was extracted with ethyl acetate (4×), and the combined organic extracts were dried over magnesium sulfate and concentrated. A solution of HCl (10% in water; 40 mL) was added and the mixture was heated at 50° C. After 15 min, the reaction mixture was cooled to ambient temperature. The precipitated solid was filtered, washed with water, and dried under reduced pressure to give the title compound. MS 318.1 (M+1).

Step C: 1-Methyl-1,3,8-triazaspiro[4.5]decane-2,4-dione

Palladium (10% on carbon; 1.0 g) was added to a solution of benzyl 1-methyl-2,4-dioxo-1,3,8-triazaspiro[4.5]decane-8-carboxylate (7.82 g, 24.6 mmol) in ethanol (100 mL). The reaction vessel was evacuated and back-filled with nitrogen (3×), then back-filled with hydrogen (1 atm). After 2 h, methanol (50 mL) was added to the reaction mixture and the mixture was continued to be stirred under hydrogen (1 atm). After 4 days, the mixture was filtered through celite, washed with acetone and concentrated. The mixture was diluted in acetic acid (50 mL). The reaction vessel was evacuated and back-filled with nitrogen (3×), then back-filled with hydrogen (1 atm). After 2 h, the mixture was filtered through celite, and concentrated to give the acetate salt of the title compound (2.98 g). MS 184.1 (M+1).

INTERMEDIATE 24

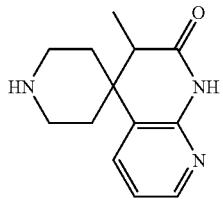

3-Methyl-1H-spiro[1,8-naphthyridine-4,4'-piperidin]-2(3H)-one

Step A: Benzyl 4-(2-methoxy-2-oxoethylidene)piperidine-1-carboxylate

Methyl (triphenylphosphoranylidene)acetate (10.0 g, 30.0 mmol) was added to a solution of benzyl 4-oxopiperidine-1-carboxylate (5.0 g, 21.4 mmol) in benzene (100 mL) at 0° C. After 1 h, the reaction mixture was heated to 75° C. After 48 h, the mixture was concentrated and ether was added. The precipitated solid was filtered off and the filtrate was concentrated. Purification by silica gel chromatography [80% hexanes/ethyl acetate→40% hexanes/ethyl acetate)] gave the title compound (5.25 g). MS 290.1 (M+1).

Step B: Benzyl 4-(2-methoxy-2-oxoethyl)-3,6-dihydropyridine-1(2H)-carboxylate 2,3,4,6,7,8,9,10-Octahydropyrimido[1,2-a]azepine (2.71 mL, 18.2 mmol) was added to a solution of benzyl 4-(2-methoxy-2-oxoethylidene)piperidine-1-carboxylate (5.25 g, 18.2 mmol) in N,N-dimethylformamide (120 mL). After 3 days, the reaction mixture was diluted with water and extracted with ether (4×). The combined organic extracts were dried over magnesium sulfate, filtered and concentrated. Purification by silica gel chromatography [100% dichloromethane→85% dichloromethane/ethyl acetate)] gave the title compound (2.43 g). MS 290.1 (M+1).

Step C: Benzyl 4-{2-[(3-bromopyridin-2-yl)amino]-2-oxoethyl}-3,6-dihydropyridine-1(2H)-carboxylate Trimethylaluminum (0.91 g, 12.61 mmol) was added to a solution of benzyl 4-(2-methoxy-2-oxoethyl)-3,6-dihydropyridine-1(2H)-carboxylate (2.43 g, 8.41 mmol) and 3-bromopyridin-2-amine (1.60 g, 9.25 mmol) in dichloroethane (45 mL) at 0° C. The reaction mixture was slowly warmed to 55° C. After 18 h, the reaction mixture was quenched with saturated aqueous sodium bicarbonate and extracted with dichloromethane (4×). The combined organic extracts were washed with Rochelle's salts (1N in water), saturated brine, dried over magnesium sulfate, filtered and concentrated. Purification by silica gel chromatography (50% hexanes/ethyl acetate→100% ethyl acetate) gave the title compound (1.91 g). MS 430.0 (M).

Step D: Benzyl 4-[2-((3-bromopyridin-2-yl) {[2-(trimethylsilyl)ethoxy]methyl}amino)-2-oxoethyl]-3,6-dihydropyridine-1(2H)-carboxylate Sodium hydride (60% dispersion in oil; 0.20 g, 5.0 mmol) was slowly added to a solution of benzyl 4-{2-[(3-bromopyridin-2-yl)amino]-2-oxoethyl}-3,6-dihydropyridine-1(2H)-carboxylate (1.91 g, 4.43 mmol) in tetrahydrofuran (15 mL) at 0° C. After 30 min, [2-(chloromethoxy)ethyl](trimethyl)silane (0.86 mL, 4.88 mmol) was added. After 4 h, additional sodium hydride (60% dispersion in oil; 0.10 g, 2.5 mmol) was added, followed by [2-(chloromethoxy)ethyl](trimethyl)silane (0.43 mL, 2.44 mmol). After 18 h, the reaction mixture was quenched with saturated ammonium chloride. The mixture was extracted with dichloromethane. The combined organic extracts were dried over magnesium sulfate, filtered and concentrated. Purification by silica gel chromatography (60% hexanes/ethyl acetate→30% hexanes/ethyl acetate) gave the title compound (1.51 g). MS 560.1 (M).

Step E: Benzyl 2-oxo-1-{[2-(trimethylsilyl)ethoxy]methyl}-2,2',3,3'-tetrahydro-1H,1'H-spiro[1,8-naphthyridine-4,4'-pyridine]-1'-carboxylate Bis(tri-t-butylphosphine) palladium(0) (9.0 mg, 0.018 mmol) was added to solution of benzyl 4-[2-((3-bromopyridin-2-yl){[2-(trimethylsilyl)ethoxy]methyl}amino)-2-oxoethyl]-3,6-dihydropyridine-1(2H)-carboxylate (0.10 g, 0.18 mmol) and dicyclohexylmethylamine (42 µL, 0.196 mmol) in dioxane (2 mL). After 5 min, the reaction mixture was heated to 50° C. After 1.5 h, additional bis(tri-t-butylphosphine)palladium(0) (9.0 mg, 0.018 mmol) was added. After 20 min, water was added and the mixture was extracted with ether (2x). The combined organic extracts were dried over magnesium sulfate, filtered and concentrated. Purification by silica gel chromatography (95% hexanes/ethyl acetate→40% hexanes/ethyl acetate) gave the title compound (68 mg). MS 480.2 (M+1).

Step F: Benzyl 3-methyl-2-oxo-1-{[2-(trimethylsilyl)ethoxy]methyl}-2,2',3,3'-tetrahydro-1H,1'H-spiro[1,8-naphthyridine-4,4'-pyridine]-1'-carboxylate Lithium hexamethyldisilylazide (1.0 M in THF; 0.135 mL, 0.135 mmol) was added to solution of benzyl 2-oxo-1-{[2-(trimethylsilyl)ethoxy]methyl}-2,2',3,3'-tetrahydro-1H,1'H-spiro[1,8-naphthyridine-4,4'-pyridine]-1'-carboxylate (50.0 mg, 0.104 mmol) in tetrahydrofuran (1 mL) at −78° C. After 40 min, iodomethane (8.0 µL, 0.135 mmol) was added and the reaction mixture was slowly warmed to ambient temperature. After 1 h, the mixture was quenched with saturated aqueous ammonium chloride and extracted with ethyl acetate (3x). The combined organic extracts were dried over magnesium sulfate, filtered and concentrated to give the title compound. MS 494.3 (M+1).

Step G: Benzyl 3-methyl-2-oxo-2,2',3,3'-tetrahydro-1H,1'H-spiro[1,8-naphthyridine-4,4'-pyridine]-1'-carboxylate Trifluoroacetic acid (4 mL, 53.8 mmol) was added to a solution of benzyl 3-methyl-2-oxo-1-{[2-(trimethylsilyl)ethoxy]methyl}-2,2',3,3'-tetrahydro-1H,1'H-spiro[1,8-naphthyridine-4,4'-pyridine]-1'-carboxylate (0.10 g, 0.20 mmol) in dichloromethane (2 mL). After 2 h, the reaction mixture was concentrated. The concentrated mixture was diluted in dichloromethane (2 mL) and ethane-1,2-diamine (4 mL) was added. After 1 h, the reaction mixture was concentrated and saturated aqueous sodium bicarbonate was added. The mixture was extracted with dichloromethane (3x). The combined organic extracts were dried over magnesium sulfate, filtered and concentrated. MS 364.1 (M+1).

Step H: 3-Methyl-1H-spiro[1,8-naphthyridine-4,4'-piperidin]-2(3H)-one

Benzyl 3-methyl-2-oxo-2,2',3,3'-tetrahydro-1H,1'H-spiro[1,8-naphthyridine-4,4'-pyridine]-1'-carboxylate (73 mg, 0.20 mmol) was diluted in ethanol (10 mL) and palladium (10% on carbon; 100 mg) was added. The reaction vessel was evacuated and back-filled with nitrogen (3x), then back-filled with hydrogen (1 atm). After 6 h, the mixture was filtered with celite, washed with ethanol and methanol. The filtrate was concentrated to give the title compound. MS 232.1 (M+1).

INTERMEDIATE 25

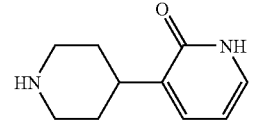

3-Piperidin-4-ylpyridin-2(1H)-one

Step A: Benzyl 4-{[(trifluoromethyl)sulfonyl]oxy}-3,6-dihydropyridine-1(2H)-carboxylate n-Butyllithium (2.5 M in THF; 10.8 mL, 27.0 mmol) was added to a solution of diisopropylamine (3.79 mL, 27.0 mmol) in tetrahydrofuran (37 mL) at −78° C. After 5 min, the reaction mixture was warmed to 0° C. for 20 min then cooled backed down to −78° C. This mixture was added to a solution of benzyl 4-oxopiperidine-1-carboxylate (5.26 g, 22.5 mmol) in tetrahydrofuran (50 mL) at −78° C. After 1 h, a solution of N-phenyl-bis(trifluoromethanesulfonimide) (8.85 g, 24.8 mmol) in tetrahydrofuran (12 mL) was added. The mixture was warmed to 0° C. After 3 h, the mixture was quenched with saturated aqueous sodium bicarbonate and concentrated. The residue was diluted with saturated aqueous sodium bicarbonate and extracted with ether. The combined organic extracts were dried over magnesium sulfate and concentrated. Purification by silica gel chromatography (100% hexanes→60% hexanes/ethyl acetate). Repurification by silica gel chromatography (100% dichloromethane→93% dichloromethane/ethyl acetate) gave the title compound (3.52 g). MS 366.0 (M+1).

Step B: Benzyl 2-methoxy-3',6'-dihydro-3,4'-bipyridine-1'(2'H)-carboxylate

Sodium carbonate (2.0 M in water; 4.0 mL, 8.09 mmol) was added to a solution of benzyl 4-{[(trifluoromethyl)sulfonyl]oxy}-3,6-dihydropyridine-1(2H)-carboxylate (1.26 g, 3.45 mmol) and (2-methoxypyridin-3-yl)boronic acid (0.58 g, 3.79 mmol) in N,N-dimethylformamide (12 mL). Dichloro[1,1'-bis(diphenylphosphino)ferrocene]palladium(II) dichloromethane adduct (0.25 g, 0.345 mmol) was added and the mixture was heated to 70° C. After 2 h, the mixture was cooled to ambient temperature and water was added. The mixture was extracted with ethyl acetate and the combined organic extracts were dried over magnesium sulfate and concentrated. Purification by silica gel chromatography (100% hexanes→50% hexanes/ethyl acetate) to give the title compound (0.815 g). MS 325.2 (M+1).

Step C: tert-Butyl 4-(2-methoxypyridin-3-yl)piperidine-1-carboxylate

Di-tert-butyl dicarbonate (0.31 g, 1.43 mmol) was added to a solution of benzyl 2-methoxy-3',6'-dihydro-3,4'-bipyridine-1'(2'H)-carboxylate (0.42 g, 1.3 mmol) in ethyl acetate (4 mL). Palladium (10% on carbon; 200 mg) was added and the reaction vessel was evacuated and back-filled with nitrogen (3×), then back-filled with hydrogen (1 atm). After 3 h, the mixture was filtered through celite and concentrated to give the title compound (416 mg). MS 293.2 (M+1).

Step D: 3-Piperidin-4-ylpyridin-2(1H)-one tert-Butyl 4-(2-methoxypyridin-3-yl)piperidine-1-carboxylate (204 mg, 0.70 mmol) was added to hydrochloric acid (6.0 M in water; 5.81 mL, 34.89 mmol). After 18 h, the reaction mixture was concentrated and dried under reduced pressure to give the title compound. MS 179.1 (M+1).

INTERMEDIATE 26

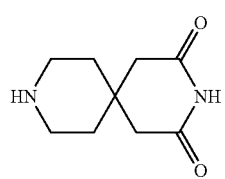

3,9-Diazaspiro[5.5]undecane-2,4-dione

Step A: 2,2'-(1-Benzylpiperidine-4,4-diyl)diacetic acid

Sodium hydroxide (173 mg, 4.30 mmol) was added to a solution of diethyl 2,2'-(1-benzylpiperidine-4,4-diyl)diacetate (J. Med. Chem. 2004, 47, 1900-1918) (0.50 g, 1.44 mmol) in methanol (5 mL). After 1 h, the reaction mixture was warmed to 50° C. After 18 h, additional sodium hydroxide (57 mg, 1.44 mmol) was added. After 2 h, hydrochloric acid (6.0 M in water; 1.02 mL, 6.10 mmol) was added and the mixture was concentrated to give the sodium chloride salt of the title compound. MS 292.1 (M+1).

Step B: 9-Benzyl-3,9-diazaspiro[5.5]undecane-2,4-dione

Urea (242 mg, 4.03 mmol) was added to 2,2'-(1-benzylpiperidine-4,4-diyl)diacetic acid (390 mg, 1.34 mmol). The mixture was heated to 160° C. After 3 h, additional urea (242 mg, 4.03 mmol) was added and the mixture was heated to 185° C. After 18 h, additional urea (242 mg, 4.03 mmol) was added. After 48 h, the reaction mixture was allowed to cool to ambient temperature and ethanol was added. After 1 h, the mixture was filtered and solid was washed with ethanol. Saturated aqueous sodium bicarbonate was added to the solid and the suspended solution was stirred until gas release was complete. The mixture was filtered and the solid was washed with water, and concentrated to give the title compound (380 mg). MS 273.1 (M+1).

Step C: 3,9-Diazaspiro[5.5]undecane-2,4-dione

Palladium hydroxide (20% on carbon; 100 mg) and acetic acid (250 µL) were added to a solution of 9-benzyl-3,9-diazaspiro[5.5]undecane-2,4-dione (0.38 g, 1.40 mmol) in ethanol (5 mL). The reaction vessel was evacuated and back-filled with nitrogen (3×), then back-filled with hydrogen (1 atm). After 18 h, the mixture was filtered and concentrated to give the acetate salt of the title compound (220 mg). MS 183.1 (M+1).

INTERMEDIATE 27

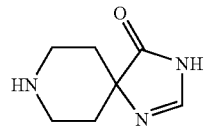

1,3,8-Triazaspiro[4.5]dec-1-en-4-one

Step A: tert-Butyl 4-(aminocarbonyl)-4-{[(benzyloxy)carbonyl]amino}piperidine-1-carboxylate To a solution of 4-{[(benzyloxy)carbonyl]amino}-1-(tert-butoxycarbonyl)piperidine-4-carboxylic acid (2.09 g, 5.52 mmol) in N,N-dimethylformamide (10 mL) were added N-(3-dimethylaminopropyl)-N'-ethylcarbodiimide hydrochloride (1.27 g, 6.63 mmol), 1-hydroxybenzotriazole hydrate (0.37 g, 2.76 mmol) and triethylamine (0.92 mL, 6.63 mmol), followed by ammonia (0.5 M in dioxane; 13.3 mL, 6.63 mmol). After 18 h, saturated aqueous sodium bicarbonate was added and the mixture was extracted with ethyl acetate. The combined organic extracts were dried over magnesium sulfate, filtered and concentrated. Purification by silica gel chromatography (100% dichloromethane→94% dichloromethane/methanol) to give the title compound (0.43 g). MS 378.2 (M+1).

Step B: 4-{[(Benzyloxy)carbonyl]amino}-1-(tert-butoxycarbonyl)piperidine-4-carboxylic acid Palladium (10% on carbon; 210 mg) was added to a solution of tert-butyl 4-(aminocarbonyl)-4-{[(benzyloxy)carbonyl]amino}piperidine-1-carboxylate (0.43 g, 1.14 mmol) in ethanol (20 mL). The reaction vessel was evacuated and back-filled with nitrogen (3×), then back-filled with hydrogen (1 atm). After 18 h, the mixture was filtered and concentrated to give the title compound (290 mg).

Step C: tert-Butyl 4-oxo-1,3,8-triazaspiro[4.5]dec-1-ene-8-carboxylate

Trimethoxymethane (230 mg, 2.16 mmol) was added to a solution of 4-{[(benzyloxy)carbonyl]amino}-1-(tert-butoxycarbonyl)piperidine-4-carboxylic acid (0.175 g, 0.72 mmol) in toluene (8 mL). The reaction mixture was heated to 90° C. After 18 h, the mixture was concentrated. Purification by silica gel chromatography (99% dichloromethane/methanol→90% dichloromethane/methanol) to give the title compound (76 mg). MS 254.1 (M+1).

Step D: 1,3,8-Triazaspiro[4.5]dec-1-en-4-one

Hydrochloric acid (4.0 N in dioxane; 4 mL, 16.0 mmol) was added to a solution of tert-butyl 4-oxo-1,3,8-triazaspiro[4.5]dec-1-ene-8-carboxylate (60 mg, 0.24 mmol) in dioxane (6 mL). After 18 h, the reaction mixture was concentrated to give the hydrochloride salt of the title compound. MS 154.1 (M+1).

INTERMEDIATE 28

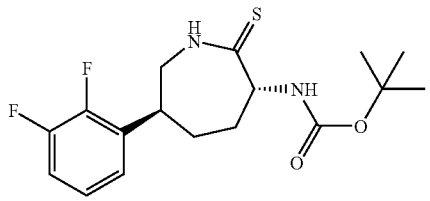

tert-Butyl (3R,6S)-6-(2,3-difluorophenyl)-2-thioxoazepan-3-ylcarbamate

Step A. 2-Bromo-N-(2,4-dimethoxybenzyl)prop-2-en-1-amine

Triethylamine (16.0 mL, 114 mmol) was added to a solution of 2,4-dimethoxybenzylamine hydrochloride (11.1 g, 54.5 mmol) and 2,3-dibromopropane (10.9 g, 54.5 mmol) in dichloromethane (200 mL). After 18 h, water was added and the mixture was extracted with dichloromethane (3×). The combined organic extracts were washed with saturated brine, dried over magnesium sulfate, filtered and concentrated. Purification by silica gel chromatography [100% dichloromethane→95% dichloromethane/5% (10% ammonium hydroxide/methanol)] gave the title compound (7.85 g).

Step B. Benzyl (1R)-1-{[(2-bromoprop-2-enyl)(2,4-dimethoxybenzyl)amino]carbonyl}but-3-enylcarbamate 1-[3-(Dimethylamino)propyl]-3-ethylcarbodiimide hydrochloride (55 mg, 0.285 mmol) was added to a solution of 2-bromo-N-(2,4-dimethoxybenzyl)prop-2-en-1-amine (73 mg, 0.256 mmol) and (2R)-2-{[(benzyloxy)carbonyl]amino}pent-4-enoic acid (71 mg, 0.285 mmol) in dichloromethane (5 mL). After 18 h the mixture was concentrated. Purification by silica gel chromatography (5% ethyl acetate/hexanes→30% ethyl acetate/hexanes) gave the title compound (77 mg). MS 517 (M+1).

Step C. Benzyl (1R)-1-{[[2-(2,3-difluorophenyl)prop-2-enyl](2,4-dimethoxybenzyl)amino]carbonyl}but-3-enylcarbamate Dichloro[1,1'-bis(diphenylphosphino)ferrocene]palladium dichloromethane adduct (0.726 g, 0.889 mmol) was added to a solution of benzyl (1R)-1-{[(2-bromoprop-2-enyl)(2,4-dimethoxybenzyl)amino]carbonyl}but-3-enylcarbamate (9.2 g, 17.8 mmol), 2,3-difluorophenylboronic acid (2.95 g, 18.7 mmol) and sodium carbonate (2M in water; 19.6 mL, 39.1 mmol) in N,N-dimethylformamide (60 mL) and the mixture was heated to 75° C. After 2 h, the mixture was allowed to cool to ambient temperature and extracted with dichloromethane (3×). The combined organic extracts were washed with saturated brine, dried over magnesium sulfate, filtered and concentrated. Purification by silica gel chromatography (5% ethyl acetate/hexanes→55% ethyl acetate/hexanes) gave the title compound (6.8 g). MS 551.2 (M+1).

Step D. Benzyl (3R)-6-(2,3-difluorophenyl)-1-(2,4-dimethoxybenzyl)-2-oxo-2,3,4,7-tetrahydro-1H-azepin-3-ylcarbamate

[1,3-bis-(2,4,6-Trimethylphenyl-2-imidazolidinylidene)dichloro(phenylmethylene)-(tricyclohexylphosphine)ruthenium] (Grubbs second generation catalyst) (2.62 g, 3.09 mmol) was added to a solution of benzyl (1R)-1-{[[2-(2,3-difluorophenyl)prop-2-enyl](2,4-dimethoxybenzyl)amino]carbonyl}but-3-enylcarbamate (6.8 g, 12.35 mmol) in dichloromethane (1800 mL) and the solution was heated to 40° C. After 48 h, additional catalyst was added (0.52 g, 0.61 mmol) and the reaction continued to heat at 40° C. for an additional 48 h. The mixture was allowed to cool to ambient temperature and concentrated. Purification by silica gel chromatography (5% ethyl acetate/hexanes→55% ethyl acetate/hexanes) gave the title compound (3.71 g). MS 523.1 (M+1).

Step E. Benzyl (3R)-6-(2,3-difluorophenyl)-2-oxo-2,3,4,7-tetrahydro-1H-azepin-3-ylcarbamate Trifluoroacetic acid (60 mL) was added to a solution of benzyl (3R)-6-(2,3-difluorophenyl)-1-(2,4-dimethoxybenzyl)-2-oxo-2,3,4,7-tetrahydro-1H-azepin-3-ylcarbamate (3.70 g, 7.08 mmol) in dichloromethane (40 mL). After 18 h, the mixture was concentrated at 25° C., methanol (150 mL) was added, and the precipitate filtered. The filtrate was concentrated, diluted with dichloromethane (100 mL), washed with water (2×), saturated aqueous sodium bicarbonate (2×), saturated brine, dried over magnesium sulfate, filtered and concentrated. Purification by silica gel chromatography (5% ethyl acetate/hexanes→65% ethyl acetate/hexanes) gave the title compound (1.75 g). MS 373.1 (M+1).

Step F. tert-Butyl (3R,6S)-6-(2,3-difluorophenyl)-2-oxoazepan-3-ylcarbamate

10% Palladium on carbon (700 mg) was added to a solution of benzyl (3R)-6-(2,3-difluorophenyl)-2-oxo-2,3,4,7-tetrahydro-1H-azepin-3-ylcarbamate (2.6 g, 6.98 mmol) and di-tert-butyl dicarbonate (5.03 g, 23.0 mmol) in toluene (200 mL). The reaction vessel was evacuated and back-filled with nitrogen (3×), then back-filled with hydrogen (1 atm). After 24 h, the mixture was filtered and concentrated. Purification by preparative reverse phase chromatography (DeltaPak C18, 15μ, 47 mm×300 mm, 70 mL/min: 80% H$_2$O/NH$_4$OAc: 20% CH$_3$CN to 100% CH$_3$CN over 60 min) afforded the pure trans title compound (1.2 g). MS 341.2 (M+1). $^1$H NMR (500 MHz, CDCl$_3$) δ 7.07-7.04 (m, 2H), 6.91-6.89 (m, 1H), 6.04 (br s, 1H), 5.93 (d, J=5.6 Hz, 1H), 4.46 (dd, J=10.5, 4.6 Hz, 1H), 3.65-3.59 (m, 1H), 3.21 (dd, J=15.1, 7.3 Hz, 1H), 3.05-3.00 (m, 1H), 2.25-2.20 (m, 1H), 2.17-2.10 (m, 2H), 1.79-1.71 (m, 1H), 1.46 (s, 9H).

Step G: tert-Butyl (3R,6S)-6-(2,3-difluorophenyl)-2-thioxoazepan-3-ylcarbamate

Lawesson's reagent [2,4-Bis(4-methoxyphenyl)-1,3-dithia-2,4-diphosphetane-2,4-disulfide] (2.90 g, 7.18 mmol) was added to a suspension of tert-butyl (3R,6S)-6-(2,3-difluorophenyl)-2-oxoazepan-3-ylcarbamate (4.79 g, 14.1 mmol) in toluene (250 mL) and the mixture was heated to 90° C. After 1 h, the reaction was allowed to cool to ambient temperature and concentrated. Purification by silica gel chromatography (100% dichloromethane→85% dichloromethane/ethyl acetate) gave a white solid. This solid was repurified by silica gel chromatography (20% ethyl acetate/hexanes→30% ethyl acetate/hexanes) to give the title compound (4.81 g). MS 357.0 (M+1). $^1$H NMR (500 MHz, CDCl$_3$) δ 8.30 (s, 1H), 7.10-7.04 (m, 2H), 6.94-6.91 (m, 1H), 6.50 (d, J=6.1 Hz, 1H), 4.62 (dd, J=10.3, 3.7 Hz, 1H), 4.13-

3.88 (m, 1H), 3.36 (dd, J=14.7, 7.1 Hz, 1H), 3.07 (t, J=11.2 Hz, 1H), 2.32-2.21 (m, 2H), 2.14-2.12 (m, 1H), 1.79-1.72 (m, 1H), 1.47 (s, 9H).

Alternatively, tert-Butyl (3R,6S)-6-(2,3-difluorophenyl)-2-oxoazepan-3-ylcarbamate (Step F of Intermediate 28 preparation) can be made in the following manner:

Step H. 1-Benzyl 5-methyl N,N-bis(tert-butoxycarbonyl)-D-glutamate

To a solution of Boc-D-Glu-OBn (50.0 g, 148.2 mmol) in DCM (400 ml) and MeOH (100 ml) was added trimethylsilyldiazomethane (88.9 mL of 2.0 M solution in hexanes, 117.8 mmol) at 0° C. dropwise via an addition funnel. After 60 min the reaction was concentrated. This residue was diluted with CH$_3$CN (400 mL) and (Boc)$_2$O (48.5 g, 222.3 mmol) was added followed by DMAP (18.1 g, 14.8 mmol). After 24 h the reaction was concentrated and purified by silica gel chromatography (10%→60% ethyl acetate/hexanes) to give the title compound (48.20 g, 72%). MS 252.2 (M+1−2Boc).

Step I. Benzyl (2R,5E)-2-[bis(tert-butoxycarbonyl)amino]-6-nitrohex-5-enoate To a −78° C. of 1-benzyl 5-methyl N,N-bis(tert-butoxycarbonyl)-D-glutamate (48.2 g, 106.8 mmol) in Et$_2$O (400 mL), was added DIBAL (133.4 mL of 1.0 M solution in toluene, 133.4 mmol) slowly so as not to let the internal temperature exceed −65° C. After 15 min, 20 mL more of DIBAL was added. After stirring for additional 20 min, water (300 mL) was added and the reaction was warmed to room temperature and stirred for 30 min. This mixture was further diluted with Et$_2$O and H$_2$O, the layers separated and the aqueous phase extracted with more Et$_2$O. The combined organics extracts were washed with a saturated aqueous solution of sodium potassium tartrate (2×), brine, dried over magnesium sulfate, filtered and concentrated to give benzyl N,N-bis(tert-butoxycarbonyl)-5-oxo-D-norvalinate (44.4 g) which was carried directly into the next step. MS 444.1 (M+Na). This material was dissolved in toluene (310 mL) and nitromethane (57.1 mL, 1.05 mol) and 1,1,3,3-tetramethylguanidine (1.3 mL, 10.5 mmol) were added at 0° C. After stirring for 30 min the nitroaldol reaction was complete, so methanesulfonyl chloride (12.2 mL, 158 mmol) was added followed triethylamine (22.0 mL, 158 mmol) at 0° C. and the reaction was allowed to warm to RT. After 1 h, 4 mL MsCl and 5.5 mL triethylamine were added. After stirring for an additional 30 min the mixture was diluted with Et$_2$O and NaHCO$_3$, the phases separated and the aqueous layer backwashed with another portion of Et$_2$O. The combined organics were dried over magnesium sulfate, filtered and concentrated to give a residue that was purified by silica gel chromatography (5%→50% ethyl acetate/hexanes) to give the title compound (34.3 g, 70%). MS 487.1 (M+Na).

Step J. Benzyl (5S)-N,N-bis(tert-butoxycarbonyl)-5-(2,3-difluorophenyl)-6-nitro-D-norleucinate A solution of benzyl (2R,5E)-2-[bis(tert-butoxycarbonyl)amino]-6-nitrohex-5-enoate (34.0 g, 73.2 mmol), 2,3-difluorophenylboronic acid (28.9 g, 183.0 mmol) and water (4.62 mL, 256.2 mmol) in dioxane (240 mL) was degassed with argon for 15 min. To this solution was added sodium bicarbonate (3.08 g, 36.6 mmol), (S)-BINAP (1.28 g, 2.05 mmol) and acetylacetanotobis(ethylene)rhodium(I) (0.472 g, 1.83 mmol). The mixture was stirred at RT for 2 min then heated to 35° C. After 4 h, 255 mg of (S)-BINAP and 94 mg of acetylacetanotobis(ethylene)rhodium(I) were added. After an additional 2 h the reaction was diluted with DCM/NaHCO$_3$, the layers separated and the aqueous phase was backwashed with another portion of DCM. The combined organics were dried over magnesium sulfate, filtered and concentrated to give a residue that was purified by silica gel chromatography (5%→60% ethyl acetate/hexanes) to give the title compound (37.0 g, 87%) contaminated with ~5% 5R isomer. MS 379.1 (M+1−2Boc).

Step K. (5S)-N$^2$,N$^2$-Bis(tert-butoxycarbonyl)-5-(2,3-difluorophenyl)-D-lysine A solution of benzyl (5S)-N,N-bis(tert-butoxycarbonyl)-5-(2,3-difluorophenyl)-6-nitro-D-norleucinate (15.5 g, 26.8 mmol) and 10% Pd/C (12.0 g) in EtOH (175 mL, SureSeal from Aldrich), was hydrogenated at 55 psi overnight. After 18 h, another 4 g of 10% Pd/C was added and the reaction hydrogenated at 55 psi for another 18 h. The reaction was filtered through Celite with more EtOH and concentrated to afford the title compound (12.0 g). MS 459.2 (M+1).

Step L. tert-Butyl (3R,6S)-6-(2,3-difluorophenyl)-2-oxoazepan-3-ylcarbamate

To a solution (5S)-N$^2$,N$^2$-bis(tert-butoxycarbonyl)-5-(2,3-difluorophenyl)-D-lysine (22.0 g, 48.0 mmol) in DCM (700 mL) were added EDC (11.0 g, 57.6 mmol) and HOAT (3.27 g, 24.0 mmol) followed by triethylamine (10.0 mL, 72.0 mmol). After 60 min, NaHCO$_3$ was added, the layers separated and the aqueous phase backwashed with DCM. The combined organics were dried over magnesium sulfate, filtered and concentrated. The residue was purified by silica gel chromatography (10% MeOH/DCM) to give the cyclized compound (18.0 g). A portion of this material (2.60 g, 5.90 mmol) was diluted DCM (60 mL) and TFA (1.20 mL, 11.8 mmol) was added. After 1 h, NaHCO$_3$ was added, the layers separated and the aqueous phase backwashed with DCM. The combined organics were dried over magnesium sulfate, filtered and concentrated and the residue purified by silica gel chromatography (5%→50% EtOAc/DCM) to give the title compound (1.14 g). MS 341.1 (M+1).

INTERMEDIATE 29

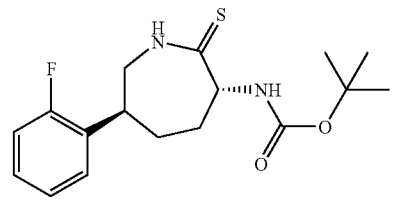

tert-Butyl [(3R,6S)-6-(2-fluorophenyl)-2-thioxoazepan-3-yl]carbamate

The title compound was prepared using a similar procedure to Intermediate 28. MS 339.2 (M+1).

INTERMEDIATE 30

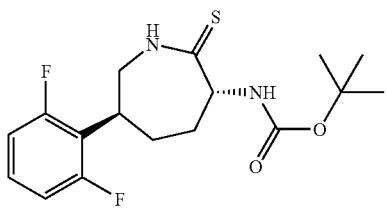

tert-Butyl [(3R,6S)-6-(2,6-difluorophenyl)-2-thioxoazepan-3-yl]carbamate

The title compound was prepared using a similar procedure to Intermediate 28. MS 357.1 (M+1).

INTERMEDIATE 31

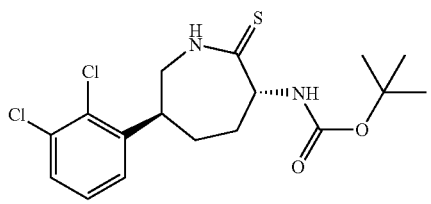

tert-Butyl [(3R,6S)-6-(2,3-dichlorophenyl)-2-thioxoazepan-3-yl]carbamate

The title compound was prepared using a similar procedure to Intermediate 28. MS 389.0 (M+1).

INTERMEDIATE 32

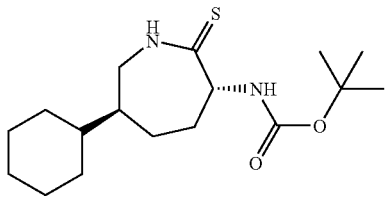

tert-Butyl [(3R,6S)-6-cyclohexyl-2-thioxoazepan-3-yl]carbamate

Step A: tert-Butyl [(3R,6S)-6-cyclohexyl-2-oxoazepan-3-yl]carbamate

Platinum oxide (300 mg, 1.32 mmol) was added to a solution of tert-butyl (3R,6S)-6-(2,3-difluorophenyl)-2-oxoazepan-3-ylcarbamate (463 mg, 1.36 mmol) in glacial acetic acid (15 mL) and the mixture hydrogenated under 50 psi hydrogen in a Parr apparatus. After 3 d, the mixture was concentrated. Saturated aqueous sodium bicarbonate was added, and the mixture was extracted with dichloromethane (3×). The combined organic extracts were washed with brine, dried with magnesium sulfate, filtered, and concentrated. Purification by silica gel chromatography (hexanes→55% ethyl acetate/hexanes) gave the title compound (210 mg). MS 311.2 (M+1).

Step B: tert-Butyl [(3R,6S)-6-cyclohexyl-2-thioxoazepan-3-yl]carbamate

Lawesson's reagent [2,4-Bis(4-methoxyphenyl)-1,3-dithia-2,4-diphosphetane-2,4-disulfide] (140 mg, 0.35 mmol) was added to a suspension of tert-butyl [(3R,6S)-6-cyclohexyl-2-oxoazepan-3-yl]carbamate (210 mg, 0.68 mmol) in toluene (8 mL) and the mixture was heated to 90° C. After 1 h, the reaction was allowed to cool to ambient temperature and concentrated. Purification by silica gel chromatography (100% dichloromethane→95% dichloromethane/ethyl acetate) gave the title compound (132 mg). MS 327.2 (M+1).

INTERMEDIATE 33

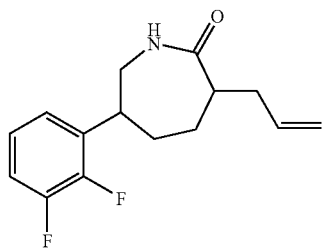

3-Allyl-6-(2,3-difluorophenyl)azepan-2-one

Step A: Ethyl 5-cyano-5-(2,3-difluorophenyl)pentanoate

Sodium hydride (60% dispersion in mineral oil; 2.9 g, 71.8 mmol) was slowly added to a solution of (2,3-difluorophenyl)acetonitrile (10.0 g, 65.3 mmol) and ethyl 4-bromobutanoate (12.7 g, 65.3 mmol) in N,N-dimethylformamide (100 mL) at 0° C. After 30 min, the reaction mixture was warmed to ambient temperature. After 3 h, water was added and the mixture was extracted with ethyl acetate (2×). The organic extracts were washed with saturated aqueous ammonium chloride, saturated brine, dried over magnesium sulfate, filtered and concentrated to give the title compound. MS 267.1 (M+1).

Step B: Ethyl 6-amino-5-(2,3-difluorophenyl)hexanoate

Raney-Nickel (2800, slurry in water; washed with ethyl alcohol (3×); 3.8 g) was added to a solution of ethyl 5-cyano-5-(2,3-difluorophenyl)pentanoate (4.75 g, 17.8 mmol) in ethanol (100 mL). Ammonia gas was bubbled to the reaction mixture and the mixture was stirred under hydrogen at 48 psi. After 18 h, the reaction was filtered and concentrated. MS 272.1 (M+1).

Step C: Ethyl 5-(2,3-difluorophenyl)-6-[(2,4-dimethoxybenzyl)amino]hexanoate 2,4-Dimethoxybenzaldehyde was added to a solution of ethyl 6-amino-5-(2,3-difluorophenyl)hexanoate (4.73 g, 17.5 mmol) in methanol (75 mL). Acetic acid was added until the pH of the reaction mixture reached pH 5. After 30 min, sodium cyanoborohydride (1.69 g, 26.9 mmol) was added. After 1 h, the mixture was diluted with ethyl acetate and saturated aqueous sodium carbonate. The mixture was extracted with ethyl acetate and the organic extracts were washed with water, saturated brine, dried over magnesium sulfate, filtered and concentrated. Purification by silica gel chromatography [100% dichloromethane→95% dichloromethane/(10% ammonium hydroxide/methanol)] gave the title compound (7.3 g). MS 422.1 (M+1).

Step D: 5-(2,3-Difluorophenyl)-6-[(2,4-dimethoxybenzyl)amino]hexanoic acid

Sodium hydroxide (1 N in water; 52 mL, 52.0 mmol) was added to a solution of ethyl 5-(2,3-difluorophenyl)-6-[(2,4-dimethoxybenzyl)amino]hexanoate (7.3 g, 17.3 mmol) in methanol (75 mL). After 1.5 h, the mixture was concentrated. The residue was azeotroped with toluene (3×) to give the sodium salt of the title compound. MS 394.1 (M+1).

Step E: 6-(2,3-Difluorophenyl)-1-(2,4-dimethoxybenzyl)azepan-2-one

N-(3-Dimethylaminopropyl)-N'-ethylcarbodiimide hydrochloride (3.65 g, 19.1 mmol) was added to a solution of the sodium salt of 5-(2,3-difluorophenyl)-6-[(2,4-dimethoxybenzyl)amino]hexanoic acid (8.58 g, 17.3 mmol) in acetonitrile (346 mL). After 2 h, hydrochloric acid (4.0 M in dioxane; 13.0 mL; 52.0 mmol) was added. After 16 h, additional N-(3-dimethylaminopropyl)-N'-ethylcarbodiimide hydrochloride (3.24 g, 16.9 mmol), 1-hydroxybenzotriazole hydrate (1.0 g, 6.53 mmol) and triethylamine (4.83 mL, 34.6 mmol) were added. After 16 h, the reaction mixture was concentrated. The mixture was diluted with saturated aqueous sodium bicarbonate and extracted with ethyl acetate. The organic extracts were washed with saturated brine, dried over magnesium sulfate, filtered and concentrated. Purification by silica gel chromatography (100% dichloromethane→96% dichloromethane/methanol) gave the title compound (4.72 g). MS 376.1 (M+1).

Step F: (3S,6S)-3-Allyl-6-(2,3-difluorophenyl)-1-(2,4-dimethoxybenzyl)azepan-2-one and (3R,6R)-3-allyl-6-(2,3-difluorophenyl)-1-(2,4-dimethoxybenzyl)azepan-2-one Lithium diisopropylamide (1.8 M in THF, heptane and ethyl benzene; 22.9 mL, 41.3 mmol) was added to a solution of 6-(2,3-difluorophenyl)-1-(2,4-dimethoxybenzyl)azepan-2-one (3.87 g, 10.3 mmol) in tetrahydrofuran (38 mL) at −78° C. After 1 h, 3-bromoprop-1-ene (3.57 mL, 41.3 mmol) was slowly added. After 1 h, the reaction mixture was quenched with saturated aqueous ammonium chloride. Saturated aqueous sodium bicarbonate was added and the mixture was extracted with ethyl acetate. The organic extracts were washed with saturated brine, dried over magnesium sulfate, filtered and concentrated. Purification by silica gel chromatography (100% hexanes→70% hexanes/ethyl acetate) gave the title compounds (350 mg). MS 416.1 (M+1).

Step G: 3-Allyl-6-(2,3-difluorophenyl)azepan-2-one

Trifluoroacetic acid (35 mL) was added to a solution of (3S,6S)-3-allyl-6-(2,3-difluorophenyl)-1-(2,4-dimethoxybenzyl)azepan-2-one and (3R,6R)-3-allyl-6-(2,3-difluorophenyl)-1-(2,4-dimethoxybenzyl)azepan-2-one (3.39 g, 8.15 mol) in dichloromethane (25 mL). After 2.5 h, the reaction mixture was concentrated. Saturated aqueous sodium bicarbonate was added and the mixture was extracted with ethyl acetate (3×). The organic extracts were washed with saturated brine, dried over magnesium sulfate, filtered and concentrated to give the title compound. Purification by silica gel chromatography (98.5% dichloromethane/methanol→97% dichloromethane/methanol) gave the mixture of racemic trans compounds (3S,6S)-3-allyl-6-(2,3-difluorophenyl)azepan-2-one and (3R,6R)-3-allyl-6-(2,3-difluorophenyl)azepan-2-one and racemic cis compounds (3S,6R)-3-allyl-6-(2,3-difluorophenyl)azepan-2-one and (3R,6S)-3-allyl-6-(2,3-difluorophenyl)azepan-2-one. MS 266.1 (M+1).

INTERMEDIATE 34

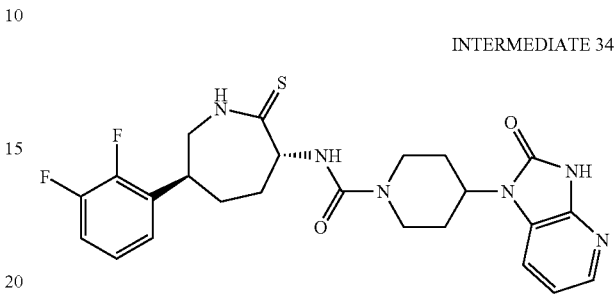

N-[(3R,6S)-6-(2,3-Difluorophenyl)-2-thioxoazepan-3-yl]-4-(2-oxo-2,3-dihydro-1H-imidazo[4,5-b]pyridin-1-yl)piperidine-1-carboxamide Step A: (3R,6S)-3-Amino-6-(2,3-difluorophenyl)azepane-2-thione Trifluoroacetic acid (5 mL, 49.6 mmol) was added to a solution of tert-butyl (3R,6S)-6-(2,3-difluorophenyl)-2-thioxoazepan-3-ylcarbamate (680 mg, 1.91 mmol) in dichloromethane (10 mL). After 1 h, the reaction was concentrated. Saturated aqueous sodium bicarbonate was added and the mixture was extracted with dichloromethane (3×). The combined organic extracts were dried over magnesium sulfate, filtered, and concentrated to give the title compound (489 g). MS 257.0 (M+1).

Step B: N-[(3R,6S)-6-(2,3-Difluorophenyl)-2-thioxoazepan-3-yl]-4-(2-oxo-2,3-dihydro-1H-imidazo[4,5-b]pyridin-1-yl)piperidine-1-carboxamide Triethylamine (0.45 mL, 3.25 mmol) was added to a solution of tert-butyl (3R,6S)-6-(2,3-difluorophenyl)-2-thioxoazepan-3-ylcarbamate (416 mg, 1.62 mmol) and 4-(2-oxo-2,3-dihydro-1H-imidazo[4,5-b]pyridin-1-yl)piperidine-1-carbonyl chloride (466 mg, 1.66 mmol) in dichloromethane (70 mL) and the mixture heated to reflux. After 18 h, the mixture was allowed to cool to ambient temperature and concentrated. Purification by silica gel chromatography (100% dichloromethane→95% dichloromethane/methanol) gave the title compound (685 mg). MS 501.0 (M+1).

INTERMEDIATE 35

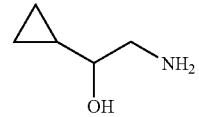

2-Amino-1-cyclopropylethanol

A solution of trimethylsilyl cyanide (8.68 mL, 65.1 mmol) and zinc (II) iodide (10 mg, 0.05 mmol) in dichloromethane (5 mL) was added dropwise to a solution of cyclopropanecarboxaldehyde (4.05 mL, 54.2 mmol) in dichloromethane (30 mL) at 0° C. After the addition was complete, the mixture was allowed to warm to ambient temperature. After 1.5 h, the mixture was concentrated. Lithium aluminum hydride (1.0 M in ether; 65.1 mL, 65.1 mmol) was added dropwise to a solution of crude cyclopropyl(hydroxy)acetonitrile in ether (40 mL) at 0° C. After the addition was complete, the mixture was warmed to ambient temperature. After 1 h, the mixture was treated sequentially with water (2.5 mL), 15% sodium hydroxide solution (2.5 mL), and water (7.5 mL). The solid was filtered and washed with dichloromethane (3×) and the filtrate concentrated to give the title compound (0.79 g). $^1$H NMR (500 MHz, CDCl$_3$) δ 2.95 (dd, J=12.5, 9.0 Hz, 1H), 2.85-2.81 (m, 1H), 2.73-2.69 (m, 1H), 1.66 (br s, 2H), 0.88-0.81 (m, 1H), 0.56-0.47 (m, 1H), 0.37-0.33 (m, 1H), 0.24-0.20 (m, 1H).

Essentially following the procedure outlined for the preparation of Intermediate 35, the Intermediates in Table 1 were prepared.

TABLE 1

| Intermediate | R | MS (M + 1) |
|---|---|---|
| 36 | isopropyl | 104 |
| 37 | thiazolyl | 145.0 |
| 38 | tetrahydrofuranyl | 132.1 |
| 39 | cyclopropylmethyl | 116.0 |
| 40 | CF$_3$-alkyl | 158.0 |
| 41 | methoxy-dimethyl | 134.1 |

TABLE 1-continued

| Intermediate | R | MS (M + 1) |
|---|---|---|
| 42 | 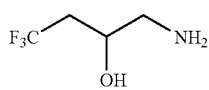 | 170.1 |
| 43 | sec-butyl | 118.0 |

INTERMEDIATE 44

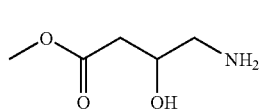

4,4,4-Trifluoro-2-hydroxybutan-1-aminium chloride 2-(2,2,2-Trifluoroethyl)oxirane (5.27 g, 41.8 mmol) was added to a solution of ammonia (2 M in methanol; 170 mL, 340 mmol) and the solution heated to 60° C. After 1.25 h, the mixture was allowed to cool to ambient temperature and concentrated to a volume of 20 mL. HCl (4 M in dioxane; 12 mL, 48 mmol) was added slowly and the mixture concentrated to give a white solid (4.0 g) that was 85% pure and contained 15% of a dimeric byproduct. MS 144.1 (M+H). $^1$H NMR (500 MHz, CD$_3$OD) δ 4.17-4.12 (m, 1H), 3.10 (dd, J=12.9, 2.9 Hz, 1H), 2.89 (dd, J=12.7, 9.8 Hz, 1H), 2.50, 2.35 (m, 2H).

INTERMEDIATE 45 methyl ester structure

2-Hydroxy-4-methoxy-4-oxobutan-1-aminium chloride

Anhydrous hydrochloric acid gas was bubbled into a suspension of 4-amino-3-hydroxybutanoic acid (0.91 g, 7.61 mmol) in methanol (150 mL) until the solution was saturated and stirred at ambient temperature. After 18 h, the solution was concentrated to give the title compound (1.32 g). MS 134 (M+1).

INTERMEDIATE 46

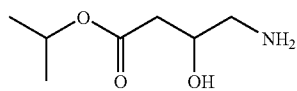

2-Hydroxy-4-isopropoxy-4-oxobutan-1-aminium chloride

Hydrochloric acid (4.0 M in dioxane; 0.4 mL, 1.6 mmol) was added to a solution of methyl 4-amino-3-hydroxybutanoate (2.8 g, 21.03 mmol) in isopropyl alcohol (50 mL) and the mixture heated to reflux. After 18 h, additional hydrochloric acid (4.0 M in dioxane, 0.4 mL, 1.6 mmol) was added. After 40 h, the reaction mixture was concentrated. MS 162.1 (M+1).

INTERMEDIATE 47

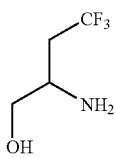

2-Amino-4,4,4-trifluorobutane-1-ol

Step A: 1-Ethoxy-4,4,4-trifluoro-1-oxobutan-2-aminium chloride

2-Amino-4,4,4-trifluorobutanoic acid (11.7 g, 52.8 mmol) was added to a saturated solution of HCl in ethanol (100 mL) and heated to 85° C. After 4 h, the mixture was allowed to cool to ambient temperature and concentrated. MS 186.0 (M+1).

Step B: 2-Amino-4,4,4-trifluorobutane-1-ol

Lithium aluminum hydride (1 M in ether; 2.32 mL, 2.32 mmol) was added to 1-ethoxy-4,4,4-trifluoro-1-oxobutan-2-aminium chloride (205 mg, 0.928 mmol) in ether (15 mL). After 1.5 h, the mixture was treated sequentially with water (0.085 mL), 15% sodium hydroxide (0.085 mL), water (0.255 mL), then filtered through celite and concentrated to give the title compound. MS 144.0 (M+1).

INTERMEDIATE 48

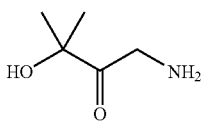

1-Amino-3-hydroxy-3-methylbutane-2-one

Step A. Di-tert-butyl (3-methylbut-2-en-1-yl)imidodicarbonate

Potassium tert-butoxide (52 mg, 0.46 mmol) was added to a solution of di-tert-butyl imidodicarbonate (100 mg, 0.46 mmol) in tetrahydrofuran (1 mL). After 5 min, 1-bromo-3-methylbut-2-ene (54 µL, 0.46 mmol) was added. After 3 h, saturated aqueous sodium bicarbonate was added and the mixture was extracted with ethyl acetate (3×). The combined organic extracts were washed with saturated brine, dried over magnesium sulfate, filtered and concentrated. MS 286.2 (M+1).

Step B. Di-tert-butyl (3-hydroxy-3-methyl-2-oxobutyl)imidodicarbonate

Potassium permanganate (114 mg, 0.72 mmol) was added to a solution of di-tert-butyl (3-methylbut-2-en-1-yl)imidodicarbonate (115 mg, 0.40 mmol) in acetone (0.8 mL), water (0.2 mL), and glacial acetic acid (20 µL). After 4 h, the reaction was quenched with saturated aqueous sodium sulfite. The mixture was adjusted to pH 5 with aqueous hydrochloric acid and extracted with ethyl acetate (3×). The combined organic extracts were washed with saturated aqueous sodium bicarbonate, saturated brine, dried over magnesium sulfate, filtered and concentrated. MS 340.1 (M+Na).

Step C. 1-Amino-3-hydroxy-3-methylbutane-2-one

Hydrochloric acid (4 M in dioxane; 1.0 mL, 4.0 mmol) was added to a solution of di-tert-butyl (3-hydroxy-3-methyl-2-oxobutyl)imidodicarbonate (102 mg, 0.32 mmol) in methanol (3 mL) at 0° C. and the mixture was allowed to warm to ambient temperature. After 2.5 h, the reaction mixture was concentrated to give the hydrochloride salt of the title compound. MS 118.0 (M+1).

INTERMEDIATE 49

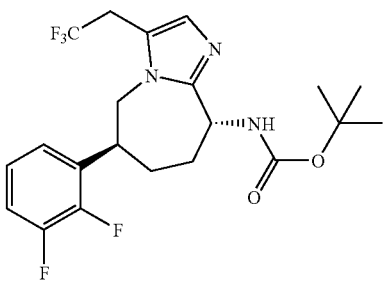

tert-Butyl [(6S,9R)-6-(2,3-difluorophenyl)-3-(2,2,2-trifluoroethyl)-6,7,8,9-tetrahydro-5H-imidazo[1,2-a]azepin-9-yl]carbamate Step A: tert-Butyl {(3R,6S)-6-(2,3-difluorophenyl-2-[(4,4,4-trifluoro-2-hydroxybutyl)imino]azepan-3-yl}carbamate Mercury(II) chloride (2.48 g, 9.12 mmol) was added to a solution of tert-butyl [(3R,6S)-6-(2,3-difluorophenyl)-2-thioxoazepan-3-yl]carbamate (2.50 g, 7.01 mmol), 4,4,4-trifluoro-2-hydroxybutan-1-aminium chloride (4.62 g, 25.7 mmol), and triethylamine (4.40 mL, 31.6 mmol) in ethanol (70 mL) at 60° C. After 1 h, the reaction was allowed to cool to ambient temperature. The mixture was filtered and concentrated. Saturated aqueous-sodium bicarbonate was added and the mixture was extracted with dichloromethane (3×). The combined organic extracts were dried over magnesium sulfate, filtered, and concentrated to give the title compound (3.45 g). MS 466.2 (M+1).

Step B: tert-Butyl [(6S,9R)-6-(2,3-difluorophenyl)-3-(2,2,2-trifluoroethyl)-6,7,8,9-tetrahydro-5H-imidazo[1,2-a]azepin-9-yl]carbamate Pyridinium dichromate (7.92 g, 21.0 mmol) was added to a solution of crude tert-butyl {(3R,6S)-6-(2,3-difluorophenyl)-2-[(4,4,4-trifluoro-2-hydroxybutyl)imino]azepan-3-yl}carbamate (3.27 g, 7.01 mmol) in acetonitrile (70 mL). After 70 h, the mixture was filtered and concentrated. Saturated aqueous sodium bicarbonate was added and the mixture was extracted with dichloromethane (3×). The combined organic extracts were dried over magnesium sulfate, filtered, and concentrated. Purification by silica gel chromatography (100% dichloromethane→96% dichloromethane/methanol) gave the title compound (2.35 g). MS 446.1 (M+1). ¹H NMR (500 MHz, CDCl₃) δ 7.14-7.09 (m, 1H), 6.97-6.94 (m, 2H), 6.33 (d, J=5.8 Hz, 1H), 4.82 (dd, J=10.0, 3.9 Hz, 1H), 4.12-4.07 (m, 1H), 3.99 (d, J=14.6 Hz, 1H), 3.37 (q, J=20.0, 10.0 Hz, 2H), 2.94 (t, J=110.2 Hz, 1H), 2.44 (d, J=13.7 Hz, 1H), 2.34-2.26 (m, 1H), 2.16-2.13 (m, 1H), 1.63-1.60 (m, 1H), 1.57 (s, 9H).

Essentially following the procedure outlined for the preparation of Intermediate 49, the Intermediates in Table 2 were prepared. In some cases the appropriate amino alcohols used in the coupling with Intermediate 28 were commercially available.

TABLE 2

| Intermediate | R¹ | R² | MS (M + 1) |
|---|---|---|---|
| 50 | CH₃ | H | 378.2 |
| 51 | cyclopropyl-C(CH₃) | H | 404.2 |
| 52 | H | -C(CH₃)-CH₂-O-benzyl | 484.1 |
| 53 | methyl ester -CH₂-C(=O)-O-CH₃ with C(CH₃) | H | 436.1 |
| 54 | isopropyl ester | H | 464.2 |
| 55 | thiazol-2-yl-C(CH₃) | H | 447.1 |
| 56 | tetrahydrofuran-3-yl-C(CH₃) | H | 434.2 |
| 57 | isobutyl | H | 392.1 |

TABLE 2-continued

| Intermediate | R¹ | R² | MS (M + 1) |
|---|---|---|---|
| 58 | methoxy-dimethyl-methyl (CH₃O-C(CH₃)₂-) | H | 436.2 |
| 59 | CF₃CH₂CH₂- | H | 460.2 |
| 60 | cyclopropyl-C(CH₃)₂- | H | 418.2 |
| 61 | (1-CF₃-cyclopropyl)-C(CH₃)- | H | 472.2 |
| 62 | sec-butyl-methyl | H | 420.2 |
| 63 | CH₃OCH₂O-C(CH₃)₂- | H | 466.2 |
| 64 | (2-methyltetrahydrofuran-2-yl) | H | 448.2 |

INTERMEDIATE 65

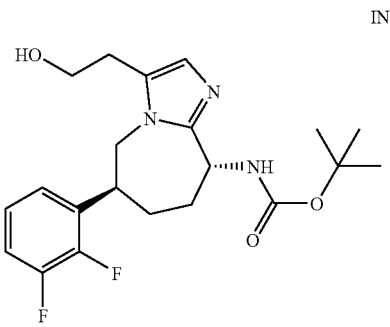

tert-Butyl (6S,9R)-6-(2,3-difluorophenyl)-3-(2-hydroxyethyl)-6,7,8,9-tetrahydro-5H-imidazo[1,2-a]azepin-9-ylcarbamate Diisobutylaluminum hydride (1.0 M in hexanes; 3.77 mL, 3.77 mmol) was added to a solution of methyl [(6S,9R)-9-[(tert-butoxycarbonyl)amino]-6-(2,3-difluorophenyl)-6,7,8,9-tetrahydro-5H-imidazo[1,2-a]azepin-3-yl]acetate (328 mg, 0.75 mmol) in dichloromethane (12 mL) at 0° C. After 1 h, saturated aqueous potassium sodium tartrate was added, and the mixture was extracted with ethyl acetate. The organic layer was washed with brine, dried over magnesium sulfate, filtered and concentrated. Purification by silica gel chromatography (100% dichloromethane→94% dichloromethane/methanol) gave the title compound (218 mg). MS 408.1 (M+1).

INTERMEDIATE 66

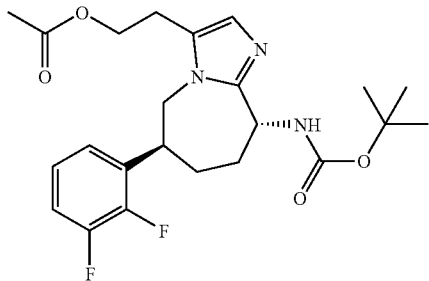

2-[(6S,9R)-9-[(tert-Butoxycarbonyl)amino]-6-(2,3-difluorophenyl)-6,7,8,9-tetrahydro-5H-imidazo[1,2-a]azepin-3-yl]ethyl acetate Acetyl chloride (24 µL, 0.344 mmol) was added to a solution of tert-butyl (6S,9R)-6-(2,3-difluorophenyl)-3-(2-hydroxyethyl)-6,7,8,9-tetrahydro-5H-imidazo[1,2-a]azepin-9-ylcarbamate (70 mg, 0.172 mmol) and triethylamine (48 µL, 0.344 mmol) in dichloromethane (6 mL) at 0° C. After 1.5 h, saturated aqueous sodium bicarbonate was added and the mixture was extracted with dichloromethane (2×). The combined organic extracts were dried over magnesium sulfate, filtered, and concentrated. Purification by silica gel chromatography (100% dichloromethane→95% dichloromethane/methanol) gave the title compound (64 mg). MS 450.2 (M+1).

INTERMEDIATE 67

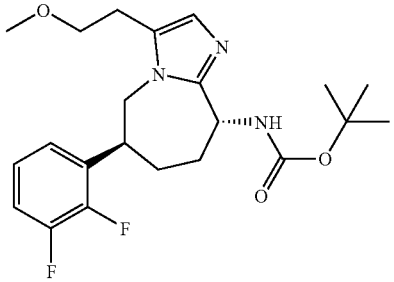

tert-Butyl (6S,9R)-6-(2,3-difluorophenyl)-3-(2-methoxyethyl)-6,7,8,9-tetrahydro-5H-imidazo[1,2-a]azepin-9-ylcarbamate Sodium hydride (60% dispersion in mineral oil; 4.0 mg, 0.112 mmol) was added to a solution of tert-butyl (6S,9R)-6-(2,3-difluorophenyl)-3-(2-hydroxyethyl)-6,7,8,9-tetrahydro-5H-imidazo[1,2-a]azepin-9-ylcarbamate (19 mg, 0.047 mmol) and iodomethane (3.0 µL, 0.051 mmol) in tetrahydrofuran (0.5 mL) at 0° C., and the mixture was allowed to warm to ambient temperature. After 18 h, additional sodium hydride (2.0 mg, 0.056 mmol) and iodomethane (3.0 µL, 0.051 mmol) were added. After 1 h, the reaction was quenched with water. Saturated aqueous sodium bicarbonate was added and the mixture was extracted with dichloromethane (2×). The combined organic extracts were dried over magnesium sulfate, filtered, and concentrated. Purification by silica gel chromatography (100% dichloromethane→94% dichloromethane/methanol) gave the title compound (6 mg). MS 422.1 (M+1).

INTERMEDIATE 68

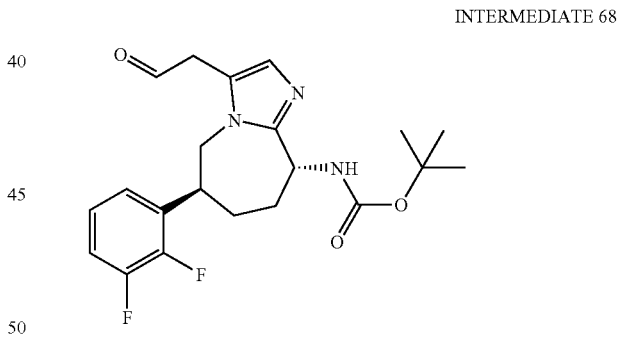

tert-Butyl (6S,9R)-6-(2,3-difluorophenyl)-3-(2-oxoethyl)-6,7,8,9-tetrahydro-5H-imidazo[1,2-a]azepin-9-ylcarbamate Diisobutylaluminum hydride (1.0 M in dichloromethane; 0.81 mL, 0.807 mmol) was added to a solution of isopropyl [(6S,9R)-9-[(tert-butoxycarbonyl)amino]-6-(2,3-difluorophenyl)-6,7,8,9-tetrahydro-5H-imidazo[1,2-a]azepin-3-yl]acetate (187 mg, 0.403 mmol) in dichloromethane (10 mL) at −78° C. After 1 h, an additional amount of diisobutylaluminum hydride (0.81 mL, 0.807 mmol) was added. After 2.5 h, saturated aqueous potassium sodium tartrate was added, and the mixture was extracted with ethyl acetate. The organic layer was washed with saturated sodium bicarbonate solution, brine, dried over magnesium sulfate, filtered and concentrated. Purification by silica gel chromatography (100% dichloromethane→95% dichloromethane/methanol) gave the title compound (120 mg). MS 406.2 (M+1).

INTERMEDIATE 69

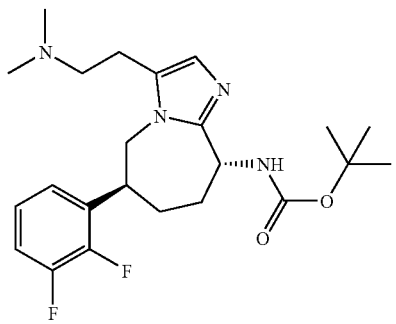

tert-Butyl (6S,9R)-6-(2,3-difluorophenyl)-3-[2-(dimethylamino)ethyl]-6,7,8,9-tetrahydro-5H-imidazo[1,2-a]azepin-9-ylcarbamate Sodium cyanoborohydride (12 mg, 0.185 mmol) was added to a solution of tert-butyl (6S,9R)-6-(2,3-difluorophenyl)-3-(2-oxoethyl)-6,7,8,9-tetrahydro-5H-imidazo[1,2-a]azepin-9-ylcarbamate (50 mg, 0.123 mmol) and dimethylamine (2.0 M in tetrahydrofuran; 0.185 mL, 0.370 mmol) in methanol (5 mL) adjusted to pH 5 with acetic acid. After 2 h, the solution was concentrated. Purification by silica gel chromatography (100% dichloromethane→92% dichloromethane/methanol) gave the title compound (45 mg). MS 435.2 (M+1).

INTERMEDIATE 70

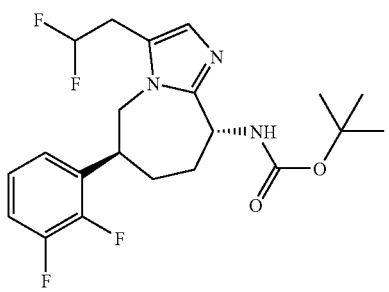

tert-Butyl (6S,9R)-3-(2,2-difluoroethyl)-6-(2,3-difluorophenyl)-6,7,8,9-tetrahydro-5H-imidazo[1,2-a]azepin-9-ylcarbamate (Diethylamino)sulfur trifluoride (92 μL, 0.696 mmol) was added to a solution of tert-butyl (6S,9R)-6-(2,3-difluorophenyl)-3-(2-oxoethyl)-6,7,8,9-tetrahydro-5H-imidazo[1,2-a]azepin-9-ylcarbamate (94 mg, 0.232 mmol) in dichloromethane (10 mL) at 0° C. After 2 h, saturated aqueous sodium bicarbonate was added and the mixture was extracted with dichloromethane (2×). The combined organic extracts were dried over sodium sulfate, filtered, and concentrated. Purification by silica gel chromatography (100% dichloromethane→95% dichloromethane/methanol) gave the title compound (67 mg). MS 428.2 (M+1).

INTERMEDIATE 71

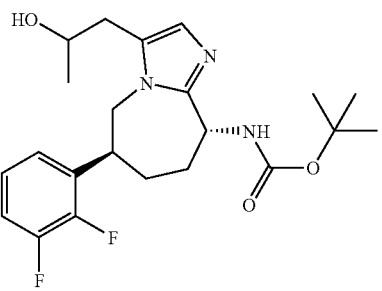

tert-Butyl (6S,9R)-6-(2,3-difluorophenyl)-3-(2-hydroxypropyl)-6,7,8,9-tetrahydro-5H-imidazo[1,2-a]azepin-9-ylcarbamate Methylmagnesium bromide (3.0 M in ether; 0.70 mL, 2.10 mmol) was added to a solution of tert-butyl (6S,9R)-6-(2,3-difluorophenyl)-3-(2-oxoethyl)-6,7,8,9-tetrahydro-5H-imidazo[1,2-a]azepin-9-ylcarbamate (85 mg, 0.210 mmol) in tetrahydrofuran (5 mL). After 2 h, the reaction was quenched with saturated aqueous ammonium chloride. Saturated aqueous sodium bicarbonate was added and the mixture was extracted with dichloromethane (3×). The combined organic extracts were dried over sodium sulfate, filtered, and concentrated. Purification by silica gel chromatography (100% dichloromethane→95% dichloromethane/methanol) gave the title compound (73 mg). MS 422.2 (M+1).

INTERMEDIATE 72

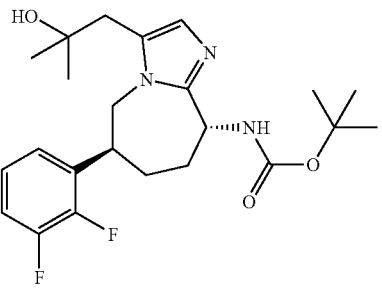

tert-Butyl (6S,9R)-6-(2,3-difluorophenyl)-3-(2-hydroxy-2-methylpropyl)-6,7,8,9-tetrahydro-5H-imidazo[1,2-a]azepin-9-ylcarbamate Step A: tert-Butyl (6S,9R)-6-(2,3-difluorophenyl)-3-(2-oxopropyl)-6,7,8,9-tetrahydro-5H-imidazo[1,2-a]azepin-9-ylcarbamate Dess-Martin reagent [1,1,1-Tris(acetyloxy)-1,1-dihydro-1,2-benziodoxol-3-(1H)-one] (257 mg, 0.605 mmol) was added to a solution of tert-butyl (6S,9R)-6-(2,3-difluorophenyl)-3-(2-hydroxypropyl)-6,7,8,9-tetrahydro-5H-imidazo[1,2-a]azepin-9-ylcarbamate (85 mg, 0.202 mmol) in dichloromethane (5 mL) at 0° C., and the mixture was allowed to warm to ambient temperature. After 4 h, the reaction was quenched with saturated aqueous sodium sulfite. Saturated aqueous sodium bicarbonate was added and the mixture was extracted with dichloromethane (3×). The combined organic extracts were dried over sodium sulfate, filtered, and concentrated. Purification by silica gel chromatography [100% dichloromethane→95% dichloromethane/5% (10% ammonium hydroxide/methanol)] gave the title compound (19 mg). MS 420.2 (M+1).

Step B: tert-Butyl (6S,9R)-6-(2,3-difluorophenyl)-3-(2-hydroxy-2-methylpropyl)-6,7,8,9-tetrahydro-5H-imidazo[1,2-a]azepin-9-ylcarbamate Methylmagnesium bromide (3.0 M in ether; 0.49 mL, 1.45 mmol) was added to a solution of tert-butyl (6S,9R)-6-(2,3-difluorophenyl)-3-(2-oxopropyl)-6,7,8,9-tetrahydro-5H-imidazo[1,2-a]azepin-9-ylcarbamate (61 mg, 0.145 mmol) in tetrahydrofuran (5 mL). After 2 h, the reaction was quenched with saturated aqueous ammonium chloride. Saturated aqueous sodium bicarbonate was added and the mixture was extracted with dichloromethane (3×). The combined organic extracts were dried over sodium sulfate, filtered, and concentrated. Purification by silica gel chromatography (100% dichloromethane→96% dichloromethane/methanol) gave the title compound (36 mg). MS 436.2 (M+1).

INTERMEDIATE 73

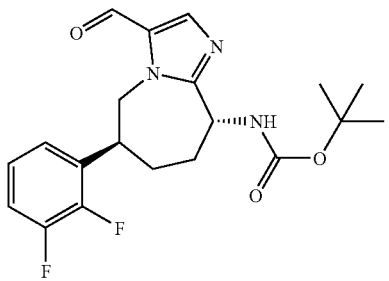

tert-Butyl (6S,9R)-6-(2,3-difluorophenyl)-3-formyl-6,7,8,9-tetrahydro-5H-imidazo[1,2-a]azepin-9-ylcarbamate Selenium dioxide (1.73 g, 15.63 mmol) was added to a solution of tert-butyl (6S,9R)-6-(2,3-difluorophenyl)-3-methyl-6,7,8,9-tetrahydro-5H-imidazo[1,2-a]azepin-9-ylcarbamate (2.95 g, 7.82 mmol) in dioxane (200 mL) and the mixture heated to reflux. After 8 h, the reaction mixture was filtered and concentrated. Purification by silica gel chromatography (100% dichloromethane→40% ethyl acetate/dichloromethane) gave the title compound (2.56 g). MS 392.2 (M+1). $^1$H NMR (500 MHz, CDCl$_3$) δ 9.69 (s, 1H), 7.68 (s, 1H), 7.13-7.06 (m, 2H), 6.96-6.93 (m, 1H), 6.26 (d, J=6.1 Hz, 1H), 5.56 (d, J=14.2 Hz, 1H), 4.91 (dd, J=9.8, 6.6 Hz, 1H), 4.13-4.08 (m, 1H), 3.02 (t, J=11.2 Hz, 1H), 2.43 (d, J=13.4 Hz, 1H), 2.28 (dd, J=24.5, 12.1 Hz, 1H), 2.18-1.16 (m, 1H), 1.50 (s, 9H).

INTERMEDIATE 74

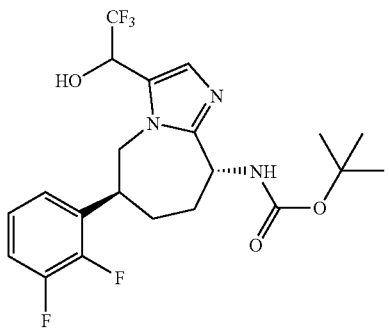

tert-Butyl (6S,9R)-6-(2,3-difluorophenyl)-3-(2,2,2-trifluoro-1-hydroxyethyl)-6,7,8,9-tetrahydro-5H-imidazo[1,2-a]azepin-9-ylcarbamate (Trifluoromethyl)trimethylsilane (0.5 M in tetrahydrofuran; 2.15 mL, 1.07 mmol) and tetrabutylammonium fluoride (1.0 M in tetrahydrofuran; 0.107 mL, 0.107 mmol) were sequentially added to neat tert-butyl (6S,9R)-6-(2,3-difluorophenyl)-3-formyl-6,7,8,9-tetrahydro-5H-imidazo[1,2-a]azepin-9-ylcarbamate (0.14 g, 0.36 mmol). After 15 min, the reaction mixture was quenched with saturated sodium bicarbonate. The mixture was extracted with dichloromethane (3×), and the combined organic extracts were washed with water, saturated brine, dried over sodium sulfate, filtered and concentrated. Purification by reverse phase HPLC (C-18, 95% water/acetonitrile→5% water/acetonitrile with 0.1% trifluoroacetic acid) gave the title compound (110 mg). MS 462.1 (M+1).

INTERMEDIATE 75

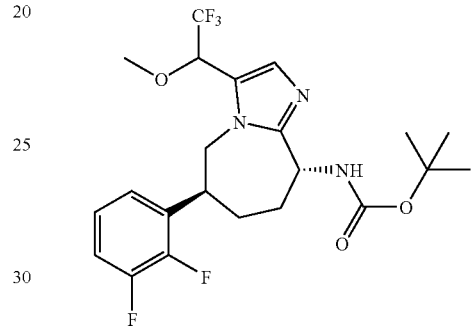

tert-Butyl (6S,9R)-6-(2,3-difluorophenyl)-3-(2,2,2-trifluoro-1-methoxyethyl)-6,7,8,9-tetrahydro-5H-imidazo[1,2-a]azepin-9-ylcarbamate Sodium hydride (60% dispersion in mineral oil; 88.3 mg, 2.21 mmol) was added to a solution of tert-butyl (6S,9R)-6-(2,3-difluorophenyl)-3-(2,2,2-trifluoro-1-hydroxyethyl)-6,7,8,9-tetrahydro-5H-imidazo[1,2-a]azepin-9-ylcarbamate (0.68 g, 1.47 mmol) and iodomethane (92.0 μL, 1.47 mmol) in tetrahydrofuran (20 mL) at 0° C. After 2 h, the mixture was allowed to warm to ambient temperature. After 2 h, additional iodomethane (92.0 μL, 1.47 mmol) and sodium hydride (60% dispersion in mineral oil; 10.0 mg, 0.27 mmol) were added. After 1 h, the reaction was quenched with water and the mixture was extracted with dichloromethane (3×). The organic layer was washed with water, saturated brine, dried over magnesium sulfate, filtered and concentrated. Purification by silica gel chromatography (100% dichloromethane→30% ethyl acetate/dichloromethane) gave the title compound (195 mg). MS 476.2 (M+1).

INTERMEDIATE 76

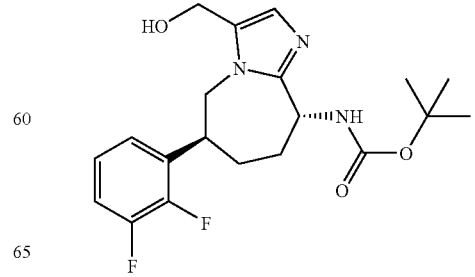

101 tert-Butyl (6S,9R)-6-(2,3-difluorophenyl)-3-hydroxymethyl)-6,7,8,9-tetrahydro-5H-imidazo[1,2-a]azepin-9-ylcarbamate Sodium borohydride (19.0 mg, 0.51 mmol) was added to a solution of tert-butyl (6S,9R)-6-(2,3-difluorophenyl)-3-formyl-6,7,8,9-tetrahydro-5H-imidazo[1,2-a]azepin-9-ylcarbamate (100 mg, 0.26 mmol) in tetrahydrofuran (3 mL). After 2 h, the reaction mixture was quenched with saturated sodium bicarbonate. The mixture was extracted with dichloromethane (3×), and the combined organic extracts were washed with water, saturated brine, dried over sodium sulfate, filtered and concentrated. MS 394.2 (M+1).

INTERMEDIATE 77

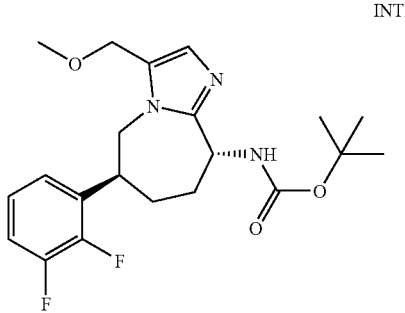

tert-Butyl (6S,9R)-6-(2,3-difluorophenyl)-3-(methoxymethyl)-6,7,8,9-tetrahydro-5H-imidazo[1,2-a]azepin-9-ylcarbamate Sodium hydride (60% dispersion in mineral oil; 25.0 mg, 0.61 mmol) was added to a solution of tert-butyl (6S,9R)-6-(2,3-difluorophenyl)-3-(hydroxymethyl)-6,7,8,9-tetrahydro-5H-imidazo[1,2-a]azepin-9-ylcarbamate (160 mg, 0.41 mmol) and iodomethane (51.0 μL, 0.81 mmol) in tetrahydrofuran (2 mL) at 0° C. After 3 h, the reaction was quenched with water and the mixture was extracted with dichloromethane (3×). The organic layer was washed with water, saturated brine, dried over magnesium sulfate, filtered and concentrated. Purification by reverse phase HPLC (C-18, 95% water/acetonitrile→5% water/acetonitrile with 0.1% trifluoroacetic acid) gave the title compound (75 mg). MS 408.2 (M+1).

INTERMEDIATE 78

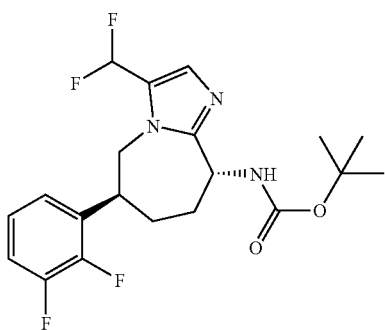

102 tert-Butyl (6S,9R)-3-(difluoromethyl)-6-(2,3-difluorophenyl)-6,7,8,9-tetrahydro-5H-imidazo[1,2-a]azepin-9-ylcarbamate (Diethylamino)sulfur trifluoride (14 μL, 0.10 mmol) was added to a solution of tert-butyl (6S,9R)-6-(2,3-difluorophenyl)-3-formyl-6,7,8,9-tetrahydro-5H-imidazo[1,2-a]azepin-9-ylcarbamate (20 mg, 0.05 mmol) in dichloromethane (1 mL) at 0° C. After 1 h, additional (diethylamino)sulfur trifluoride (14 μL, 0.10 mmol) was added. After 16 h, the reaction mixture was quenched with saturated sodium bicarbonate. The mixture was extracted with dichloromethane (3×), and the combined organic extracts were washed with water, saturated brine, dried over sodium sulfate, filtered and concentrated. Purification by silica gel chromatography (100% dichloromethane→7% methanol/dichloromethane) gave the title compound (18 mg). MS 414.1 (M+1).

INTERMEDIATE 79

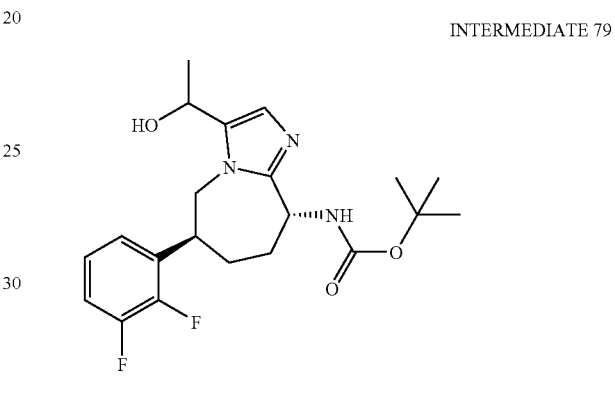

tert-Butyl (6S,9R)-6-(2,3-difluorophenyl)-3-(1-hydroxyethyl)-6,7,8,9-tetrahydro-5H-imidazo[1,2-a]azepin-9-ylcarbamate Methylmagnesium bromide (3.0 M in ether; 0.33 mL, 1.0 mmol) was added to a solution of tert-butyl (6S,9R)-6-(2,3-difluorophenyl)-3-formyl-6,7,8,9-tetrahydro-5H-imidazo[1,2-a]azepin-9-ylcarbamate (130 mg, 0.33 mmol) in tetrahydrofuran (3 mL) at 0° C. After 10 min, the reaction was quenched with water and the mixture was extracted with dichloromethane (3×). The organic layer was washed with water, saturated brine, dried over magnesium sulfate, filtered and concentrated. MS 408.1 (M+1).

INTERMEDIATE 80

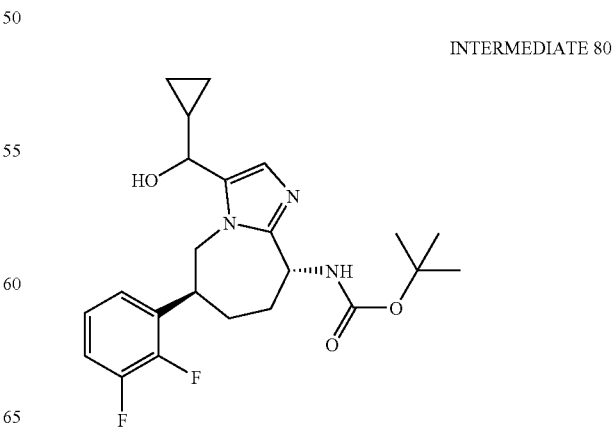

103 tert-Butyl (6S,9R)-3-[cyclopropyl(hydroxy)methyl]-6-(2,3-difluorophenyl)-6,7,8,9-tetrahydro-5H-imidazo[1,2-a]azepin-9-ylcarbamate Cyclopropylmagnesium bromide (0.5 M in tetrahydrofuran; 1.53 mL, 0.77 mmol) was added to a solution of tert-butyl (6S,9R)-6-(2,3-difluorophenyl)-3-formyl-6,7,8,9-tetrahydro-5H-imidazo[1,2-a]azepin-9-ylcarbamate (60 mg, 0.15 mmol) in tetrahydrofuran (1 mL) at 0° C. After 30 min, the reaction was quenched with water and the mixture was extracted with dichloromethane (3×). The organic layer was washed with water, saturated brine, dried over magnesium sulfate, filtered and concentrated. MS 434.2 (M+1).

INTERMEDIATE 81

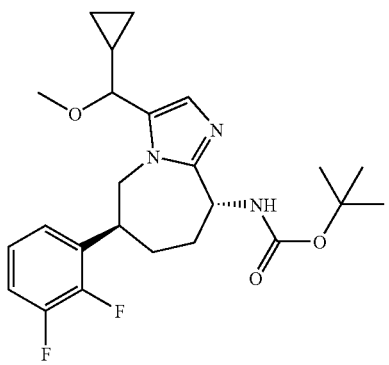

tert-Butyl (6S,9R)-3-[cyclopropyl(methoxy)methyl]-6-(2,3-difluorophenyl)-6,7,8,9-tetrahydro-5H-imidazo[1,2-a]azepin-9-ylcarbamate Iodomethane (9.0 µL, 0.15 mmol) was added to a solution of tert-butyl (6S,9R)-3-[cyclopropyl(hydroxy)methyl]-6-(2,3-difluorophenyl)-6,7,8,9-tetrahydro-5H-imidazo[1,2-a]azepin-9-ylcarbamate (66 mg, 0.15 mmol) and sodium hydride (60% dispersion in mineral oil; 8.3 mg, 0.23 mmol) in tetrahydrofuran (1 mL) at 0° C. After 1 h, the mixture was allowed to warm to ambient temperature. After 2 h, additional iodomethane (6.0 µL, 0.10 mmol) and sodium hydride (60% dispersion in mineral oil; 3.0 mg, 0.08 mmol) were added. After 1 h, the reaction was quenched with water and the mixture was extracted with dichloromethane (3×). The organic layer was washed with water, saturated brine, dried over magnesium sulfate, filtered and concentrated. Purification by reverse phase HPLC (C-18, 95% water/acetonitrile→5% water/acetonitrile with 0.1% trifluoroacetic acid) gave the title compound (23 mg). MS 448.2 (M+1).

INTERMEDIATE 82

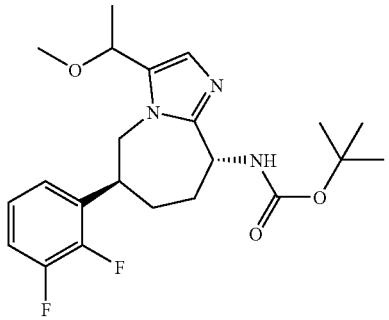

104 tert-Butyl (6S,9R)-6-(2,3-difluorophenyl)-3-(1-methoxyethyl)-6,7,8,9-tetrahydro-5H-imidazo[1,2-a]azepin-9-ylcarbamate Iodomethane (6.0 µL, 0.10 mmol) was added to a solution of tert-butyl (6S,9R)-6-(2,3-difluorophenyl)-3-(1-hydroxyethyl)-6,7,8,9-tetrahydro-5H-imidazo[1,2-a]azepin-9-ylcarbamate (40 mg, 0.10 mmol) and sodium hydride (60% dispersion in mineral oil; 6.7 mg, 0.15 mmol) in tetrahydrofuran (1 mL) at 0° C. After 2 h, the mixture was allowed to warm to ambient temperature. Additional iodomethane (6.0 µL, 0.10 mmol) and sodium hydride (60% dispersion in mineral oil; 2.2 mg, 0.05 mmol) were added every 1.5 h over a total of 4.5 h, after which the reaction was quenched with water and the mixture was extracted with dichloromethane (3×). The organic layer was washed with water, saturated brine, dried over magnesium sulfate, filtered and concentrated. Purification by reverse phase HPLC (C-18, 95% water/acetonitrile→5% water/acetonitrile with 0.1% trifluoroacetic acid) gave the title compound (16 mg). MS 422.2 (M+1).

INTERMEDIATE 83

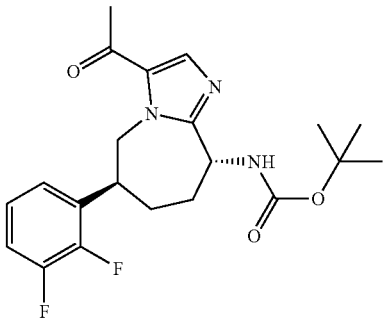

tert-Butyl (6S,9R)-3-acetyl-6-(2,3-difluorophenyl)-6,7,8,9-tetrahydro-5H-imidazo[1,2-a]azepin-9-ylcarbamate Pyridinium dichromate (0.96 g, 2.55 mmol) was added to a solution of tert-butyl (6S,9R)-6-(2,3-difluorophenyl)-3-(1-hydroxyethyl)-6,7,8,9-tetrahydro-5H-imidazo[1,2-a]azepin-9-ylcarbamate (0.52 g, 1.28 mmol) in acetonitrile (10 mL). After 18 h, the reaction was filtered through celite and concentrated. Saturated sodium carbonate was added and the mixture was extracted with dichloromethane (3×). The organic layer was washed with water, saturated brine, dried over magnesium sulfate, filtered and concentrated. Purification by silica gel chromatography (100% dichloromethane→40% ethyl acetate/dichloromethane) gave the title compound (0.38 g). MS 406.1 (M+1).

INTERMEDIATE 84

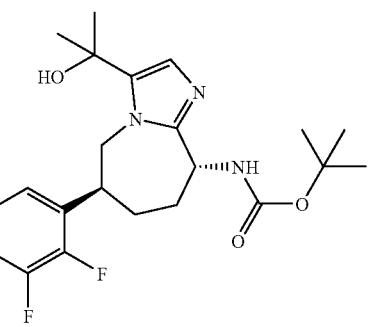

tert-Butyl (6S,9R)-6-(2,3-difluorophenyl)-3-(1-hydroxy-1-methylethyl)-6,7,8,9-tetrahydro-5H-imidazo[1,2-a]azepin-9-ylcarbamate Methylmagnesium bromide (3.0 M in ether; 90 µL, 0.27 mmol) was added to a solution of tert-butyl (6S,9R)-3-acetyl-6-(2,3-difluorophenyl)-6,7,8,9-tetrahydro-5H-imidazo[1,2-a]azepin-9-ylcarbamate (22 mg, 0.05 mmol) in tetrahydrofuran (1 mL) at 0° C., and the reaction mixture was allowed to warm to ambient temperature. After 30 min, the reaction was quenched with water and the mixture was extracted with dichloromethane (3×). The organic layer was washed with water, saturated brine, dried over magnesium sulfate, filtered and concentrated. Purification by reverse phase HPLC (C-18, 95% water/acetonitrile→5% water/acetonitrile with 0.1% trifluoroacetic acid) gave the title compound (15 mg). MS 422.2 (M+1).

Alternatively, Intermediate 84 can be prepared as follows:

The hydrochloride salt of 1-amino-3-hydroxy-3-methylbutane-2-one (108 mg, 0.70 mmol) was added to a solution of tert-butyl [(3R,6S)-6-(2,3-difluorophenyl)-2-thioxoazepan-3-yl]carbamate (100 mg, 0.28 mmol) in anhydrous ethanol (2.8 mL) and the mixture heated to 60° C. Mercury(II) chloride (152 mg, 0.56 mmol) was added, followed immediately by triethylamine (0.20 mL, 1.40 mmol). After 23 h, the reaction was filtered and washed with methanol, then concentrated. Saturated aqueous sodium bicarbonate was added and the mixture was extracted with dichloromethane (3×). The combined organic extracts were washed with saturated brine, dried over magnesium sulfate, filtered and concentrated. Purification by silica gel chromatography (100% dichloromethane→95% dichloromethane/methanol) gave the title compound (85 mg). MS 422.2 (M+1).

INTERMEDIATE 85

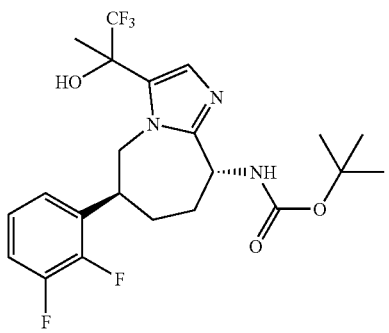

tert-Butyl (6S,9R)-6-(2,3-difluorophenyl)-3-(2,2,2-trifluoro-1-hydroxy-1-methylethyl)-6,7,8,9-tetrahydro-5H-imidazo[1,2-a]azepin-9-ylcarbamate (Trifluoromethyl)trimethylsilane (0.273 mL, 1.85 mmol) and tetrabutylammonium fluoride (1.0 M in tetrahydrofuran; 74 µL, 0.074 mmol) were sequentially added to a solution of tert-butyl (6S,9R)-3-acetyl-6-(2,3-difluorophenyl)-6,7,8,9-tetrahydro-5H-imidazo[1,2-a]azepin-9-ylcarbamate (150 mg, 0.37 mmol) in tetrahydrofuran (1 mL). After 5 min, additional (trifluoromethyl)trimethylsilane (100 µL, 0.678 mmol) and tetrabutylammonium fluoride (1.0 M in tetrahydrofuran; 25 µL, 0.025 mmol) were added. After 30 min, the reaction mixture was quenched with saturated sodium bicarbonate. The mixture was extracted with dichloromethane (3×), and the combined organic extracts were washed with water, saturated brine, dried over sodium sulfate, filtered and concentrated. Purification by reverse phase HPLC (C-18, 95% water/acetonitrile→5% water/acetonitrile with 0.1% trifluoroacetic acid) gave the title compound (55 mg). MS 476.2 (M+1).

INTERMEDIATE 86

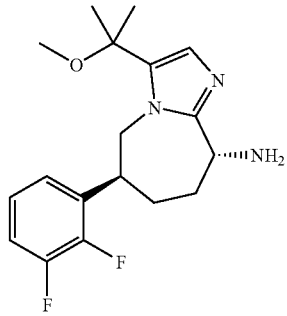

(6S,9R)-6-(2,3-Difluorophenyl)-3-(1-methoxy-1-methylethyl)-6,7,8,9-tetrahydro-5H-imidazo[1,2-a]azepin-9-amine Methanesulfonic acid (77 µL, 1.19 mmol) was added to a solution of tert-butyl (6S,9R)-6-(2,3-difluorophenyl)-3-(1-hydroxy-1-methylethyl)-6,7,8,9-tetrahydro-5H-imidazo[1,2-a]azepin-9-ylcarbamate (100 mg, 0.24 mmol) in methanol (5 mL) and the mixture heated to 60° C. After 18 h, the reaction mixture was quenched with saturated aqueous sodium bicarbonate. The mixture was extracted with ethyl acetate (3×), and the combined organic extracts were washed with saturated brine, dried over sodium sulfate, filtered and concentrated. MS 336.2 (M+1).

Essentially following the procedure outlined for the preparation of Intermediate 86, the Intermediates in Table 3 were prepared.

TABLE 3

| Intermediate | R | MS (M + 1) |
|---|---|---|
| 87 | HO~~~O~~~ | 366.1 |
| 88 | ~~~O~~~ | 350.2 |

TABLE 3-continued

| Intermediate | R | MS (M + 1) |
|---|---|---|
| 89 | (methoxyethoxy-dimethylmethyl group) | 380.2 |
| 90 | (2,2,2-trifluoroethoxy-dimethylmethyl group) F₃C | 404.3 |
| 91 | (isopropoxy-dimethylmethyl group) | 364.2 |
| 92 | (tetrahydrofuran-3-yloxy-dimethylmethyl group) | 392.2 |
| 93 | (methoxy-diethylmethyl group) | 364.2 |

INTERMEDIATE 94

Methyl (6S,9R)-9-[(tert-butoxycarbonyl)amino]-6-(2,3-difluorophenyl)-6,7,8,9-tetrahydro-5H-imidazo[1,2-a]azepine-3-carboxylate Step A: (6S,9R)-9-[(tert-Butoxycarbonyl)amino]-6-(2,3-difluorophenyl)-6,7,8,9-tetrahydro-5H-imidazo[1,2-a]azepine-3-carboxylic acid Sodium dihydrogen phosphate (127 mg, 0.92 mmol) and sodium chlorite (42 mg, 0.46 mmol) were added to a solution of tert-butyl (6S,9R)-6-(2,3-difluorophenyl)-3-formyl-6,7,8,9-tetrahydro-5H-imidazo[1,2-a]azepin-9-ylcarbamate (45 mg, 0.12 mmol) in tetrahydrofuran (0.8 mL), water (0.8 mL), tert-butanol (0.2 mL), and 2-methyl-2-butene (0.2 mL). After 3 h of vigorously stirring, the reaction mixture was quenched with saturated solution of ammonium chloride. The mixture was extracted with ethyl acetate (3×), and the combined organic extracts were washed with water, saturated brine, dried over sodium sulfate, filtered and concentrated. MS 408.1 (M+1).

Step B: Methyl (6S,9R)-9-[(tert-butoxycarbonyl)amino]-6-(2,3-difluorophenyl)-6,7,8,9-tetrahydro-5H-imidazo[1,2-a]azepine-3-carboxylate (Trimethylsilyl)diazomethane (2.0 M in ether; 173 µL, 0.35 mmol) was added to a solution of (6S,9R)-9-[(tert-butoxycarbonyl)amino]-6-(2,3-difluorophenyl)-6,7,8,9-tetrahydro-5H-imidazo[1,2-a]azepine-3-carboxylic acid (47 mg, 0.12 mmol) in dichloromethane (1.5 mL) and methanol (0.5 mL). After 1 h, additional (trimethylsilyl)diazomethane (2.0 M in diethyl ether; 50 µL, 0.10 mmol) was added. After 4 h, the reaction mixture was concentrated. MS 422.2 (M+1).

INTERMEDIATE 95 tert-Butyl [(6S,9R)-6-(2,3-difluorophenyl)-3-(1-hydroxycyclopropyl)-6,7,8,9-tetrahydro-5H-imidazo[1,2-a]azepin-9-yl]carbamate Ethylmagnesium bromide (3 M in ether; 0.17 mL, 0.51 mmol) was added dropwise over 15 min to a solution of titanium(IV) isopropoxide (0.08 mL, 0.26 mmol) and methyl (6S,9R)-9-[(tert-butoxycarbonyl)amino]-6-(2,3-difluorophenyl)-6,7,8,9-tetrahydro-5H-imidazo[1,2-a]azepine-3-carboxylate (54 mg, 0.13 mmol) in ether (0.9 mL) at 0° C. After 1.5 h, additional titanium(IV) isopropoxide (0.08 mL, 0.26 mmol) and ethylmagnesium bromide (3 M in ether; 0.17 mL, 0.51 mmol) were added. After 1.5 h, the mixture was quenched with saturated aqueous sodium bicarbonate and extracted with ethyl acetate (3×). The combined organic layers were washed with saturated brine, dried with magnesium

INTERMEDIATE 96

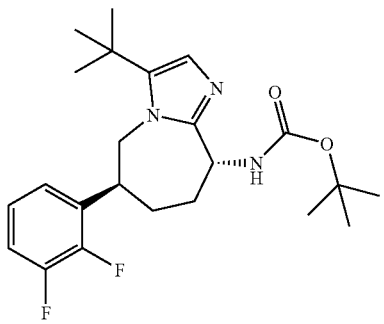

tert-Butyl [(6S,9R)-3-tert-butyl-6-(2,3-difluorophenyl)-6,7,8,9-tetrahydro-5H-imidazo[1,2-a]azepin-9-yl]carbamate Mercury(II) chloride (10 mg, 0.036 mmol) was added to a solution of tert-butyl [(3R,6S)-6-(2,3-difluorophenyl)-2-thioxoazepan-3-yl]carbamate (10 mg, 0.028 mmol), hydrobromide salt of 1-amino-3,3-dimethylbutan-2-one (11 mg, 0.056 mmol), and triethylamine (10 μL, 0.07 mmol) in ethanol (1 mL) at 70° C. After 18 h, the reaction was allowed to cool to ambient temperature. The mixture was filtered and concentrated. Purification by silica gel chromatography (100% dichloromethane→95% dichloromethane/methanol) gave the title compound (14 mg). MS 420.2 (M+1).

INTERMEDIATE 97

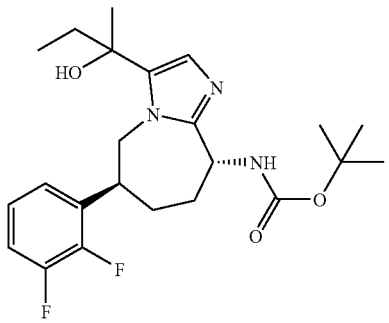

tert-Butyl [(6S,9R)-6-(2,3-difluorophenyl)-3-(1-hydroxy-1-methylpropyl)-6,7,8,9-tetrahydro-5H-imidazo[1,2-a]azepin-9-yl]carbamate Ethylmagnesium bromide (3.0 M in ether; 82.0 μL, 0.247 mmol) was added to a solution of tert-butyl (6S,9R)-3-acetyl-6-(2,3-difluorophenyl)-6,7,8,9-tetrahydro-5H-imidazo[1,2-a]azepin-9-ylcarbamate (25 mg, 0.062 mmol) in tetrahydrofuran (1 mL) at 0° C. After 10 min, the reaction mixture was quenched with water and the mixture was extracted with dichloromethane (3x). The organic layer was washed with water, saturated brine, dried over magnesium sulfate, filtered and concentrated. Purification by silica gel chromatography (100% dichloromethane→60% dichloromethane/ethyl acetate) gave the title compound (17 mg). MS 436.2 (M+1).

INTERMEDIATE 98 and INTERMEDIATE 99

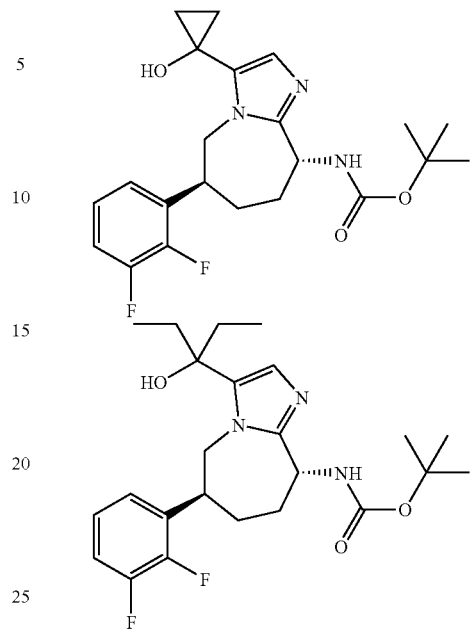

tert-Butyl [(6S,9R)-6-(2,3-difluorophenyl)-3-(1-hydroxycyclopropyl)-6,7,8,9-tetrahydro-5H-imidazo[1,2-a]azepin-9-yl]carbamate and tert-butyl [(6S,9R)-6-(2,3-difluorophenyl)-3-(1-ethyl-1-hydroxypropyl)-6,7,8,9-tetrahydro-5H-imidazo[1,2-a]azepin-9-yl]carbamate Ethylmagnesium bromide (3 M in ether; 0.32 mL, 0.95 mmol) was added dropwise to a solution of titanium (IV) isopropoxide (0.141 mL, 0.475 mmol) and methyl (6S,9R)-9-[(tert-butoxycarbonyl)amino]-6-(2,3-difluorophenyl)-6,7,8,9-tetrahydro-5H-imidazo[1,2-a]azepine-3-carboxylate (100 mg, 0.237 mmol) in tetrahydrofuran (4 mL) at 0° C. After 40 min, additional titanium(IV) isopropoxide (0.141 mL, 0.475 mmol) and ethylmagnesium bromide (3 M in ether; 0.316 mL, 0.95 mmol) were added. After 40 min, additional ethylmagnesium bromide (3 M in ether; 0.316 mL, 0.95 mmol) was added. After 40 min, the mixture was quenched with saturated aqueous ammonium chloride and saturated aqueous sodium bicarbonate and mixture was extracted with ethyl acetate (3x). The combined organic layers were washed with saturated brine, dried with magnesium sulfate, filtered, and concentrated. Purification by silica gel chromatography (100% dichloromethane→95% dichloromethane/ethyl acetate) gave a mixture of tert-butyl [(6S,9R)-6-(2,3-difluorophenyl)-3-(1-hydroxycyclopropyl)-6,7,8,9-tetrahydro-5H-imidazo[1,2-a]azepin-9-yl]carbamate (62 mg) MS 420.2 (M+1) and tert-butyl [(6S,9R)-6-(2,3-difluorophenyl)-3-(1-ethyl-1-hydroxypropyl)-6,7,8,9-tetrahydro-5H-imidazo[1,2-a]azepin-9-yl]carbamate (18 mg) MS 450.2 (M+1).

INTERMEDIATE 100

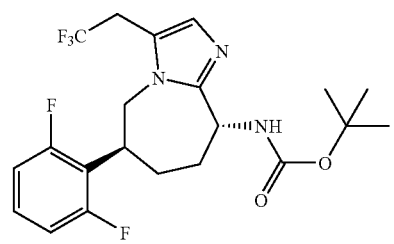

tert-Butyl [(6S,9R)-6-(2,6-difluorophenyl)-3-(2,2,2-trifluoroethyl)-6,7,8,9-tetrahydro-5H-imidazo[1,2-a]azepin-9-yl]carbamate Step A: tert-Butyl {(2Z,3R,6S)-6-(2,6-difluorophenyl)-2-[(4,4,4-trifluoro-2-hydroxybutyl)imino]azepan-3-yl}carbamate Mercury(II) chloride (538 mg, 1.98 mmol) was added to a solution of tert-butyl [(3R,6S)-6-(2,6-difluorophenyl)-2-thioxoazepan-3-yl]carbamate (353 mg, 0.99 mmol), 4,4,4-trifluoro-2-hydroxybutan-1-aminium chloride (498 mg, 2.77 mmol), and triethylamine (0.61 mL, 4.36 mmol) in ethanol (10 mL) at 55° C. After 2 h, the reaction was allowed to cool to ambient temperature. The mixture was filtered and concentrated. Saturated aqueous sodium bicarbonate was added and the mixture was extracted with dichloromethane (2×). The combined organic extracts were dried over magnesium sulfate, filtered, and concentrated to give the title compound. MS 466.2 (M+1).

Step B: tert-Butyl [(6S,9R)-6-(2,6-difluorophenyl)-3-(2,2,2-trifluoroethyl)-6,7,8,9-tetrahydro-5H-imidazo[1,2-a]azepin-9-yl]carbamate Pyridinium dichromate (2.24 g, 5.94 mmol) was added to a solution of tert-butyl {(2Z,3R,6S)-6-(2,6-difluorophenyl)-2-[(4,4,4-trifluoro-2-hydroxybutyl)imino]azepan-3-yl}carbamate (461 mg, 0.99 mmol) in acetonitrile (20 mL). After 18 h, the mixture was filtered and concentrated. Saturated aqueous sodium bicarbonate was added and the mixture was extracted with dichloromethane (3×). The combined organic extracts were dried over magnesium sulfate, filtered, and concentrated. Purification by silica gel chromatography (80% hexanes/ethyl acetate→50% hexanes/ethyl acetate) gave the title compound. MS 446.2 (M+1).

Essentially following the procedure outlined for the preparation of Intermediate 100, the Intermediates in Table 4 were prepared.

TABLE 4

| Intermediate | R | MS (M + 1) |
|---|---|---|
| 101 | 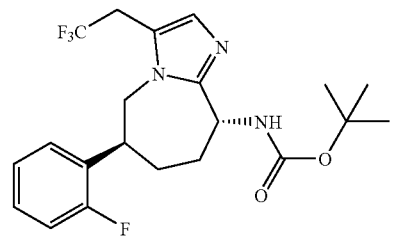 | 392.2 |
| 102 | | 436.2 |

INTERMEDIATE 103

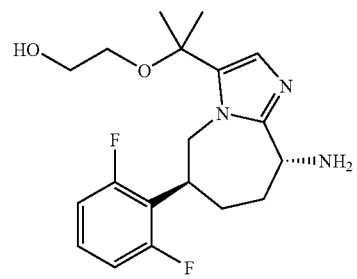

2-{1-[(6S,9R)-9-Amino-6-(2,6-difluorophenyl)-6,7,8,9-tetrahydro-5H-imidazo[1,2-a]azepin-3-yl]-1-methylethoxy}ethanol Methanesulfonic acid (78 μL, 1.19 mmol) was added to a solution of tert-butyl [(6S,9R)-6-(2,6-difluorophenyl)-3-(1-methoxy-1-methylethyl)-6,7,8,9-tetrahydro-5H-imidazo[1,2-a]azepin-9-yl]carbamate (104 mg, 0.24 mmol) in ethylene glycol (4 mL) and the mixture heated to 60° C. After 18 h, the reaction mixture was concentrated. Saturated aqueous sodium bicarbonate was added and the mixture was extracted with dichloromethane (3×), and the combined organic extracts were washed with saturated brine, dried over sodium sulfate, filtered and concentrated. MS 366.1 (M+1).

INTERMEDIATE 104

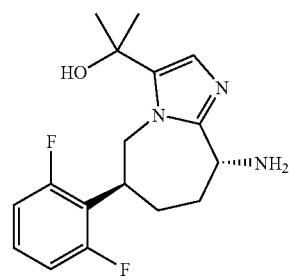

2-[(6S,9R)-9-Amino-6-(2,6-difluorophenyl)-6,7,8,9-tetrahydro-5H-imidazo[1,2-a]azepin-3-yl]propan-2-ol Intermediate 104 can be prepared following the procedure outlined for the preparation of Intermediate 103 using water in place of ethylene glycol. MS 322.1 (M+1).

INTERMEDIATE 105

113 tert-Butyl [(6S,9R)-6-(2-fluorophenyl)-3-(2,2,2-trifluoroethyl)-6,7,8,9-tetrahydro-5H-imidazo[1,2-a]azepin-9-yl]carbamate Prepared essentially following the procedure outlined for the preparation of Intermediate 100. MS 428.2 (M+1).

INTERMEDIATE 106

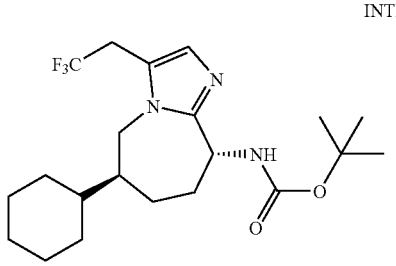

tert-Butyl [(6S,9R)-6-cyclohexyl-3-(2,2,2-trifluoroethyl)-6,7,8,9-tetrahydro-5H-imidazo[1,2-a]azepin-9-yl]carbamate Prepared essentially following the procedure outlined for the preparation of Intermediate 100. MS 416.3 (M+1).

INTERMEDIATE 107

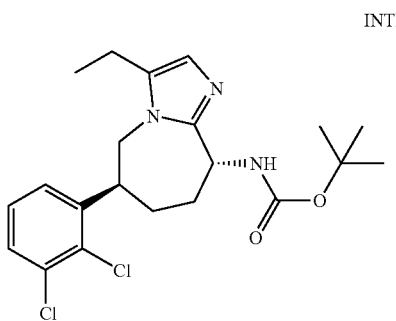

tert-Butyl [(6S,9R)-6-(2,3-dichlorophenyl)-3-ethyl-6,7,8,9-tetrahydro-5H-imidazo[1,2-a]azepin-9-yl]carbamate Prepared essentially following the procedure outlined for the preparation of Intermediate 100. MS 424.1 (M+1).

INTERMEDIATE 108

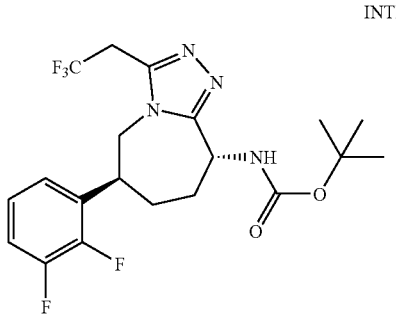

114 tert-Butyl (6S,9R)-6-(2,3-difluorophenyl)-3-(2,2,2-trifluoroethyl)-6,7,8,9-tetrahydro-5H-[1,2,4]triazolo[4,3-a]azepin-9-ylcarbamate Step A: tert-Butyl (3R,6S)-6-(2,3-difluorophenyl)-2-hydrazonoazepan-3-ylcarbamate Hydrazine monohydrate (2.23 mL, 46.0 mmol) was added to a solution of tert-butyl (3R,6S)-6-(2,3-difluorophenyl)-2-thioxoazepan-3-ylcarbamate (546 mg, 1.53 mmol) in methanol (25 mL). After 30 min, the mixture was concentrated. Saturated aqueous sodium bicarbonate was added and the mixture was extracted with dichloromethane (3×). The combined organic extracts were dried over sodium sulfate, filtered, and concentrated to give the title compound (548 mg). MS 355.2 (M+1).

Step B: tert-Butyl (6S,9R)-6-(2,3-difluorophenyl)-3-(2,2,2-trifluoroethyl)-6,7,8,9-tetrahydro-5H-[1,2,4]triazolo[4,3-a]azepin-9-ylcarbamate Triethylamine (0.259 mL, 1.86 mmol) was added to a solution of tert-butyl (3R,6S)-6-(2,3-difluorophenyl)-2-hydrazonoazepan-3-ylcarbamate (548 mg, 1.55 mmol), 3,3,3-trifluoropropionic acid (0.205 mL, 2.32 mmol), 1-(3-dimethylaminopropyl)-3-ethylcarbodimmide hydrochloride (356 mg, 1.86 mmol), and 1-hydroxy-7-azabenzotriazole (253 mg, 1.86 mmol) in dichloromethane (55 mL). After 18 h, saturated aqueous sodium bicarbonate was added and the mixture was extracted with dichloromethane (3×). The combined organic extracts were dried over sodium sulfate, filtered, and concentrated. Purification by silica gel chromatography (100% dichloromethane→96% dichloromethane/methanol) gave the title compound (618 mg). MS 447.1 (M+1).

Essentially following the procedure outlined for the preparation of Intermediate 108, the Intermediates in Table 5 were prepared.

TABLE 5

| Intermediate | R | MS (M + 1) |
|---|---|---|
| 109 |  | 473.2 |
| 110 |  | 437.2 |

TABLE 5-continued

| Intermediate | R | MS (M + 1) |
|---|---|---|
| 111 | HO-C(CH3)2-CH2- | 423.2 |

INTERMEDIATE 112

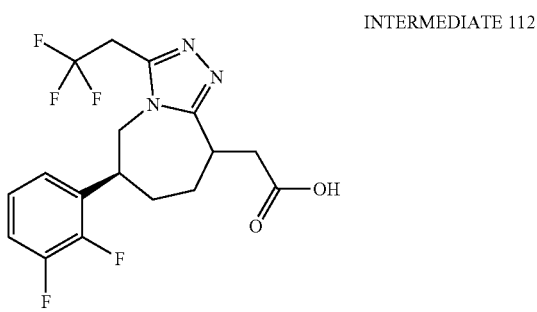

[6-(2,3-Difluorophenyl-3-(2,2,2-trifluoroethyl)-6,7,8,
9-tetrahydro-5H-[1,2,4]triazolo[4,3-a]azepin-9-yl]
acetic acid Step A: 3-Allyl-6-
(2,3-difluorophenyl)azepane-2-thione Lawesson's reagent [2,4-bis(4-methoxyphenyl)-1,3-dithia-2,4-diphosphetane-2,4-disulfide] (649 mg, 1.61 mmol) was added to a suspension 3-allyl-6-(2,3-difluorophenyl)azepan-2-one (426 mg, 1.61 mmol) in toluene (10 mL). After 3 h, the reaction mixture was heated to 45° C. After 30 min, the mixture was concentrated in a cold water bath. Purification by silica gel chromatography (100% hexanes→70% hexanes/ethyl acetate) gave the title compound (257 mg). MS 282.1 (M+1).

Step B: (2Z)-3-Allyl-6-(2,3-difluorophenyl)azepan-
2-one hydrazone

Hydrazine (anhydrous; 1.11 mL, 35.40 mmol) was added to a solution of 3-allyl-6-(2,3-difluorophenyl)azepane-2-thione (249 mg, 0.885 mmol) in ethanol (8 mL). After 4 h, the reaction mixture was concentrated. The residue was diluted with saturated aqueous sodium bicarbonate and extracted with dichloromethane (3×). The organic extracts were dried over sodium sulfate, filtered and concentrated to give the title compound. (MS 280.2 (M+1).

Step C: 9-Allyl-6-(2,3-difluorophenyl)-3-(2,2,2-trifluoroethyl)-6,7,8,9-tetrahydro-5H-[1,2,4]triazolo[4,3-a]azepine Triethylamine (142 μL, 1.02 mmol), N-(3-dimethylaminopropyl)-N'-ethylcarbodiimide hydrochloride (196 mg, 1.02 mmol), and 1-hydroxy-7-azabenzotriazole (139 mg, 1.02 mmol) were added to a solution of (2Z)-3-allyl-6-(2,3-difluorophenyl)azepan-2-one hydrazone (285 mg, 1.02 mmol) and 3,3,3-trifluoropropanoic acid (90 μL, 1.02 mmol) in acetonitrile (25 mL). After 18 h, additional triethylamine (0.14 mL, 1.02 mmol), N-(3-dimethylaminopropyl)-N'-ethylcarbodiimide hydrochloride (100 mg, 0.52 mmol), 1-hydroxy-7-azabenzotriazole (70 mg, 0.51 mmol) and 3,3,3-trifluoropropanoic acid (45 μL, 0.51 mmol) were added. After 5.5 h, the reaction mixture was heated to 60° C. After 2.5 h, the mixture was cooled to ambient temperature. After 18 h, the reaction mixture was diluted with ethyl acetate and saturated aqueous sodium bicarbonate. The mixture was extracted with ethyl acetate, washed with saturated brine, dried with sodium sulfate, filtered and concentrated. Purification by reverse phase HPLC (100% water→100% acetonitrile with 0.1% trifluoroacetic acid) gave the title compounds (275 mg). MS 372.1 (M+1).

Step D: [6-(2,3-Difluorophenyl)-3-(2,2,2-trifluoroethyl)-6,7,8,9-tetrahydro-5H-[1,2,4]triazolo[4,3-a]
azepin-9-yl]acetic acid Sodium periodate (191 mg, 0.89 mmol) in water (7.77 mL) was added to a solution of 9-allyl-6-(2,3-difluorophenyl)-3-(2,2,2-trifluoroethyl)-6,7,8,9-tetrahydro-5H-[1,2,4]triazolo[4,3-a]azepine (83 mg, 0.224 mmol) in tetrahydrofuran (7 mL). The pH of the reaction mixture was adjusted to pH 7.5 with sodium carbonate (0.5 M; 0.20 mL) and potassium permanganate (7 mg, 0.045 mmol) was added. After 3.5 h, additional potassium permanganate (7 mg, 0.045 mmol) and potassium carbonate (0.20 mL) were added. After 18 h, saturated aqueous sodium sulfite and dichloromethane were added and the pH of the solution was adjusted to pH 5 with hydrochloric acid. The mixture was extracted with dichloromethane (5×). The combined organic extracts were dried over magnesium sulfate, filtered, and concentrated to give the hydrochloride salt of the title compounds. MS 390.1 (M+1).

Essentially following the procedure outlined for the preparation of Intermediate 112, the Intermediates in Table 6 were prepared. Cis and trans diastereomers can be separated after step B, step C or step D by reverse phase chromatography.

TABLE 6

| Intermediate | R | MS (M + 1) |
|---|---|---|
| 113 | CH3O-C(CH3)2- | 380.1 |

TABLE 6-continued

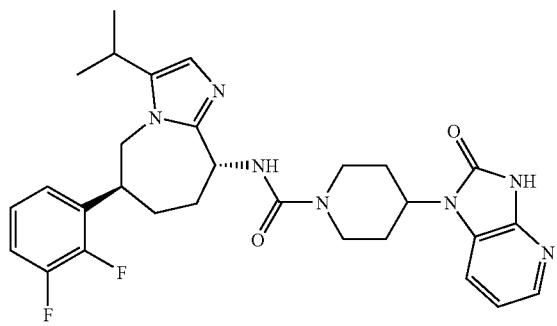

| Intermediate | R | MS (M + 1) |
|---|---|---|
| 114 | F₃C— (cyclopropyl with CF₃) | 416.0 |

Example 1

N-[(6S,9R)-6-(2,3-Difluorophenyl)-3-isopropyl-6,7,8,9-tetrahydro-5H-imidazo[1,2-a]azepin-9-yl]-4-(2-oxo-2,3-dihydro-1H-imidazo[4,5-b]pyridin-1-yl)piperidine-1-carboxamide Step A: N-{(3R,6S)-6-(2,3-Difluorophenyl)-2-[(2-hydroxy-3-methylbutyl)imino]azepan-3-yl}-4-(2-oxo-2,3-dihydro-1H-imidazo[4,5-b]pyridin-1-yl)piperidine-1-carboxamide Mercury(II) chloride (85 mg, 0.314 mmol) was added to a solution of N-[(3R,6S)-6-(2,3-difluorophenyl)-2-thioxoazepan-3-yl]-4-(2-oxo-2,3-dihydro-1H-imidazo[4,5-b]pyridin-1-yl)piperidine-1-carboxamide (105 mg, 0.210 mmol) and 1-amino-3-methylbutan-2-ol (122 mg, 1.18 mmol) in methanol (7 mL) at 55° C. After 1 h, the reaction was allowed to cool to ambient temperature. The mixture was filtered and concentrated. Purification by reverse phase HPLC (C-18, 90% water/acetonitrile→100% acetonitrile with 0.1% trifluoroacetic acid) gave the title compound as a trifluoroacetate salt (164 mg). MS 570.2 (M+1).

Step B: N-[(6S,9R)-6-(2,3-Difluorophenyl)-3-isopropyl-6,7,8,9-tetrahydro-5H-imidazo[1,2-a]azepin-9-yl]-4-(2-oxo-2,3-dihydro-1H-imidazo[4,5-b]pyridin-1-yl)piperidine-1-carboxamide Dess-Martin reagent [1,1,1-tris(acetyloxy)-1,1-dihydro-1,2-benziodoxol-3-(1)-one] (174 mg, 0.411 mmol) was added to a solution of the trifluoroacetate salt of N-{(3R,6S)-6-(2,3-difluorophenyl)-2-[(2-hydroxy-3-methylbutyl)imino]azepan-3-yl}-4-(2-oxo-2,3-dihydro-1H-imidazo[4,5-b]pyridin-1-yl)piperidine-1-carboxamide (164 mg, 0.206 mmol) and acetic acid (24 μL, 0.411 mmol) in dichloromethane (10 mL). After 1 h, sodium sulfite (100 mg, 0.793 mmol) and ethanol (10 mL) were added and the mixture was heated to 80° C. After 1 h, the reaction was allowed to cool to ambient temperature and concentrated. Saturated aqueous sodium bicarbonate was added and the mixture was extracted with dichloromethane (3×). The combined organic extracts were dried over sodium sulfate, filtered, and concentrated. Purification by silica gel chromatography [100% dichloromethane→93% dichloromethane/methanol)] gave the title compound (76 mg). MS 550.2748 (M+1).

Essentially following the procedure outlined for the preparation of Example 1, the Examples in Table 7 were prepared.

TABLE 7

| Example | R¹ | R² | MS (M + 1) |
|---|---|---|---|
| 2 | H | H | 508.2269 |
| 3 | isopropyl | H | 536.2578 |
| 4 | benzyl(α-methyl) | H | 584.2524 |
| 5 | H | CH₂C(CH₃)₂CF₃ | 590.1 |
| 6 | H | CH₃ | 522.2420 |
| 7 | CH₂C(CH₃)₂CF₃ | H | 590.2287 |
| 8 | cyclopropyl-C(CH₃)₂ | H | 548.2595 |
| 9 | CH₃ | H | 522.2379 |

Example 10

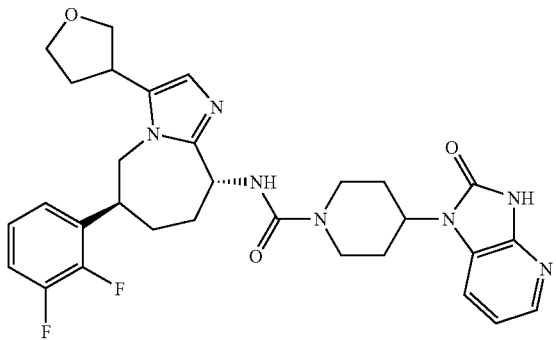

N-[(6S,9R)-6-(2,3-Difluorophenyl)-3-(tetrahydrofuran-3-yl)-6,7,8,9-tetrahydro-5H-imidazo[1,2-a]azepin-9-yl]-4-(2-oxo-2,3-dihydro-1H-imidazo[4,5-b]pyridin-1-yl)piperidine-1-carboxamide

Step A: (6S,9R)-6-(2,3-Difluorophenyl)-3-(tetrahydrofuran-3-yl)-6,7,8,9-tetrahydro-5H-imidazo[1,2-a]azepin-9-amine Hydrochloric acid (4.0 M in dioxane; 3 mL, 12.0 mmol) was added to a solution of tert-butyl [(6S,9R)-6-(2,3-difluorophenyl)-3-(tetrahydrofuran-3-yl)-6,7,8,9-tetrahydro-5H-imidazo[1,2-a]azepin-9-yl]carbamate (113 mg, 0.261 mmol) in 1,4-dioxane (3 mL). After 2.5 h, the reaction was concentrated to give the title compound as a bis hydrochloride salt (117 mg). MS 334.2 (M+1).

Step B: N-[(6S,9R)-6-(2,3-Difluorophenyl)-3-(tetrahydrofuran-3-yl)-6,7,8,9-tetrahydro-5H-imidazo[1,2-a]azepin-9-yl]-4-(2-oxo-2,3-dihydro-1H-imidazo[4,5-b]pyridin-1-yl)piperidine-1-carboxamide Triethylamine (43 µL, 0.310 mmol) was added to a solution of the bis hydrochloride salt of (6S,9R)-6-(2,3-difluorophenyl)-3-(tetrahydrofuran-3-yl)-6,7,8,9-tetrahydro-5H-imidazo[1,2-a]azepin-9-amine (42 mg, 0.103 mmol) and 4-nitrophenyl chloroformate (21 mg, 104 mmol) in tetrahydrofuran (3 mL) at 0° C. After 30 min, 2-oxo-1-piperidinium-4-yl-2,3-dihydro-1H-imidazo[4,5-b]pyridin-4-ium dichloride (45 mg, 0.155 mmol), triethylamine (43 µL, 0.310 mmol) and dichloromethane (3 mL) were added and the mixture allowed to warm to ambient temperature. After 18 h, the reaction was concentrated. Purification by reverse phase HPLC (C-18, 90% water/acetonitrile→100% acetonitrile with 0.1% trifluoroacetic acid) gave the title compound (35 mg). MS 578.2702 (M+1).

Essentially following the procedure outlined for the preparation of Example 10, the Examples in Table 8 were prepared.

TABLE 8

| Example | R¹ | R² | MS (M + 1) |
|---|---|---|---|
| 11 | H | —CH₂—O—CH₂—C₆H₅ | 628.2 |
| 12 | H | —C(CH₃)₂—OH | 538.2 |
| 13 | CH₃O—C(O)—CH₂—C(CH₃)₂— | H | 580.2457 |
| 14 | HO—C(O)—CH₂—C(CH₃)₂— | H | 566.2332 |

TABLE 8-continued
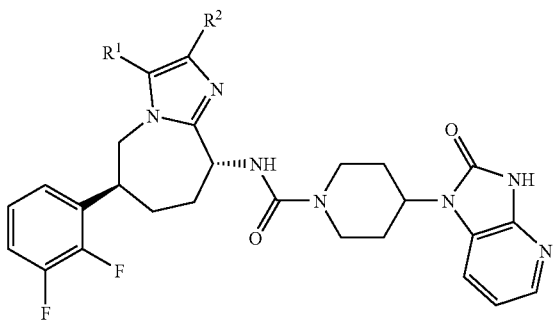
| Example | R[1] | R[2] | MS (M + 1) |
|---|---|---|---|
| 15 | N,N-dimethylcarbamoyl-CH2-C(CH3)< | H | 593.2812 |
| 16 | HO-CH2CH2-C(CH3)< | H | 552.2540 |
| 17 | MeO-CH2CH2-C(CH3)< | H | 566.2728 |
| 18 | F-CH2CH2-C(CH3)< | H | 554.2464 |
| 19 | CHF2-CH2-C(CH3)< | H | 571.2441 |
| 20 | HO-CH2-C(CH3)< | H | 538.2 |
| 21 | AcO-CH2CH2-C(CH3)< | H | 594.2623 |
| 22 | MeO-CH2-C(CH3)< | H | 552.2564 |
| 23 | CF3-CH(OH)-C(CH3)< | H | 606.2213 |
| 24 | CF3-CH(OMe)-C(CH3)< | H | 620.2445 |
| 25 | OHC-C(CH3)< | H | 536.2 |

TABLE 8-continued
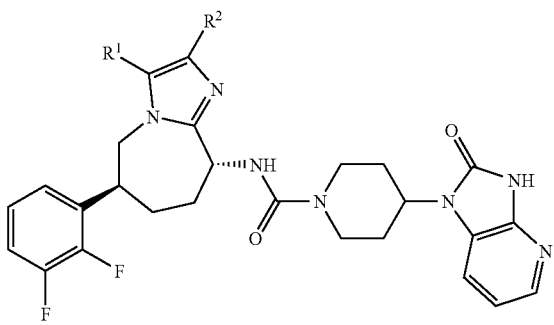
| Example | R¹ | R² | MS (M + 1) |
|---|---|---|---|
| 26 | (acetyl-dimethyl group) | H | 550.2407 |
| 27 | (methoxy-isopropyl group) | H | 566.2674 |
| 28 | (hydroxy-isopropyl group) | H | 552.2504 |
| 29 | (difluoromethyl-methyl group) | H | 558.2272 |
| 30 | (2-hydroxy-2-methylpropyl group) | H | 566.2673 |
| 31 | (methoxy-dimethyl group) | H | 580.3 |
| 32 | (CF₃, HO, dimethyl group) | H | 620.2459 |
| 33 | (isopropyl ester group) | H | 608.2767 |
| 34 | (dimethylaminoethyl-methyl group) | H | 579.2958 |

TABLE 8-continued

| Example | R¹ | R² | MS (M + 1) |
|---------|----|----|------------|
| 35 | cyclopropyl-CH(OMe)-C(CH₃)- | H | 592.2826 |
| 36 | cyclopropyl-CH(OH)-C(CH₃)- | H | 578.2728 |
| 37 | MeO-C(O)-C(CH₃)- | H | 566.2349 |
| 38 | HO-C(O)-C(CH₃)- | H | 552.2191 |
| 39 | (CH₃)₂N-C(O)-C(CH₃)- | H | 579.3 |
| 40 | morpholine-C(O)-C(CH₃)- | H | 621.3 |
| 41 | HO-CH(CH₃)-C(CH₃)- | H | 566.2734 |
| 42 | HO-C(CH₃)₂-C(CH₃)- | H | 580.2892 |
| 43 | thiazol-2-yl-C(CH₃)- | H | 591.2132 |

TABLE 8-continued

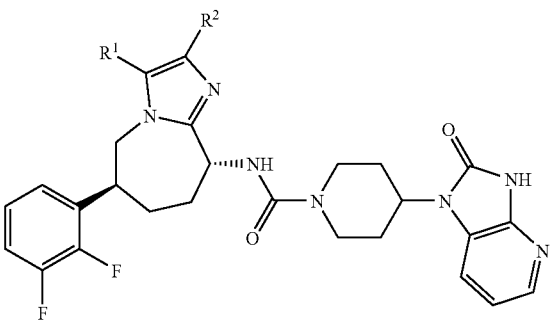

| Example | R¹ | R² | MS (M + 1) |
|---------|----|----|-----------|
| 44 | HO-[cyclopropyl-C(CH₃)-] | H | 564.2 |
| 45 | F₃C-[cyclopropyl-C(CH₃)-] | H | 616.3 |
| 46 | F₃C-CH₂-C(CH₃)- | H | 604.2424 |

Example 47

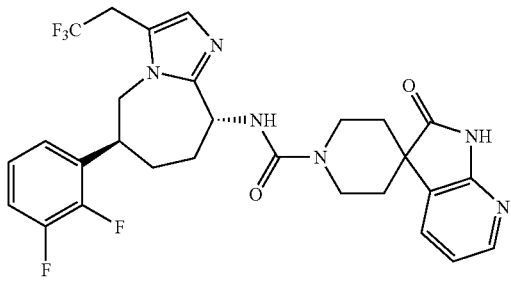

N-[(6S,9R)-6-(2,3-Difluorophenyl)-3-(2,2,2-trifluoroethyl)-6,7,8,9-tetrahydro-5H-imidazo[1,2-a]azepin-9-yl]-2'-oxo-1',2'-dihydro-1H-spiro[piperidine-4,3'-pyrrolo[2,3-b]pyridine]-1-carboxamide

Step A: (6S,9R)-6-(2,3-Difluorophenyl)-3-(2,2,2-trifluoroethyl)-6,7,8,9-tetrahydro-5H-imidazo[1,2-a]azepin-9-amine Hydrochloric acid (4.0 M in dioxane; 4.0 mL, 16.0 mmol) was added to a solution of tert-butyl (6S,9R)-6-(2,3-difluorophenyl)-3-(2,2,2-trifluoroethyl)-6,7,8,9-tetrahydro-5H-imidazo[1,2-a]azepin-9-ylcarbamate (100 mg, 0.224 mmol) in dioxane (2 mL). After 1 h, the reaction mixture was concentrated to give the hydrochloride salt of the title compound. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-2'-oxo-1',2'-dihydro-1H-spiro[piperidine-4,3'-pyrrolo[2,3-b]pyridine]-1-carboxamide Triethylamine (94 µL, 0.673 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (94 mg, 0.224 mmol) and 4-nitrophenyl chloroformate (45 mg, 0.224 mmol) in tetrahydrofuran (3 mL) at 0° C. After 1 h, 2'-oxo-2,2'-dihydrospiro[piperidine-4,3'-pyrrolo[2,3-b]pyridine] dichloride (62 mg, 0.224 mmol) and triethylamine (94 µL, 0.673 mmol) were added and the mixture allowed to warm to ambient temperature. After 1 h, saturated aqueous sodium carbonate was added and the mixture was extracted with dichloromethane. The organic layer was washed with saturated aqueous sodium bicarbonate (3×), saturated brine, dried over sodium sulfate, filtered and concentrated. Purification by silica gel chromatography [100% dichloromethane→93% dichloromethane/methanol] gave the title compound (62 mg). MS 575.2179 (M+1). ¹H NMR (500 MHz, CDCl₃) δ 8.33 (s, 1H), 8.18 (dd, J=5.1, 1.5 Hz, 1H), 7.56 (dd, J=7.6, 1.5 Hz, 1H), 7.15-7.12 (m, 2H), 7.02-6.98 (m, 2H), 6.95 (s, 1H), 6.62 (d, J=3.4 Hz, 1H), 5.05 (dd, J=9.5, 4.9 Hz, 1H), 4.16 (J=13.8, 10.6 Hz, 1H), 4.03 (d, J=14.7 Hz, 1H), 3.40-3.93 (m, 2H), 3.84-3.72 (m, 2H), 3.41 (dd, J=19.9, 9.9 Hz, 2H), 2.99 (t, J=11.7 Hz, 1H), 2.56-2.53 (m, 1H), 2.39-2.34 (m, 1H), 2.20-2.17 (m, 1H), 2.04-2.01 (m, 2H), 1.93-1.58 (m, 2H).

Essentially following the procedure outlined for the preparation of Example 47, the Examples in Table 9 were prepared.

TABLE 9

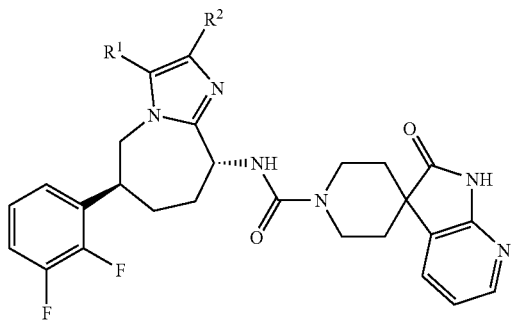

| Example | R¹ | R² | MS (M + 1) |
|---|---|---|---|
| 48 | (ethyl/methyl branched) | H | 521.1 |
| 49 | HO-CH₂CH₂-C(CH₃)- | H | 537.2423 |
| 50 | cyclopropyl-C(CH₃)- | H | 533.2457 |
| 51 | tetrahydrofuran-3-yl with methyl | H | 563.2591 |
| 52 | CH₃O-CH(CF₃)- | H | 605.2337 |
| 53 | HO-C(CH₃)₂-C(CH₃)- | H | 551.2630 |
| 54 | CH₃O-C(CH₃)₂-C(CH₃)- | H | 565.2745 |
| 55 | CH₃O-CH₂-C(CH₃)- | H | 537.2400 |
| 56 | HO-C(CF₃)(CH₃)-C(CH₃)- | H | 605.2267 |
| 57 | F₃C-cyclopropyl-C(CH₃)- | H | 601.3 |
| 58 | HO-CH₂CH₂-O-C(CH₃)₂- | H | 595.2832 |
| 59 | F₃C-CH₂CH₂-C(CH₃)- | H | 589.2298 |
| 60 | cyclopropyl-CH₂-C(CH₃)- | H | 547.2650 |

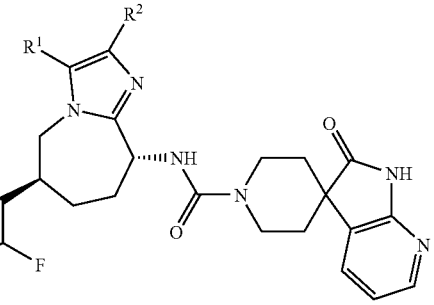

Example 61

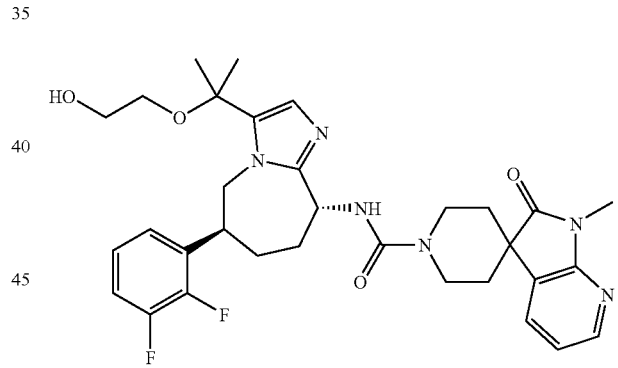

N-{(6S,9R)-6-(2,3-Difluorophenyl)-3-[1-(2-hydroxyethoxy)-1-methylethyl]-6,7,8,9-tetrahydro-5H-imidazo[1,2-a]azepin-9-yl}-1'-methyl-2'-oxo-1',2'-dihydro-1H-spiro[piperidine-4,3'-pyrrolo[2,3-b]pyridine]-1-carboxamide Triethylamine (14 μL, 0.104 mmol) was added to a solution of 2-{1-[(6S,9R)-9-amino-6-(2,3-difluorophenyl)-6,7,8,9-tetrahydro-5H-imidazo[1,2-a]azepin-3-yl]-1-methylethoxy}ethanol (38 mg, 0.104 mmol) and 4-nitrophenyl chloroformate (21 mg, 0.104 mmol) in tetrahydrofuran (3 mL) at 0° C. After 1 h, 1'-methylspiro[piperidine-4,3'-pyrrolo[2,3-b]pyridin]-2'(1'H)-one (23 mg, 0.104 mmol) and triethylamine (42 μL, 0.31 mmol) were added and the mixture was allowed to warm to ambient temperature. After 16 h, saturated aqueous sodium carbonate was added and the mixture was extracted with ethyl acetate (3×). The organic layer was washed with saturated brine, dried over magnesium sulfate, filtered and concentrated. Purification by silica gel chromatography (100% dichloromethane→92% dichloromethane/methanol) gave the title compound (41 mg). MS 609.3013 (M+1).

Example 62

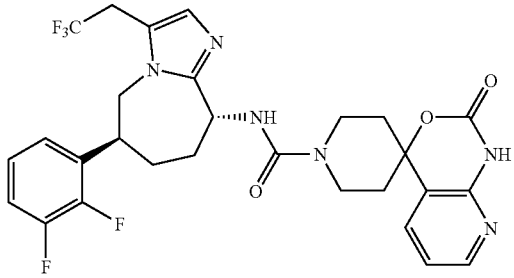

N-[(6S,9R)-6-[2,3-Difluorophenyl)-3-(2,2,2-trifluoroethyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Trifluoroacetic acid (2 mL) was added to a solution of tert-butyl (6S,9R)-6-(2,3-difluorophenyl)-3-(2,2,2-trifluoroethyl)-6,7,8,9-tetrahydro-5H-imidazo[1,2-a]azepin-9-ylcarbamate (50 mg, 0.112 mmol) in dichloromethane (2 mL). After 1 h, saturated sodium bicarbonate was added. The mixture was extracted with dichloromethane (3×), and the combined organic extracts were washed with saturated brine, dried over sodium sulfate, filtered and concentrated. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide Triethylamine (16 µL, 0.11 mmol) was added to a solution of (6S,9R)-6-(2,3-difluorophenyl)-3-(2,2,2-trifluoroethyl)-6,7,8,9-tetrahydro-5H-imidazo[1,2-a]azepin-9-amine (38 mg, 0.11 mmol) and 4-nitrophenyl chloroformate (23 mg, 0.11 mmol) in tetrahydrofuran (2 mL) at 0° C. After 1 h, spiro[piperidine-4,4'-pyrido[2,3-d][1,3]oxazin]-2'(1'H)-one (25 mg, 0.11 mmol) and triethylamine (47 µL, 0.33 mmol) were added and the mixture allowed to warm to ambient temperature. After 1 h, saturated aqueous sodium carbonate was added and the mixture was extracted with dichloromethane. The organic layer was washed with saturated aqueous sodium bicarbonate (3×), saturated brine, dried over sodium sulfate, filtered and concentrated. Purification by silica gel chromatography (100% dichloromethane→93% dichloromethane/methanol) gave the title compound (46 mg). MS 591.2132 (M+1). $^1$H NMR (500 MHz, CDCl$_3$) δ 9.07 (s, 1H), 8.33 (dd, J=4.9, 1.5 Hz, 1H), 7.46 (d, J=7.0 Hz, 1H), 7.15-7.11 (m, 2H), 7.08 (dd, J=7.6, 4.9 Hz, 1H), 7.01-6.99 (m, 1H), 6.96 (s, 1H), 6.62 (d, J=5.1 Hz, 1H), 5.32-5.00 (m, 1H), 4.17-4.12 (m, 2H), 4.10-4.07 (m, 1H), 4.03 (d, J=14.7 Hz, 1H), 3.51 (dd, J=25.2, 12.5 Hz, 2H), 3.41 (dd, J=19.9, 9.9 Hz, 2H), 2.98 (t, J=11.2 Hz, 1H), 2.53-2.49 (m, 1H), 2.38-2.35 (m, 1H), 2.21-2.18 (m, 3H), 2.09-1.97 (m, 2H), 1.61-1.59 (m, 1H).

Example 63

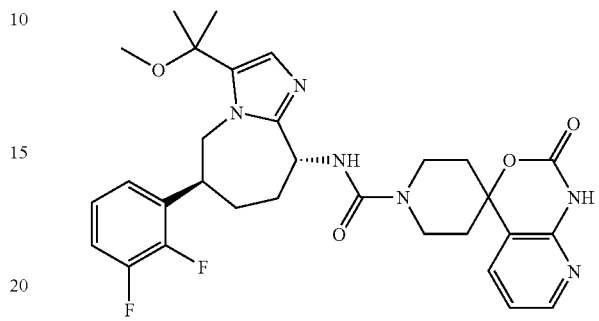

N-[(6S,9R)-6-(2,3-difluorophenyl)-3-(1-methoxy-1-methylethyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide Triethylamine (52 µL, 0.38 mmol) was added to a solution of (6S,9R)-6-(2,3-difluorophenyl)-3-(1-methoxy-1-methylethyl)-6,7,8,9-tetrahydro-5H-imidazo[1,2-a]azepin-9-amine (0.14 g, 0.42 mmol) and 4-nitrophenyl chloroformate (93 mg, 0.46 mmol) in tetrahydrofuran (10 mL) at 0° C. After 30 min, spiro[piperidine-4,4'-pyrido[2,3-d][1,3]oxazin]-2'(1'H)-one (101 mg, 0.46 mmol) and triethylamine (126 µL, 1.25 mmol) were added and the mixture allowed to warm to ambient temperature. After 1 h, saturated aqueous sodium carbonate was added and the mixture was extracted with dichloromethane. The organic layer was washed with saturated aqueous sodium bicarbonate (3×), saturated brine, dried over sodium sulfate, filtered and concentrated. Purification by silica gel chromatography (100% dichloromethane→93% dichloromethane/methanol) gave the title compound (149 mg). MS 581.2657 (M+1). $^1$H NMR (500 MHz, CDCl$_3$) δ 8.68 (s, 1H), 8.31 (d, J=5.1 Hz, 1H), 7.45 (d, J=7.6 Hz, 1H), 9.29-7.07 (m, 3H), 6.99-6.97 (m, 1H), 6.78 (s, 1H), 6.65 (d, J=4.9 Hz, 1H), 5.01 (dd, J=10.3, 4.2 Hz, 1H), 4.89 (d, J=14.4 Hz, 1H), 4.15-4.08 (m, 3H), 3.53-3.48 (m, 2H), 3.07 (s, 3H), 3.03 (t, J=11.1 Hz, 1H), 2.48 (d, J=13.2 Hz, 1H), 2.31-2.29 (m, 1H), 2.21-2.18 (m, 2H), 2.13-2.11 (m, 1H), 2.08-1.97 (m, 2H), 1.60 (br s, 1H), 1.54 (s, 3H), 1.52 (s, 3H).

Example 64

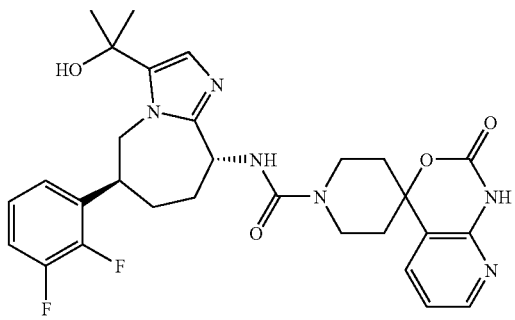

N-[(6S,9R)-6-(2,3-Difluorophenyl)-3-(1-hydroxy-1-methylethyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide Step A: 2-[(6S,9R)-9-Amino-6-(2,3-difluorophenyl)-6,7,8,9-tetrahydro-5H-imidazo[1,2-a]azepin-3-yl]propan-2-ol Trifluoroacetic acid (2 mL, 26.9 mmol) was added to a solution of tert-butyl [(6S,9R)-6-(2,3-difluorophenyl)-3-(1-hydroxy-1-methylethyl)-6,7,8,9-tetrahydro-5H-imidazo[1,2-a]azepin-9-yl]carbamate (100 mg, 0.24 mmol) in dichloromethane (3 mL). After 1 h, saturated aqueous sodium bicarbonate was added and the mixture was extracted with dichloromethane (3×). The combined organic extracts were washed with saturated brine, dried over magnesium sulfate, filtered and concentrated. MS 322.2 (M+1).

Step B: N-[(6S,9R)-6-(2,3-Difluorophenyl)-3-(2,2,2-trifluoro-1-hydroxyethyl)-6,7,8,9-tetrahydro-5H-imidazo[1,2-a]azepin-9-yl]-1'-methyl-2'-oxo-1',2'-dihydro-1H-spiro[piperidine-4,4'-pyrido[2,3-d][1,3]oxazine]-1-carboxamide Triethylamine (31 µL, 0.23 mmol) was added to a solution of 2-[(6S,9R)-9-amino-6-(2,3-difluorophenyl)-6,7,8,9-tetrahydro-5H-imidazo[1,2-a]azepin-3-yl]propan-2-ol (76 mg, 0.24 mmol) and 4-nitrophenyl chloroformate (50 mg, 0.25 mmol) in tetrahydrofuran (3 mL) at 0° C. After 20 min, spiro[piperidine-4,4'-pyrido[2,3-d][1,3]oxazin]-2'(1'H)-one (57 mg, 0.26 mmol) and triethylamine (99 µL, 0.71 mmol) were added and the mixture was allowed to warm to ambient temperature. After 1 h, saturated aqueous sodium carbonate was added and the mixture was extracted with dichloromethane (3×). The organic extracts were washed with saturated brine, dried over magnesium sulfate, filtered and concentrated. Purification by silica gel chromatography (100% dichloromethane→93% dichloromethane/methanol) gave the title compound (92 mg). MS 567.2534 (M+1). $^1$H NMR (500 MHz, CDCl$_3$) δ 8.27 (dd, J=5.4, 1.5 Hz, 1H), 7.88 (dd, J=7.7, 1.6 Hz, 1H), 7.36 (s, 1H), 7.26-7.22 (m, 3H), 5.37-5.32 (m, 2H), 4.65 (dd, J=14.4, 10.5 Hz, 1H), 4.26 (d, J=13.2 Hz, 1H), 4.15 (d, J=13.9 Hz, 1H), 3.51-3.46 (m, 1H), 3.41-3.35 (m, 1H), 3.33-3.27 (m, 2H), 2.42-2.36 (m, 1H), 2.29-2.27 (m, 1H), 2.23-2.19 (m, 4H), 2.17-2.09 (m, 1H), 1.62 (s, 3H), 1.60 (s, 3H).

Essentially following the procedure outlined for the preparation of Examples 62-64, the Examples in Table 10 were prepared.

TABLE 10

| Example | R$^1$ | R$^2$ | MS (M + 1) |
|---|---|---|---|
| 65 | cyclopropyl | H | 549.2434 |
| 66 | methoxycarbonylmethyl (dimethyl) | H | 581.2294 |
| 67 | HOOC-CH$_2$-C(CH$_3$)$_2$- | H | 567.2158 |
| 68 | CHF$_2$-CH$_2$- | H | 573.2268 |
| 69 | tetrahydrofuran-3-yl | H | 579.2252 |
| 70 | 1-(trifluoromethyl)cyclopropyl | H | 617.3 |
| 71 | CF$_3$CH$_2$C(CH$_3$)$_2$- | H | 605.2253 |
| 72 | ethoxy-dimethyl | H | 595.2850 |
| 73 | cyclopropylmethyl | H | 563.2608 |
| 74 | CF$_3$CH$_2$O-C(CH$_3$)$_2$- | H | 649.2541 |
| 75 | HOCH$_2$CH$_2$O-C(CH$_3$)$_2$- | H | 611.2783 |

TABLE 10-continued

| Example | R¹ | R² | MS (M+1) |
|---|---|---|---|
| 76 | methoxyethoxy-dimethylmethyl | H | 625.2942 |
| 77 | CF₃, OMe, methyl | H | 621.2248 |
| 78 | CF₃, HO, methyl | H | 607.2087 |
| 79 | CF₃, HO, methyl | H | 621.2231 |
| 80 | CF₃, HO, methyl | H | 621.2228 |
| 81 | HO-CH₂-C(CH₃)₂- | H | 539.2210 |
| 82 | MeO-CH₂-C(CH₃)₂- | H | 553.2382 |
| 83 | HO-CH(CH₃)-C(CH₃)₂- | H | 553.2406 |
| 84 | iPrO-C(CH₃)₂-C(CH₃)₂- | H | 609.3016 |
| 85 | MeO-CH(CH₃)-C(CH₃)₂- | H | 567.2546 |
| 86 | MeO-CH₂-O-C(CH₃)₂- | H | 611.2798 |
| 87 | 2-methyltetrahydrofuran-2-yl | H | 593.2636 |
| 88 | tetrahydrofuran-3-yloxy-C(CH₃)₂- | H | 637.2969 |
| 89 | Et-C(OH)(CH₃)- | H | 581.2726 |
| 90 | sec-butyl methyl | H | 565.2724 |
| 91 | tBu-C(CH₃)₂- | H | 565.2765 |
| 92 | Et₂C(OH)- | H | 595.2838 |
| 93 | 1-hydroxycyclopropyl-C(CH₃)- | H | 565.2419 |
| 94 | MeO-CH₂-C(Et)₂- | H | 609.3017 |

Example 95

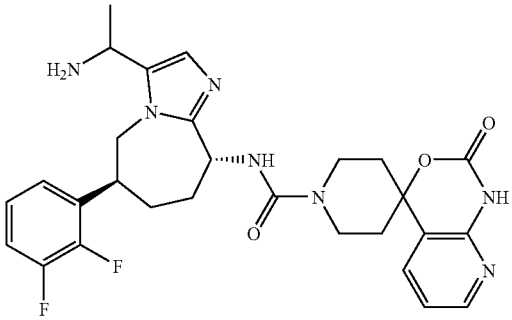

N-[(6S,9R)-3-(1-Aminoethyl)-6-(2,3-difluorophenyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide Step A: tert-Butyl [(6S,9R)-3-{(E)-[(tert-butylsulfinyl)imino]methyl}-6-(2,3-difluorophenyl)-6,7,8,9-tetrahydro-5H-imidazo[1,2-a]azepin-9-yl]carbamate Titanium (IV) ethoxide (239 mg, 1.05 mmol) was added to a solution of tert-butyl [(6S,9R)-6-(2,3-difluorophenyl)-3-formyl-6,7,8,9-tetrahydro-5H-imidazo[1,2-a]azepin-9-yl]carbamate (205 mg, 0.524 mmol) and (R)-2-methylpropane-2-sulfinamide (79 mg, 0.655 mmol) in tetrahydrofuran (8 mL). The reaction mixture was heated to 60° C. After 6 h, the reaction mixture was allowed to cool to ambient temperature. Saturated sodium bicarbonate was added and the mixture was extracted with dichlormethane (3×). The organic extracts were dried with magnesium sulfate, filtered and concentrated. Purification by silica gel chromatography (100% dichloromethane→95% dichloromethane/methanol) gave the title compound (252 mg). MS 495.2 (M+1).

Step B: tert-Butyl [(6S,9R)-3-{1-[(tert-butylsulfinyl)amino]ethyl}-6-(2,3-difluorophenyl)-6,7,8,9-tetrahydro-5H-imidazo[1,2-a]azepin-9-yl]carbamate Methylmagnesium bromide (0.24 mL, 0.71 mmol) was added to a solution of tert-butyl [(6S,9R)-3-{(E)-[(tert-butylsulfinyl)imino]methyl}-6-(2,3-difluorophenyl)-6,7,8,9-tetrahydro-5H-imidazo[1,2-a]azepin-9-yl]carbamate (117 mg, 0.24 mmol) in tetrahydrofuran (4 mL) at 0° C. After 5 min, the mixture was warmed to ambient temperature. After 1.5 h, additional methylmagnesium bromide (0.24 mL, 0.71 mmol) was added. After 1.5 h, the reaction mixture was cooled to 0° C. and quenched with saturated aqueous ammonium chloride and water. The mixture was extracted with ethyl acetate (3×). The organic extracts were washed with saturated brine, dried with magnesium sulfate, filtered and concentrated. Purification by silica gel chromatography (100% dichloromethane→94% dichloromethane/methanol) gave the title compound (144 mg). MS 511.2 (M+1).

Step C: N-{1-[(6S,9R)-9-Amino-6-(2,3-difluorophenyl)-6,7,8,9-tetrahydro-5H-imidazo[1,2-a]azepin-3-yl]ethyl}-2-methylpropane-2-sulfinamide Trifluoroacetic acid (1 mL, 13.5 mmol) was added to a solution of tert-butyl [(6S,9R)-3-{1-[(tert-butylsulfinyl)amino]ethyl}-6-(2,3-difluorophenyl)-6,7,8,9-tetrahydro-5H-imidazo[1,2-a]azepin-9-yl]carbamate (144 mg, 0.28 mmol) in dichloromethane (5 mL). After 1.5 h, saturated aqueous sodium bicarbonate was added and the mixture was extracted with dichloromethane (3×). The combined organic extracts were washed with saturated brine, dried over magnesium sulfate, filtered and concentrated. MS 411.1 (M+1).

Step D: N-[(6S,9R)-3-{1-[(tert-Butylsulfinyl)amino]ethyl}-6-(2,3-difluorophenyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide Triethylamine (14 μL, 0.097 mmol) was added to a solution of N-{1-[(6S,9R)-9-amino-6-(2,3-difluorophenyl)-6,7,8,9-tetrahydro-5H-imidazo[1,2-a]azepin-3-yl]ethyl}-2-methylpropane-2-sulfinamide (40 mg, 0.097 mmol) and 4-nitrophenyl chloroformate (20 mg, 0.097 mmol) in tetrahydrofuran (3 mL) at 0° C. After 10 min, the hydrochloride salt of spiro[piperidine-4,4'-pyrido[2,3-d][1,3]oxazin]-2'(1'H)-one (43 mg, 0.146 mmol) and triethylamine (28 μL, 0.194 mmol) were added and the mixture allowed to warm to ambient temperature. After 1.5 h, saturated aqueous sodium carbonate was added and the mixture was extracted with dichloromethane (3×). The organic extracts were washed with saturated brine, dried over magnesium sulfate, filtered and concentrated. Purification by silica gel chromatography (100% dichloromethane→90% dichloromethane/methanol) gave the title compound (65 mg). MS 656.3 (M+1).

Step E: N-[(6S,9R)-3-(1-Aminoethyl)-6-(2,3-difluorophenyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide Hydrochloric acid (4.0 M in dioxane; 0.50 mL, 2.0 mmol) was added to a solution of N-[(6S,9R)-3-{1-[(tert-butylsulfinyl)amino]ethyl}-6-(2,3-difluorophenyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide (65 mg, 0.099 mmol) in methanol (7 mL). After 16 h, the reaction mixture was concentrated. Purification by reverse phase HPLC (C-18, 100% water→100% acetonitrile with 0.1% trifluoroacetic acid) gave the title compound (44 mg). MS 552.2558 (M+1).

Example 96

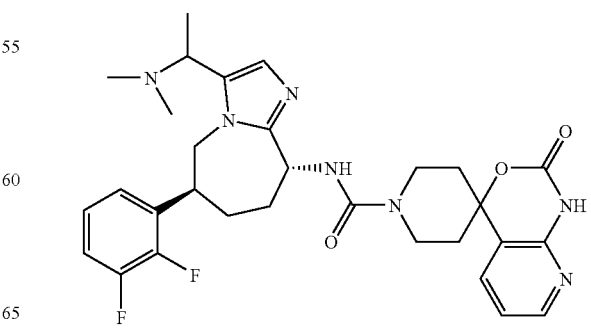

N-{(6S,9R)-6-(2,3-Difluorophenyl)-3-[1-(dimethylamino)ethyl]-6,7,8,9-tetrahydro-5H-imidazo[1,2-a]azepin-9-yl}-2'-oxo-1',2'-dihydro-1H-spiro[piperidine-4,4'-pyrido[2,3-d][1,3]oxazine]-1-carboxamide Sodium cyanoborohydride (5.0 mg, 0.080 mmol) was added to a solution of the hydrochloride salt of N-[(6S,9R)-3-(1-aminoethyl)-6-(2,3-difluorophenyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide (15 mg, 0.023 mmol) and formaldehyde (37% solution in methanol; 27 µL, 0.363 mmol) in methanol (1 mL). After 16 h, the reaction mixture was concentrated. Purification by reverse phase HPLC (100% water→100% acetonitrile with 0.1% trifluoroacetic acid) gave the title compound (15 mg). MS 580.2858 (M+1).

Example 97

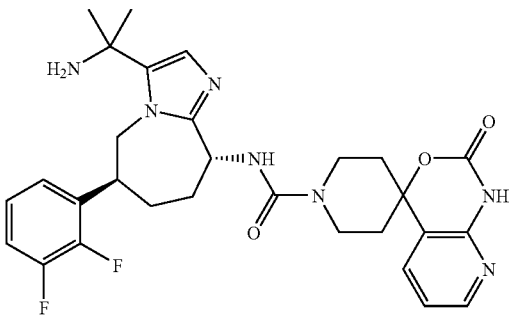

N-[(6S,9R)-3-(1-Amino-1-methylethyl)-6-(2,3-difluorophenyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide Step A: (6S,9R)-3-(1-Azido-1-methylethyl)-6-(2,3-difluorophenyl)-6,7,8,9-tetrahydro-5H-imidazo[1,2-a]azepin-9-amine Methanesulfonic acid (0.30 mL, 4.63 mmol) was added to a solution of tert-butyl [(6S,9R)-6-(2,3-difluorophenyl)-3-(1-methoxy-1-methylethyl)-6,7,8,9-tetrahydro-5H-imidazo[1,2-a]azepin-9-yl]carbamate (50 mg, 0.115 mmol) and sodium azide (170 mg, 2.62 mmol) in chloroform (10 mL). After 1 h, additional methanesulfonic acid (0.95 mL, 14.65 mmol) was added. After 16 h, the reaction mixture was concentrated. Purification by reverse phase HPLC (100% water→100% acetonitrile with 0.1% trifluoroacetic acid) gave the title compound (38 mg). MS 347.1 (M+1).

Step B: N-[(6S,9R)-3-(1-Azido-1-methylethyl)-6-(2,3-difluorophenyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide Triethylamine (15 µL, 0.11 mmol) was added to a solution of (6S,9R)-3-(1-azido-1-methylethyl)-6-(2,3-difluorophenyl)-6,7,8,9-tetrahydro-5H-imidazo[1,2-a]azepin-9-amine (38 mg, 0.11 mmol) and 4-nitrophenyl chloroformate (22 mg, 0.11 mmol) in tetrahydrofuran (5 mL) at 0° C. After 30 min, additional 4-nitrophenyl chloroformate (5 mg, 0.025 mmol) was added. After 10 min, the hydrochloride salt of spiro[piperidine-4,4'-pyrido[2,3-d][1,3]oxazin]-2'(1'H)-one (50 mg, 0.171 mmol) and triethylamine (40 µL, 0.287 mmol) were added and the mixture was allowed to warm to ambient temperature. After 16 h, saturated aqueous sodium carbonate was added and the mixture was extracted with ethyl acetate (3×). The organic extracts were washed with saturated brine, dried over magnesium sulfate, filtered and concentrated. Purification by silica gel chromatography (100% dichloromethane→92% dichloromethane/methanol) gave the title compound (37 mg). MS 592.2 (M+1).

Step C: N-[(6S,9R)-3-(1-Amino-1-methylethyl)-6-(2,3-difluorophenyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide Palladium (10% on carbon; 10 mg) was added to a solution of N-[(6S,9R)-3-(1-azido-1-methylethyl)-6-(2,3-difluorophenyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide (37 mg, 0.063 mmol) in ethyl acetate (5 mL). The reaction vessel was evacuated and back-filled with nitrogen (3×), then back-filled with hydrogen (1 atm). After 3 h, methanol (5 mL) was added. After 18 h, the mixture was filtered and concentrated. Purification by reverse phase HPLC (100% water→100% acetonitrile with 0.1% trifluoroacetic acid) gave the title compound. MS 566.2725 (M+1).

Example 98

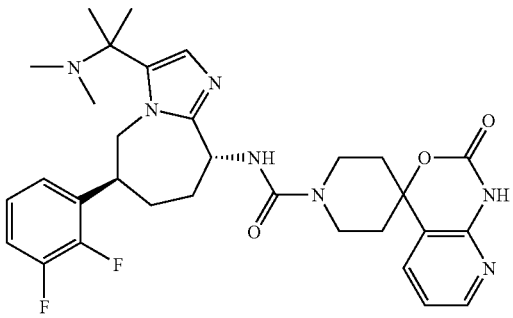

N-{(6S,9R)-6-(2,3-Difluorophenyl)-3-[1-(dimethylamino)-1-methylethyl]-6,7,8,9-tetrahydro-5H-imidazo[1,2-a]azepin-9-yl}-2'-oxo-1',2'-dihydro-1H-spiro[piperidine-4,4'-pyrido[2,3-d][1,3]oxazine]-1-carboxamide Sodium cyanoborohydride (6.0 mg, 0.093 mmol) was added to a solution of the hydrochloride salt of N-[(6S,9R)-3-(1-amino-1-methylethyl)-6-(2,3-difluorophenyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide (18 mg, 0.027 mmol) and formaldehyde (37% solution in methanol; 32 μL, 0.427 mmol) in methanol (1.5 mL). After 1 h, the reaction mixture was concentrated. Purification by reverse phase HPLC (100% water→100% acetonitrile with 0.1% trifluoroacetic acid) gave the title compound (14 mg). MS 594.2992 (M+1).

Example 99

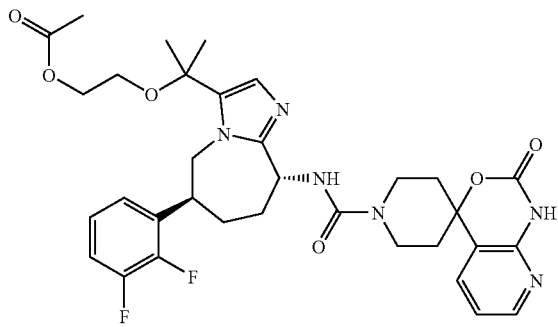

2-[1-((6S,9R)-6-(2,3-Difluorophenyl)-9-{[(2'-oxo-1', 2'-dihydro-1H-spiro[piperidine-4,4'-pyrido[2,3-d][1, 3]oxazin]-1-yl)carbonyl]amino}-6,7,8,9-tetrahydro-5H-imidazo[1,2-a]azepin-3-yl)-1-methylethoxy] ethyl acetate Triethylamine (28 μL, 0.20 mmol) was added to a solution of N-{(6S,9R)-6-(2,3-difluorophenyl)-3-[1-(2-hydroxyethoxy)-1-methylethyl]-6,7,8,9-tetrahydro-5H-imidazo[1,2-a]azepin-9-yl}-2'-oxo-1',2'-dihydro-1H-spiro[piperidine-4, 4'-pyrido[2,3-d][1,3]oxazine]-1-carboxamide (61 mg, 0.10 mmol) and acetyl chloride (14.0 μL, 0.204 mmol) in dichloromethane (5 mL) at 0° C. After 45 min, additional acetyl chloride (7.0 μL, 0.102 mmol) and triethylamine (14 μL, 0.10 mmol) were added. After 20 min, additional acetyl chloride (5.0 μL, 0.07 mmol) was added. After 1 h, the reaction mixture was quenched with water. Saturated aqueous sodium bicarbonate was added and the mixture was extracted with dichloromethane (2×). The organic extracts were dried with magnesium sulfate, filtered and concentrated. Purification by reverse phase HPLC (100% water→100% acetonitrile with 0.1% trifluoroacetic acid) gave the title compound (35 mg). MS 653.2920 (M+1).

Example 100

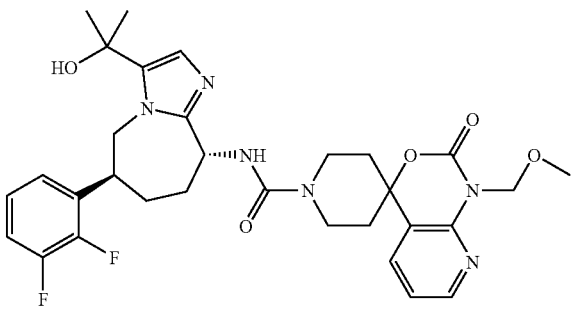

N-[(6S,9R)-6-(2,3-Difluorophenyl)-3-(1-hydroxy-1-methylethyl)-6,7,8,9-tetrahydro-5H-imidazo[1,2-a] azepin-9-yl]-1'-(methoxymethyl)-2'-oxo-1',2'-dihydro-1H-spiro[piperidine-4,4'-pyrido[2,3-d][1,3] oxazine]-1-carboxamide Step A: N-[(6S,9R)-6-(2,3-Difluorophenyl)-3-(1-hydroxy-1-methylethyl)-6,7,8,9-tetrahydro-5H-imidazo[1,2-a]azepin-9-yl]-1'-(methoxymethyl)-2'-oxo-1',2'-dihydro-1H-spiro[piperidine-4,4'-pyrido[2,3-d] [1,3]oxazine]-1-carboxamide Triethylamine (18 μL, 0.126 mmol) was added to a solution of 2-[(6S,9R)-9-amino-6-(2,3-difluorophenyl)-6,7,8,9-tetrahydro-5H-imidazo[1,2-a]azepin-3-yl]propan-2-ol (45 mg, 0.140 mmol) and 4-nitrophenyl chloroformate (31 mg, 0.154 mmol) in tetrahydrofuran (4 mL) at 0° C. After 1 h, 1'-(methoxymethyl)spiro[piperidine-4,4'-pyrido[2,3-d][1,3] oxazin]-2'(1'H)-one (41 mg, 0.154 mmol) and triethylamine (39 μL, 0.378 mmol) were added and the mixture allowed to warm to ambient temperature. After 3 h, saturated aqueous sodium carbonate was added and the mixture was extracted with dichloromethane. The organic layer was washed with saturated aqueous sodium bicarbonate (3×), saturated brine, dried over sodium sulfate, filtered and concentrated. Purification by silica gel chromatography [100% dichloromethane 93% dichloromethane/methanol] gave the title compound (69 mg). MS 611.2780 (M+1).

Example 101

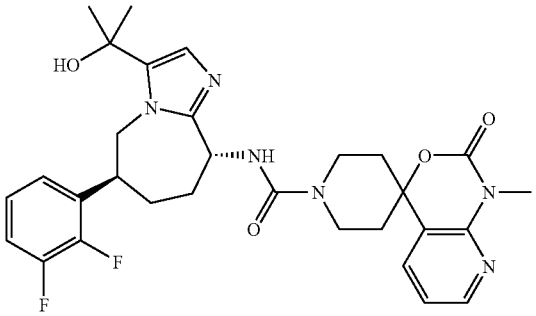

N-[(6S,9R)-6-(2,3-Difluorophenyl)-3-(1-hydroxy-1-methylethyl)-6,7,8,9-tetrahydro-5H-imidazo[1,2-a] azepin-9-yl]-1'-methyl-2'-oxo-1',2'-dihydro-1H-spiro [piperidine-4,4'-pyrido[2,3-d][1,3]oxazine]-1-carboxamide Step A: N-[(6S,9R)-6-(2,3-Difluorophenyl)-3-(1-hydroxy-1-methylethyl)-6,7,8,9-tetrahydro-5H-imidazo[1,2-a]azepin-9-yl]-1'-methyl-2'-oxo-1',2'-dihydro-1H-spiro[piperidine-4,4'-pyrido[2,3-d][1,3] oxazine]-1-carboxamide Triethylamine (18 μL, 0.126 mmol) was added to a solution of 2-[(6S,9R)-9-amino-6-(2,3-difluorophenyl)-6,7,8,9-tetrahydro-5H-imidazo[1,2-a]azepin-3-yl]propan-2-ol (45 mg, 0.140 mmol) and 4-nitrophenyl chloroformate (31 mg, 0.154 mmol) in tetrahydrofuran (4 mL) at 0° C. After 1 h, 1'-methylspiro[piperidine-4,4'-pyrido[2,3-d][1,3]oxazin]-2'(1'H)-one (36 mg, 0.154 mmol) and triethylamine (39 μL, 0.378 mmol) were added and the mixture allowed to warm to ambient temperature. After 3 h, saturated aqueous sodium carbonate was added and the mixture was extracted with dichloromethane. The organic layer was washed with saturated aqueous sodium bicarbonate (3×), saturated brine, dried over sodium sulfate, filtered and concentrated. Purification by silica gel chromatography [100% dichloromethane→93% dichloromethane/methanol] gave the title compound (69 mg). MS 581.2690 (M+1).

Essentially following the procedure outlined for the preparation of Example 101, the Examples in Table 11 were prepared

TABLE 11

| Example | R | MS (M + 1) |
|---|---|---|
| 102 | HO~~~O~~~ (structure) | 625.2981 |
| 103 | CF₃, HO (structure) | 621.2298 |

Example 104

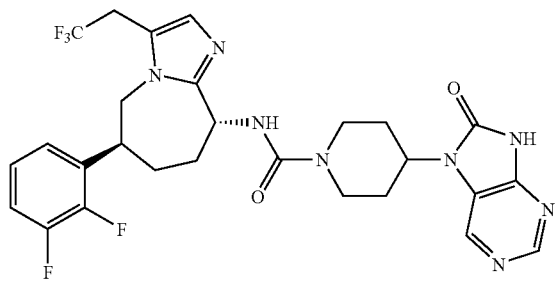

N-[(6S,9R)-6-(2,3-Difluorophenyl)-3-(2,2,2-trifluoroethyl)-6,7,8,9-tetrahydro-5H-imidazo[1,2-a]azepin-9-yl]-4-(8-oxo-8,9-dihydro-7H-purin-7-yl)piperidine-1-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Hydrochloric acid (4.0 M in dioxane; 2.0 mL, 8.0 mmol) was added to a solution of tert-butyl (6S,9R)-6-(2,3-difluorophenyl)-3-(2,2,2-trifluoroethyl)-6,7,8,9-tetrahydro-5H-imidazo[1,2-a]azepin-9-ylcarbamate (100 mg, 0.224 mmol) in dioxane (1 mL). After 1 h, the reaction mixture was concentrated to give the hydrochloride salt of the title compound. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-4-(8-oxo-8,9-dihydro-7H-purin-7-yl)piperidine-1-carboxamide Triethylamine (94 µL, 0.673 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (94 mg, 0.224 mmol) and 4-nitrophenyl chloroformate (45 mg, 0.224 mmol) in tetrahydrofuran (3 mL) at 0° C. After 1 h, 8-oxo-7-piperidinium-4-yl-8,9-dihydro-7H-purin-3-ium dichloride (66 mg, 0.224 mmol) and triethylamine (94 µL, 0.673 mmol) were added and the mixture allowed to warm to ambient temperature. After 1 h, saturated aqueous sodium carbonate was added and the mixture was extracted with dichloromethane. The organic layer was washed with saturated aqueous sodium bicarbonate (3×), saturated brine, dried over sodium sulfate, filtered and concentrated. Purification by reverse phase HPLC (C-18, 95% water/acetonitrile→5% water/acetonitrile with 0.1% trifluoroacetic acid) gave the title compound (76 mg). MS 591.2214 (M+1).

Essentially following the procedure outlined for the preparation of Example 104, the Examples in Table 12 were prepared.

TABLE 12

| Example | R¹ | R² | MS (M + 1) |
|---|---|---|---|
| 105 | cyclopropyl | H | 549.2566 |
| 106 | isopropyl | H | 537.2521 |
| 107 | tetrahydrofuranyl | H | 579.2660 |
| 108 | HO~~~O~~~ | H | 611.2928 |

Example 109

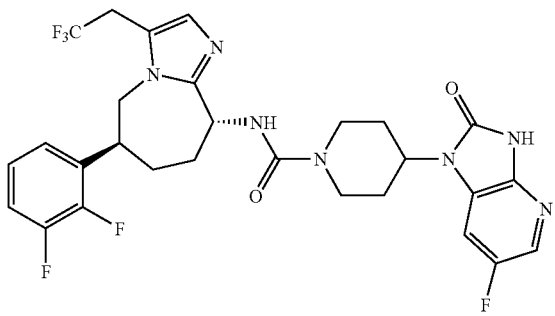

N-[(6S,9R)-6-(2,3-Difluorophenyl)-3-(2,2,2-trifluoroethyl)-6,7,8,9-tetrahydro-5H-imidazo[1,2-a]azepin-9-yl]-4-(6-fluoro-2-oxo-2,3-dihydro-1H-imidazo[4,5-b]pyridin-1-yl)piperidine-1-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Hydrochloric acid (4.0 M in dioxane; 2.0 mL, 8.0 mmol) was added to a solution of tert-butyl (6S,9R)-6-(2,3-difluorophenyl)-3-(2,2,2-trifluoroethyl)-6,7,8,9-tetrahydro-5H-imidazo[1,2-a]azepin-9-ylcarbamate (20 mg, 0.045 mmol) in dioxane (1 mL). After 1 h, the reaction mixture was concentrated to give the hydrochloride salt of the title compound. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-4-(6-fluoro-2-oxo-2,3-dihydro-1H-imidazo[4,5-b]pyridin-1-yl)piperidine-1-carboxamide Triethylamine (19 μL, 0.135 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (18.8 mg, 0.045 mmol) and 4-nitrophenyl chloroformate (9.0 mg, 0.045 mmol) in tetrahydrofuran (2 mL) at 0° C. After 1 h, 6-fluoro-2-oxo-1-piperidinium-4-yl-2,3-dihydro-1H-imidazo[4,5-b]pyridin-4-ium dichloride (14 mg, 0.045 mmol) and triethylamine (19 μL, 0.135 mmol) were added and the mixture allowed to warm to ambient temperature. After 1 h, saturated aqueous sodium carbonate was added and the mixture was extracted with dichloromethane. The organic layer was washed with saturated aqueous sodium bicarbonate (3×), saturated brine, dried over sodium sulfate, filtered and concentrated. Purification by reverse phase HPLC (C-18, 95% water/acetonitrile→5% water/acetonitrile with 0.1% trifluoroacetic acid) gave the title compound (12.5 mg). MS 608.2229 (M+1).

Example 110

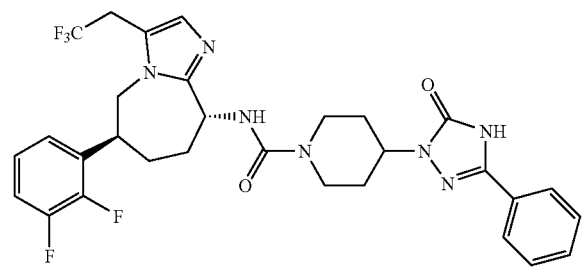

N-[(6S,9R)-6-(2,3-Difluorophenyl)-3-(2,2,2-trifluoroethyl)-6,7,8,9-tetrahydro-5H-imidazo-[1,2-a]azepin-9-yl]-4-(5-oxo-3-phenyl-4,5-dihydro-1H-1,2,4-triazol-1-yl)piperidine-1-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Hydrochloric acid (4.0 M in dioxane; 2.0 mL, 8.0 mmol) was added to a solution of tert-butyl (6S,9R)-6-(2,3-difluorophenyl)-3-(2,2,2-trifluoroethyl)-6,7,8,9-tetrahydro-5H-imidazo[1,2-a]azepin-9-ylcarbamate (20 mg, 0.045 mmol) in dioxane (1 mL). After 1 h, the reaction mixture was concentrated to give the hydrochloride salt of the title compound. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-4-(5-oxo-3-phenyl-4,5-dihydro-1H-1,2,4-triazol-1-yl)piperidine-1-carboxamide Triethylamine (19 μL, 0.135 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (18.8 mg, 0.045 mmol) and 4-nitrophenyl chloroformate (9.0 mg, 0.045 mmol) in tetrahydrofuran (2 mL) at 0° C. After 1 h, 5-phenyl-2-piperidin-4-yl-2,4-dihydro-3H-1,2,4-triazol-3-one (11 mg, 0.045 mmol) and triethylamine (19 μL, 0.135 mmol) were added and the mixture allowed to warm to ambient temperature. After 1 h, saturated aqueous sodium carbonate was added and the mixture was extracted with dichloromethane. The organic layer was washed with saturated aqueous sodium bicarbonate (3×), saturated brine, dried over sodium sulfate, filtered and concentrated. Purification by reverse phase HPLC (C-18, 95% water/acetonitrile→5% water/acetonitrile with 0.1% trifluoroacetic acid) gave the title compound (11 mg). MS 616.2509 (M+1).

Example 111

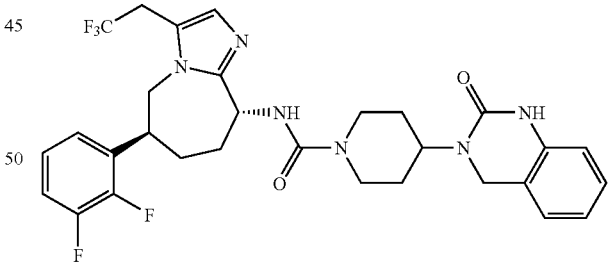

N-[(6S,9R)-6-(2,3-Difluorophenyl)-3-(2,2,2-trifluoroethyl)-6,7,8,9-tetrahydro-5H-imidazo[1,2-a]azepin-9-yl]-4-(5-oxo-3-phenyl-4,5-dihydro-1H-1,2,4-triazol-1-yl)piperidine-1-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Hydrochloric acid (4.0 M in dioxane; 2.0 mL, 8.0 mmol) was added to a solution of tert-butyl (6S,9R)-6-(2,3-difluorophenyl)-3-(2,2,2-trifluoroethyl)-6,7,8,9-tetrahydro-5H-imidazo[1,2-a]azepin-9-ylcarbamate (20 mg, 0.045 mmol) in dioxane (1 mL). After 1 h, the reaction mixture was concentrated to give the hydrochloride salt of the title compound. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-4-(5-oxo-3-phenyl-4,5-dihydro-1H-1,2,4-triazol-1-yl)piperidine-1-carboxamide Triethylamine (19 µL, 0.135 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (18.8 mg, 0.045 mmol) and 4-nitrophenyl chloroformate (9.0 mg, 0.045 mmol) in tetrahydrofuran (2 mL) at 0° C. After 1 h, 3-piperidin-4-yl-3,4-dihydroquinazolin-2(1H)-one (10 mg, 0.045 mmol) and triethylamine (19 µL, 0.135 mmol) were added and the mixture allowed to warm to ambient temperature. After 1 h, saturated aqueous sodium carbonate was added and the mixture was extracted with dichloromethane. The organic layer was washed with saturated aqueous sodium bicarbonate (3×), saturated brine, dried over sodium sulfate, filtered and concentrated. Purification by reverse phase HPLC (C-18, 95% water/acetonitrile→5% water/acetonitrile with 0.1% trifluoroacetic acid) gave the title compound (7.8 mg). MS 603.2536 (M+1).

Example 112

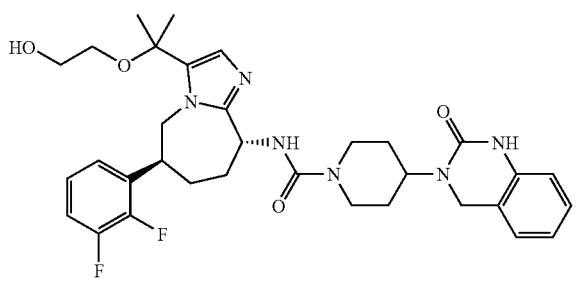

N-{(6S,9R)-6-(2,3-Difluorophenyl)-3-[1-(2-hydroxyethoxy)-1-methylethyl]-6,7,8,9-tetrahydro-5H-imidazo[1,2-a]azepin-9-yl}-4-(2-oxo-1,4-dihydroquinazolin-3(2H)-yl)piperidine-1-carboxamide Triethylamine (5.0 µL, 0.037 mmol) was added to a solution of 2-{1-[(6S,9R)-9-amino-6-(2,3-difluorophenyl)-6,7,8,9-tetrahydro-5H-imidazo[1,2-a]azepin-3-yl]-1-methylethoxy}ethanol (15.0 mg, 0.041 mmol) and 4-nitrophenyl chloroformate (9.0 mg, 0.045 mmol) in tetrahydrofuran (1 mL) at 0° C. After 15 min, 3-piperidin-4-yl-3,4-dihydroquinazolin-2(1H)-one (9.0 mg, 0.041 mmol) and triethylamine (17 µL, 0.12 mmol) were added and the mixture was allowed to warm to ambient temperature. After 1 h, saturated aqueous sodium carbonate was added and the mixture was extracted with dichloromethane (3×). The organic layer was washed with saturated brine, dried over magnesium sulfate, filtered and concentrated. Purification by reverse phase HPLC (95% water/acetonitrile→5% water/acetonitrile with 0.1% trifluoroacetic acid) gave the title compound (8.5 mg). MS 623.3163 (M+1).

Example 113

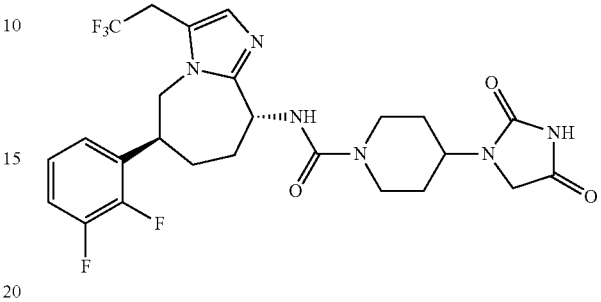

N-[(6S,9R)-6-(2,3-Difluorophenyl)-3-(2,2,2-trifluoroethyl)-6,7,8,9-tetrahydro-5H-imidazo[1,2-a]azepin-9-yl]-4-(2,4-dioxoimidazolidin-1-yl)piperidine-1-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Trifluoroacetic acid (2 mL) was added to a solution of tert-butyl (6S,9R)-6-(2,3-difluorophenyl)-3-(2,2,2-trifluoroethyl)-6,7,8,9-tetrahydro-5H-imidazo[1,2-a]azepin-9-ylcarbamate (50 mg, 0.112 mmol) in dichloromethane (2 mL). After 1 h, saturated sodium bicarbonate was added. The mixture was extracted with dichloromethane (3×), and the combined organic extracts were washed with saturated brine, dried over sodium sulfate, filtered and concentrated. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-4-(2,4-dioxoimidazolidin-1-yl)piperidine-1-carboxamide Triethylamine (16 µL, 0.11 mmol) was added to a solution of (6S,9R)-6-(2,3-difluorophenyl)-3-(2,2,2-trifluoroethyl)-6,7,8,9-tetrahydro-5H-imidazo[1,2-a]azepin-9-amine (38 mg, 0.11 mmol) and 4-nitrophenyl chloroformate (23 mg, 0.11 mmol) in tetrahydrofuran (2 mL) at 0° C. After 1 h, 1-piperidin-4-ylimidazolidine-2,4-dione (21 mg, 0.11 mmol) and triethylamine (47 µL, 0.33 mmol) were added and the mixture allowed to warm to ambient temperature. After 1 h, saturated aqueous sodium carbonate was added and the mixture was extracted with dichloromethane. The organic layer was washed with saturated aqueous sodium bicarbonate (3×), saturated brine, dried over sodium sulfate, filtered and concentrated. Purification by silica gel chromatography [100% dichloromethane→93% dichloromethane/methanol] gave the title compound (36 mg). MS 555.2126 (M+1).

Essentially following the procedure outlined for the preparation of Example 113, the Examples in Table 13 were prepared.

TABLE 13

![Structure with R1, R2 substituents on imidazo-azepine core]

| Example | R¹ | R² | MS (M + 1) |
|---------|----|----|------------|
| 114 | F₃C-cyclopropyl-CH₂- | H | 581.2318 |
| 115 | CH₃O-C(CH₃)₂-CH₂- | H | 545.2709 |
| 116 | HO-C(CH₃)₂-CH₂- | H | 531.2541 |
| 117 | cyclopropyl-CH₂-CH₂- | H | 527.2591 |
| 118 | F₃C-CH(CH₃)-CH₂- | H | 569.2255 |
| 119 | HO-CH₂CH₂-O-C(CH₃)₂-CH₂- | H | 575.2775 |

Example 120

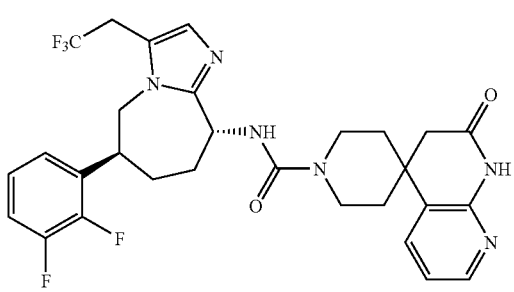

N-[(6S,9R)-6-(2,3-Difluorophenol)-3-(2,2,2-trifluoroethyl)-6,7,8,9-tetrahydro-5H-imidazo[1,2-a]azepin-9-yl]-2-oxo-2,3-dihydro-1H,1'H-spiro[1,8-naphthyridine-4,4'-piperidine]-1'-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Trifluoroacetic acid (2 mL) was added to a solution of tert-butyl (6S,9R)-6-(2,3-difluorophenyl)-3-(2,2,2-trifluoroethyl)-6,7,8,9-tetrahydro-5H-imidazo[1,2-a]azepin-9-ylcarbamate (50 mg, 0.112 mmol) in dichloromethane (2 mL). After 1 h, saturated sodium bicarbonate was added. The mixture was extracted with dichloromethane (3×), and the combined organic extracts were washed with saturated brine, dried over sodium sulfate, filtered and concentrated. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-2-oxo-2,3-dihydro-1H,1'H-spiro[1,8-naphthyridine-4,4'-piperidine]-1'-carboxamide Triethylamine (24 μL, 0.174 mmol) was added to a solution of (6S,9R)-6-(2,3-difluorophenyl)-3-(2,2,2-trifluoroethyl)-6,7,8,9-tetrahydro-5H-imidazo[1,2-a]azepin-9-amine (30 mg, 0.087 mmol) and 4-nitrophenyl chloroformate (18 mg, 0.091 mmol) in tetrahydrofuran (1 mL) at 0° C. After 1 h, 1H-spiro[1,8-naphthyridine-4,4'-piperidin]-2(3H)-one (21 mg, 0.096 mmol), triethylamine (48 μL, 0.348 mmol) and dichloromethane (1 mL) were added and the mixture allowed to warm to ambient temperature. After 1 h, saturated aqueous sodium carbonate was added and the mixture was extracted with dichloromethane. The organic layer was washed with saturated aqueous sodium bicarbonate (3×), saturated brine, dried over sodium sulfate, filtered and concentrated. Purification by silica gel chromatography [100% dichloromethane→88% dichloromethane/methanol] gave the title compound (9.5 mg). MS 589.2369 (M+1).

Example 121

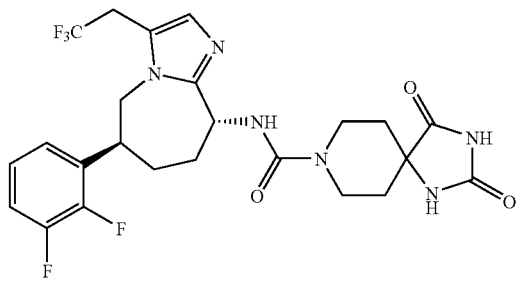

N-[(6S,9R)-6-(2,3-Difluorophenyl)-3-(2,2,2-trifluoroethyl)-6,7,8,9-tetrahydro-5H-imidazo[1,2-a]azepin-9-yl]-2,4-dioxo-1,3,8-triazaspiro[4.5]decane-8-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Trifluoroacetic acid (2 mL) was added to a solution of tert-butyl (6S,9R)-6-(2,3-difluorophenyl)-3-(2,2,2-trifluoroethyl)-6,7,8,9-tetrahydro-5H-imidazo[1,2-a]azepin-9-ylcarbamate (50 mg, 0.112 mmol) in dichloromethane (2 mL). After 1 h, saturated sodium bicarbonate was added. The mixture was extracted with dichloromethane (3×), and the combined organic extracts were washed with saturated brine, dried over sodium sulfate, filtered and concentrated. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-2,4-dioxo-1,3,8-triazaspiro[4.5]decane-8-carboxamide Triethylamine (12 µL, 0.087 mmol) was added to a solution of (6S,9R)-6-(2,3-difluorophenyl)-3-(2,2,2-trifluoroethyl)-6,7,8,9-tetrahydro-5H-imidazo[1,2-a]azepin-9-amine (30 mg, 0.087 mmol) and 4-nitrophenyl chloroformate (18 mg, 0.091 mmol) in tetrahydrofuran (1 mL) at 0° C. After 1 h, 1,3,8-triazaspiro[4.5]decane-2,4-dione (15 mg, 0.091 mmol), triethylamine (48 µL, 0.348 mmol) and N,N-dimethylformamide (1 mL) were added and the mixture heated to 40° C. After 18 h, saturated aqueous sodium carbonate was added and the mixture was extracted with dichloromethane. The organic layer was washed with saturated aqueous sodium bicarbonate (3×), saturated brine, dried over sodium sulfate, filtered and concentrated. Purification by silica gel chromatography [100% dichloromethane→88% dichloromethane/methanol] gave the title compound (12 mg). MS 541.1955 (M+1).

Example 122

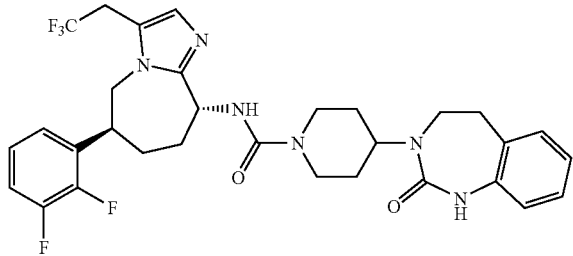

N-[(6S,9R)-6-(2,3-Difluorophenyl)-3-(2,2,2-trifluoroethyl)-6,7,8,9-tetrahydro-5H-imidazo[1,2-a]azepin-9-yl]-4-(2-oxo-1,2,4,5-tetrahydro-3H-1,3-benzodiazepin-3-yl)piperidine-1-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Trifluoroacetic acid (1 mL, 13.5 mmol) was added to a solution of tert-butyl [(6S,9R)-6-(2,3-difluorophenyl)-3-(2,2,2-trifluoroethyl)-6,7,8,9-tetrahydro-5H-imidazo[1,2-a]azepin-9-yl]carbamate (110 mg, 0.57 mmol) in dichloromethane (2 mL). After 2 h, saturated aqueous sodium bicarbonate was added and the mixture was extracted with dichloromethane (3×). The combined organic extracts were washed with saturated brine, dried over magnesium sulfate, filtered and concentrated. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-4-(2-oxo-1,2,4,5-tetrahydro-3H-1,3-benzodiazepin-3-yl)piperidine-1-carboxamide Triethylamine (7.0 µL, 0.05 mmol) was added to a solution of (6S,9R)-6-(2,3-difluorophenyl)-3-(2,2,2-trifluoroethyl)-6,7,8,9-tetrahydro-5H-imidazo[1,2-a]azepin-9-amine (17 mg, 0.05 mmol) and 4-nitrophenyl chloroformate (10.0 mg, 0.05 mmol) in tetrahydrofuran (3 mL) at 0° C. After 20 min, the hydrochloride salt of 3-piperidin-4-yl-1,3,4,5-tetrahydro-2H-1,3-benzodiazepin-2-one (14 mg, 0.05 mmol) and triethylamine (21 µL, 0.15 mmol) were added and the mixture allowed to warm to ambient temperature. After 1 h, saturated aqueous sodium carbonate was added and the mixture was extracted with dichloromethane (3×). The organic layer was washed with saturated brine, dried over magnesium sulfate, filtered and concentrated. Purification by silica gel chromatography (100% dichloromethane→93% dichloromethane/methanol) gave the title compound (22 mg). MS 617.2609 (M+1).

Essentially following the procedure outlined for the preparation of Example 122, the Examples in Table 14 were prepared.

TABLE 14

| Example | R¹ | R² | MS (M + 1) |
|---|---|---|---|
| 123 | ![F3C-cyclopropyl] | H | 643.2844 |
| 124 | ![HO-C(CH3)2] | H | 593.3057 |
| 125 | ![MeO-C(CH3)2] | H | 607.3168 |
| 126 | ![HO-CH2CH2-O-C(CH3)2] | H | 637.3306 |

Example 127

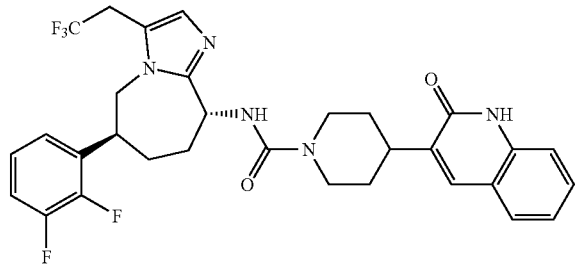

N-[(6S,9R)-6-(2,3-Difluorophenyl)-3-(2,2,2-trifluoroethyl)-6,7,8,9-tetrahydro-5H-imidazo[1,2-a]azepin-9-yl]-4-(2-oxo-1,2-dihydroquinolin-3-yl)piperidine-1-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Trifluoroacetic acid (1 mL, 13.5 mmol) was added to a solution of tert-butyl [(6S,9R)-6-(2,3-difluorophenyl)-3-(2,2,2-trifluoroethyl)-6,7,8,9-tetrahydro-5H-imidazo[1,2-a]azepin-9-yl]carbamate (110 mg, 0.57 mmol) in dichloromethane (2 mL). After 2 h, saturated aqueous sodium bicarbonate was added and the mixture was extracted with dichloromethane (3×). The combined organic extracts were washed with saturated brine, dried over magnesium sulfate, filtered and concentrated. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-4-(2-oxo-1,2-dihydroquinolin-3-yl)piperidine-1-carboxamide Triethylamine (5.0 µL, 0.035 mmol) was added to a solution of (6S,9R)-6-(2,3-difluorophenyl)-3-(2,2,2-trifluoroethyl)-6,7,8,9-tetrahydro-5H-imidazo[1,2-a]azepin-9-amine (12.0 mg, 0.035 mmol) and 4-nitrophenyl chloroformate (7.0 mg, 0.035 mmol) in tetrahydrofuran (3 mL) at 0° C. After 20 min, 3-piperidin-4-ylquinolin-2(1H)-one (8.0 mg, 0.035 mmol) and triethylamine (15 µL, 0.11 mmol) were added and the mixture allowed to warm to ambient temperature. After 1 h, saturated aqueous sodium carbonate was added and the mixture was extracted with dichloromethane (3×). The organic layer was washed with saturated brine, dried over magnesium sulfate, filtered and concentrated. Purification by silica gel chromatography (100% dichloromethane→93% dichloromethane/methanol) gave the title compound (17 mg). MS 600.2340 (M+1).

Essentially following the procedure outlined for the preparation of Example 127, the Examples in Table 15 were prepared.

TABLE 15

| Example | R¹ | R² | MS (M + 1) |
|---------|----|----|------------|
| 128 | HO-CH₂CH₂-O-C(CH₃)₂- | H | 620.3049 |
| 129 | HO-C(CH₃)₂- | H | 576.2749 |
| 130 | F₃C-cyclopropyl- | H | 626.2516 |
| 131 | CH₃O-C(CH₃)₂- | H | 590.2894 |

Example 132

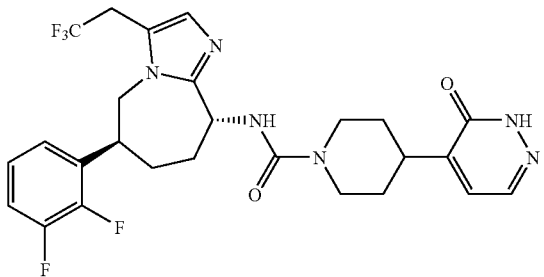

N-[(6S,9R)-6-(2,3-Difluorophenyl)-3-(2,2,2-trifluoroethyl)-6,7,8,9-tetrahydro-5H-imidazo[1,2-a]azepin-9-yl]-4-(3-oxo-2,3-dihydropyridazin-4-yl)piperidine-1-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Hydrochloric acid (4.0 M in dioxane; 1 mL, 4.0 mmol) was added to a solution of tert-butyl [(6S,9R)-6-(2,3-difluorophenyl)-3-(2,2,2-trifluoroethyl)-6,7,8,9-tetrahydro-5H-imidazo[1,2-a]azepin-9-yl]carbamate (36.0 mg, 0.081 mmol) in dioxane (1 mL). After 18 h, the reaction mixture was concentrated to give the hydrochloride salt of the title compound. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-4-(3-oxo-2,3-dihydropyridazin-4-yl)piperidine-1-carboxamide Triethylamine (37 µL, 0.50 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (70 mg, 0.167 mmol) and 4-nitrophenyl chloroformate (34 mg, 0.167 mmol) in tetrahydrofuran (1 mL) at 0° C. After 15 min, a solution of 4-piperidin-4-ylpyridazin-3(2H)-one (30 mg, 0.167 mmol) in dichloromethane (1 mL) and triethylamine (49 µL, 0.67 mmol) were added and the mixture allowed to warm to ambient temperature. After 4 h, saturated aqueous sodium carbonate was added and the mixture was extracted with ethyl acetate (3×). The organic layer was washed with saturated aqueous sodium bicarbonate (3×), saturated brine, dried over magnesium sulfate, filtered and concentrated. Purification by silica gel chromatography (100% dichloromethane→90% dichloromethane/methanol) gave the title compound (51 mg). MS 551.2152 (M+1).

Essentially following the procedure outlined for the preparation of Example 132, the Examples in Table 16 were prepared.

TABLE 16

| Example | R¹ | R² | MS (M + 1) |
|---|---|---|---|
| 133 | F₃C-CH₂-CH₂- | H | 565.2329 |
| 134 | MeO-C(CH₃)₂- | H | 541.2760 |
| 135 | F₃C-cyclopropyl- | H | 577.2360 |
| 136 | (CH₃)₂CH- | H | 527.2597 |

Example 137

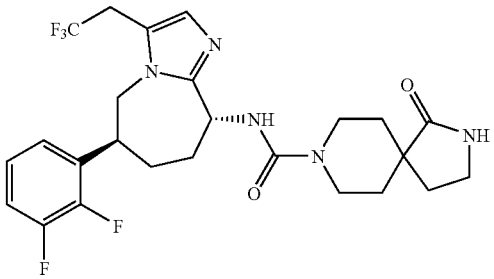

N-[(6S,9R)-6-(2,3-Difluorophenyl)-3-(2,2,2-trifluoroethyl)-6,7,8,9-tetrahydro-5H-imidazo[1,2-a]azepin-9-yl]-1-oxo-2,8-diazaspiro[4.5]decane-8-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Hydrochloric acid (4.0 M in dioxane; 1 mL, 4.0 mmol) was added to a solution of tert-butyl [(6S,9R)-6-(2,3-difluorophenyl)-3-(2,2,2-trifluoroethyl)-6,7,8,9-tetrahydro-5H-imidazo[1,2-a]azepin-9-yl]carbamate (36.0 mg, 0.081 mmol) in dioxane (1 mL). After 18 h, the reaction mixture was concentrated to give the hydrochloride salt of the title compound. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-1-oxo-2,8-diazaspiro[4.5]decane-8-carboxamide Triethylamine (32.2 µL, 0.23 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (32 mg, 0.077 mmol) and 4-nitrophenyl chloroformate (15 mg, 0.077 mmol) in tetrahydrofuran (1 mL) at 0° C. After 15 min, a solution of the hydrochloride salt of 2,8-diazaspiro[4.5]decan-1-one (15 mg, 0.077 mmol) in dichloromethane (1 mL) and triethylamine (43 µL, 0.31 mmol) were added and the mixture allowed to warm to ambient temperature. After 72 h, saturated aqueous sodium carbonate was added and the mixture was extracted with ethyl acetate (3×). The organic layer was washed with saturated aqueous sodium bicarbonate (3×), saturated brine, dried over magnesium sulfate, filtered and concentrated. Purification by silica gel chromatography (100% dichloromethane→87% dichloromethane/methanol) gave the title compound (13 mg). MS 526.2204 (M+1).

Essentially following the procedure outlined for the preparation of Example 137, the Examples in Table 17 were prepared.

TABLE 17

| Example | R¹ | R² | MS (M + 1) |
|---|---|---|---|
| 138 | HO-C(CH₃)₂- | H | 502.2641 |
| 139 | MeO-C(CH₃)₂- | H | 516.2807 |

Example 140

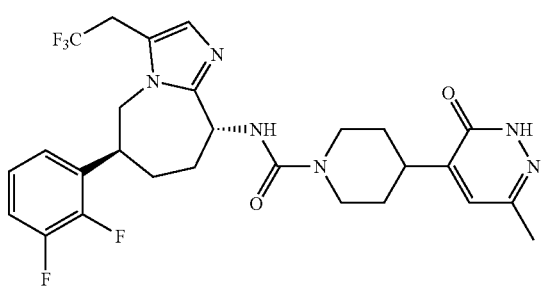

N-[(6S,9R)-6-(2,3-Difluorophenyl)-3-(2,2,2-trifluoroethyl)-6,7,8,9-tetrahydro-5H-imidazo[1,2-a]azepin-9-yl]-4-(6-methyl-3-oxo-2,3-dihydropyridazin-4-yl)piperidine-1-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Hydrochloric acid (4.0 M in dioxane; 1 mL, 4.0 mmol) was added to a solution of tert-butyl [(6S,9R)-6-(2,3-difluorophenyl)-3-(2,2,2-trifluoroethyl)-6,7,8,9-tetrahydro-5H-imidazo[1,2-a]azepin-9-yl]carbamate (36 mg, 0.081 mmol) in dioxane (1 mL). After 18 h, the mixture was concentrated to give the hydrochloride salt of the title compound. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-4-(6-methyl-3-oxo-2,3-dihydropyridazin-4-yl)piperidine-1-carboxamide Triethylamine (33.0 μL, 0.24 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (33.0 mg, 0.079 mmol) and 4-nitrophenyl chloroformate (16.0 mg, 0.079 mmol) in tetrahydrofuran (1 mL) at 0° C. After 15 min, a solution of 6-methyl-4-piperidin-4-ylpyridazin-3(2H)-one (15.0 mg, 0.079 mmol) in dichloromethane (1 mL) and triethylamine (22 μL, 0.16 mmol) were added and the mixture allowed to warm to ambient temperature. After 4 h, saturated aqueous sodium carbonate was added and the mixture was extracted with ethyl acetate (3×). The organic layer was washed with saturated aqueous sodium bicarbonate (3×), saturated brine, dried over magnesium sulfate, filtered and concentrated. Purification by silica gel chromatography (100% dichloromethane→90% dichloromethane/methanol) gave the title compound (22 mg). MS 565.2306 (M+1).

Essentially following the procedure outlined for the preparation of Example 140, the Examples in Table 18 were prepared.

TABLE 18

| Example | R¹ | R² | MS (M + 1) |
|---|---|---|---|
| 141 | HO-C(CH₃)₂- | H | 541.2 |
| 142 | HO-CH₂CH₂-O-C(CH₃)₂- | H | 585.3020 |
| 143 | MeO-C(CH₃)₂- | H | 555.2885 |

Example 144

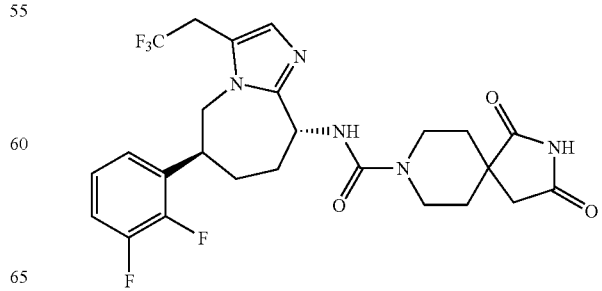

N-[(6S,9R)-6-(2,3-Difluorophenyl)-3-(2,2,2-trifluoroethyl)-6,7,8,9-tetrahydro-5H-imidazo[1,2-a]azepin-9-yl]-1,3-dioxo-2,8-diazaspiro[4.5]decane-8-carboxamide

Step A: (6S,9R)-6-(2,3-Difluorophenyl)-3-(2,2,2-trifluoroethyl-6,7,8,9-tetrahydro-5H-imidazo[1,2-a]azepin-9-amine Hydrochloric acid (4.0 M in dioxane; 1 mL, 4.0 mmol) was added to a solution of tert-butyl [(6S,9R)-6-(2,3-difluorophenyl)-3-(2,2,2-trifluoroethyl)-6,7,8,9-tetrahydro-5H-imidazo[1,2-a]azepin-9-yl]carbamate (36 mg, 0.081 mmol) in dioxane (1 mL). After 18 h, the mixture was concentrated to give the hydrochloride salt of the title compound. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-1,3-dioxo-2,8-diazaspiro[4.5]decane-8-carboxamide Triethylamine (0.28 mL, 1.97 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (275 mg, 0.66 mmol) and 4-nitrophenyl chloroformate (139 mg, 0.69 mmol) in tetrahydrofuran (2.5 mL) at 0° C. After 15 min, a solution of the acetate salt of 2,8-diazaspiro[4.5]decane-1,3-dione (WO 2004/076455) (180 mg, 0.79 mmol) in dichloromethane (2.5 mL) and triethylamine (0.28 mL, 1.97 mmol) were added and the mixture was allowed to warm to ambient temperature. After 2 h, saturated aqueous sodium carbonate was added and the mixture was extracted with ethyl acetate (3×). The organic layer was washed with saturated aqueous sodium bicarbonate (3×), saturated brine, dried over magnesium sulfate, filtered and concentrated. Purification by silica gel chromatography (100% dichloromethane→90% dichloromethane/methanol) gave the title compound (213 mg). MS 540.2005 (M+1).

Essentially following the procedure outlined for the preparation of Example 144, the Examples in Table 19 were prepared.

TABLE 19

| Example | R | MS (M + 1) |
|---|---|---|
| 145 | ![F3C-cyclopropyl] | 566.2230 |
| 146 | 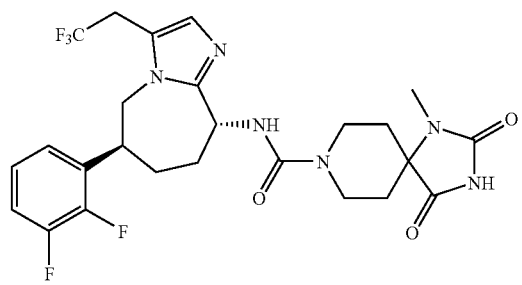 | 530.2582 |

Example 147

N-[(6S,9R)-6-(2,3-Difluorophenyl)-3-(2,2,2-trifluoroethyl)-6,7,8,9-tetrahydro-5H-imidazo[1,2-a]azepin-9-yl]-1-methyl-2,4-dioxo-1,3,8-triazaspiro[4.5]decane-8-carboxamide

Step A: (6S,9R)-6-(2,3-Difluorophenyl)-3-(2,2,2-trifluoroethyl)-6,7,8,9-tetrahydro-5H-imidazo[1,2-a]azepin-9-amine Trifluoroacetic acid (1 mL, 13.5 mmol) was added to a solution of tert-butyl [(6S,9R)-6-(2,3-difluorophenyl)-3-(2,2,2-trifluoroethyl)-6,7,8,9-tetrahydro-5H-imidazo[1,2-a]azepin-9-yl]carbamate (120 mg, 0.27 mmol) in dichloromethane (2 mL). After 1 h, the mixture was concentrated and saturated aqueous sodium bicarbonate was added. The mixture was extracted with dichloromethane (3×), and the combined organic extracts were washed with saturated brine, dried over magnesium sulfate, filtered and concentrated. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-1-methyl-2,4-dioxo-1,3,8-triazaspiro[4.5]decane-8-carboxamide Triethylamine (70 µL, 0.50 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2- a]azepin-9-amine (70 mg, 0.167 mmol) and 4-nitrophenyl chloroformate (34 mg, 0.167 mmol) in tetrahydrofuran (2 mL) at 0° C. After 15 min, a solution of 1-methyl-1,3,8-triazaspiro[4.5]decane-2,4-dione (31 mg, 0.167 mmol) in dichloromethane (2 mL) and triethylamine (93 μL, 0.67 mmol) were added and the mixture was allowed to warn to ambient temperature. After 4 h, saturated aqueous sodium carbonate was added and the mixture was extracted with ethyl acetate. The organic layer was washed with saturated aqueous sodium bicarbonate (3×), saturated brine, dried over magnesium sulfate, filtered and concentrated. Purification by silica gel chromatography (100% dichloromethane→90% dichloromethane/methanol) gave the title compound (33 mg). MS 555.2107 (M+1).

Example 148

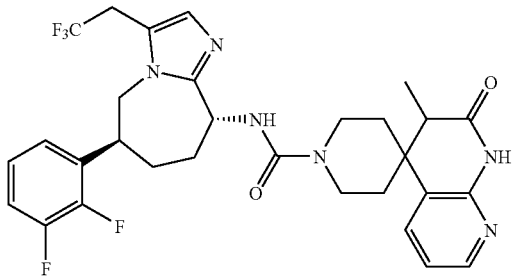

N-[(6S,9R)-6-(2,3-Difluorophenyl)-3-(2,2,2-trifluoroethyl)-6,7,8,9-tetrahydro-5H-imidazo[1,2-a]azepin-9-yl]-3-methyl-2-oxo-2,3-dihydro-1H,1'H-spiro[1,8-naphthyridine-4,4'-piperidine]-1'-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Trifluoroacetic acid (1 mL, 13.5 mmol) was added to a solution of tert-butyl [(6S,9R)-6-(2,3-difluorophenyl)-3-(2,2,2-trifluoroethyl)-6,7,8,9-tetrahydro-5H-imidazo[1,2-a]azepin-9-yl]carbamate (120 mg, 0.27 mmol) in dichloromethane (2 mL). After 1 h, the mixture was concentrated and saturated aqueous sodium bicarbonate was added. The mixture was extracted with dichloromethane (3×), and the combined organic extracts were washed with saturated brine, dried over magnesium sulfate, filtered and concentrated. MS 346.1 (M+1).

Step B: N-[(6S,9R)-6-(2,3-Difluorophenyl-3-(2,2,2-trifluoroethyl)-6,7,8,9-tetrahydro-5H-imidazo[1,2-a]azepin-9-yl]-3-methyl-2-oxo-2,3-dihydro-1H,1'H-spiro[1,8-naphthyridine-4,4'-piperidine]-1'-carboxamide Triethylamine (30 μL, 0.22 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (30 mg, 0.07 mmol) and 4-nitrophenyl chloroformate (14 mg, 0.07 mmol) in tetrahydrofuran (1 mL) at 0° C. After 15 min, a solution of 3-methyl-1H-spiro[1,8-naphthyridine-4,4'-piperidin]-2(3H)-one (17 mg, 0.07 mmol) in dichloromethane (1 mL) and triethylamine (40 μL, 0.29 mmol) were added and the mixture was allowed to warm to ambient temperature. After 72 h, saturated aqueous sodium carbonate was added and the mixture was extracted with ethyl acetate. The organic layer was washed with saturated aqueous sodium bicarbonate (3×), saturated brine, dried over magnesium sulfate, filtered and concentrated. Purification by silica gel chromatography (100% dichloromethane→90% dichloromethane/methanol) gave the title compound (10.9 mg). MS 603.2451 (M+1).

Example 149

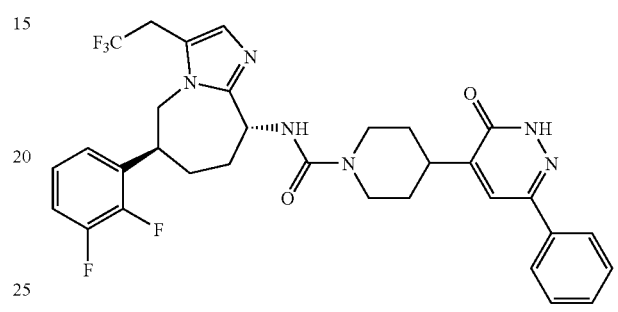

N-[(6S,9R)-6-(2,3-Difluorophenyl)-3-(2,2,2-trifluoroethyl)-6,7,8,9-tetrahydro-5H-imidazo[1,2-a]azepin-9-yl]-4-(3-oxo-6-phenyl-2,3-dihydropyridazin-4-yl)piperidine-1-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Trifluoroacetic acid (1 mL, 13.5 mmol) was added to a solution of tert-butyl [(6S,9R)-6-(2,3-difluorophenyl)-3-(2,2,2-trifluoroethyl)-6,7,8,9-tetrahydro-5H-imidazo[1,2-a]azepin-9-yl]carbamate (120 mg, 0.27 mmol) in dichloromethane (2 mL). After 1 h, the mixture was concentrated and saturated aqueous sodium bicarbonate was added. The mixture was extracted with dichloromethane (3×), and the combined organic extracts were washed with saturated brine, dried over magnesium sulfate, filtered and concentrated. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-4-(3-oxo-6-phenyl-2,3-dihydropyridazin-4-yl)piperidine-1-carboxamide Triethylamine (33 μL, 0.24 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (33 mg, 0.08 mmol) and 4-nitrophenyl chloroformate (16 mg, 0.08 mmol) in tetrahydrofuran (1 mL) at 0° C. After 15 min, a solution of 6-phenyl-4-piperidin-4-ylpyridazin-3(2H)-one (20 mg, 0.08 mmol) in dichloromethane (1 mL) and triethylamine (22 μL, 0.16 mmol) were added and the mixture allowed to warm to ambient temperature. After 2 h, saturated aqueous sodium carbonate was added and the mixture was extracted with ethyl acetate. The organic layer was washed with saturated aqueous sodium bicarbonate (3×), saturated brine, dried over magnesium sulfate, filtered and concentrated. Purification by silica gel chromatography (100% dichloromethane→90% dichloromethane/methanol) gave the title compound (22 mg). MS 627.2498 (M+1).

Example 150 and Example 151

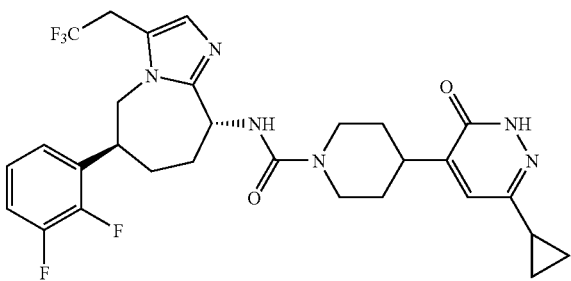

4-(6-Cyclopropyl-3-oxo-2,3-dihydropyridazin-4-yl)-
N-[(6S,9R)-6-(2,3-difluorophenyl)-3-(2,2,2-trifluoroethyl)-6,7,8,9-tetrahydro-5H-imidazo[1,2-a]
azepin-9-yl]piperidine-1-carboxamide and N-[(6S,9R)-6-(2,3-difluorophenyl)-3-(2,2,2-trifluoroethyl)-6,7,8,9-tetrahydro-5H-imidazo[1,2-a]azepin-9-yl]-4-
(3-oxo-6-propyl-2,3-dihydropyridazin-4-yl)
piperidine-1-carboxamide Step A: (6S,9R)-6-(2,3-Difluorophenyl)-3-(2,2,2-trifluoroethyl)-6,7,8,9-tetrahydro-5H-imidazo[1,2-a]
azepin-9-amine Hydrochloric acid (4.0 M in dioxane; 1 mL, 4.0 mmol) was added to a solution of tert-butyl [(6S,9R)-6-(2,3-difluorophenyl)-3-(2,2,2-trifluoroethyl)-6,7,8,9-tetrahydro-5H-imidazo[1,2-a]azepin-9-yl]carbamate (36 mg, 0.081 mmol) in dioxane (1 mL). After 18 h, the reaction mixture was concentrated to give the hydrochloride salt of the title compound. MS 346.1 (M+1).

Step B: 4-(6-Cyclopropyl-3-oxo-2,3-dihydropyridazin-4-yl)-N-[(6S,9R)-6-(2,3-difluorophenyl)-3-(2,2,2-trifluoroethyl)-6,7,8,9-tetrahydro-5H-imidazo[1,2-a]azepin-9-yl]piperidine-1-carboxamide and N-[(6S,9R)-6-(2,3-difluorophenyl)-3-(2,2,2-trifluoroethyl)-6,7,8,9-tetrahydro-5H-imidazo[1,2-a]
azepin-9-yl]-4-(3-oxo-6-propyl-2,3-dihydropyridazin-4-yl)piperidine-1-carboxamide Triethylamine (34 µL, 0.24 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (36 mg, 0.081 mmol) and 4-nitrophenyl chloroformate (16 mg, 0.081 mmol) in dichloromethane (1 mL) at 0° C. After 15 min, a solution of a mixture of 6-cyclopropyl-4-piperidin-4-ylpyridazin-3(2H)-one and 4-piperidin-4-yl-6-propylpyridazin-3(2H)-one (18 mg, 0.081 mmol) in dichloromethane (1 mL) and triethylamine (11 µL, 0.08 mmol) were added and the mixture allowed to warm to ambient temperature. After 3 h, saturated aqueous sodium carbonate was added and the mixture was extracted with ethyl acetate. The organic layer was washed with saturated aqueous sodium bicarbonate (3×), saturated brine, dried over magnesium sulfate, filtered and concentrated. Purification by silica gel chromatography (100% dichloromethane→90% dichloromethane/methanol) gave 4-(6-cyclopropyl-3-oxo-2,3-dihydropyridazin-4-yl)-N-[(6S,9R)-6-(2,3-difluorophenyl)-3-(2,2,2-trifluoroethyl)-6,7,8,9-tetrahydro-5H-imidazo[1,2-a]
azepin-9-yl]piperidine-1-carboxamide (11 mg); MS 591.2507 (M+1) and N-[(6S,9R)-6-(2,3-difluorophenyl)-3-(2,2,2-trifluoroethyl)-6,7,8,9-tetrahydro-5H-imidazo[1,2-a]
azepin-9-yl]-4-(3-oxo-6-propyl-2,3-dihydropyridazin-4-yl)
piperidine-1-carboxamide (14 mg); MS 593.2689 (M+1).

Example 152

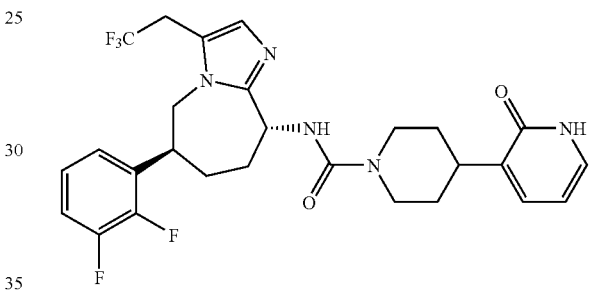

N-[(6S,9R)-6-(2,3-Difluorophenyl)-3-(2,2,2-trifluoroethyl)-6,7,8,9-tetrahydro-5H-imidazo[1,2-a]
azepin-9-yl]-4-(2-oxo-1,2-dihydropyridin-3-yl)piperidine-1-carboxamide Step A: (6S,9R)-6-(2,3-Difluorophenyl)-3-(2,2,2-trifluoroethyl)-6,7,8,9-tetrahydro-5H-imidazo[1,2-a]
azepin-9-amine Trifluoroacetic acid (1 mL, 13.5 mmol) was added to a solution of tert-butyl [(6S,9R)-6-(2,3-difluorophenyl)-3-(2,2,2-trifluoroethyl)-6,7,8,9-tetrahydro-5H-imidazo[1,2-a]
azepin-9-yl]carbamate (120 mg, 0.27 mmol) in dichloromethane (2 mL). After 1 h, the mixture was concentrated and saturated sodium bicarbonate was added. The mixture was extracted with dichloromethane (3×), and the combined organic extracts were washed with saturated brine, dried over magnesium sulfate, filtered and concentrated. MS 346.1 (M+1).

Step B: N-[(6S,9R)-6-(2,3-Difluorophenyl)-3-(2,2,2-trifluoroethyl)-6,7,8,9-tetrahydro-5H-imidazo[1,2-a]
azepin-9-yl]-4-(2-oxo-1,2-dihydropyridin-3-yl)piperidine-1-carboxamide Triethylamine (40 µL, 0.285 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (33 mg, 0.095 mmol) and 4-nitrophenyl chloroformate (19 mg, 0.095 mmol) in dichloromethane (2 mL) at 0° C. After 15 min, a solution of the hydrochloride salt of 3-piperidin-4-ylpyridin-2(1H)-one (23 mg, 0.105 mmol) in dichloromethane (1 mL) and triethylamine (26 µL, 0.19 mmol) were added and the mixture was allowed to warm to ambient temperature. After 3 h, saturated aqueous sodium carbonate was added and the mixture was extracted with ethyl acetate. The organic layer was washed with saturated aqueous sodium bicarbonate (3×), saturated brine, dried over magnesium sulfate, filtered and concentrated. Purification by silica gel chromatography (100% dichloromethane→90% dichloromethane/methanol) gave the title compound (8.5 mg). MS 650.2244 (M+1).

Example 153

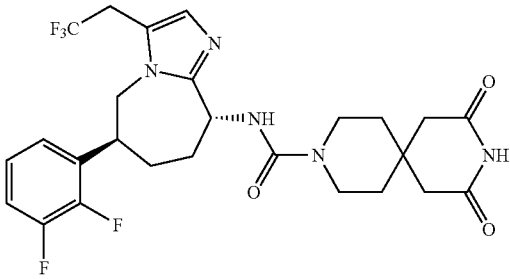

N-[(6S,9R)-6-(2,3-Difluorophenyl)-3-(2,2,2-trifluoroethyl)-6,7,8,9-tetrahydro-5H-imidazo[1,2-a]azepin-9-yl]-8,10-dioxo-3,9-diazaspiro[5.5]undecane-3-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Trifluoroacetic acid (1 mL, 13.5 mmol) was added to a solution of tert-butyl [(6S,9R)-6-(2,3-difluorophenyl)-3-(2,2,2-trifluoroethyl)-6,7,8,9-tetrahydro-5H-imidazo[1,2-a]azepin-9-yl]carbamate (120 mg, 0.27 mmol) in dichloromethane (2 mL). After 1 h, the reaction mixture was concentrated and saturated aqueous sodium bicarbonate was added. The mixture was extracted with dichloromethane (3×), and the combined organic extracts were washed with saturated brine, dried over magnesium sulfate, filtered and concentrated. MS 346.1 (M+1).

Step B: N-[(6S,9R)-6-(2,3-Difluorophenyl)-3-(2,2,2-trifluoroethyl-6,7,8,9-tetrahydro-5H-imidazo[1,2-a]azepin-9-yl]-8,10-dioxo-3,9-diazaspiro[5.5]undecane-3-carboxamide Triethylamine (30.3 µL, 0.215 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (30 mg, 0.072 mmol) and 4-nitrophenyl chloroformate (15 mg, 0.075 mmol) in tetrahydrofuran (0.5 mL) at 0° C. After 15 min, a solution of the acetate salt of 3,9-diazaspiro[5.5]undecane-2,4-dione (19 mg, 0.079 mmol) in dichloromethane (1 mL) and triethylamine (30.3 µL, 0.215 mmol) were added and the mixture allowed to warm to ambient temperature. After 2 h, saturated aqueous sodium carbonate was added and the mixture was extracted with ethyl acetate. The organic layer was washed with saturated aqueous sodium bicarbonate (3×), saturated brine, dried over magnesium sulfate, filtered and concentrated. Purification by silica gel chromatography (100% dichloromethane→90% dichloromethane/methanol) gave the title compound (17.4 mg). MS 554.2196 (M+1).

Example 154

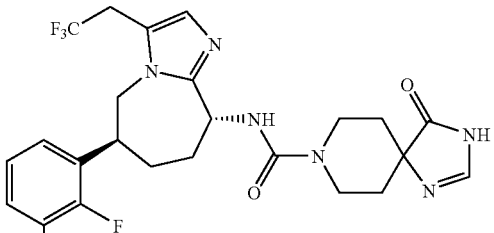

N-[(6S,9R)-6-(2,3-Difluorophenyl)-3-(2,2,2-trifluoroethyl)-6,7,8,9-tetrahydro-5H-imidazo[1,2-a]azepin-9-yl]-4-oxo-1,3,8-triazaspiro[4.5]dec-1-ene-8-carboxamide Step A: (6S,9R)-6-(2,3-Difluorophenyl)-3-(2,2,2-trifluoroethyl)-6,7,8,9-tetrahydro-5H-imidazo[1,2-a]azepin-9-amine Hydrochloric acid (4.0 M in dioxane; 4 mL, 16.0 mmol) was added to a solution of tert-butyl [(6S,9R)-6-(2,3-difluorophenyl)-3-(2,2,2-trifluoroethyl)-6,7,8,9-tetrahydro-5H-imidazo[1,2-a]azepin-9-yl]carbamate (27 mg, 0.061 mmol) in dioxane (4 mL). After 18 h, the reaction mixture was concentrated to give the hydrochloride salt of the title compound. MS 346.2 (M+1).

Step B: N-[(6S,9R)-6-(2,3-Difluorophenyl)-3-(2,2,2-trifluoroethyl)-6,7,8,9-tetrahydro-5H-imidazo[1,2-a]azepin-9-yl]-4-oxo-1,3,8-triazaspiro[4.5]dec-1-ene-8-carboxamide Triethylamine (42 µL, 0.30 mmol) was added to a solution of the hydrochloride salt of (6S,9R)-6-(2,3-difluorophenyl)-3-(2,2,2-trifluoroethyl)-6,7,8,9-tetrahydro-5H-imidazo[1,2-a]azepin-9-amine (25 mg, 0.061 mmol) and 4-nitrophenyl chloroformate (14 mg, 0.070 mmol) in tetrahydrofuran (5 mL) at 0° C. After 40 min, the hydrochloride salt of 1,3,8-triazaspiro[4.5]dec-1-en-4-one (21 mg, 0.091 mmol), triethylamine (34 µL, 0.24 mmol) and chloroform (5 mL) were added and the mixture allowed to warm to ambient temperature. After 18 h, saturated aqueous sodium carbonate was added and the mixture was extracted with dichloromethane. The organic extracts were washed with saturated aqueous sodium bicarbonate (3×), saturated brine, dried over magnesium sulfate, filtered and concentrated. Purification by silica gel chromatography (100% dichloromethane→85% dichloromethane/methanol) gave the title compound (22 mg). MS 525.2000 (M+1).

Example 155

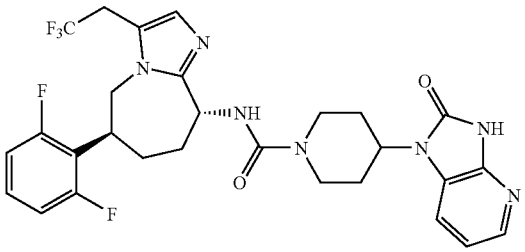

N-[(6S,9R)-6-(2,6-Difluorophenyl)-3-(2,2,2-trifluoroethyl)-6,7,8,9-tetrahydro-5H-imidazo[1,2-a]azepin-9-yl]-4-(2-oxo-2,3-dihydro-1H-imidazo[4,5-b]pyridin-1-yl)piperidine-1-carboxamide Prepared essentially following the procedure outlined for the preparation of Example 10. MS 590.2326 (M+1).

Example 156

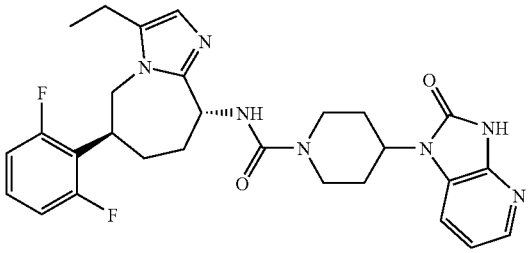

N-[(6S,9R)-6-(2,6-Difluorophenyl)-3-ethyl-6,7,8,9-tetrahydro-5H-imidazo[1,2-a]azepin-9-yl]-4-(2-oxo-2,3-dihydro-1H-imidazo[4,5-b]pyridin-1-yl)piperidine-1-carboxamide Prepared essentially following the procedure outlined for the preparation of Example 10. MS 536.2557 (M+1).

Example 157

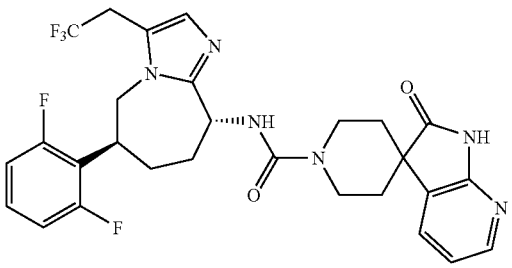

N-[(6S,9R)-6-(2,6-Difluorophenyl)-3-(2,2,2-trifluoroethyl)-6,7,8,9-tetrahydro-5H-imidazo[1,2-a]azepin-9-yl]-2'-oxo-1',2'-dihydro-1H-spiro[piperidine-4,3'-pyrrolo[2,3-b]pyridine]-1-carboxamide Prepared essentially following the procedure outlined for the preparation of Example 47. MS 575.2227 (M+1).

Example 158

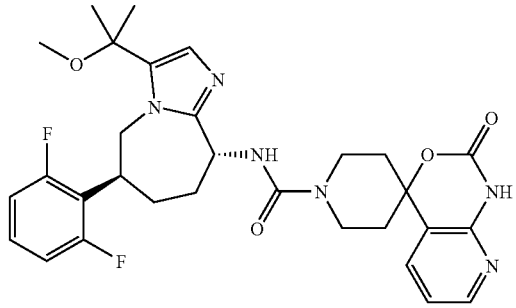

N-[(6S,9R)-6-(2,6-Difluorophenyl)-3-(2,2,2-trifluoroethyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide Step A: (6S,9R)-6-(2,6-Difluorophenyl)-3-(1-methoxy-1-methylethyl)-6,7,8,9-tetrahydro-5H-imidazo[1,2-a]azepin-9-amine Sulfuric acid (0.15 mL, 2.85 mmol) was added to a solution of tert-butyl [(6S,9R)-6-(2,6-difluorophenyl)-3-(1-hydroxy-1-methylethyl)-6,7,8,9-tetrahydro-5H-imidazo[1,2-a]azepin-9-yl]carbamate (120 mg, 0.285 mmol) in methanol (1.5 mL). The reaction mixture was heated to 60° C. After 3 h, the reaction was quenched with saturated aqueous sodium bicarbonate. The mixture was extracted with dichloromethane (3×), washed with saturated brine, dried over magnesium sulfate, filtered and concentrated. MS 336.2 (M+1).

Step B: N-[(6S,9R)-6-(2,6-Difluorophenyl)-3-(2,2,2-trifluoroethyl)-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide Triethylamine (38 µL, 0.27 mmol) was added to a solution of (6S,9R)-6-(2,6-difluorophenyl)-3-(1-methoxy-1-methylethyl)-6,7,8,9-tetrahydro-5H-imidazo[1,2-a]azepin-9-amine (95 mg, 0.28 mmol) and 4-nitrophenyl chloroformate (60 mg, 0.30 mmol) in tetrahydrofuran (4 mL) at 0° C. After 15 min, spiro[piperidine-4,4'-pyrido[2,3-d][1,3]oxazin]-2'(1'H)-one (68 mg, 0.31 mmol) and triethylamine (120 µL, 0.85 mmol) were added and the mixture allowed to warm to ambient temperature. After 16 h, saturated aqueous sodium carbonate was added and the mixture was extracted with dichloromethane. The organic extracts were washed with saturated aqueous sodium bicarbonate (3×), saturated brine, dried over sodium sulfate, filtered and concentrated. Purification by silica gel chromatography (100% dichloromethane→93% dichloromethane/methanol) gave the title compound (128 mg). MS 581.2702 (M+1).

Essentially following the procedure outlined for the preparation of Example 158, the Examples in Table 20 were prepared.

TABLE 20

| Example | R¹ | R² | MS (M + 1) |
|---|---|---|---|
| 159 | HO-CH₂CH₂-O-C(CH₃)₂- | H | 611.2832 |
| 160 | F₃C-CH₂- | H | 591.2164 |
| 161 | HO-C(CH₃)₂- | H | 567.2545 |

Example 162

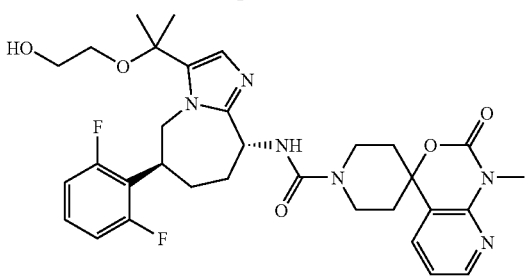

N-{(6S,9R)-6-(2,6-Difluorophenyl)-3-[1-(2-hydroxyethoxy)-1-methylethyl]-6,7,8,9-tetrahydro-5H-imidazo[1,2-a]azepin-9-yl}-1'-methyl-2'-oxo-1',2'-dihydro-1H-spiro[piperidine-4,4'-pyrido[2,3-d][1,3]oxazine]-1-carboxamide Step A: 2-{1-[(6S,9R)-9-Amino-6-(2,6-difluorophenyl)-6,7,8,9-tetrahydro-5H-imidazo[1,2-a]azepin-3-yl]-1-methylethoxy}ethanol Methanesulfonic acid (78 µL, 1.19 mmol) was added to a solution of tert-butyl [(6S,9R)-6-(2,6-difluorophenyl)-3-(1-methoxy-1-methylethyl)-6,7,8,9-tetrahydro-5H-imidazo[1,2-a]azepin-9-yl]carbamate (104 mg, 0.24 mmol) in ethylene glycol (4 mL). The reaction mixture was heated to 60° C. After 18 h, the mixture was allowed to cool to ambient temperature and saturated aqueous sodium bicarbonate was added. The mixture was extracted with dichloromethane (3×). The organic extracts were washed with saturated aqueous sodium bicarbonate, saturated brine, dried over magnesium sulfate, filtered and concentrated to give the title compound. MS 366.1 (M+1).

Step B: N-{(6S,9R)-6-(2,6-Difluorophenyl)-3-[1-(2-hydroxyethoxy)-1-methylethyl]-6,7,8,9-tetrahydro-5H-imidazo[1,2-a]azepin-9-yl}-1'-methyl-2'-oxo-1',2'-dihydro-1H-spiro[piperidine-4,4'-pyrido[2,3-d][1,3]oxazine]-1-carboxamide Triethylamine (53 µL, 0.38 mmol) was added to a solution of 2-{1-[(6S,9R)-9-amino-6-(2,6-difluorophenyl)-6,7,8,9-tetrahydro-5H-imidazo[1,2-a]azepin-3-yl]-1-methylethoxy}ethanol (63 mg, 0.17 mmol) and 4-nitrophenyl chloroformate (38 mg, 0.19 mmol) in tetrahydrofuran (10 mL) at 0° C. After 20 min, 1'-methylspiro[piperidine-4,4'-pyrido[2,3-d][1,3]oxazin]-2'(1'H)-one (60 mg, 0.26 mmol), triethylamine (96.4 µL, 0.67 mmol) and chloroform (10 mL) were added and the mixture was heated to 40° C. After 16 h, the reaction mixture was allowed to cool to ambient temperature. Saturated aqueous sodium carbonate was added and the mixture was extracted with dichloromethane (3×). The organic extracts were washed with saturated aqueous sodium bicarbonate, saturated brine, dried over magnesium sulfate, filtered and concentrated. Purification by silica gel chromatography (100% dichloromethane→91% dichloromethane/methanol) gave the title compound (64 mg). MS 625.2989 (M+1).

Example 163

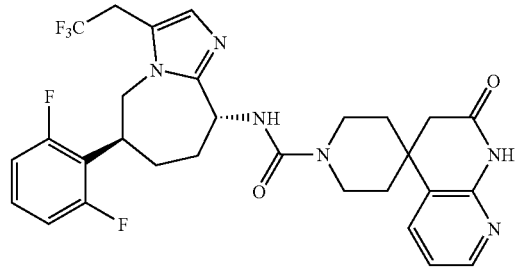

N-[(6S,9R)-6-(2,6-Difluorophenyl)-3-(2,2,2-trifluoroethyl)-6,7,8,9-tetrahydro-5H-imidazo[1,2-a]azepin-9-yl]-2-oxo-2,3-dihydro-1H,1'H-spiro[1,8-naphthyridine-4,4'-piperidine]-1'-carboxamide Prepared essentially following the procedure outlined for the preparation of Example 120. MS 589.2314 (M+1).

Example 164

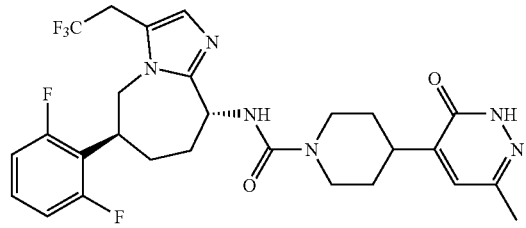

N-[(6S,9R)-6-(2,6-Difluorophenyl)-3-(2,2,2-trifluoroethyl)-6,7,8,9-tetrahydro-5H-imidazo[1,2-a]azepin-9-yl]-4-(6-methyl-3-oxo-2,3-dihydropyridazin-4-yl)piperidine-1-carboxamide Step A: (6S,9R)-6-(2,6-Difluorophenyl)-3-L2,2,2-trifluoroethyl)-6,7,8,9-tetrahydro-5H-imidazo[1,2-a]azepin-9-amine Hydrochloric acid (4.0 M in dioxane; 5.0 mL, 20.0 mmol) was added to a solution of tert-butyl [(6S,9R)-6-(2,6-difluorophenyl)-3-(2,2,2-trifluoroethyl)-6,7,8,9-tetrahydro-5H-imidazo[1,2-a]azepin-9-yl]carbamate (265 mg, 0.60 mmol) in dioxane (5 mL). After 18 h, the reaction mixture was concentrated to give the hydrochloride salt of the title compound. MS 346.1 (M+1).

Step B: N-[(6S,9R)-6-(2,6-Difluorophenyl)-3-(2,2,2-trifluoroethyl)-6,7,8,9-tetrahydro-5H-imidazo[1,2-a]azepin-9-yl]-4-(6-methyl-3-oxo-2,3-dihydropyridazin-4-yl)piperidine-1-carboxamide Triethylamine (22 μL, 0.16 mmol) was added to a solution of the hydrochloride salt of (6S,9R)-6-(2,6-difluorophenyl)-3-(2,2,2-trifluoroethyl)-6,7,8,9-tetrahydro-5H-imidazo[1,2-a]azepin-9-amine (15 mg, 0.04 mmol) and 4-nitrophenyl chloroformate (19 mg, 0.043 mmol) in tetrahydrofuran (5 mL) at 0° C. After 30 min, 6-methyl-4-piperidin-4-ylpyridazin-3(2H)-one (15 mg, 0.08 mmol), triethylamine (22 μL, 0.16 mmol) and chloroform (5 mL) were added and the mixture was heated to 50° C. After 30 min, the reaction mixture was allowed to cool to ambient temperature. Saturated aqueous sodium carbonate was added and the mixture was extracted with dichloromethane. The organic layer was washed with saturated aqueous sodium bicarbonate (3×), saturated brine, dried over magnesium sulfate, filtered and concentrated. Purification by silica gel chromatography (100% dichloromethane→90% dichloromethane/methanol) gave the title compound (15 mg). MS 565.2346 (M+1).

Example 165

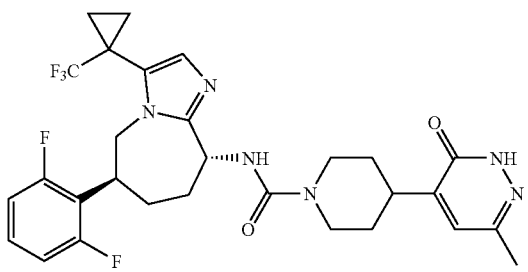

N-{(6S,9R)-6-(2,6-Difluorophenyl)-3-[1-(trifluoromethyl)cyclopropyl]-6,7,8,9-tetrahydro-5H-imidazo[1,2-a]azepin-9-yl}-4-(6-methyl-3-oxo-2,3-dihydropyridazin-4-yl)piperidine-1-carboxamide Step A: (6S,9R)-6-(2,6-Difluorophenyl)-3-[1-(trifluoromethyl)cyclopropyl]-6,7,8,9-tetrahydro-5H-imidazo[1,2-a]azepin-9-amine Hydrochloric acid (4.0 M in dioxane; 3 mL, 12.0 mmol) was added to a solution of tert-butyl {(6S,9R)-6-(2,6-difluorophenyl)-3-[1-(trifluoromethyl)cyclopropyl]-6,7,8,9-tetrahydro-5H-imidazo[1,2-a]azepin-9-yl}carbamate (40 mg, 0.085 mmol) in dioxane (3 mL). After 2 h, the reaction mixture was concentrated to give the hydrochloride salt of the title compound. MS 372.1 (M+1).

Step B: N-{(6S,9R)-6-(2,6-Difluorophenyl)-3-[1-(trifluoromethyl)cyclopropyl]-6,7,8,9-tetrahydro-5H-imidazo[1,2-a]azepin-9-yl}-4-(6-methyl-3-oxo-2,3-dihydropyridazin-4-yl)piperidine-1-carboxamide Triethylamine (55 μL, 0.39 mmol) was added to a solution of the hydrochloride salt of (6S,9R)-6-(2,6-difluorophenyl)-3-[1-(trifluoromethyl)cyclopropyl]-6,7,8,9-tetrahydro-5H-imidazo[1,2-a]azepin-9-amine (40 mg, 0.10 mmol) and 4-nitrophenyl chloroformate (22 mg, 0.11 mmol) in tetrahydrofuran (5 mL) at 0° C. After 30 min, 6-methyl-4-piperidin-4-ylpyridazin-3(2H)-one (38 mg, 0.20 mmol), triethylamine (55 μL, 0.39 mmol) and chloroform (5 mL) were added and the mixture was heated to 50° C. After 30 min, the reaction mixture was allowed to cool to ambient temperature. Saturated aqueous sodium carbonate was added and the mixture was extracted with dichloromethane. The organic extracts were washed with saturated aqueous sodium bicarbonate (3×), saturated brine, dried over magnesium sulfate, filtered and concentrated. Purification by silica gel chromatography (100% dichloromethane→90% dichloromethane/methanol) gave the title compound (15 mg). MS 591.2536 (M+1).

Example 166

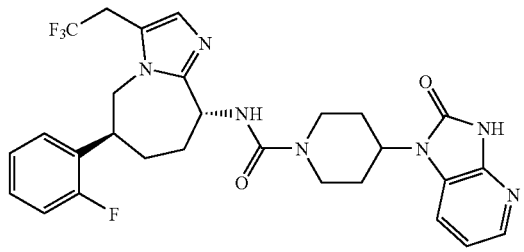

N-[(6S,9R)-6-(2-Fluorophenyl)-3-(2,2,2-trifluoroethyl)-6,7,8,9-tetrahydro-5H-imidazo[1,2-a]azepin-9-yl]-4-(2-oxo-2,3-dihydro-1H-imidazo[4,5-b]pyridin-1-yl)piperidine-1-carboxamide Prepared essentially following the procedure outlined for the preparation of Example 10. MS 572.2377 (M+1).

Example 167

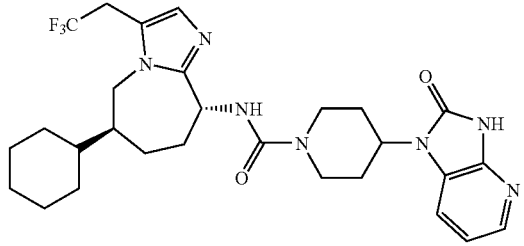

N-[(6S,9R)-6-Cyclohexyl-3-(2,2,2-trifluoroethyl)-6,7,8,9-tetrahydro-5H-imidazo[1,2-a]azepin-9-yl]-4-(2-oxo-2,3-dihydro-1H-imidazo[4,5-b]pyridin-1-yl)piperidine-1-carboxamide Prepared essentially following the procedure outlined for the preparation of Example 10. MS 560.2974 (M+1).

Example 168

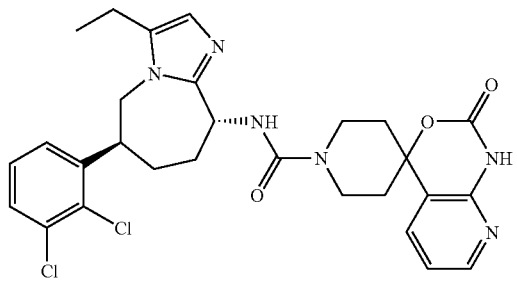

N-[(6S,9R)-6-(2,3-Dichlorophenyl)-3-ethyl-6,7,8,9-tetrahydro-5H-imidazo[1,2-a]azepin-9-yl]-2'-oxo-1',2'-dihydro-1H-spiro[piperidine-4,4'-pyrido[2,3-d][1,3]oxazine]-1-carboxamide Prepared essentially following the procedure outlined for the preparation of Example 62. MS 569.1784 (M+1).

Example 169

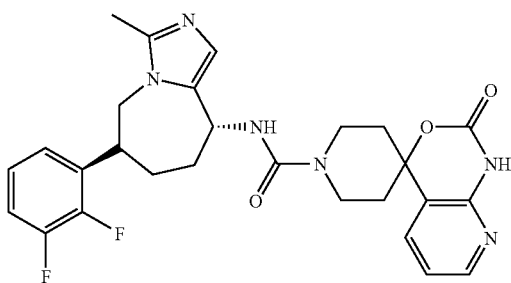

N-[(6S,9R)-6-(2,3-Difluorophenyl)-3-methyl-6,7,8,9-tetrahydro-5H-imidazo[1,5-a]azepin-9-yl]-2'-oxo-1',2'-dihydro-1H-spiro[piperidine-4,4'-pyrido[2,3-d][1,3]oxazine]-1-carboxamide Step A: tert-Butyl [(3R,6S)-2-cyano-6-(2,3-difluorophenyl)azepan-3-yl]carbamate A solution of tert-butyl [(3R,6S)-6-(2,3-difluorophenyl)-2-oxoazepan-3-yl]carbamate (0.67 g, 1.97 mmol) in tetrahydrofuran (10 mL) was slowly added to a solution of zirconocene chloride hydride (0.76 g, 2.95 mmol) in tetrahydrofuran (5.0 mL) at −20° C. After 15 min, the mixture was allowed to warm to ambient temperature. After 3 h, trimethylsilanecarbonitrile (1.31 mL, 9.84 mmol) was added. After 16 h, saturated aqueous sodium bicarbonate was added and the mixture was extracted with dichloromethane (3×). The combined organic extracts were washed with Rochelle's salt (1.0 M in water), brine, dried over sodium sulfate, filtered, and concentrated. MS 352.1 (M+1).

Step B: tert-Butyl [(3R,6S)-1-acetyl-2-cyano-6-(2,3-difluorophenyl)azepan-3-yl]carbamate Triethylamine (1.29 mL, 9.25 mmol) was added to a solution of tert-butyl [(3R,6S)-2-cyano-6-(2,3-difluorophenyl)azepan-3-yl]carbamate (0.65 g, 1.85 mmol) in dichloromethane (20 mL) at 0° C. Acetic anhydride (0.53 mL, 5.55 mmol) was added and the mixture was allowed to warm to ambient temperature. After 16 h, saturated aqueous sodium bicarbonate was added and the mixture was extracted with dichloromethane (3×). The combined organic extracts were dried over sodium sulfate, filtered, and concentrated. Purification by silica gel chromatography (99% dichloromethane/ethyl acetate→70% dichloromethane/ethyl acetate) gave the title compound (144 mg). MS 394.1 (M+1).

Step C: tert-Butyl [(3R,6S)-1-acetyl-2-(aminomethyl)-6-(2,3-difluorophenyl)azepan-3-yl]carbamate Raney-Nickel (2800, slurry in water; washed with ethyl alcohol (2×); 0.5 g) was added to a solution of tert-butyl [(3R,6S)-1-acetyl-2-cyano-6-(2,3-difluorophenyl)azepan-3-yl]carbamate (80.0 mg, 0.20 mmol) in ethanol (10 mL). Ammonia gas was bubbled to the reaction mixture for 3 minutes and the mixture was stirred under hydrogen at 40 psi. After 4 h, the reaction mixture was filtered and concentrated. MS 398.2 (M+1).

Step D: tert-Butyl[(6S,9R)-6-(2,3-difluorophenyl)-3-methyl-5,6,7,8,9,9a-hexahydro-1H-imidazo[1,5-a]azepin-9-yl]carbamate A solution of tert-butyl [(3R,6S)-1-acetyl-2-(aminomethyl)-6-(2,3-difluorophenyl)azepan-3-yl]carbamate (22 mg, 0.055 mmol) in acetic acid (3 mL) was heated to 80° C. After 6 h, the reaction mixture was allowed to cool to ambient temperature. Saturated aqueous sodium bicarbonate was added and the mixture was extracted with dichloromethane (3×). The combined organic extracts were dried over sodium sulfate, filtered, and concentrated. MS 380.1 (M+1).

Step E: tert-Butyl [(6S,9R)-6-(2,3-difluorophenyl)-3-methyl-6,7,8,9-tetrahydro-5H-imidazo[1,5-a]azepin-9-yl]carbamate Manganese(IV) oxide (46.0 mg, 0.53 mmol) was added to a solution of tert-butyl [(6S,9R)-6-(2,3-difluorophenyl)-3-methyl-5,6,7,8,9,9a-hexahydro-1H-imidazo[1,5-a]azepin-9-yl]carbamate (20.0 mg, 0.053 mmol) in toluene (7 mL). The reaction mixture was heated to reflux. After 8 h, additional manganese (IV) oxide (46.0 mg, 0.53 mmol) was added. After 16 h, the reaction mixture was allowed to cool to ambient temperature. The mixture was filtered, washed with methanol, and concentrated. Purification by preparative thin layer chromatography (9% methanol/dichloromethane) gave the title compound (5 mg). MS 378.1 (M+1).

Step F: (6S,9R)-6-(2,3-Difluorophenyl)-3-methyl-6,7,8,9-tetrahydro-5H-imidazo[1,5-a]azepin-9-amine Hydrochloric acid (4.0 M in dioxane; 3.0 mL, 12.0 mmol) was added to a solution of tert-butyl [(6S,9R)-6-(2,3-difluorophenyl)-3-methyl-6,7,8,9-tetrahydro-5H-imidazo[1,5-a]azepin-9-yl]carbamate (33 mg, 0.087 mmol) in dichloromethane (3 mL). After 2 h, the reaction mixture was concentrated to give the hydrochloride salt of the title compound. MS 278.1 (M+1).

Step G: N-[(6S,9R)-6-(2,3-Difluorophenyl)-3-methyl-6,7,8,9-tetrahydro-5H-imidazo[1,5-a]azepin-9-yl]-2'-oxo-1',2'-dihydro-1H-spiro[piperidine-4,4'-pyrido[2,3-d][1,3]oxazine]-1-carboxamide Triethylamine (66 µL, 0.476 mmol) was added to a solution of the hydrochloride salt of (6S,9R)-6-(2,3-difluorophenyl)-3-methyl-6,7,8,9-tetrahydro-5H-imidazo[1,5-a]azepin-9-amine (30.0 mg, 0.108 mmol) and 4-nitrophenyl chloroformate (31.0 mg, 0.152 mmol) in tetrahydrofuran (10 mL) at 0° C. After 20 min, the hydrochloride salt of spiro[piperidine-4,4'-pyrido[2,3-d][1,3]oxazin]-2'(1'H)-one (95 mg, 0.325 mmol), triethylamine (66 µL, 0.476 mmol), and trichloromethane (10 mL) were added. The reaction mixture was heated to 40° C. After 16 h, the mixture was allowed to cooled to ambient temperature and concentrated. Saturated aqueous sodium carbonate was added and the mixture was extracted with dichloromethane. The organic layer was washed with saturated aqueous sodium bicarbonate (3×), saturated brine, dried over sodium sulfate, filtered and concentrated. Purification by reverse phase HPLC (C-18, 95% water/acetonitrile→5% water/acetonitrile with 0.1% trifluoroacetic acid) gave the title compound (3.55 mg). MS 523.2274 (M+1).

Example 170

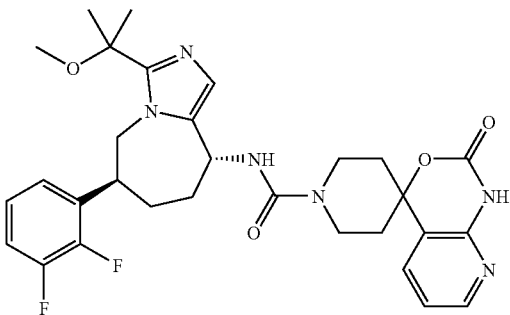

N-[(6S,9R)-6-(2,3-Difluorophenyl)-3-(1-methoxy-1-methylethyl)-6,7,8,9-tetrahydro-5H-imidazo[1,5-a]azepin-9-yl]-2'-oxo-1',2'-dihydro-1H-spiro[piperidine-4,4'-pyrido[2,3-d][1,3]oxazine]-1-carboxamide Prepared essentially following the procedure outlined for the preparation of Example 169. MS 581.2660 (M+1).

Example 171

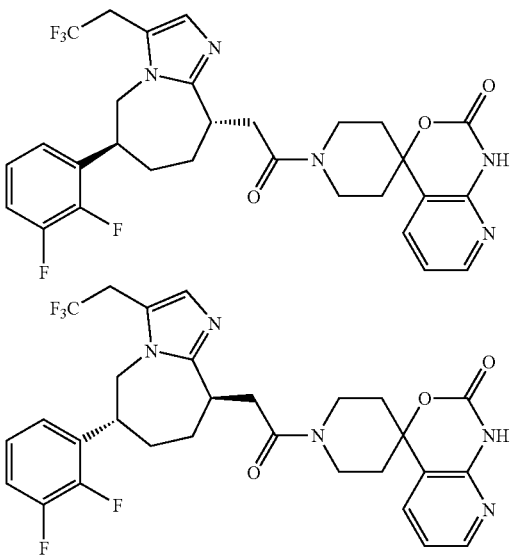

1-{[(6S,9S)-6-(2,3-Difluorophenyl)-3-(2,2,2-trifluoroethyl)-6,7,8,9-tetrahydro-5H-imidazo[1,2-a]azepin-9-yl]acetyl}spiro[piperidine-4,4'-pyrido[2,3-d][1,3]oxazin]-2'(1'H)-one and 1-{[(6R,9R)-6-(2,3-difluorophenyl)-3-(2,2,2-trifluoroethyl)-6,7,8,9-tetrahydro-5H-imidazo[1,2-a]azepin-9-yl]acetyl}spiro[piperidine-4,4'-pyrido[2,3-d][1,3]oxazin]-2'(1'H)-one Step A: (3S,6S)-3-Allyl-6-(2,3-difluorophenyl)azepan-2-one and (3R,6R)-3-allyl-6-(2,3-difluorophenyl)azepan-2-one Lawesson's reagent [2,4-bis(4-methoxyphenyl)-1,3-dithia-2,4-diphosphetane-2,4-disulfide] (0.97 g, 2.39 mmol) was added to a suspension of (3S,6S)-3-allyl-6-(2,3-difluorophenyl)azepan-2-one and (3R,6R)-3-allyl-6-(2,3-difluorophenyl)azepan-2-one (634 mg, 2.39 mmol) in toluene (50 mL). After 18 h, the reaction mixture was concentrated in a cold water bath. Purification by silica gel chromatography (100% hexanes→70% hexanes/ethyl acetate) gave the title compounds (372 mg). MS 282.1 (M+1).

Step B: 1-{[(2Z,3S,6S)-3-Allyl-6-(2,3-difluorophenyl)azepan-2-ylidene]amino}-4,4,4-trifluorobutane-2-ol and 1-{[(2Z,3R,6R)-3-allyl-6-(2,3-difluorophenyl)azepan-2-ylidene]amino}-4,4,4-trifluorobutane-2-ol Mercury(II) chloride (96 mg, 0.36 mmol) was added to a solution of (3S,6S)-3-allyl-6-(2,3-difluorophenyl)azepan-2-one and (3R,6R)-3-allyl-6-(2,3-difluorophenyl)azepan-2-one (100 mg, 0.36 mmol), the hydrochloride salt of 1-amino-4,4,4-trifluorobutane-2-ol (167 mg, 0.93 mmol), and triethylamine (150 μL, 1.07 mmol) in ethanol (2 mL) at 60° C. After 5 min, the reaction was allowed to cool to ambient temperature. The mixture was filtered and concentrated. Saturated aqueous sodium bicarbonate was added and the mixture was extracted with dichloromethane (3×). The combined organic extracts were dried over magnesium sulfate, filtered, and concentrated to give the title compounds. MS 391.1 (M+1).

Step C: (6S,9S)-9-Allyl-6-(2,3-Difluorophenyl)-3-(2,2,2-trifluoroethyl)-6,7,8,9-tetrahydro-5H-imidazo[1,2-a]azepine and (6R,9R)-9-allyl-6-(2,3-difluorophenyl)-3-(2,2,2-trifluoroethyl)-6,7,8,9-tetrahydro-5H-imidazo[1,2-a]azepine Pyridinium dichromate (296 mg, 0.79 mmol) was added to a solution of 1-{[(2Z,3S,6S)-3-allyl-6-(2,3-difluorophenyl)azepan-2-ylidene]amino}-4,4,4-trifluorobutane-2-ol and 1-{[(2Z,3R,6R)-3-allyl-6-(2,3-difluorophenyl)azepan-2-ylidene]amino}-4,4,4-trifluorobutane-2-ol (123 g, 0.32 mmol) in acetonitrile (10 mL). After 48 h, additional pyridinium dichromate (296 mg, 0.79 mmol) was added. After 18 h, the mixture was filtered. Saturated aqueous sodium bicarbonate was added and the mixture was extracted with dichloromethane (3×). The combined organic extracts were dried over magnesium sulfate, filtered, and concentrated. Purification by silica gel chromatography (100% dichloromethane→96% dichloromethane/methanol). Repurification by reverse phase HPLC (95% water/acetonitrile→5% water/acetonitrile with 0.1% trifluoroacetic acid) gave the title compounds (51 mg). MS 371.1 (M+1).

Step D: [(6S,9S)-6-(2,3-Difluorophenyl)-3-(2,2,2-trifluoroethyl)-6,7,8,9-tetrahydro-5H-imidazo[1,2-a]azepin-9-yl]acetic acid and [(6R,9R)-6-(2,3-difluorophenyl)-3-(2,2,2-trifluoroethyl)-6,7,8,9-tetrahydro-5H-imidazo[1,2-a]azepin-9-yl]acetic acid Sodium periodate (265 mg, 1.24 mmol) and potassium permanganate (22 mg, 0.14 mmol) were added to a solution of (6S,9S)-9-allyl-6-(2,3-difluorophenyl)-3-(2,2,2-trifluoroethyl)-6,7,8,9-tetrahydro-5H-imidazo[1,2-a]azepine and (6R,9R)-9-allyl-6-(2,3-difluorophenyl)-3-(2,2,2-trifluoroethyl)-6,7,8,9-tetrahydro-5H-imidazo[1,2-a]azepine (51 mg, 0.14 mmol) in tetrahydrofuran (3 mL) and water (5 mL). After 16 h, saturated aqueous sodium sulfite and dichloromethane were added and the pH of the solution was adjusted to pH 4 with hydrochloric acid. The mixture was extracted with dichloromethane (3×). The combined organic extracts were dried over magnesium sulfate, filtered, and concentrated to give the hydrochloride salt of the title compounds. MS 389.0 (M+1).

Step E: 1-{[(6S,9S)-6-(2,3-Difluorophenyl)-3-(2,2,2-trifluoroethyl)-6,7,8,9-tetrahydro-5H-imidazo[1,2-a]azepin-9-yl]acetyl}spiro[piperidine-4,4'-pyrido[2,3-d][1,3]oxazin]-2'(1'H)-one and 1-{[(6R,9R)-6-(2,3-difluorophenyl)-3-(2,2,2-trifluoroethyl-6,7,8,9-tetrahydro-5H-imidazo[1,2-a]azepin-9-yl]acetyl}spiro[piperidine-4,4'-pyrido[2,3-d][1,3]oxazin]-2'(1'H)-one Triethylamine (70 µL, 0.50 mmol), N-(3-dimethylaminopropyl)-N'-ethylcarbodiimide hydrochloride (33 mg, 0.17 mmol), and 1-hydroxy-7-azabenzotriazole (20 mg, 0.144 mmol) were added to a solution of the hydrochloride salt of [(6S,9S)-6-(2,3-difluorophenyl)-3-(2,2,2-trifluoroethyl)-6,7,8,9-tetrahydro-5H-imidazo[1,2-a]azepin-9-yl]acetic acid and the hydrochloride salt of [(6R,9R)-6-(2,3-difluorophenyl)-3-(2,2,2-trifluoroethyl)-6,7,8,9-tetrahydro-5H-imidazo[1,2-a]azepin-9-yl]acetic acid (61 mg, 0.144 mmol), and spiro[piperidine-4,4'-pyrido[2,3-d][1,3]oxazin]-2'(1'H)-one (38 mg, 0.17 mmol) in dichloromethane (5 mL). After 18 h, the reaction mixture was heated to 45° C. After 1.5 h, the mixture was concentrated. Purification by reverse phase HPLC (95% water/acetonitrile→5% water/acetonitrile with 0.1% trifluoroacetic acid) gave the title compound as a racemic mixture (34 mg). MS 590.2207 (M+1).

Example 172

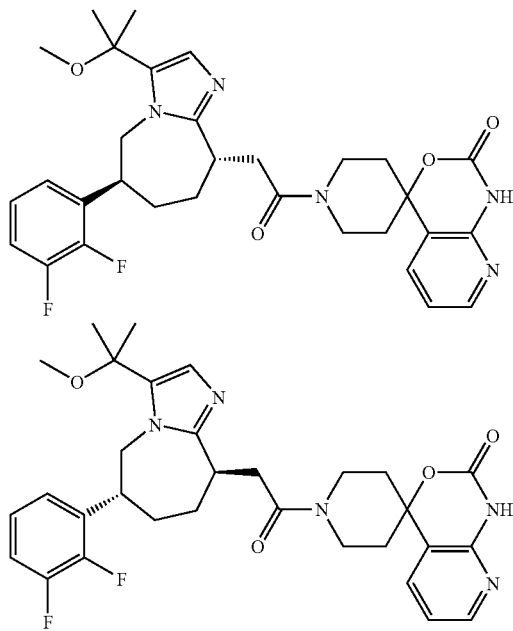

1-{[(6S,9S)-6-(2,3-Difluorophenyl)-3-(1-methoxy-1-methylethyl)-6,7,8,9-tetrahydro-5H-imidazo[1,2-a]azepin-9-yl]acetyl}spiro[piperidine-4,4'-pyrido[2,3-d][1,3]oxazin]-2'(1'H)-one and 1-{[(6R,9R)-6-(2,3-difluorophenyl)-3-(1-methoxy-1-methylethyl)-6,7,8,9-tetrahydro-5H-imidazo[1,2-a]azepin-9-yl]acetyl}spiro[piperidine-4,4'-pyrido[2,3-d][1,3]oxazin]-2'(1'H)-one Step A: (3S,6S)-3-Allyl-6-(2,3-difluorophenyl)azepan-2-one and (3R,6R)-3-allyl-6-(2,3-difluorophenyl)azepan-2-one Lawesson's reagent [2,4-bis(4-methoxyphenyl)-1,3-dithia-2,4-diphosphetane-2,4-disulfide] (0.97 g, 2.39 mmol) was added to a suspension of (3S,6S)-3-allyl-6-(2,3-difluorophenyl)azepan-2-one and (3R,6R)-3-allyl-6-(2,3-difluorophenyl)azepan-2-one (634 mg, 2.39 mmol) in toluene (50 mL). After 18 h, the reaction mixture was concentrated in a cold water bath. Purification by silica gel chromatography (100% hexanes→70% hexanes/ethyl acetate) gave the title compound (372 mg). MS 282.1 (M+1).

Step B: 1-{[(2Z,3S,6S)-3-Allyl-6-(2,3-difluorophenyl)azepan-2-ylidene]amino}-3-methoxy-3-methylbutane-2-ol and 1-{[(2Z,3R,6R)-3-allyl-6-(2,3-difluorophenyl)azepan-2-ylidene]amino}-3-methoxy-3-methylbutane-2-ol Mercury(II) chloride (96 mg, 0.36 mmol) was added to a solution of (3S,6S)-3-allyl-6-(2,3-difluorophenyl)azepan-2-one and (3R,6R)-3-allyl-6-(2,3-difluorophenyl)azepan-2-one (100 mg, 0.36 mmol), and 1-amino-3-methoxy-3-methylbutane-2-ol (174 mg, 1.31 mmol) in ethanol (2 mL) at 60° C. After 30 min, the reaction was allowed to cool to ambient temperature. The mixture was filtered and concentrated. Saturated aqueous sodium bicarbonate was added and the mixture was extracted with dichloromethane (3×). The combined organic extracts were dried over magnesium sulfate, filtered, and concentrated to give the title compound. MS 381.2 (M+1).

Step C: (6S,9S)-9-Allyl-6-(2,3-difluorophenyl)-3-(1-methoxy-1-methylethyl)-6,7,8,9-tetrahydro-5H-imidazo[1,2-a]azepine and (6R,9R)-9-allyl-6-(2,3-difluorophenyl)-3-(1-methoxy-1-methylethyl)-6,7,8,9-tetrahydro-5H-imidazo[1,2-a]azepine Pyridinium dichromate (383 mg, 1.02 mmol) was added to a solution of 1-{[(2Z,3S,6S)-3-allyl-6-(2,3-difluorophenyl)azepan-2-ylidene]amino}-3-methoxy-3-methylbutane-2-ol and 1-{[(2Z,3R,6R)-3-allyl-6-(2,3-difluorophenyl)azepan-2-ylidene]amino}-3-methoxy-3-methylbutan-2-ol (155 g, 0.41 mmol) in acetonitrile (15 mL). After 48 h, additional pyridinium dichromate (383 mg, 1.02 mmol) was added. After 18 h, the mixture was filtered and concentrated. Saturated aqueous sodium bicarbonate was added and the mixture was extracted with dichloromethane (3×). The combined organic extracts were dried over magnesium sulfate, filtered, and concentrated. Purification by silica gel chromatography (100% dichloromethane→96% dichloromethane/methanol) gave the title compound (23 mg). MS 361.2 (M+1).

Step D: [(6S,9S)-6-(2,3-Difluorophenyl)-3-(1-methoxy-1-methylethyl)-6,7,8,9-tetrahydro-5H-imidazo[1,2-a]azepin-9-yl]acetic acid and [(6R,9R)-6-(2,3-difluorophenyl)-3-(1-methoxy-1-methylethyl)-6,7,8,9-tetrahydro-5H-imidazo[1,2-a]azepin-9-yl]acetic acid Sodium periodate (123 mg, 0.57 mmol) and potassium permanganate (10 mg, 0.064 mmol) were added to a solution of (6S,9S)-9-allyl-6-(2,3-difluorophenyl)-3-(1-methoxy-1-methylethyl)-6,7,8,9-tetrahydro-5H-imidazo[1,2-a]azepine and (6R,9R)-9-allyl-6-(2,3-difluorophenyl)-3-(1-methoxy-1-methylethyl)-6,7,8,9-tetrahydro-5H-imidazo[1,2-a]azepine (23 mg, 0.064 mmol) in tetrahydrofuran (3 mL) and water (3 mL). After 16 h, additional potassium permanganate (10 mg, 0.064 mmol) and water (2 mL) were added. After 2 h, saturated aqueous sodium sulfite and dichloromethane were added and the pH of the solution was adjusted to pH 4 with hydrochloric acid. The mixture was extracted with dichloromethane (3×). The combined organic extracts were dried over magnesium sulfate, filtered, and concentrated to give the hydrochloride salt of the title compounds. MS 389.0 (M+1).

Step E: 1-{[(6S,9S)-6-(2,3-Difluorophenyl)-3-(1-methoxy-1-methylethyl)-6,7,8,9-tetrahydro-5H-imidazo[1,2-a]azepin-9-yl]acetyl}spiro[piperidine-4,4'-pyrido[2,3-d][1,3]oxazin]-2'(1'H)-one and 1-{[(6R,9R)-6-(2,3-difluorophenyl)-3-(1-methoxy-1-methylethyl)-6,7,8,9-tetrahydro-5H-imidazo[1,2-a]azepin-9-yl]acetyl}spiro[piperidine-4,4'-pyrido[2,3-d][1,3]oxazin]-2'(1'H)-one Triethylamine (31 μL, 0.22 mmol), N-(3-dimethylaminopropyl)-N'-ethylcarbodiimide hydrochloride (14 mg, 0.075 mmol), and 1-hydroxy-7-azabenzotriazole (9.0 mg, 0.063 mmol) were added to a solution of the hydrochloride salt of [(6S,9S)-6-(2,3-difluorophenyl)-3-(1-methoxy-1-methylethyl)-6,7,8,9-tetrahydro-5H-imidazo[1,2-a]azepin-9-yl]acetic acid and the hydrochloride salt of [(6R,9R)-6-(2,3-difluorophenyl)-3-(1-methoxy-1-methylethyl)-6,7,8,9-tetrahydro-5H-imidazo[1,2-a]azepin-9-yl]acetic acid (26 mg, 0.063 mmol), and spiro[piperidine-4,4'-pyrido[2,3-d][1,3]oxazin]-2'(1'H)-one (16 mg, 0.075 mmol) in dichloromethane (3 mL) at 45° C. After 1.5 h, the mixture was concentrated. Purification by reverse phase HPLC (95% water/acetonitrile→5% water/acetonitrile with 0.1% trifluoroacetic acid) gave the title compound as a racemic mixture (15 mg). MS 580.2704 (M+1).

Example 173

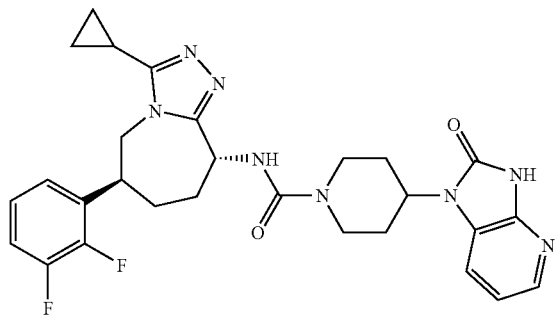

N-[(6S,9R)-3-Cyclopropyl-6-(2,3-difluorophenyl)-6,7,8,9-tetrahydro-5H-[1,2,4]triazolo[4,3-a]azepin-9-yl]-4-(2-oxo-2,3-dihydro-1H-imidazo[4,5-b]pyridin-1-yl)piperidine-1-carboxamide Step A: N-[(3R,6S)-6-(2,3-Difluorophenyl)-2-hydrazonoazepan-3-yl]-4-(2-oxo-2,3-dihydro-1H-imidazo[4,5-b]pyridin-1-yl)piperidine-1-carboxamide Hydrazine monohydrate (1.46 mL, 30.1 mmol) was added to a solution of N-[(3R,6S)-6-(2,3-difluorophenyl)-2-thioxoazepan-3-yl]-4-(2-oxo-2,3-dihydro-1H-imidazo[4,5-b]pyridin-1-yl)piperidine-1-carboxamide (502 mg, 1.00 mmol) in methanol (20 mL). After 30 min, the reaction was concentrated. Saturated aqueous sodium bicarbonate was added and the mixture was extracted with dichloromethane (3×). The combined organic extracts were dried over sodium sulfate, filtered, and concentrated to give the title compound (515 mg). MS 499.1 (M+1).

Step B: N-[(6S,9R)-3-Cyclopropyl-6-(2,3-difluorophenyl)-6,7,8,9-tetrahydro-5H-[1,2,4]triazolo[4,3-a]azepin-9-yl]-4-(2-oxo-2,3-dihydro-1H-imidazo[4,5-b]pyridin-1-yl)piperidine-1-carboxamide Triethylamine (20 μL, 0.142 mmol) was added to a solution of N-[(3R,6S)-6-(2,3-difluorophenyl)-2-hydrazonoazepan-3-yl]-4-(2-oxo-2,3-dihydro-1H-imidazo[4,5-b]pyridin-1-yl)piperidine-1-carboxamide (59 mg, 0.118 mmol) and cyclopropanecarbonyl chloride (11 μL, 0.124 mmol) in dichloromethane (1 mL) and the mixture heated to 45° C. After 20 h, the reaction was concentrated. Saturated aqueous sodium bicarbonate was added and the mixture was extracted with dichloromethane (3×). The combined organic extracts were dried over sodium sulfate, filtered, and concentrated. Purification by silica gel chromatography [100% dichloromethane→95% dichloromethane/(10% ammonium hydroxide/methanol)] gave the title compound (57 mg). MS 549.2524 (M+1).

Essentially following the procedure outlined for the preparation of Example 173, the Examples in Table 21 were prepared

TABLE 21

| Example | R | MS (M + 1) |
|---|---|---|
| 174 | H | 509.2231 |
| 175 | methoxymethyl-CH(CH3)- | 553.2490 |
| 176 | phenyl-C(CH3)2- | 585.2509 |
| 177 | isopropyl branched | 537.2552 |
| 178 | 2,2-difluorocyclopropyl-C(CH3)2- | 585.2315 |
| 179 | CF3-cyclopropyl | 617.2420 |

Example 180

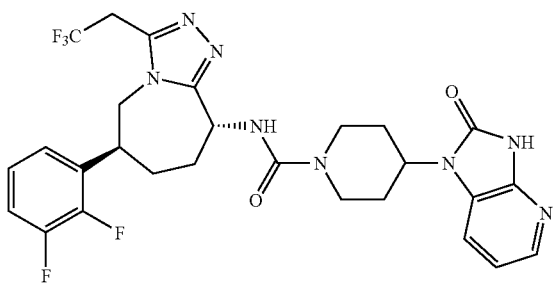

N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-4-(2-oxo-2,3-dihydro-1H-imidazo[4,5-b]pyridin-1-yl)piperidine-1-carboxamide Step A: (6S,9R)-6-(2,3-Difluorophenyl)-3-(2,2,2-trifluoroethyl)-6,7,8,9-tetrahydro-5H-[1,2,4]triazolo[4,3-a]azepin-9-amine Hydrochloric acid (4.0 M in dioxane; 10 mL, 40.1 mmol) was added to a solution of tert-butyl [(6S,9R)-6-(2,3-difluorophenyl)-3-(2,2,2-trifluoroethyl)-6,7,8,9-tetrahydro-5H-[1,2,4]triazolo[4,3-a]azepin-9-yl]carbamate (618 mg, 1.384 mmol) in 1,4-dioxane (5 mL). After 1 h, the reaction was concentrated to give the title compound as a bis hydrochloride salt (584 mg). MS 347.1 (M+1).

Step B: N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-4-(2-oxo-2,3-dihydro-1H-imidazo[4,5-b]pyridin-1-yl)piperidine-1-carboxamide Triethylamine (58 µL, 0.417 mmol) was added to a solution of the bis hydrochloride salt of (6S,9R)-6-(2,3-difluorophenyl)-3-(2,2,2-trifluoroethyl)-6,7,8,9-tetrahydro-5H-[1,2,4]triazolo[4,3-a]azepin-9-amine (50 mg, 0.119 mmol) and 4-nitrophenyl chloroformate (25 mg, 125 mmol) in tetrahydrofuran (4 mL) at 0° C. After 15 min, 2-oxo-1-piperidinium-4-yl-2,3-dihydro-1H-imidazo[4,5-b]pyridin-4-ium dichloride (52 mg, 0.179 mmol), triethylamine (58 µL, 0.417 mmol) and dichloromethane (3 mL) were added and the mixture allowed to warm to ambient temperature. After 5 h, the reaction was concentrated. Purification by reverse phase HPLC (C-18, 90% water/acetonitrile→100% acetonitrile with 0.1% trifluoroacetic acid) gave the title compound (38 mg). MS 591.2223 (M+1).

Example 181

N-{(6S,9R)-6-(2,3-Difluorophenyl)-3-[1-(trifluoromethyl cyclopropyl]-6,7,8,9-tetrahydro-5H-[1,2,4]triazolo[4,3-a]azepin-9-yl}-4-(3-methyl-2-oxo-2,3-dihydro-1H-imidazo[4,5-b]pyridin-1-yl)piperidine-1-carboxamide Step A: (6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-amine Trifluoroacetic acid (7.5 mL, 101.3 mmol) was added to a solution of tert-butyl {(6S,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}carbamate (0.38 g, 0.80 mmol) in dichloromethane (15 mL). After 1 h, the reaction mixture was quenched with saturated aqueous sodium bicarbonate and the mixture was extracted with dichloromethane (3×). The combined organic extracts were washed with saturated brine, dried over magnesium sulfate, filtered and concentrated to give the title compound. MS 373.1 (M+1).

Step B: N-{(6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-yl}-4-(3-methyl-2-oxo-2,3-dihydro-1H-imidazo[4,5-b]pyridin-1-yl)piperidine-1-carboxamide 1,1'-Carbonyldiimidazole (24.0 mg, 0.15 mmol) was added to a solution of (6S,9R)-6-(2,3-difluorophenyl)-3-[1-(trifluoromethyl)cyclopropyl]-6,7,8,9-tetrahydro-5H-[1,2,4]triazolo[4,3-a]azepin-9-amine (28 mg, 0.075 mmol) and in tetrahydrofuran (1.0 mL) at 0° C. After 30 min, additional 1,1'-carbonyldiimidazole (11.0 mg, 0.068 mmol) was added. After 30 min, 3-methyl-1-piperidin-4-yl-1,3-dihydro-2H-imidazo[4,5-b]pyridin-2-one (26 mg, 0.113 mmol) was added and the mixture was heated to 60° C. After 1 h, additional 3-methyl-1-piperidin-4-yl-1,3-dihydro-2H-imidazo[4,5-b]pyridin-2-one (23 mg, 0.099 mmol) was added. After 1 h, the reaction mixture was concentrated. Purification by reverse phase HPLC (100% water→100% acetonitrile with 0.1% trifluoroacetic acid) gave the title compound (33 mg). MS 631.2566 (M+1).

Example 182

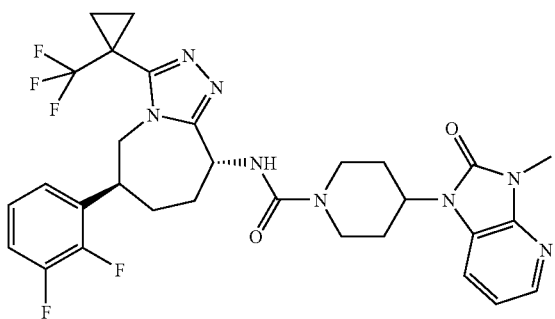

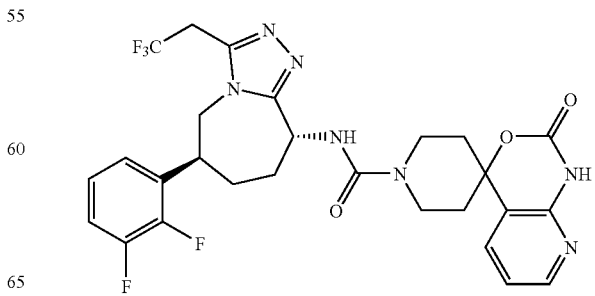

183

N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-2'-oxo-1',2'-dihydro-1H-spiro[piperidine-4,4'-pyrido[2,3-d][1,3]oxazine]-1-carboxamide

Step A: (6S,9R)-6-(2,3-Difluorophenyl)-3-(2,2,2-trifluoroethyl)-6,7,8,9-tetrahydro-5H-[1,2,4]triazolo[4,3-a]azepin-9-amine Hydrochloric acid (4.0 M in dioxane; 10 mL, 40.1 mmol) was added to a solution of tert-butyl [(6S,9R)-6-(2,3-difluorophenyl)-3-(2,2,2-trifluoroethyl)-6,7,8,9-tetrahydro-5H-[1,2,4]triazolo[4,3-a]azepin-9-yl]carbamate (618 mg, 1.384 mmol) in 1,4-dioxane (5 mL). After 1 h, the reaction was concentrated to give the title compound as a bis hydrochloride salt (584 mg). MS 347.1 (M+1).

Step B: N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-2'-oxo-1',2'-dihydro-1H-spiro[piperidine-4,4'-pyrido[2,3-d][1,3]oxazine]-1-carboxamide Triethylamine (42 µL, 0.298 mmol) was added to a solution of the bis hydrochloride salt of (6S,9R)-6-(2,3-difluorophenyl)-3-(2,2,2-trifluoroethyl)-6,7,8,9-tetrahydro-5H-[1,2,4]triazolo[4,3-a]azepin-9-amine (50 mg, 0.119 mmol) and 1,1'-carbonyldiimidazole (29 mg, 0.179 mmol) in tetrahydrofuran (2 mL) at 0° C. After 1 h, spiro[piperidine-4,4'-pyrido[2,3-a][1,3]oxazin]-2'(1'H)-one (33 mg, 0.149 mmol) and dichloromethane (3 mL) were added and the mixture heated to 60° C. After 2.5 h, saturated aqueous sodium bicarbonate was added and the mixture was extracted with dichloromethane (3×). The combined organic extracts were dried over sodium sulfate, filtered, and concentrated. Purification by reverse phase HPLC (C-18, 90% water/acetonitrile→100% acetonitrile with 0.1% trifluoroacetic acid) gave the title compound (37 mg). MS 592.2087 (M+1).

Essentially following the procedure outlined for the preparation of Example 182, the Examples in Table 22 were prepared.

TABLE 22

| Example | R | MS (M + 1) |
|---------|---|------------|
| 183 | (cyclopropyl-CF₃)-C(CH₃)- | 618.2251 |
| 184 | (CH₃O)-C(CH₃)₂- | 542.2682 |

Example 185

N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-1'-methyl-2'-oxo-1',2'-dihydro-1H-spiro[piperidine-4,4'-pyrido[2,3-d][1,3]oxazine]-1-carboxamide

Step A: N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-1'-methyl-2'-oxo-1',2'-dihydro-1H-spiro[piperidine-4,4'-pyrido[2,3-a][1,3]oxazine]-1-carboxamide Triethylamine (13 µL, 0.092 mmol) was added to a solution of (6S,9R)-6-(2,3-difluorophenyl)-3-(2,2,2-trifluoroethyl)-6,7,8,9-tetrahydro-5H-[1,2,4]triazolo[4,3-a]azepin-9-amine (32 mg, 0.092 mmol) and 1,1'-carbonyldiimidazole (29 mg, 0.179 mmol) in tetrahydrofuran (1 mL) at 0° C. After 1 h, 1'-methylspiro[piperidine-4,4'-pyrido[2,3-d][1,3]oxazin]-2'(1'H)-one (26 mg, 0.111 mmol) and dichloromethane (1 mL) were added and the mixture heated to 60° C. After 1 h, saturated aqueous sodium bicarbonate was added and the mixture was extracted with dichloromethane (3×). The combined organic extracts were dried over sodium sulfate, filtered, and concentrated. Purification by reverse phase HPLC (C-18, 90% water/acetonitrile→100% acetonitrile with 0.1% trifluoroacetic acid) gave the title compound (28 mg). MS 606.2231 (M+1).

Example 186

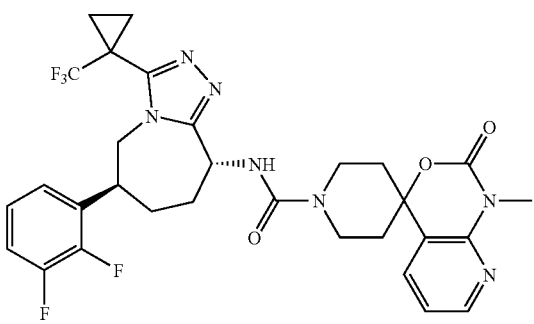

N-{(6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-yl}-1'-methyl-2'-oxo-1',2'-dihydro-1H-spiro[piperidine-4,4'-pyrido[2,3-d][1,3]oxazine]-1-carboxamide Step A: N-{(6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-yl}-1'-methyl-2'-oxo-1',2'-dihydro-1H-spiro[piperidine-4,4'-pyrido[2,3-d][1,3]oxazine]-1-carboxamide Triethylamine (39 µL, 0.281 mmol) was added to a solution of the bis HCl salt of (6S,9R)-6-(2,3-difluorophenyl)-3-[1-(trifluoromethyl)cyclopropyl]-6,7,8,9-tetrahydro-5H-[1,2,4]triazolo[4,3-a]azepin-9-amine (50 mg, 0.112 mmol) and 1,1'-carbonyldiimidazole (32 mg, 0.197 mmol) in tetrahydrofuran (1 mL) at 0° C. After 1 h, 1'-methylspiro[piperidine-4,4'-pyrido[2,3-d][1,3]oxazin]-2'(1'H)-one (31 mg, 0.135 mmol) and dichloromethane (1 mL) were added and the mixture heated to 60° C. After 3 h, saturated aqueous sodium bicarbonate was added and the mixture was extracted with dichloromethane (3×). The combined organic extracts were dried over sodium sulfate, filtered, and concentrated. Purification by reverse phase HPLC (C-18, 90% water/acetonitrile→100% acetonitrile with 0.1% trifluoroacetic acid) gave the title compound (64 mg). MS 632.2384 (M+1).

Example 187

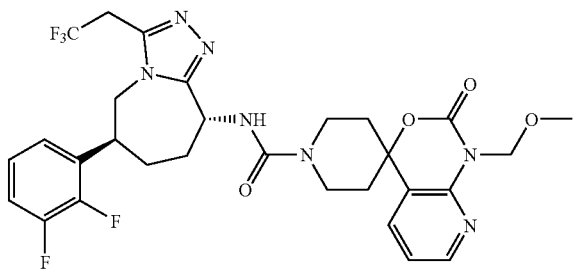

N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-1'-(methoxymethyl)-2'-oxo-1',2'-dihydro-1H-spiro[piperidine-4,4'-pyrido[2,3-d][1,3]oxazine]-1-carboxamide Step A: N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-1'-(methoxymethyl)-2'-oxo-1',2'-dihydro-1H-spiro[piperidine-4,4'-pyrido[2,3-d][1,3]oxazine]-1-carboxamide Triethylamine (26 µL, 0.185 mmol) was added to a solution of the bis hydrochloride salt of (6S,9R)-6-(2,3-difluorophenyl)-3-(2,2,2-trifluoroethyl)-6,7,8,9-tetrahydro-5H-[1,2,4]triazolo[4,3-a]azepin-9-amine (31 mg, 0.074 mmol) and 1,1'-carbonyldiimidazole (21 mg, 0.129 mmol) in tetrahydrofuran (1 mL) at 0° C. After 1 h, 1'-(methoxymethyl)spiro[piperidine-4,4'-pyrido[2,3-d][1,3]oxazin]-2'(1'H)-one (23 mg, 0.089 mmol) and dichloromethane (1 mL) were added and the mixture heated to 60° C. After 2.5 h, saturated aqueous sodium bicarbonate was added and the mixture was extracted with dichloromethane (3×). The combined organic extracts were dried over sodium sulfate, filtered, and concentrated. Purification by reverse phase HPLC (C-18, 90% water/acetonitrile→100% acetonitrile with 0.1% trifluoroacetic acid) gave the title compound (42 mg). MS 636.2330 (M+1).

Example 188

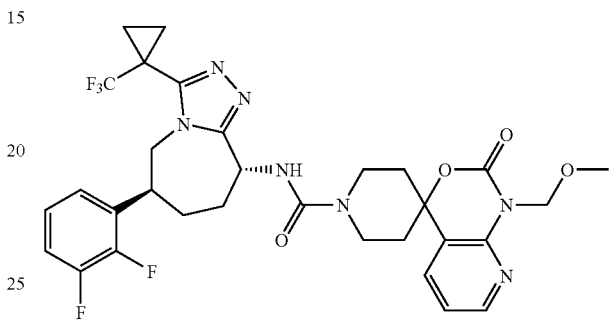

N-{(6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-yl}-1'-(methoxymethyl)-2'-oxo-1',2'-dihydro-1H-spiro[piperidine-4,4'-pyrido[2,3-d][1,3]oxazine]-1-carboxamide Step A: N-{(6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-yl}-1'-(methoxymethyl)-2'-oxo-1',2'-dihydro-1H-spiro[piperidine-4,4'-pyrido[2,3-d][1,3]oxazine]-1-carboxamide Triethylamine (39 µL, 0.281 mmol) was added to a solution of the bis HCl salt of (6S,9R)-6-(2,3-difluorophenyl)-3-[1-(trifluoromethyl)cyclopropyl]-6,7,8,9-tetrahydro-5H-[1,2,4]triazolo[4,3-a]azepin-9-amine (50 mg, 0.112 mmol) and 1,1'-carbonyldiimidazole (32 mg, 0.197 mmol) in tetrahydrofuran (1 mL) at 0° C. After 1 h, 1'-(methoxymethyl)spiro[piperidine-4,4'-pyrido[2,3-d][1,3]oxazin]-2'(1'H)-one (35 mg, 0.135 mmol) and dichloromethane (1 mL) were added and the mixture heated to 60° C. After 2.5 h, saturated aqueous sodium bicarbonate was added and the mixture was extracted with dichloromethane (3×). The combined organic extracts were dried over sodium sulfate, filtered, and concentrated. Purification by reverse phase HPLC (C-18, 90% water/acetonitrile→100% acetonitrile with 0.1% trifluoroacetic acid) gave the title compound (64 mg). MS 662.2487 (M+1).

Example 189

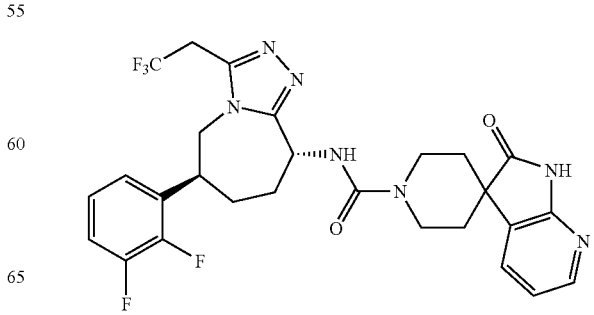

N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-2'-oxo-1',2'-dihydro-1H-spiro[piperidine-4,3'-pyrrolo[2,3-b]pyridine]-1-carboxamide Step A: (6S,9R)-6-(2,3-Difluorophenyl-3-(2,2,2-trifluoroethyl)-6,7,8,9-tetrahydro-5H-[1,2,4]triazolo[4,3-a]azepin-9-amine Hydrochloric acid (4.0 M in dioxane; 10 mL, 40.1 mmol) was added to a solution of tert-butyl [(6S,9R)-6-(2,3-difluorophenyl)-3-(2,2,2-trifluoroethyl)-6,7,8,9-tetrahydro-5H-[1,2,4]triazolo[4,3-a]azepin-9-yl]carbamate (618 mg, 1.384 mmol) in 1,4-dioxane (5 mL). After 1 h, the reaction was concentrated to give the title compound as a bis hydrochloride salt (584 mg). MS 347.1 (M+1).

Step B: N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-2'-oxo-1',2'-dihydro-1H-spiro[piperidine-4,3'-pyrrolo[2,3-b]pyridine]-1-carboxamide Triethylamine (52 μL, 0.370 mmol) was added to a solution of the bis hydrochloride salt of (6S,9R)-6-(2,3-difluorophenyl)-3-(2,2,2-trifluoroethyl)-6,7,8,9-tetrahydro-5H-[1,2,4]triazolo[4,3-a]azepin-9-amine (62 mg, 0.148 mmol) and 1,1'-carbonyldiimidazole (48 mg, 0.296 mmol) in tetrahydrofuran (5 mL) at 0° C. After 30 min, 2'-oxo-1',2'-dihydrospiro[piperidine-4,3'-pyrrolo[2,3-b]pyridine]dichloride (51 mg, 0.185 mmol) and dichloromethane (3 mL) were added and the mixture heated to 60° C. After 1.5 h, the reaction was concentrated. Purification by reverse phase HPLC (C-18, 90% water/acetonitrile→100% acetonitrile with 0.1% trifluoroacetic acid) gave the title compound (33 mg). MS 576.2143 (M+1).

Example 190

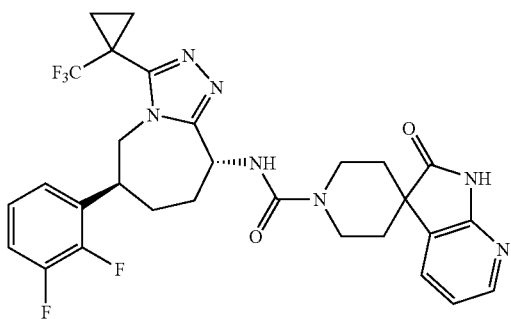

N-{(6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-yl}-2'-oxo-1',2'-dihydro-1H-spiro[piperidine-4,3'-pyrrolo[2,3-b]pyridine]-1-carboxamide Step A: (6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-amine Hydrochloric acid (4.0 M in dioxane; 5 mL, 20.0 mmol) was added to a solution of tert-butyl {(6S,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}carbamate (440 mg, 0.93 mmol) in 1,4-dioxane (5 mL). After 1.5 h, the reaction mixture was concentrated to give the bis hydrochloride salt of the title compound (425 mg). MS 347.1 (M+1).

Step B: N-{(6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-yl}-2'-oxo-1',2'-dihydro-1H-spiro[piperidine-4,3'-pyrrolo[2,3-b]pyridine]-1-carboxamide Triethylamine (39 μL, 0.28 mmol) was added to a solution of the bis hydrochloride salt of (6S,9R)-6-(2,3-difluorophenyl)-3-[1-(trifluoromethyl)cyclopropyl]-6,7,8,9-tetrahydro-5H-[1,2,4]triazolo[4,3-a]azepin-9-amine (50 mg, 0.112 mmol) and 1,1'-carbonyldiimidazole (32 mg, 0.197 mmol) in tetrahydrofuran (1.5 mL) at 0° C. After 30 min, additional 1,1'-carbonyldiimidazole (10 mg, 0.062 mmol) was added. After 15 min, 2'-oxo-1',2'-dihydrospiro[piperidine-4,3'-pyrrolo[2,3-b]pyridine]dichloride (37 mg, 0.135 mmol), triethylamine (39 μL, 0.28 mmol) and dichloromethane (1.5 mL) were added and the mixture heated to 60° C. After 1.5 h, the reaction mixture was allowed to cool to ambient temperature and concentrated. Purification by reverse phase HPLC (C-18, 10% acetonitrile/water→100% acetonitrile with 0.1% trifluoroacetic acid) gave the title compound (38 mg). MS 602.2306 (M+1).

Example 191

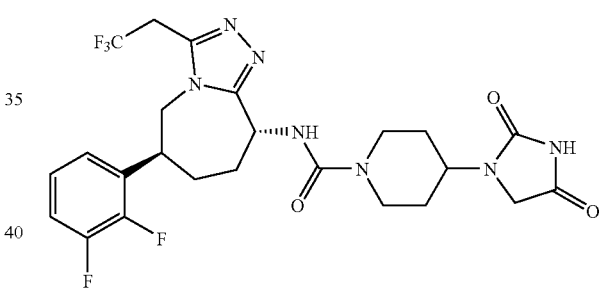

N-[(6S,9R)-6-(2,3-Difluorophenyl-3-(2,2,2-trifluoroethyl-6,7,8,9-tetrahydro-5H-[1,2,4]triazolo[4,3-a]azepin-9-yl]-4-(2,4-dioxoimidazolidin-1-yl)piperidine-1-carboxamide Step A: (6S,9R)-6-(2,3-Difluorophenyl)-3-(2,2,2-trifluoroethyl)-6,7,8,9-tetrahydro-5H-[1,2,4]triazolo[4,3-a]azepin-9-amine Hydrochloric acid (4.0 M in dioxane; 10 mL, 40.1 mmol) was added to a solution of tert-butyl [(6S,9R)-6-(2,3-difluorophenyl)-3-(2,2,2-trifluoroethyl)-6,7,8,9-tetrahydro-5H-[1,2,4]triazolo[4,3-a]azepin-9-yl]carbamate (618 mg, 1.384 mmol) in 1,4-dioxane (5 mL). After 1 h, the reaction was concentrated to give the title compound as a bis hydrochloride salt (584 mg). MS 347.1 (M+1).

Step B: N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-4-(2,4-dioxoimidazolidin-1-yl)piperidine-1-carboxamide Triethylamine (42 μL, 0.298 mmol) was added to a solution of the bis hydrochloride salt of (6S,9R)-6-(2,3-difluorophenyl)-3-(2,2,2-trifluoroethyl)-6,7,8,9-tetrahydro-5H-[1,2,4]triazolo[4,3-a]azepin-9-amine (50 mg, 0.119 mmol) and 1,1'-carbonyldiimidazole (44 mg, 0.271 mmol) in tetrahydrofuran (4 mL) at 0° C. After 1 h, 1-piperidin-4-ylimidazolidine-2,4-dione (27 mg, 0.149 mmol) and dichloromethane (3 mL) were added and the mixture heated to 60° C. After 2 h, the reaction was concentrated. Purification by reverse phase HPLC (C-18, 90% water/acetonitrile→100% acetonitrile with 0.1% trifluoroacetic acid) gave the title compound (28 mg). MS 556.2126 (M+1).

Example 192

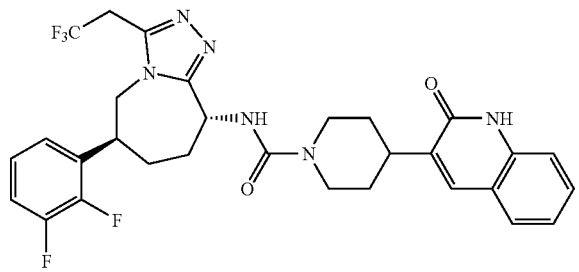

N-[(6S,9R)-6-(2,3-Difluorophenyl)-3-(2,2,2-trifluoroethyl-6,7,8,9-tetrahydro-5H-[1,2,4]triazolo[4,3-a]azepin-9-yl]-4-(2-oxo-1,2-dihydroquinolin-3-yl)piperidine-1-carboxamide Step A: (6S,9R)-6-(2,3-Difluorophenyl)-3-(2,2,2-trifluoroethyl)-6,7,8,9-tetrahydro-5H [1,2,4]triazolo[4,3-a]azepin-9-amine Hydrochloric acid (4.0 M in dioxane; 10 mL, 40 mmol) was added to a solution of tert-butyl [(6S,9R)-6-(2,3-difluorophenyl)-3-(2,2,2-trifluoroethyl)-6,7,8,9-tetrahydro-5H-[1,2,4]triazolo[4,3-a]azepin-9-yl]carbamate (618 mg, 1.38 mmol) in 1,4-dioxane (5 mL). After 1 h, the reaction mixture was concentrated to give the bis hydrochloride salt of the title compound (584 mg). MS 347.1 (M+1).

Step B: N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-4-(2-oxo-1,2-dihydroquinolin-3-yl)piperidine-1-carboxamide Triethylamine (50 µL, 0.358 mmol) was added to a solution of the bis hydrochloride salt of (6S,9R)-6-(2,3-difluorophenyl)-3-(2,2,2-trifluoroethyl)-6,7,8,9-tetrahydro-5H-[1,2,4]triazolo[4,3-a]azepin-9-amine (60 mg, 0.143 mmol) and 1,1'-carbonyldiimidazole (41 mg, 0.25 mmol) in tetrahydrofuran (3 mL) at 0° C. After 25 min, 3-piperidin-4-ylquinolin-2(1H)-one (33 mg, 0.143 mmol) and dichloromethane (3 mL) were added and the mixture heated to 60° C. After 16 h, saturated aqueous sodium bicarbonate was added and the mixture was extracted with dichloromethane (3×). The organic layer was washed with saturated brine, dried over magnesium sulfate, filtered and concentrated. Purification by silica gel chromatography [100% dichloromethane→95% dichloromethane/ (10% ammonium hydroxide/methanol)]. Repurification by reverse phase HPLC (C-18, 10% acetonitrile/water→100% acetonitrile with 0.1% trifluoroacetic acid) gave the title compound (57.5 mg). MS 601.2312 (M+1).

Essentially following the procedure outlined for the preparation of Example 192, the Examples in Table 23 were prepared.

TABLE 23

| Example | R | MS (M + 1) |
|---------|---|------------|
| 193 | ![cyclopropyl-CF3] | 627.2510 |
| 194 | ![OMe-dimethyl] | 591.2901 |
| 195 | ![HO-dimethyl] | 577.2717 |

Example 196

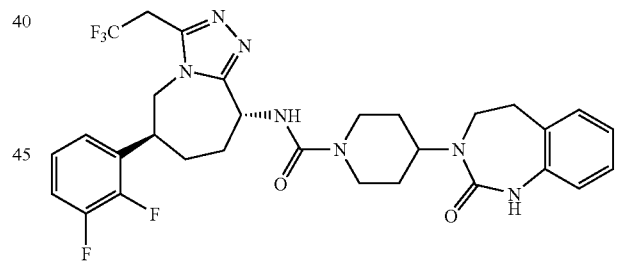

N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-4-(2-oxo-1,2,4,5-tetrahydro-3H-1,3-benzodiazepin-3-yl)piperidine-1-carboxamide Step A: (6S,9R)-6-(2,3-Difluorophenyl)-3-(2,2,2-trifluoroethyl)-6,7,8,9-tetrahydro-5H-[1,2,4]triazolo[4,3-a]azepin-9-amine Hydrochloric acid (4.0 M in dioxane; 10 mL, 40 mmol) was added to a solution of tert-butyl [(6S,9R)-6-(2,3-difluorophenyl)-3-(2,2,2-trifluoroethyl)-6,7,8,9-tetrahydro-5H-[1,2,4]triazolo[4,3-a]azepin-9-yl]carbamate (618 mg, 1.38 mmol) in 1,4-dioxane (5 mL). After 1 h, the reaction mixture was concentrated to give the bis hydrochloride salt of the title compound (584 mg). MS 347.1 (M+1).

191

Step B: N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-4-(2-oxo-1,2,4,5-tetrahydro-3H-1,3-benzodiazepin-3-yl)piperidine-1-carboxamide Triethylamine (50 μL, 0.358 mmol) was added to a solution of the bis hydrochloride salt of (6S,9R)-6-(2,3-difluorophenyl)-3-(2,2,2-trifluoroethyl)-6,7,8,9-tetrahydro-5H-[1,2,4]triazolo[4,3-a]azepin-9-amine (60 mg, 0.143 mmol) and 1,1'-carbonyldiimidazole (41 mg, 0.25 mmol) in tetrahydrofuran (3 mL) at 0° C. After 25 min, the hydrochloride salt of 3-piperidin-4-yl-1,3,4,5-tetrahydro-2H-1,3-benzodiazepin-2-one (40 mg, 0.143 mmol) and dichloromethane (3 mL) were added and the mixture was heated to 60° C. After 16 h, the reaction mixture was allowed to cool to ambient temperature and concentrated. Purification by reverse phase HPLC (C-18, 10% acetonitrile/water→100% acetonitrile with 0.1% trifluoroacetic acid) gave the title compound (53 mg). MS 618.2572 (M+1).

Essentially following the procedure outlined for the preparation of Example 196, the Examples in Table 24 were prepared.

TABLE 24

| Example | R | MS (M + 1) |
|---|---|---|
| 197 | F₃C-C(cyclopropyl)- | 644.2767 |
| 198 | (CH₃)₂C(OCH₃)- | 608.3130 |
| 199 | (CH₃)₂C(OH)- | 594.2960 |

192

Example 200

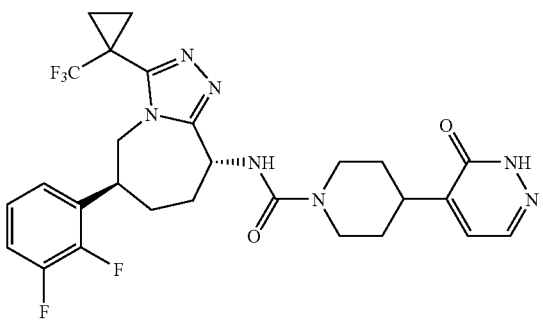

N-{(6S,9R)-6-(2,3-Difluorophenyl-3-[1-(trifluoromethyl)cyclopropyl]-6,7,8,9-tetrahydro-5H-[1,2,4]triazolo[4,3-a]azepin-9-yl}-4-(3-oxo-2,3-dihydropyridazin-4-yl)piperidine-1-carboxamide Step A: (6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-amine Hydrochloric acid (4.0 M in dioxane; 5 mL, 20.0 mmol) was added to a solution of tert-butyl {(6S,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}carbamate (440 mg, 0.93 mmol) in 1,4-dioxane (5 mL). After 1.5 h, the reaction was concentrated to give the bis hydrochloride salt of the title compound (425 mg). MS 347.1 (M+1).

Step B: N-{(6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-yl}-4-(3-oxo-2,3-dihydropyridazin-4-yl)piperidine-1-carboxamide Triethylamine (16 μL, 0.112 mmol) was added to a solution of the bis hydrochloride salt of (6S,9R)-6-(2,3-difluorophenyl)-3-[1-(trifluoromethyl)cyclopropyl]-6,7,8,9-tetrahydro-5H-[1,2,4]triazolo[4,3-a]azepin-9-amine (20 mg, 0.045 mmol) and 1,1'-carbonyldiimidazole (13 mg, 0.079 mmol) in tetrahydrofuran (1.0 mL) at 0° C. After 20 min, additional 1,1'-carbonyldiimidazole (7.3 mg, 0.045 mmol) was added. After 30 min, 4-piperidin-4-ylpyridazin-3(2H)-one (10 mg, 0.056 mmol) and dichloromethane (1.0 mL) were added and the mixture was heated to 60° C. After 16 h, the reaction was allowed to cool to ambient temperature and concentrated. Purification by reverse phase HPLC (C-18, 10% acetonitrile/water→100% acetonitrile with 0.1% trifluoroacetic acid) gave the title compound (20 mg). MS 578.2315 (M+1).

Essentially following the procedure outlined for the preparation of Example 200, the Examples in Table 25 were prepared.

TABLE 25

| Example | R | MS (M + 1) |
|---|---|---|
| 201 | methoxy-dimethyl group | 542.2628 |
| 202 | hydroxy-dimethyl group | 528.2508 |

Example 203

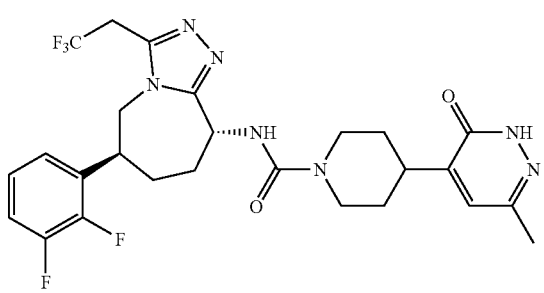

N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-4-(6-methyl-3-oxo-2,3-dihydropyridazin-4-yl)piperidine-1-carboxamide Step A: (6S,9R)-6-(2,3-Difluorophenyl)-3-(2,2,2-trifluoroethyl)-6,7,8,9-tetrahydro-5H-[1,2,4]triazolo[4,3-a]azepin-9-amine Hydrochloric acid (4.0 M in dioxane; 10 mL, 40 mmol) was added to a solution of tert-butyl [(6S,9R)-6-(2,3-difluorophenyl)-3-(2,2,2-trifluoroethyl)-6,7,8,9-tetrahydro-5H-[1,2,4]triazolo[4,3-a]azepin-9-yl]carbamate (618 mg, 1.38 mmol) in dioxane (5 mL). After 1 h, the reaction mixture was concentrated to give the bis hydrochloride salt of the title compound (584 mg). MS 347.1 (M+1).

Step B: N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-4-(6-methyl-3-oxo-2,3-dihydropyridazin-4-yl)piperidine-1-carboxamide Triethylamine (42 μL, 0.298 mmol) was added to a solution of the bis hydrochloride salt of (6S,9R)-6-(2,3-difluorophenyl)-3-(2,2,2-trifluoroethyl)-6,7,8,9-tetrahydro-5H-[1,2,4]triazolo[4,3-a]azepin-9-amine (50 mg, 0.119 mmol) and 1,1'-carbonyldiimidazole (34 mg, 0.209 mmol) in tetrahydrofuran (2 mL) at 0° C. After 15 min, additional 1,1'-carbonyldiimidazole (10 mg, 0.062 mmol). After 30 min, 6-methyl-4-piperidin-4-ylpyridazin-3(2H)-one (28 mg, 0.143 mmol) and dichloromethane (3 mL) were added and the mixture heated to 60° C. After 1 h, the reaction mixture was allowed to cool to ambient temperature and concentrated. Purification by reverse phase HPLC (C-18, 10% acetonitrile/water→100% acetonitrile with 0.1% trifluoroacetic acid) gave the title compound (54 mg). MS 566.2313 (M+1).

Essentially following the procedure outlined for the preparation of Example 203, the Examples in Table 26 were prepared.

TABLE 26

| Example | R | MS (M + 1) |
|---|---|---|
| 204 | methoxy-dimethyl group | 556.2847 |
| 205 | trifluoromethyl-cyclopropyl group | 592.2462 |

Example 206

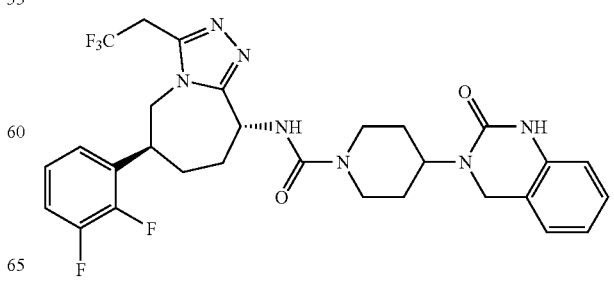

N-[(6S,9R)-6-(23-Difluorophenyl)-3-(2,2,2-trifluoroethyl)-6,7,8,9-tetrahydro-5H-[1,2,4]triazolo[4,3-a]azepin-9-yl]-4-(2-oxo-1,4-dihydroquinazolin-3(2H)-yl)piperidine-1-carboxamide Step A: (6S,9R)-6-(2,3-Difluorophenyl)-3-(2,2,2-trifluoroethyl)-6,7,8,9-tetrahydro-5H-[1,2,4]triazolo[4,3-a]azepin-9-amine Hydrochloric acid (4.0 M in dioxane; 10 mL, 40 mmol) was added to a solution of tert-butyl [(6S,9R)-6-(2,3-difluorophenyl)-3-(2,2,2-trifluoroethyl)-6,7,8,9-tetrahydro-5H-[1,2,4]triazolo[4,3-a]azepin-9-yl]carbamate (618 mg, 1.38 mmol) in dioxane (5 mL). After 1 h, the reaction mixture was concentrated to give the bis hydrochloride salt of the title compound (584 mg). MS 347.1 (M+1).

Step B: N-[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]-4-(2-oxo-1,4-dihydroquinazolin-3(2H)-yl)piperidine-1-carboxamide Triethylamine (50 μL, 0.356 mmol) was added to a solution of the bis hydrochloride salt of (6S,9R)-6-(2,3-difluorophenyl)-3-(2,2,2-trifluoroethyl)-6,7,8,9-tetrahydro-5H-[1,2,4]triazolo[4,3-a]azepin-9-amine (60 mg, 0.143 mmol) and 1,1'-carbonyldiimidazole (41 mg, 0.25 mmol) in tetrahydrofuran (3 mL) at 0° C. After 25 min, the hydrochloride salt of 3-piperidin-4-yl-3,4-dihydroquinazolin-2(1H)-one (38 mg, 0.143 mmol) and dichloromethane (3 mL) were added and the mixture heated to 60° C. After 16 h, the reaction mixture was allowed to cool to ambient temperature and concentrated. Purification by reverse phase HPLC (C-18, 10% acetonitrile/water→100% acetonitrile with 0.1% trifluoroacetic acid) gave the title compound (54 mg). MS 604.2404 (M+1).

Example 207

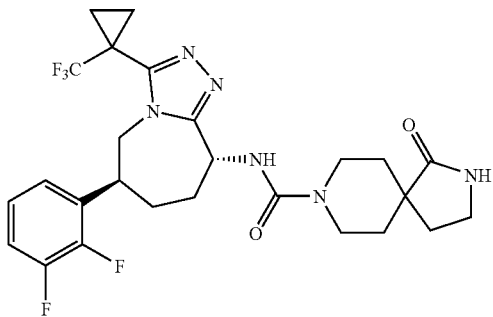

N-{(6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-yl}-1-oxo-2,8-diazaspiro[4,5]decane-8-carboxamide Step A: (6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-amine Hydrochloric acid (4.0 M in dioxane; 5 mL, 20.0 mmol) was added to a solution of tert-butyl {(6S,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}carbamate (440 mg, 0.93 mmol) in 1,4-dioxane (5 mL). After 1.5 h, the reaction mixture was concentrated to give the bis hydrochloride salt of the title compound (425 mg). MS 347.1 (M+1).

Step B: N-{(6S,9R)-6-(2,3-Difluorophenyl)-3-[1-(trifluoromethyl)cyclopropyl]-6,7,8,9-tetrahydro-5H-[1,2,4]triazolo[4,3-a]azepin-9-yl}-1-oxo-2,8-diazaspiro[4,5]decane-8-carboxamide Triethylamine (16 μL, 0.112 mmol) was added to a solution of the bis hydrochloride salt of (6S,9R)-6-(2,3-difluorophenyl)-3-[1-(trifluoromethyl)cyclopropyl]-6,7,8,9-tetrahydro-5H-[1,2,4]triazolo[4,3-a]azepin-9-amine (20 mg, 0.045 mmol) and 1,1'-carbonyldiimidazole (13 mg, 0.079 mmol) in tetrahydrofuran (1.0 mL) at 0° C. After 20 min, additional 1,1'-carbonyldiimidazole (7.3 mg, 0.045 mmol) was added. After 30 min, the hydrochloride salt of 2,8-diazaspiro[4.5]decan-1-one (11 mg, 0.056 mmol) and dichloromethane (1.0 mL) were added and the mixture was heated to 60° C. After 16 h, the reaction was concentrated. Purification by reverse phase HPLC (C-18, 10% acetonitrile/water→100% acetonitrile with 0.1% trifluoroacetic acid) gave the title compound (14 mg). MS 553.2315 (M+1).

Example 208

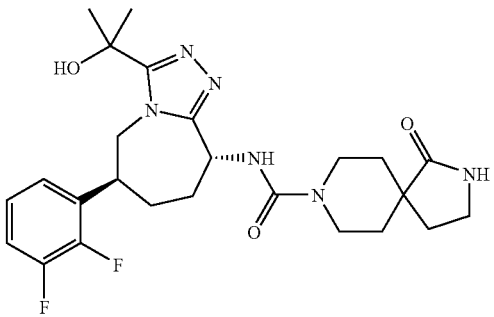

N-[(6S,9R)-6-(2,3-Difluorophenyl)-3-(1-hydroxy-1-methylethyl)-6,7,8,9-tetrahydro-5H-[1,2,4]triazolo[4,3-a]azepin-9-yl]-1-oxo-2,8-diazaspiro[4.5]decane-8-carboxamide Step A: 2-[(6S,9R)-9-Amino-6-(2,3-difluorophenyl)-6,7,8,9-tetrahydro-5H-[1,2,4]triazolo[4,3-a]azepin-3-yl]propan-2-ol Hydrochloric acid (4.0 M in dioxane; 5 mL, 20.0 mmol) was added to a solution of tert-butyl [(6S,9R)-6-(2,3-difluorophenyl)-3-(1-hydroxy-1-methylethyl)-6,7,8,9-tetrahydro-5H-[1,2,4]triazolo[4,3-a]azepin-9-yl]carbamate (176 mg, 0.417 mmol) in 1,4-dioxane (5 mL). After 1 h, the reaction mixture was concentrated to give the bis hydrochloride salt of the title compound (175 mg). MS 323.1 (M+1).

Step B: N-[(6S,9R)-6-(2,3-Difluorophenyl)-3-(1-hydroxy-1-methylethyl)-6,7,8,9-tetrahydro-5H-[1,2,4]triazolo[4,3-a]azepin-9-yl]-1-oxo-2,8-diazaspiro[4.5]decane-8-carboxamide Triethylamine (18 μL, 0.126 mmol) was added to a solution of the bis hydrochloride salt of 2-[(6S,9R)-9-amino-6-(2,3-difluorophenyl)-6,7,8,9-tetrahydro-5H-[1,2,4]triazolo[4,3-a]azepin-3-yl]propan-2-ol (20 mg, 0.051 mmol) and 1,1'-carbonyldiimidazole (14 mg, 0.09 mmol) in tetrahydrofuran (1.0 mL) at 0° C. After 10 min, additional 1,1'-carbonyldiimidazole (8.0 mg, 0.05 mmol) was added. After 30 min, the hydrochloride salt of 2,8-diazaspiro[4.5]decan-1-one (12 mg, 0.06 mmol) and dichloromethane (1.0 mL) were added and the mixture was heated to 60° C. After 16 h, the reaction was concentrated. Purification by reverse phase HPLC (C-18, 10% acetonitrile/water→100% acetonitrile with 0.1% trifluoroacetic acid) gave the title compound (20 mg). MS 503.2570 (M+1).

Example 209

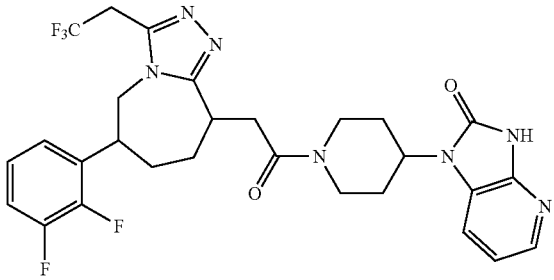

1-(1-{[6-(2,3-Difluorophenyl)-3-(2,2,2-trifluoroethyl)-6,7,8,9-tetrahydro-5H-[1,2,4]triazolo[4,3-a]azepin-9-yl]acetyl}piperidin-4-yl)-1,3-dihydro-2H-imidazo[4,5-b]pyridin-2-one Triethylamine (146 µL, 1.044 mmol), N-(3-dimethylaminopropyl)-N'-ethylcarbodiimide hydrochloride (69 mg, 0.358 mmol), and 1-hydroxy-7-azabenzotriazole (41 mg, 0.298 mmol) were added to a solution of the hydrochloride salt of [6-(2,3-difluorophenyl)-3-(2,2,2-trifluoroethyl)-6,7,8,9-tetrahydro-5H-[1,2,4]triazolo[4,3-a]azepin-9-yl]acetic acid (127 mg, 0.298 mmol) and 2-oxo-1-piperidinium-4-yl-2,3-dihydro-1H-imidazo[4,5-b]pyridin-4-ium dichloride (87 mg, 0.298 mmol) in acetonitrile (3 mL) and N,N-dimethylformamide (1 mL). After 4 h, the reaction mixture was diluted with ethyl acetate and saturated aqueous sodium bicarbonate. The mixture was extracted with ethyl acetate, washed with saturated brine, dried with sodium sulfate, filtered and concentrated to give the title compound. Purification by reverse phase HPLC (100% water→100% acetonitrile with 0.1% trifluoroacetic acid) gave racemic cis compounds 1-(1-{[(6S,9R)-6-(2,3-difluorophenyl)-3-(2,2,2-trifluoroethyl)-6,7,8,9-tetrahydro-5H-[1,2,4]triazolo[4,3-a]azepin-9-yl]acetyl}piperidin-4-yl)-1,3-dihydro-2H-imidazo[4,5-b]pyridin-2-one and 1-(1-{[(6R,9S)-6-(2,3-difluorophenyl)-3-(2,2,2-trifluoroethyl)-6,7,8,9-tetrahydro-5H-[1,2,4]triazolo[4,3-a]azepin-9-yl]acetyl}piperidin-4-yl)-1,3-dihydro-2H-imidazo[4,5-b]pyridin-2-one; MS 590.2299 (M+1), and racemic trans compounds 1-(1-{[(6S,9S)-6-(2,3-difluorophenyl)-3-(2,2,2-trifluoroethyl)-6,7,8,9-tetrahydro-5H-[1,2,4]triazolo[4,3-a]azepin-9-yl]acetyl}piperidin-4-yl)-1,3-dihydro-2H-imidazo[4,5-b]pyridin-2-one and 1-(1-{[(6R,9R)-6-(2,3-difluorophenyl)-3-(2,2,2-trifluoroethyl)-6,7,8,9-tetrahydro-5H-[1,2,4]triazolo[4,3-a]azepin-9-yl]acetyl}piperidin-4-yl)-1,3-dihydro-2H-imidazo[4,5-b]pyridin-2-one; MS 590.2293 (M+1). The trans enantiomers were separated by Chiralpak OD column (2×35 cm), 60% hexanes (0.1% diethylamine)/ethanol at 6 mL/min.

Example 210

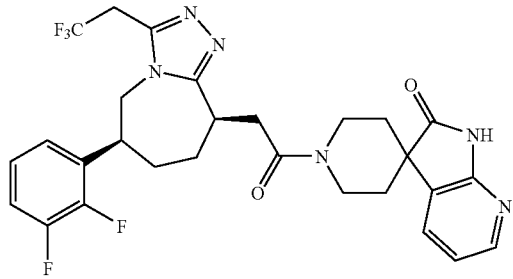

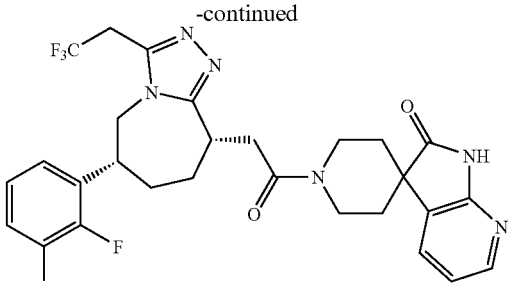

1-{[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]acetyl}spiro[piperidine-4,3'-pyrrolo[2,3-b]pyridin]-2'(1'H)-one and 1-{[(6R,9S)-6-(2,3-difluorophenyl)-3-(2,2,2-trifluoroethyl)-6,7,8,9-tetrahydro-5H-[1,2,4]triazolo[4,3-a]azepin-9-yl]acetyl}spiro[piperidine-4,3'-pyrrolo[2,3-b]pyridin]-2'(1'H)-one Triethylamine (17 µL, 0.123 mmol), N-(3-dimethylaminopropyl)-N'-ethylcarbodiimide hydrochloride (8.0 mg, 0.042 mmol), and 1-hydroxy-7-azabenzotriazole (5.0 mg, 0.035 mmol) were added to a solution of the hydrochloride salt of [(6S,9R)-6-(2,3-difluorophenyl)-3-(2,2,2-trifluoroethyl)-6,7,8,9-tetrahydro-5H-[1,2,4]triazolo[4,3-a]azepin-9-yl]acetic acid and the hydrochloride salt of [(6R,9S)-6-(2,3-difluorophenyl)-3-(2,2,2-trifluoroethyl)-6,7,8,9-tetrahydro-5H-[1,2,4]triazolo[4,3-a]azepin-9-yl]acetic acid (15.0 mg, 0.035 mmol) and 2'-oxo-1',2'-dihydrospiro[piperidine-4,3'-pyrrolo[2,3-b]pyridine]dichloride (13 mg, 0.046 mmol) in N,N-dimethylformamide (0.5 mL). After 18 h, trifluoroacetic acid (20 µL) was added. Purification by reverse phase HPLC (100% water→100% acetonitrile with 0.1% trifluoroacetic acid) gave the title compound as a racemic mixture (12 mg). MS 575.2197 (M+1).

Example 211

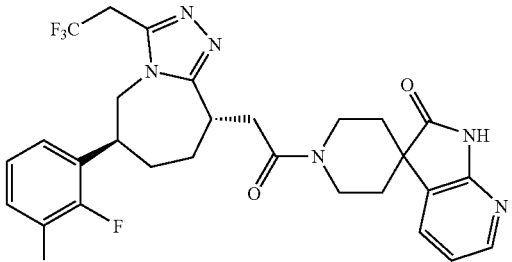

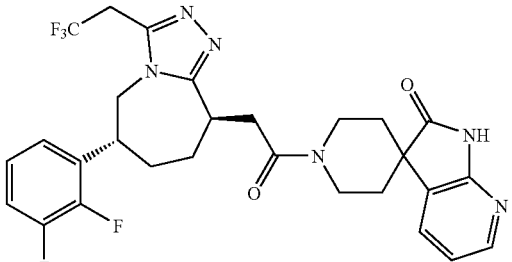

1-{[(6S,9S)-6-(2,3-Difluorophenyl)-3-(2,2,2-trifluoroethyl)-6,7,8,9-tetrahydro-5H-[1,2,4]triazolo[4,3-a]azepin-9-yl]acetyl}spiro[piperidine-4,3'-pyrrolo[2,3-b]pyridin]-2'(1'H)-one and 1-{[(6R,9R)-6-(2,3-difluorophenyl)-3-(2,2,2-trifluoroethyl)-6,7,8,9-tetrahydro-5H-[1,2,4]triazolo[4,3-a]azepin-9-yl]acetyl}spiro[piperidine-4,3'-pyrrolo[2,3-b]pyridin]-2'(1'H)-one Triethylamine (17 µL, 0.123 mmol), N-(3-dimethylaminopropyl)-N'-ethylcarbodiimide hydrochloride (8.0 mg, 0.042 mmol), and 1-hydroxy-7-azabenzotriazole (5.0 mg, 0.035 mmol) were added to a solution of the hydrochloride salt of [(6S,9S)-6-(2,3-difluorophenyl)-3-(2,2,2-trifluoroethyl)-6,7,8,9-tetrahydro-5H-[1,2,4]triazolo[4,3-a]azepin-9-yl]acetic acid and the hydrochloride salt of [(6R,9R)-6-(2,3-difluorophenyl)-3-(2,2,2-trifluoroethyl)-6,7,8,9-tetrahydro-5H-[1,2,4]triazolo[4,3-a]azepin-9-yl]acetic acid (15.0 mg, 0.035 mmol) and 2'-oxo-1',2'-dihydrospiro[piperidine-4,3'-pyrrolo[2,3-b]pyridine]dichloride (13 mg, 0.046 mmol) in N,N-dimethylformamide (0.5 mL). After 18 h, trifluoroacetic acid (20 µL) was added. Purification by reverse phase HPLC (100% water→100% acetonitrile with 0.1% trifluoroacetic acid) gave the title compound as a racemic mixture (12 mg). MS 575.2196 (M+1).

Example 212

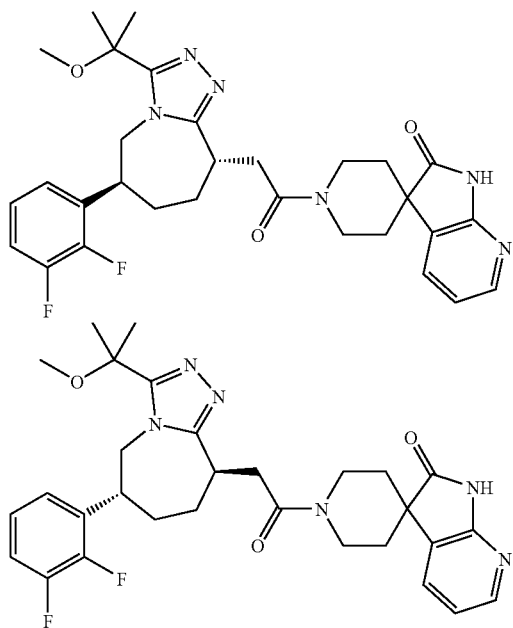

1-{[(6S,9S)-6-(2,3-Difluorophenyl)-3-(1-methoxy-1-methylethyl)-6,7,8,9-tetrahydro-5H-[1,2,4]triazolo[4,3-a]azepin-9-yl]acetyl}spiro[piperidine-4,3'-pyrrolo[2,3-b]pyridin]-2'(1'H)-one and 1-{[(6R,9R)-6-(2,3-difluorophenyl)-3-(1-methoxy-1-methylethyl)-6,7,8,9-tetrahydro-5H-[1,2,4]triazolo[4,3-a]azepin-9-yl]acetyl}spiro[piperidine-4,3'-pyrrolo[23-b]pyridin]-2'(1'H)-one Triethylamine (12 µL, 0.084 mmol), N-(3-dimethylaminopropyl)-N'-ethylcarbodiimide hydrochloride (6.0 mg, 0.029 mmol), and 1-hydroxy-7-azabenzotriazole (3.0 mg, 0.024 mmol) were added to a solution of the hydrochloride salt of [(6S,9S)-6-(2,3-difluorophenyl)-3-(1-methoxy-1-methylethyl)-6,7,8,9-tetrahydro-5H-[1,2,4]triazolo[4,3-a]azepin-9-yl]acetic acid and the hydrochloride salt of [(6R,9R)-6-(2,3-difluorophenyl)-3-(1-methoxy-1-methylethyl)-6,7,8,9-tetrahydro-5H-[1,2,4]triazolo[4,3-a]azepin-9-yl]acetic acid (10.0 mg, 0.024 mmol) and 2'-oxo-1',2'-dihydrospiro[piperidine-4,3'-pyrrolo[2,3-b]pyridine]dichloride (8 mg, 0.029 mmol) in N,N-dimethylformamide (0.5 mL). After 18 h, trifluoroacetic acid (20 µL) was added. Purification by reverse phase HPLC (100% water→100% acetonitrile with 0.1% trifluoroacetic acid) gave the title compound as a racemic mixture (9 mg). MS 565.2752 (M+1).

Example 213

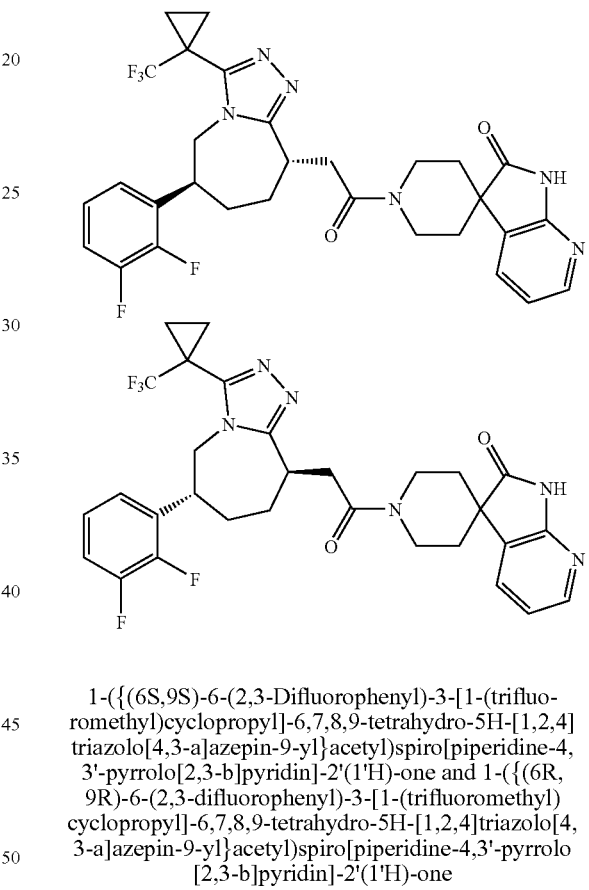

1-({(6S,9S)-6-(2,3-Difluorophenyl)-3-[1-(trifluoromethyl)cyclopropyl]-6,7,8,9-tetrahydro-5H-[1,2,4]triazolo[4,3-a]azepin-9-yl}acetyl)spiro[piperidine-4,3'-pyrrolo[2,3-b]pyridin]-2'(1'H)-one and 1-({(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}acetyl)spiro[piperidine-4,3'-pyrrolo[2,3-b]pyridin]-2'(1'H)-one Triethylamine (21 µL, 0.149 mmol), N-(3-dimethylaminopropyl)-N'-ethylcarbodiimide hydrochloride (8.0 mg, 0.040 mmol), and 1-hydroxy-7-azabenzotriazole (5.0 mg, 0.033 mmol) were added to a solution the hydrochloride salt of {(6S,9S)-6-(2,3-difluorophenyl)-3-[1-(trifluoromethyl)cyclopropyl]-6,7,8,9-tetrahydro-5H-[1,2,4]triazolo[4,3-a]azepin-9-yl}acetic acid and the hydrochloride salt of {(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}acetic acid (15.0 mg, 0.033 mmol) and 2'-oxo-1',2'-dihydrospiro[piperidine-4,3'-pyrrolo[2,3-b]pyridine]dichloride (11 mg, 0.040 mmol) in N,N-dimethylformamide (0.25 mL). After 18 h, trifluoroacetic acid (20 µL) was added. Purification by reverse phase HPLC (100% water 100% acetonitrile with 0.1% trifluoroacetic acid) gave the title compound as a racemic mixture (14 mg). MS 601.2370 (M+1).

Example 214

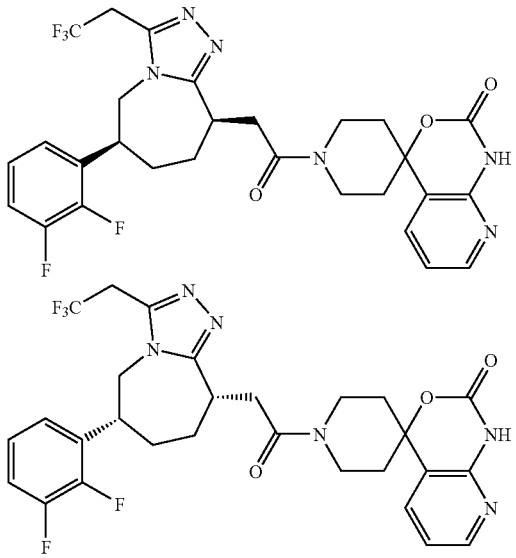

1-{[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]acetyl}spiro[piperidine-4,4'-pyrido[2,3-d][1,3]oxazin]-2'(1'H-one and 1-{[(6R,9S)-6-(2,3-difluorophenyl)-3-(2,2,2-trifluoroethyl)-6,7,8,9-tetrahydro-5H-[1,2,4]triazolo[4,3-a]azepin-9-yl]acetyl}spiro[piperidine-4,4'-pyrido[2,3-d][1,3]oxazin]-2'(1'H)-one Triethylamine (17 µL, 0.123 mmol), N-(3-dimethylaminopropyl)-N'-ethylcarbodiimide hydrochloride (8.0 mg, 0.042 mmol), and 1-hydroxy-7-azabenzotriazole (5.0 mg, 0.035 mmol) were added to a solution of the hydrochloride salt of [(6S,9R)-6-(2,3-difluorophenyl)-3-(2,2,2-trifluoroethyl)-6,7,8,9-tetrahydro-5H-[1,2,4]triazolo[4,3-a]azepin-9-yl]acetic acid and the hydrochloride salt of [(6R,9S)-6-(2,3-difluorophenyl)-3-(2,2,2-trifluoroethyl)-6,7,8,9-tetrahydro-5H-[1,2,4]triazolo[4,3-a]azepin-9-yl]acetic acid (15.0 mg, 0.035 mmol) and spiro[piperidine-4,4'-pyrido[2,3-d][1,3]oxazin]-2'(1'H)-one (9.0 mg, 0.042 mmol) in N,N-dimethylformamide (0.5 mL). After 18 h, trifluoroacetic acid (20 µL) was added. Purification by reverse phase HPLC (100% water→100% acetonitrile with 0.1% trifluoroacetic acid) gave the title compound as a racemic mixture (18 mg). MS 591.2157 (M+1).

Example 215

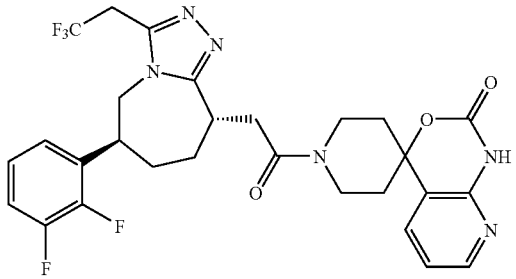

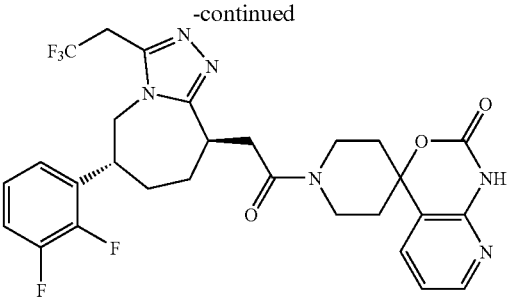

1-{[(6S,9S)-6-(2,3-Difluorophenyl)-3-(2,2,2-trifluoroethyl)-6,7,8,9-tetrahydro-5H-[1,2,4]triazolo[4,3-a]azepin-9-yl]acetyl}spiro[piperidine-4,4'-pyrido[2,3-d][1,3]oxazin]-2'(1'H)-one and 1-{[(6R,9R)-6-(2,3-difluorophenyl)-3-(2,2,2-trifluoroethyl)-6,7,8,9-tetrahydro-5H-[1,2,4]triazolo[4,3-a]azepin-9-yl]acetyl}spiro[piperidine-4,4'-pyrido[2,3-d][1,3]oxazin]-2'(1'H)-one Triethylamine (17 µL, 0.123 mmol), N-(3-dimethylaminopropyl)-N'-ethylcarbodiimide hydrochloride (8.0 mg, 0.042 mmol), and 1-hydroxy-7-azabenzotriazole (5.0 mg, 0.035 mmol) were added to a solution of the hydrochloride salt of [(6S,9S)-6-(2,3-difluorophenyl)-3-(2,2,2-trifluoroethyl)-6,7,8,9-tetrahydro-5H-[1,2,4]triazolo[4,3-a]azepin-9-yl]acetic acid and the hydrochloride salt of [(6R,9R)-6-(2,3-difluorophenyl)-3-(2,2,2-trifluoroethyl)-6,7,8,9-tetrahydro-5H-[1,2,4]triazolo[4,3-a]azepin-9-yl]acetic acid (15.0 mg, 0.035 mmol) and spiro[piperidine-4,4'-pyrido[2,3-d][1,3]oxazin]-2'(1'H)-one (9.0 mg, 0.042 mmol) in N,N-dimethylformamide (0.5 mL). After 18 h, trifluoroacetic acid (20 µL) was added. Purification by reverse phase HPLC (100% water→100% acetonitrile with 0.1% trifluoroacetic acid) gave the title compound as a racemic mixture (17 mg). MS 591.2166 (M+1).

Example 216

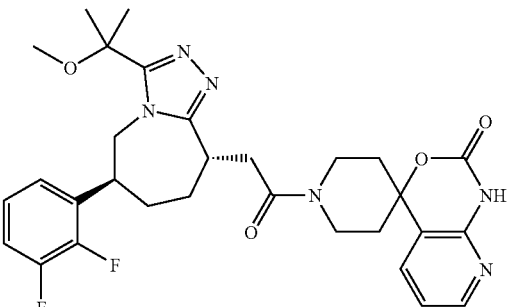

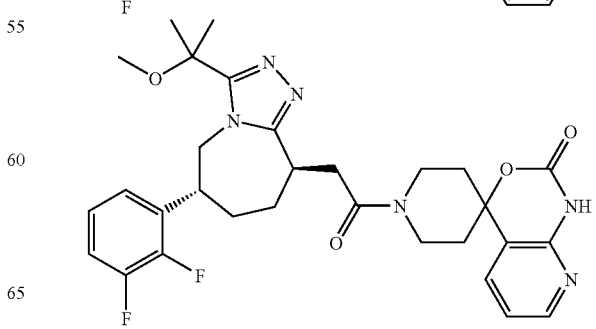

1-{[(6S,9S)-6-(2,3-Difluorophenyl)-3-(1-methoxy-1-methylethyl)-6,7,8,9-tetrahydro-5H-[1,2,4]triazolo[4,3-a]azepin-9-yl]acetyl}spiro[piperidine-4,4'-pyrido[2,3-d][1,3]oxazin]-2'(1'H)-one and 1-{[(6R,9R)-6-(2,3-difluorophenyl)-3-(1-methoxy-1-methylethyl)-6,7,8,9-tetrahydro-5H-[1,2,4]triazolo[4,3-a]azepin-9-yl]acetyl}spiro[piperidine-4,4'-pyrido[2,3-d][1,3]oxazin]-2'(1'H)-one Triethylamine (41 µL, 0.295 mmol), N-(3-dimethylaminopropyl)-N'-ethylcarbodiimide hydrochloride (19.0 mg, 0.101 mmol), and 1-hydroxy-7-azabenzotriazole (11.0 mg, 0.084 mmol) were added to a solution of the hydrochloride salt of [(6S,9S)-6-(2,3-difluorophenyl)-3-(1-methoxy-1-methylethyl)-6,7,8,9-tetrahydro-5H-[1,2,4]triazolo[4,3-a]azepin-9-yl]acetic acid and the hydrochloride salt of [(6R,9R)-6-(2,3-difluorophenyl)-3-(1-methoxy-1-methylethyl)-6,7,8,9-tetrahydro-5H-[1,2,4]triazolo[4,3-a]azepin-9-yl]acetic acid (35.0 mg, 0.084 mmol) and spiro[piperidine-4,4'-pyrido[2,3-d][1,3]oxazin]-2'(1'H)-one (22.0 mg, 0.101 mmol) in N,N-dimethylformamide (0.5 mL) and acetonitrile (3 mL). After 18 h, trifluoroacetic acid (20 µL) was added. Purification by reverse phase HPLC (100% water→100% acetonitrile with 0.1% trifluoroacetic acid) gave the title compound as a racemic mixture (36 mg). MS 581.2698 (M+1).

Example 217

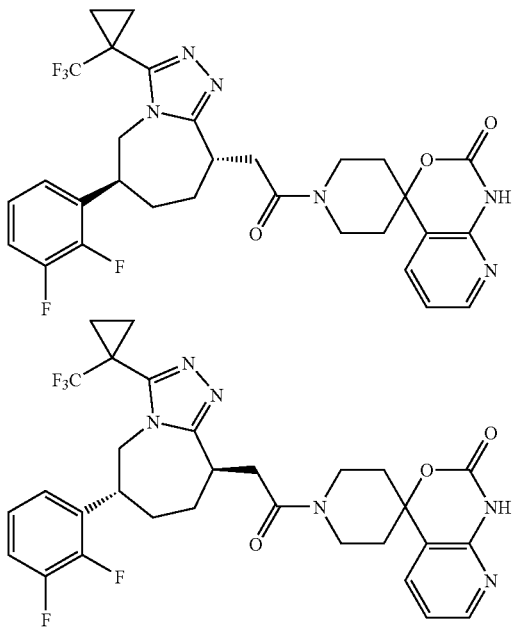

1-({(6S,9S)-6-(2,3-Difluorophenyl)-3-[1-(trifluoromethyl)cyclopropyl]-6,7,8,9-tetrahydro-5H-[1,2,4]triazolo[4,3-a]azepin-9-yl}acetyl)spiro[piperidine-4,4'-pyrido[2,3-d][1,3]oxazin]-2'(1'H)-one and 1-({(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}acetyl)spiro[piperidine-4,4'-pyrido[2,3-d][1,3]oxazin]-2'(1'H)-one Triethylamine (43 µL, 0.31 mmol), N-(3-dimethylaminopropyl)-N'-ethylcarbodiimide hydrochloride (20.0 mg, 0.106 mmol), and 1-hydroxy-7-azabenzotriazole (12.0 mg, 0.089 mmol) were added to a solution of the hydrochloride salt of {(6S,9S)-6-(2,3-difluorophenyl)-3-[1-(trifluoromethyl)cyclopropyl]-6,7,8,9-tetrahydro-5H-[1,2,4]triazolo[4,3-a]azepin-9-yl}acetic acid and the hydrochloride salt of {(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}acetic acid (40.0 mg, 0.089 mmol) and spiro[piperidine-4,4'-pyrido[2,3-d][1,3]oxazin]-2'(1'H)-one (23.0 mg, 0.106 mmol) in N,N-dimethylformamide (0.5 mL). After 18 h, trifluoroacetic acid (20 µL) was added. Purification by reverse phase HPLC (100% water→100% acetonitrile with 0.1% trifluoroacetic acid) gave the title compound as a racemic mixture (46 mg). MS 617.2322 (M+1).

Example 218

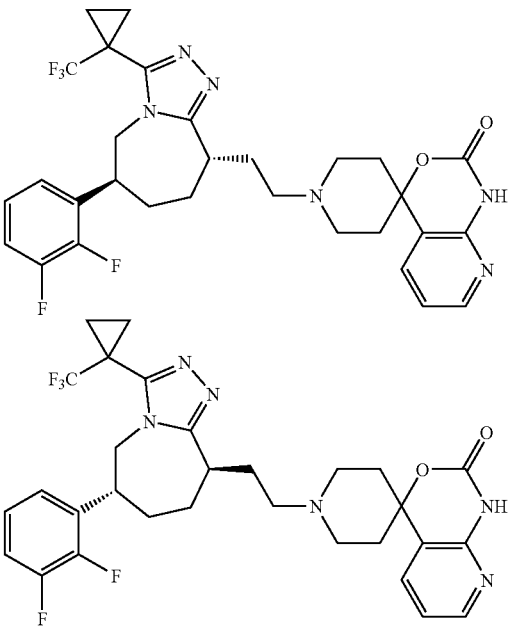

1-(2-{(6S,9S)-6-(2,3-Difluorophenyl)-3-[1-(trifluoromethyl)cyclopropyl]-6,7,8,9-tetrahydro-5H-[1,2,4]triazolo[4,3-a]azepin-9-yl}ethyl)spiro[piperidine-4,4'-pyrido[2,3-d][1,3]oxazin]-2'(1'H)-one and 1-(2-{(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}ethyl)spiro[piperidine-4,4'-pyrido[2,3-d][1,3]oxazin]-2'(1'H)-one Step A: Methyl {(6S,9S)-6-(2,3-difluorophenyl)-3-[1-(trifluoromethyl)cyclopropyl]-6,7,8,9-tetrahydro-5H-[1,2,4]triazolo[4,3-a]azepin-9-yl}acetate and methyl {(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}acetate Trimethylsilyl diazomethane (0.22 mL, 0.438 mmol) was added to a solution of the hydrochloride salt of {(6S,9S)-6-(2,3-difluorophenyl)-3-[1-(trifluoromethyl)cyclopropyl]-6,7,8,9-tetrahydro-5H-[1,2,4]triazolo[4,3-a]azepin-9-yl}acetic acid and the hydrochloride salt of {(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}acetic acid (33 mg, 0.073 mmol) in dichloromethane (3 mL) and methanol (1 mL) at 0° C. After 30 min, the reaction mixture was concentrated. Purification by reverse phase HPLC (100% water→100% acetonitrile with 0.1% trifluoroacetic acid) gave the title compounds (23 mg). MS 430.1 (M+1).

Step B: {(6S,9S)-6-(2,3-Difluorophenyl)-3-[1-(trifluoromethyl)cyclopropyl]-6,7,8,9-tetrahydro-5H-[1,2,4]triazolo[4,3-a]azepin-9-yl}acetaldehyde and {(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}acetaldehyde Diisobutylaluminum chloride (1.0 M in hexanes; 0.25 mL, 0.252 mmol) was added to a solution of methyl {(6S,9S)-6-(2,3-difluorophenyl)-3-[1-(trifluoromethyl)cyclopropyl]-6,7,8,9-tetrahydro-5H-[1,2,4]triazolo[4,3-a]azepin-9-yl}acetate and methyl {(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}acetate (18 mg, 0.042 mmol) in dichloromethane (2 mL) at −78° C. Two additional portions of diisobutylaluminum chloride (0.25 mL, 0.252 mmol) was added. After 1.5 h, the reaction mixture was quenched with Rochelle's salt (3 mL) at −78° C. Ethyl acetate was added and the mixture was allowed to warm to ambient temperature. The mixture was extracted with ethyl acetate, washed with saturated brine, dried over sodium sulfate, filtered and concentrated to give the title compound. MS 400.1 (M+1).

Step C: 1-(2-{(6S,9S)-6-(2,3-Difluorophenyl)-3-[1-(trifluoromethyl)cyclopropyl]-6,7,8,9-tetrahydro-5H-[1,2,4]triazolo[4,3-a]azepin-9-yl}ethyl)spiro[piperidine-4,4'-pyrido[2,3-d][1,3]oxazin]-2'(1'H)-one and 1-(2-{(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}ethyl)spiro[piperidine-4,4'-pyrido[2,3-a][1,3]oxazin]-2'(1'H)-one Sodium cyanoborohydride (7.0 mg, 0.111 mmol) was added to a solution of {(6S,9S)-6-(2,3-Difluorophenyl)-3-[1-(trifluoromethyl)cyclopropyl]-6,7,8,9-tetrahydro-5H-[1,2,4]triazolo[4,3-a]azepin-9-yl}acetaldehyde and {(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}acetaldehyde (22.0 mg, 0.055 mmol), and spiro[piperidine-4,4'-pyrido[2,3-d][1,3]oxazin]-2'(1'H)-one (12.0 mg, 0.055 mmol) in methanol (3 mL). The reaction mixture was adjusted to pH 3 with acetic acid. After 20 min, the mixture was concentrated. Purification by reverse phase HPLC (10% acetonitrile/water→100% acetonitrile with 0.1% trifluoroacetic acid) gave the title compound as a racemic mixture (17 mg). MS 603.2528 (M+1).

Example 219

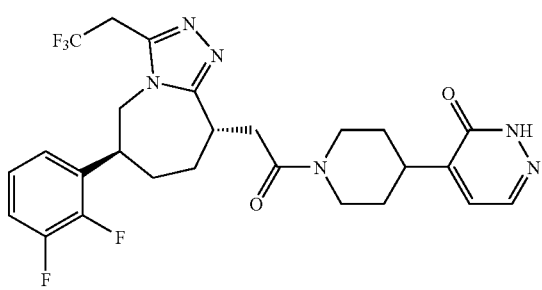

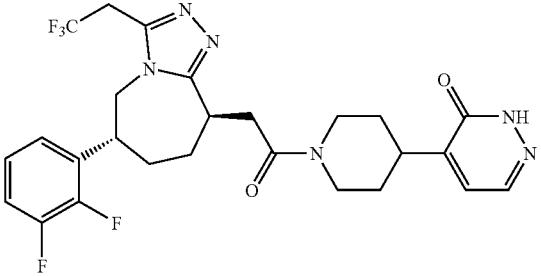

4-(1-{[(6S,9S)-6-(2,3-Difluorophenyl)-3-(2,2,2-trifluoroethyl)-6,7,8,9-tetrahydro-5H-[1,2,4]triazolo[4,3-a]azepin-9-yl]acetyl}piperidin-4-yl pyridazin-3(2H)-one and 4-(1-{[(6R,9R)-6-(2,3-difluorophenyl)-3-(2,2,2-trifluoroethyl)-6,7,8,9-tetrahydro-5H-[1,2,4]triazolo [4,3-a]azepin-9-yl]acetyl}piperidin-4-yl)pyridazin-3(2H)-one Triethylamine (17 μL, 0.123 mmol), N-(3-dimethylaminopropyl)-N'-ethylcarbodiimide hydrochloride (8.0 mg, 0.042 mmol), and 1-hydroxy-7-azabeizotriazole (5.0 mg, 0.035 mmol) were added to a solution of the hydrochloride salt of [(6S,9S)-6-(2,3-difluorophenyl)-3-(2,2,2-trifluoroethyl)-6,7,8,9-tetrahydro-5H-[1,2,4]triazolo[4,3-a]azepin-9-yl]acetic acid and the hydrochloride salt of [(6R,9R)-6-(2,3-difluorophenyl)-3-(2,2,2-trifluoroethyl)-6,7,8,9-tetrahydro-5H-[1,2,4]triazolo[4,3-a]azepin-9-yl]acetic acid (15.0 mg, 0.035 mmol), and 4-piperidin-4-ylpyridazin-3(2H)-one (8.0 mg, 0.046 mmol) in N,N-dimethylformamide (0.5 mL). After 18 h, trifluoroacetic acid (20 μL) was added. Purification by reverse phase HPLC (100% water→100% acetonitrile with 0.1% trifluoroacetic acid) gave the title compound as a racemic mixture (15 mg). MS 551.2190 (M+1).

Example 220

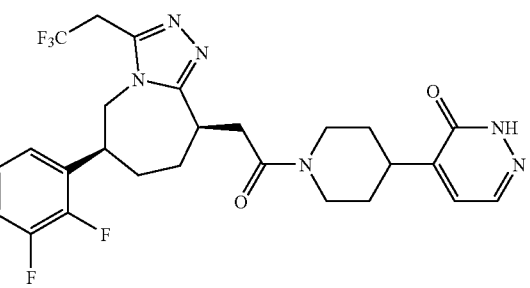

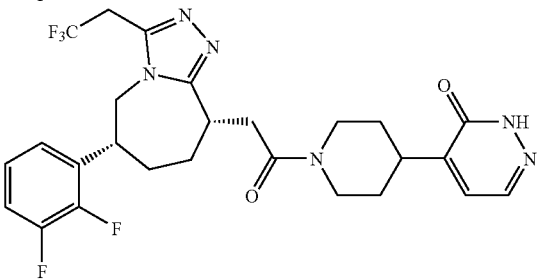

4-(1-{[(6S,9R)-6-(23-Difluorophenyl)-3-(2,2,2-trifluoroethyl)-6,7,8,9-tetrahydro-5H-[1,2,4]triazolo[4,3-a]azepin-9-yl]acetyl}piperidin-4-yl pyridazin-3(2H)-one and 4-(1-{[(6R,9S)-6-(2,3-difluorophenyl)-3-(2,2,2-trifluoroethyl)-6,7,8,9-tetrahydro-5H-[1,2,4]triazolo[4,3-a]azepin-9-yl]acetyl}piperidin-4-yl)pyridazin-3(2H)-one Triethylamine (17 µL, 0.123 mmol), N-(3-dimethylaminopropyl)-N'-ethylcarbodiimide hydrochloride (8.0 mg, 0.042 mmol), the 1-hydroxy-7-azabenzotriazole (5.0 mg, 0.035 mmol) were added to a solution of the hydrochloride salt of [(6S,9R)-6-(2,3-difluorophenyl)-3-(2,2,2-trifluoroethyl)-6,7,8,9-tetrahydro-5H-[1,2,4]triazolo[4,3-a]azepin-9-yl]acetic acid and the hydrochloride salt of [(6R,9S)-6-(2,3-difluorophenyl)-3-(2,2,2-trifluoroethyl)-6,7,8,9-tetrahydro-5H-[1,2,4]triazolo[4,3-a]azepin-9-yl]acetic acid (15.0 mg, 0.035 mmol), and 4-piperidin-4-ylpyridazin-3(2H)-one (8.0 mg, 0.046 mmol) in N,N-dimethylformamide (0.5 mL). After 18 h, trifluoroacetic acid (20 µL) was added. Purification by reverse phase HPLC (100% water→100% acetonitrile with 0.1% trifluoroacetic acid) acid gave the title compound as a racemic mixture (16 mg). MS 551.2199 (M+1).

Example 221

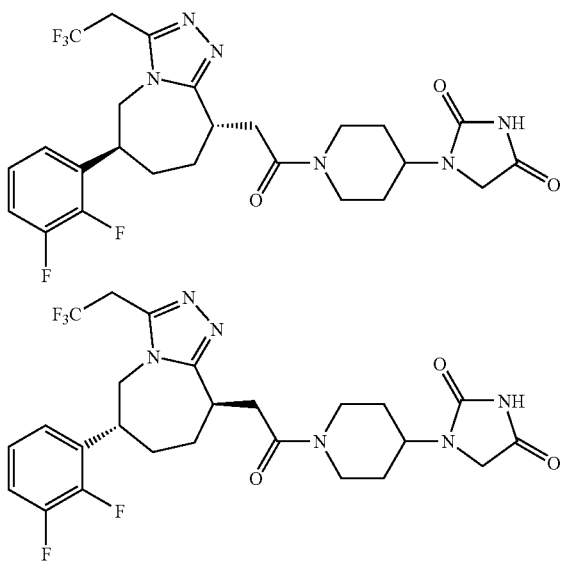

1-(1-{[(6S,9S)-6-(2,3-Difluorophenyl)-3-(2,2,2-trifluoroethyl-6,7,8,9-tetrahydro-5H-[1,2,4]triazolo[4,3-a]azepin-9-yl]acetyl}piperidin-4-yl)imidazolidine-2,4-dione and 1-(1-{[(6R,9R)-6-(2,3-difluorophenyl)-3-(2,2,2-trifluoroethyl)-6,7,8,9-tetrahydro-5H-[1,2,4]triazolo[4,3-a]azepin-9-yl]acetyl}piperidin-4-yl)imidazolidine-2,4-dione Triethylamine (17 µL, 0.123 mmol), N-(3-dimethylaminopropyl)-N'-ethylcarbodiimide hydrochloride (8.0 mg, 0.042 mmol), and 1-hydroxy-7-azabenzotriazole (5.0 mg, 0.035 mmol) were added to a solution the hydrochloride salt of [(6S,9S)-6-(2,3-difluorophenyl)-3-(2,2,2-trifluoroethyl)-6,7,8,9-tetrahydro-5H-[1,2,4]triazolo[4,3-a]azepin-9-yl]acetic acid and the hydrochloride salt of [(6R,9R)-6-(2,3-difluorophenyl)-3-(2,2,2-trifluoroethyl)-6,7,8,9-tetrahydro-5H-[1,2,4]triazolo[4,3-a]azepin-9-yl]acetic acid (15.0 mg, 0.035 mmol), and 1-piperidin-4-ylimidazolidine-2,4-dione (10 mg, 0.056 mmol) in N,N-dimethylformamide (0.5 mL). After 18 h, trifluoroacetic acid (20 µL) was added. Purification by reverse phase HPLC (100% water→100% acetonitrile with 0.1% trifluoroacetic acid) gave the title compound as a racemic mixture (16 mg). MS 555.2144 (M+1).

Example 222

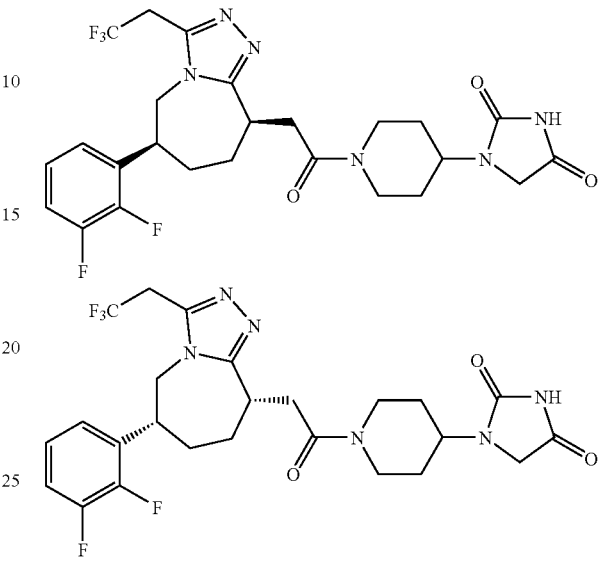

1-(1-{[(6S,9R)-6-(2,3-Difluorophenyl)-3-(2,2,2-trifluoroethyl)-6,7,8,9-tetrahydro-5H-[1,2,4]triazolo[4,3-a]azepin-9-yl]acetyl}piperidin-4-yl)imidazolidine-2,4-dione and 1-(1-{[(6R,9S)-6-(2,3-difluorophenyl)-3-(2,2,2-trifluoroethyl)-6,7,8,9-tetrahydro-5H-[1,2,4]triazolo[4,3-a]azepin-9-yl]acetyl}piperidin-4-yl)imidazolidine-2,4-dione Triethylamine (17 µL, 0.123 mmol), N-(3-dimethylaminopropyl)-N'-ethylcarbodiimide hydrochloride (8.0 mg, 0.042 mmol), the 1-hydroxy-7-azabenzotriazole (5.0 mg, 0.035 mmol) were added to a solution of the hydrochloride salt of [(6S,9R)-6-(2,3-difluorophenyl)-3-(2,2,2-trifluoroethyl)-6,7,8,9-tetrahydro-5H-[1,2,4]triazolo[4,3-a]azepin-9-yl]acetic acid and the hydrochloride salt of [(6R,9S)-6-(2,3-difluorophenyl)-3-(2,2,2-trifluoroethyl)-6,7,8,9-tetrahydro-5H-[1,2,4]triazolo[4,3-a]azepin-9-yl]acetic acid (15.0 mg, 0.035 mmol) and 1-piperidin-4-ylimidazolidine-2,4-dione (10 mg, 0.053 mmol) in N,N-dimethylformamide (0.5 mL). After 18 h, trifluoroacetic acid (20 µL) was added. Purification by reverse phase HPLC (100% water→100% acetonitrile with 0.1% trifluoroacetic acid) gave the title compound as a racemic mixture (16 mg). MS 555.2161 (M+1).

Example 223

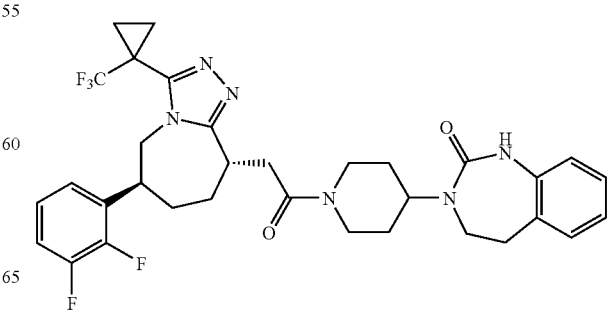

-continued

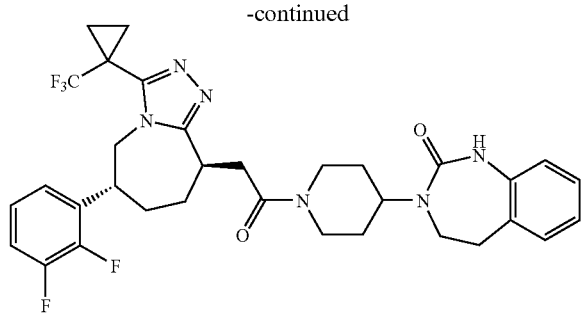

3-[1-({(6S,9S)-6-(2,3-Difluorophenyl)-3-[1-(trifluoromethyl)cyclopropyl]-6,7,8,9-tetrahydro-5H-[1,2,4]triazolo[4,3-a]azepin-9-yl}acetyl)piperidin-4-yl]-1,3,4,5-tetrahydro-2H-1,3-benzodiazepin-2-one and 3-[1-({(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}acetyl)piperidin-4-yl]-1,3,4,5-tetrahydro-2H-1,3-benzodiazepin-2-one Triethylamine (16 µL, 0.116 mmol), N-(3-dimethylaminopropyl)-N'-ethylcarbodiimide hydrochloride (8.0 mg, 0.040 mmol), and 1-hydroxy-7-azabenzotriazole (5.0 mg, 0.033 mmol) were added to a solution of the hydrochloride salt of {(6S,9S)-6-(2,3-difluorophenyl)-3-[1-(trifluoromethyl)cyclopropyl]-6,7,8,9-tetrahydro-5H-[1,2,4]triazolo[4,3-a]azepin-9-yl}acetic acid and the hydrochloride salt of {(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}acetic acid (15.0 mg, 0.033 mmol), and 4-(2-oxo-1,2,4,5-tetrahydro-3H-1,3-benzodiazepin-3-yl)piperidinium chloride (11.0 mg, 0.040 mmol) in N,N-dimethylformamide (0.5 mL). After 18 h, trifluoroacetic acid (20 µL) was added. Purification by reverse phase HPLC (100% water 100% acetonitrile with 0.1% trifluoroacetic acid) gave the title compound as a racemic mixture (17 mg). MS 643.2833 (M+1).

Example 224

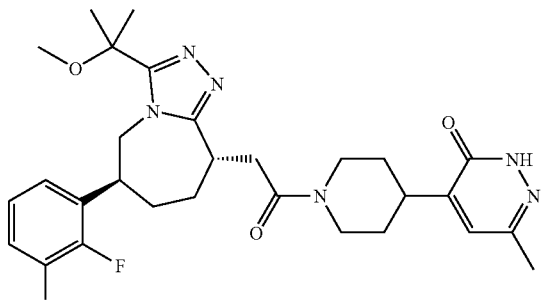

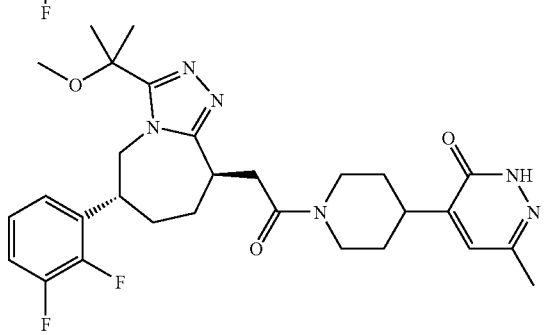

4-(1-{[(6S,9S)-6-(2,3-Difluorophenyl)-3-(1-methoxy-1-methylethyl)-6,7,8,9-tetrahydro-5H-[1,2,4]triazolo[4,3-a]azepin-9-yl]acetyl}piperidin-4-yl)-6-methylpyridazin-3(2H)-one and 4-(1-{[(6R,9R)-6-(2,3-difluorophenyl)-3-(1-methoxy-1-methylethyl)-6,7,8,9-tetrahydro-5H-[1,2,4]triazolo[4,3-a]azepin-9-yl]acetyl}piperidin-4-yl)-6-methylpyridazin-3(2H)-one Triethylamine (3.0 µL, 0.024 mmol), N-(3-dimethylaminopropyl)-N'-ethylcarbodiimide hydrochloride (5.0 mg, 0.024 mmol), and 1-hydroxy-7-azabenzotriazole (3.0 mg, 0.024 mmol) were added to a solution of the hydrochloride salt of [(6S,9S)-6-(2,3-difluorophenyl)-3-(1-methoxy-1-methylethyl)-6,7,8,9-tetrahydro-5H-[1,2,4]triazolo[4,3-a]azepin-9-yl]acetic acid and the hydrochloride salt of [(6R,9R)-6-(2,3-difluorophenyl)-3-(1-methoxy-1-methylethyl)-6,7,8,9-tetrahydro-5H-[1,2,4]triazolo[4,3-a]azepin-9-yl]acetic acid (10.0 mg, 0.024 mmol), and 6-methyl-4-piperidin-4-ylpyridazin-3(2H)-one (6.0 mg, 0.029 mmol) in N,N-dimethylformamide (0.5 mL). After 18 h, trifluoroacetic acid (20 µL) was added. Purification by reverse phase HPLC (100% water→100% acetonitrile with 0.1% trifluoroacetic acid) acid gave the title compound as a racemic mixture (6 mg). MS 555.2909 (M+1).

Example 225

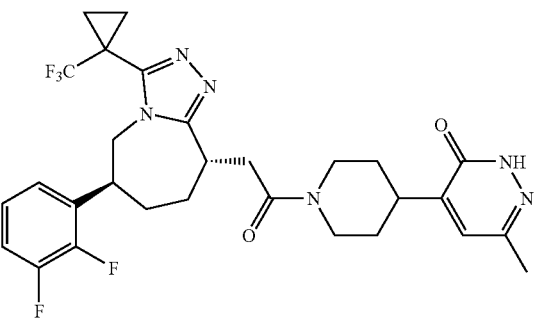

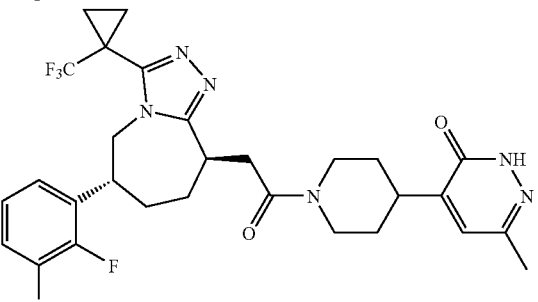

4-[1-({(6S,9S)-6-(2,3-Difluorophenyl)-3-[1-(trifluoromethyl)cyclopropyl]-6,7,8,9-tetrahydro-5H-[1,2,4]triazolo[4,3-a]azepin-9-yl}acetyl)piperidin-4-yl]-6-methylpyridazin-3(2H)-one and 4-[1-({(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}acetyl)piperidin-4-yl]-6-methylpyridazin-3(2H)-one Triethylamine (43.0 µL, 0.31 mmol), N-(3-dimethylaminopropyl)-N'-ethylcarbodiimide hydrochloride (20.0 mg, 0.106 mmol), and 1-hydroxy-7-azabenzotriazole (12.0 mg, 0.089 mmol) were added to a solution of the hydrochloride salt of {(6S,9S)-6-(2,3-difluorophenyl)-3-[1-(trifluoromethyl)cyclopropyl]-6,7,8,9-tetrahydro-5H-[1,2,4]triazolo[4,3-a]azepin-9-yl}acetic acid and the hydrochloride salt of {(6R,9R)-6-(2,3-difluorophenyl)-3-[1-(trifluoromethyl)cyclopropyl]-6,7,8,9-tetrahydro-5H-[1,2,4]triazolo[4,3-a]azepin-9-yl}acetic acid (40.0 mg, 0.089 mmol), and 6-methyl-4-piperidin-4-ylpyridazin-3(2H)-one (21.0 mg, 0.106 mmol) in N,N-dimethylformamide (0.5 mL). After 18 h, trifluoroacetic acid (20 μL) was added. Purification by reverse phase HPLC (100% water→100% acetonitrile with 0.1% trifluoroacetic acid) gave the title compound as a racemic mixture (45 mg). MS 591.2520 (M+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I:

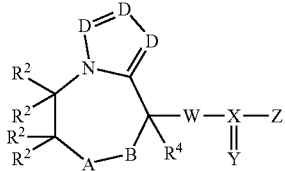

I wherein:

Z is selected from:

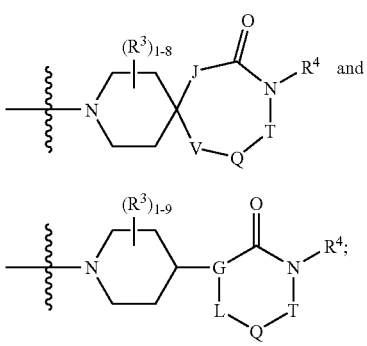

Z1

Z2

A is $C(R^2)_2$;
B is $(C(R^2)_2)_n$;
D is independently selected from N and $C(R^1)$;

$R^1$ is independently selected from:
1) H, $C_1$-$C_6$ alkyl, $C_2$-$C_6$ alkenyl, $C_2$-$C_6$ alkynyl, $C_{3-6}$ cycloalkyl, and heterocycle, said $C_1$-$C_6$ alkyl, $C_2$-$C_6$ alkenyl, $C_2$-$C_6$ alkynyl, $C_{3-6}$ cycloalkyl, and heterocycle unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10})SO_2 R^{11}$,
   r) $S(O)_m R^{10}$,
   s) CN,
   t) $NR^{10}R^{11}$,
   u) $N(R^{10})(CO)NR^4 R^{11}$, and,
   v) $O(CO)R^4$;
2) aryl or heteroaryl, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10})SO_2 R^{11}$,
   r) $S(O)_m R^{10}$,
   s) CN,
   t) $NR^{10}R^{11}$,
   u) $N(R^{10})(CO)NR^4 R^{11}$, and
   v) $O(CO)R^4$;

$R^2$ is independently selected from:
1) H, $C_1$-$C_6$ alkyl, $C_2$-$C_6$ alkenyl, $C_2$-$C_6$ alkynyl, $C_{3-6}$ cycloalkyl and heterocycle, said $C_1$-$C_6$ alkyl, $C_2$-$C_6$ alkenyl, $C_2$-$C_6$ alkynyl, $C_{3-6}$ cycloalkyl and heterocycle unsubstituted or substituted with one or more substituents each independently selected from:
   a) $C_{1-6}$ alkyl,
   b) $C_{3-6}$ cycloalkyl, c) aryl, unsubstituted or substituted with 1-5 substituents where the substituents are independently selected from $R^4$,
d) heteroaryl, unsubstituted or substituted with 1-5 substituents each independently selected from $R^4$,
e) heterocycle, unsubstituted or substituted with 1-5 substituents each independently selected from $R^4$,
f) $(F)_p C_{1-3}$ alkyl,
g) halogen,
h) $OR^4$,
i) $O(CH_2)_s OR^4$,
j) $CO_2 R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_m R^{10}$,
s) CN,
t) $NR^{10}R^{11}$,
u) $N(R^{10})(CO)NR^4R^{11}$, and,
v) $O(CO)R^4$;
2) aryl or heteroaryl, unsubstituted or substituted with one or more substituents each independently selected from:
a) $C_{1-6}$ alkyl,
b) $C_{3-6}$ cycloalkyl,
c) aryl, unsubstituted or substituted with 1-5 substituents where the substituents are independently selected from $R^4$,
d) heteroaryl, unsubstituted or substituted with 1-5 substituents each independently selected from $R^4$,
e) heterocycle, unsubstituted or substituted with 1-5 substituents each independently selected from $R^4$,
f) $(F)_p C_{1-3}$ alkyl,
g) halogen,
h) $OR^4$,
i) $O(CH_2)_s OR^4$,
j) $CO_2 R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_m R^{10}$,
s) CN,
t) $NR^{10}R^{11}$,
u) $N(R^{10})(CO)NR^4R^{11}$, and
v) $O(CO)R^4$;
$R^{10}$ and $R^{11}$ are independently selected from: H, $C_{1-6}$ alkyl, $(F)_p C_{1-6}$ alkyl, $C_{3-6}$ cycloalkyl, aryl, heteroaryl, and benzyl, said $C_{1-6}$ alkyl, $(F)_p C_{1-6}$ alkyl, $C_{3-6}$ cycloalkyl, aryl, heteroaryl, and benzyl unsubstituted or substituted with halogen, hydroxy or $C_1$-$C_6$ alkoxy, and where $R^{10}$ and $R^{11}$ are attached to the same nitrogen atom they may optionally join to form a ring selected from:
azetidinyl, pyrrolidinyl, piperidinyl, piperazinyl, or morpholinyl, which is ring is unsubstituted or substituted with 1-5 substituents each independently selected from $R^4$;
$R^4$ is independently selected from: H, $C_{1-6}$ alkyl, $(F)_p C_{1-6}$ alkyl, $C_{3-6}$ cycloalkyl, aryl, heteroaryl and benzyl, said $C_{1-6}$ alkyl, $(F)_p C_{1-6}$ alkyl, $C_{3-6}$ cycloalkyl, aryl, heteroaryl and benzyl unsubstituted or substituted with halogen, hydroxy or $C_1$-$C_6$ alkoxy;
W is O, $NR^4$ or $C(R^4)_2$;
X is C or S;
Y is O, $(R^4)_2$, NCN, $NSO_2CH_3$ or $NCONH_2$, or Y is $O_2$ when X is S;
$R^6$ is independently selected from H and:
a) $C_{1-6}$ alkyl,
b) $C_{3-6}$ cycloalkyl,
c) aryl, unsubstituted or substituted with 1-5 substituents where the substituents are independently selected from $R^4$,
d) heteroaryl, unsubstituted or substituted with 1-5 substituents each independently selected from $R^4$,
e) heterocycle, unsubstituted or substituted with 1-5 substituents each independently selected from $R^4$,
f) $(F)_p C_{1-3}$ alkyl,
g) halogen,
h) $OR^4$,
i) $O(CH_2)_s OR^4$,
j) $CO_2 R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10}) SO_2R^{11}$,
r) $S(O)_m R^{10}$,
s) CN,
t) $NR^{10}R^{11}$,
u) $N(R^{10})(CO)NR^4R^{11}$, and
v) $O(CO)R^4$;
J is a bond, $C(R^6)_2$, O or $NR^6$;
V is selected from a bond, $C(R^6)_2$, O, $S(O)_m$, $NR^6$, $C(R^6)_2$-$C(R^6)_2$, $C(R^6)=C(R^6)$, $C(R^6)_2$-$N(R^6)$, $C(R^6)=N$, $N(R^6)$—$C(R^6)_2$, $N=C(R^6)$, and $N(R^6)$—$N(R^6)$;
G-L is selected from: N, N—$C(R^6)_2$, C=$C(R^6)$, C=N, $C(R^6)$, $C(R^6)$—$C(R^6)_2$, $C(R^6)$—$C(R^6)_2$—$C(R^6)_2$, C=$C(R^6)$—$C(R^6)_2$, $C(R^6)$—$C(R^6)$=$C(R^6)$, $C(R^6)$—$C(R^6)_2$—$N(R^6)$, C=$C(R^6)$—$N(R^6)$, $C(R^6)$—$C(R^6)$=N, $C(R^6)$—$N(R^6)$—$C(R^6)_2$, C=N—$C(R^6)_2$, $C(R^6)$—N=$C(R^6)$, $C(R^6)$—$N(R^6)$—$N(R^6)$, C=N—$N(R^6)$, N—$C(R^6)_2$—$C(R^6)_2$, N—$C(R^6)$=$C(R^6)$, N—$C(R^6)_2$—$N(R^6)$, N—$C(R^6)$=N, N—$N(R^6)$—$C(R^6)_2$ and N—N=$C(R^6)$;
Q is independently selected from:
(1) =$C(R^{7a})$—,
(2) —$C(R^{7a})_2$—,
(3) —C(=O)—,
(4) —$S(O)_m$—,
(5) =N—, and
(6) —$N(R^{7a})$—;
T is independently selected from:
(1) =$C(R^{7b})$—,
(2) —$C(R^{7b})_2$—,
(3) —C(=O)—,
(4) —$S(O)_m$—,
(5) =N—, and
(6) —$N(R^{7b})$—;
$R^3$ is independently selected from H, substituted or unsubstituted $C_1$-$C_3$ alkyl, F, CN and $CO_2R^4$;
$R^{7a}$ and $R^{7b}$ are each independently selected from $R^2$, where $R^{7a}$ and $R^{7b}$ and the atom or atoms to which they are attached optionally join to form a ring selected from C$_{3-6}$ cycloalkyl, aryl, heterocycle, and heteroaryl, which ring is unsubstituted or substituted with 1-10 substituents each each independently selected from R$^6$;

p is selected from an integer in the range of 0 to 2 times q plus 1, for a substituent with q carbons;

m is 0, 1 or 2;

n is 1;

s is 1, 2 or 3;

and pharmaceutically acceptable salts and individual diastereomers thereof.

2. The compound of claim 1 having the Formula Ia:

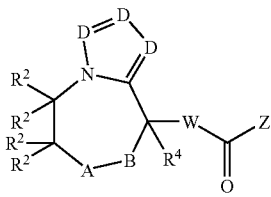

Ia wherein:
A is C(R$^2$)$_2$;
B is (C(R$^2$)$_2$)$_n$;
n is 1;
and pharmaceutically acceptable salts and individual stereoisomers thereof 3. The compound of claim 1 having the Formula Id:

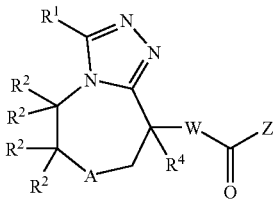

Id wherein:
A is C(R$^2$)$_2$;
and pharmaceutically acceptable salts and individual stereoisomers thereof.

4. The compound of claim 1 having the Formula Ie:

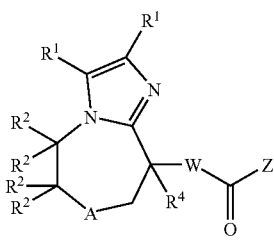

Ie wherein:
A is C(R$^2$)$_2$;
and pharmaceutically acceptable salts and individual stereoisomers thereof.

5. The compound of claim 1 having the Formula If:

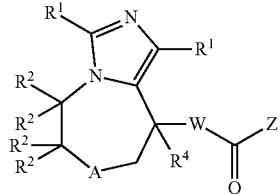

If wherein:
A is C(R$^2$)$_2$;
and pharmaceutically acceptable salts and individual stereoisomers thereof.

6. The compound of claim 1, wherein:

R$^1$ is selected from:
1) H, C$_1$-C$_6$ alkyl, C$_{3-6}$ cycloalkyl and heterocycle, said C$_1$-C$_6$ alkyl, C$_{3-6}$ cycloalkyl and heterocycle unsubstituted or substituted with one or more substituents each independently selected from:
  a) C$_{1-6}$ alkyl,
  b) C$_{3-6}$ cycloalkyl,
  c) aryl, unsubstituted or substituted with 1-5 substituents where the substituents are independently selected from R$^4$,
  d) heteroaryl, unsubstituted or substituted with 1-5 substituents each independently selected from R$^4$,
  e) heterocycle, unsubstituted or substituted with 1-5 substituents each independently selected from R$^4$,
  f) (F)$_p$C$_{1-3}$ alkyl,
  g) halogen,
  h) OR$^4$,
  i) O(CH$_2$)$_s$OR$^4$,
  j) CO$_2$R$^4$,
  k) CN,
  l) NR$^{10}$R$^{11}$, and
  m) O(CO)R$^4$; and
2) aryl or heteroaryl, unsubstituted or substituted with one or more substituents independently selected from:
  a) C$_{1-6}$ alkyl,
  b) C$_{3-6}$ cycloalkyl,
  c) (F)$_p$C$_{1-3}$ alkyl,
  d) halogen,
  e) OR$^4$,
  f) CO$_2$R$^4$,
  g) (CO)NR$^{10}$R$^{11}$,
  h) SO$_2$NR$^{10}$R$^{11}$,
  i) N(R$^{10}$)SO$_2$R$^{11}$,
  j) S(O)$_m$R$^{10}$,
  k) CN,
  l) NR$^{10}$R$^{11}$, and,
  m) O(CO)R$^4$;

R$^2$ is selected from:
1) H, C$_1$-C$_6$ alkyl, C$_2$-C$_6$ alkynyl, C$_{3-6}$ cycloalkyl and heterocycle, said C$_1$-C$_6$ alkyl, C$_2$-C$_6$ alkynyl, C$_{3-6}$ cycloalkyl and heterocycle unsubstituted or substituted with one or more substituents each independently selected from:
  a) C$_{1-6}$ alkyl,
  b) C$_{3-6}$ cycloalkyl,
  c) aryl, unsubstituted or substituted with 1-5 sustituents where the substituents are independently selected from R$^4$, d) heteroaryl, unsubstituted or substituted with 1-5 substituents each independently selected from $R^4$,
e) heterocycle, unsubstituted or substituted with 1-5 substituents each independently selected from $R^4$,
f) $(F)_pC_{1-3}$ alkyl,
g) halogen,
h) $OR^4$,
i) $O(CH_2)_sOR^4$,
j) $CO_2R^4$,
k) $S(O)_mR^{10}$,
l) CN,
m) $NR^{10}R^{11}$, and
n) $O(CO)R^4$; and 2) aryl or heteroaryl, unsubstituted or substituted with one more substituents independently selected from:
a) $C_{1-6}$ alkyl,
b) $C_{3-6}$ cycloalkyl,
c) $(F)_pC_{1-3}$ alkyl,
d) halogen,
e) $OR^4$,
f) $CO_2R^4$,
g) $(CO)NR^{10}R^{11}$,
h) $SO_2NR^{10}R^{11}$,
i) $N(R^{10})SO_2R^{11}$,
j) $S(O)_mR^{10}$,
k) CN,
l) $NR^{10}R^{11}$, and
m) $O(CO)R^4$;

$R^{10}$ and $R^{11}$ are independently selected from: H, $C_{1-6}$ alkyl, $(F)_pC_{1-6}$ alkyl, $C_{3-6}$ cycloalkyl, aryl, heteroaryl and benzyl, said $C_{1-6}$ alkyl, $(F)_pC_{1-6}$ alkyl, $C_{3-6}$ cycloalkyl, aryl, heteroaryl and benzyl unsubstituted or substituted with halogen, hydroxy or $C_1$-$C_6$ alkoxy, and where $R^{10}$ and $R^{11}$ are attached to the same nitrogen atom they may optionally join to form a ring selected from:
azetidinyl, pyrrolidinyl, piperidinyl, piperazinyl and morpholinyl, which ring is unsubstituted or substituted with 1-5 substituents each independently selected from $R^4$;

$R^4$ is independently selected from: H, $C_{1-6}$ alkyl, $(F)_pC_{1-6}$ alkyl, $C_{3-6}$ cycloalkyl, aryl, heteroaryl and benzyl, said $C_{1-6}$ alkyl, $(F)_pC_{1-6}$ alkyl, $C_{3-6}$ cycloalkyl, aryl, heteroaryl and benzyl unsubstituted or substituted with halogen, hydroxy or $C_1$-$C_6$ alkoxy;

W is O, $NR^4$ or $C(R^4)2$;

$R^6$ is independently selected from H and:
a) $C_{1-6}$ alkyl,
b) $C_{3-6}$ cycloalkyl,
c) $(F)_pC_{1-3}$ alkyl,
d) halogen,
e) $OR^4$,
f) $CO_2R^4$,
g) $(CO)NR^{10}R^{11}$,
h) $SO_2NR^{10}R^{11}$,
i) $N(R^{10}) SO_2R^{11}$,
j) $S(O)_mR^{10}$,
k) CN,
l) $NR^{10}R^{11}$ and
m) $O(CO)R^4$; and Z is Z1 and:
J is a bond and V is a bond, or
J is a bond, V is a bond and T is —C(=O)—, or
J is a bond, V is a bond, $C(R^6)_2$, O, $S(O)_m$, $NR^6$, $C(R^6)_2$—$C(R^6)_2$, $C(R^6)$=$C(R^6)$, $C(R^6)_2$—$N(R^6)$, $C(R^6)$=N, $N(R^6)$—$C(R^6)_2$, N=$C(R^6)$ or $N(R^6)$—N($R^6$), or
J is a bond, $C(R^6)_2$, O, or $NR^6$, and V is a bond,
or Z is Z2 and G-L is selected from N, N—$C(R^6)_2$, C=C($R^6$), C=N and N—$C(R^6)_2$—$C(R^6)_2$;

Q is selected from:
(1) =$C(R^{7a})$—,
(2) —$C(R^{7a})_2$—,
(3) —C(=O)—,
(4) —$S(O)_m$—,
(5) =N—, and
(6) —$N(R^{7a})$—;

T is selected from:
(1) =$C(R^{7b})$—,
(2) —$C(R^{7b})_2$—,
(3) —C(=O)—,
(4) —$S(O)_m$—,
(5) =N—, and
(6) —$N(R^{7b})$—;

$R^3$ is independently selected from H, substituted or unsubstituted $C_1$-$C_3$ alkyl, F, CN and $CO_2R^4$;

$R^{7a}$ and $R^{7b}$ are each independently selected from $R^2$, where $R^{7a}$ and $R^{7b}$ and the atom or atoms to which they are attached optionally join to form a ring selected from $C_{3-6}$cycloalkyl, aryl, heterocycle, and heteroaryl, which ring is unsubstituted or substituted with 1-10 substituents each each independently selected from $R^6$;

p is selected from an integer in the range of 0 to 2 times q plus 1, for a substituent with q carbons;

m is 0, 1 or 2;

s is 1, 2 or 3;

and pharmaceutically acceptable salts and individual stereoisomers thereof.

7. The compound of claim 1, wherein $R^1$ is selected from:
1) H, $C_1$-$C_6$ alkyl, $C_{3-6}$ cycloalkyl and heterocycle, said $C_1$-$C_6$ alkyl, $C_{3-6}$ cycloalkyl and heterocycle unsubstituted or substituted with one or more substituents each independently selected from:
a) $C_{1-6}$ alkyl,
b) $C_{3-6}$ cycloalkyl,
c) phenyl, unsubstituted or substituted with 1-5 substituents each independently selected from $R^4$,
d) heteroaryl, unsubstituted or substituted with 1-5 substituents each independently selected from $R^4$, and where heteroaryl is selected from:
imidazole, isoxazole, oxazole, pyrazine, pyrazole, pyridazine, pyridine, pyrimidine, and thiazole;
e) heterocycle, unsubstituted or substituted with 1-5 substituents each independently selected from $R^4$, and where heterocycle is selected from:
azetidine, dioxane, dioxolane, morpholine, oxetane, piperazine, piperidine, pyrrolidine, tetrahydrofuran, and tetrahydropyran;
f) $(F)_pC_{1-3}$ alkyl,
g) halogen,
h) $OR^4$,
i) $O(CH_2)_sOR^4$,
j) $CO_2R^4$,
k) CN,
l) $NR^{10}R^{11}$,
m) $O(CO)R^4$;

2) aryl or heteroaryl, selected from: phenyl, imidazole, isoxazole, oxazole, pyrazine, pyrazole, pyridazine, pyridine, pyrimidine, and thiazole, unsubstituted or substituted with one or more substituents each independently selected from:
a) $C_{1-6}$ alkyl,
b) $C_{3-6}$ cycloalkyl,
c) $(F)_pC_{1-3}$ alkyl,
d) halogen,
e) $OR^4$,
f) $CO_2R^4$, g) $(CO)NR^{10}R^{11}$,
h) $SO_2NR^{10}R^{11}$,
i) $N(R^{10})SO_2R^{11}$,
j) $S(O)_mR^{10}$,
k) CN,
l) $NR^{10}R^{11}$, and
m) $O(CO)R^4$;

$R^2$ is selected from:

1) H, $C_1$-$C_6$ alkyl, $C_{3-6}$ cycloalkyl and heterocycle, said $C_1$-$C_6$ alkyl, $C_{3-6}$ cycloalkyl and heterocycle unsubstituted or substituted with one or more substituents each independently selected from:
   a) $C_{1-6}$ alkyl,
   b) $C_{3-6}$ cycloalkyl,
   c) phenyl, unsubstituted or substituted with 1-5 substituents each independently selected from $R^4$,
   d) heteroaryl, unsubstituted or substituted with 1-5 substituents each independently selected from $R^4$, and where heteroaryl is selected from: benzimidazole, benzothiophene, furan, imidazole, indole, isoxazole, oxazole, pyrazine, pyrazole, pyridazine, pyridine, pyrimidine, pyrrole, thiazole, thiophene, and triazole;
   e) heterocycle, unsubstituted or substituted with 1-5 substituents where the substituents are independently selected from $R^4$, and where heterocycle is selected from: azetidine, imidazolidine, imidazoline, isoxazoline, isoxazolidine, morpholine, oxazoline, oxazolidine, oxetane, pyrazolidine, pyrazoline, pyrroline, tetrahydrofuran, tetrahydropyran, thiazoline, and thiazolidine;
   f) $(F)_pC_{1-3}$ alkyl,
   g) halogen,
   h) $OR^4$,
   i) $O(CH_2)_sOR^4$,
   j) $CO_2R^4$,
   k) CN,
   l) $NR^{10}R^{11}$, and
   m) $O(CO)R^4$; and 2) aryl or heteroaryl, selected from:
   phenyl, benzimidazole, benzothiophene, furan, imidazole, indole, isoxazole, oxazole, pyrazine, pyrazole, pyridazine, pyridine, pyrimidine, pyrrole, thiazole, thiophene, and triazole, unsubstituted or substituted with one or more substituents each independently selected from:
   a) $C_{1-6}$ alkyl,
   b) $C_{3-6}$ cycloalkyl,
   c) $(F)_pC_{1-3}$ alkyl,
   d) halogen,
   e) $OR^4$,
   f) $CO_2R^4$,
   g) $(CO)NR^{10}R^{11}$,
   h) $SO_2NR^{10}R^{11}$,
   i) $N(R^{10})SO_2R^{11}$,
   j) $S(O)_mR^{10}$,
   k) CN,
   l) $NR^{10}R^{11}$, and
   m) $O(CO)R^4$, $R^{10}$ and $R^{11}$ are independently selected from: H, $C_{1-6}$ alkyl, $(F)_pC_{1-6}$ alkyl, $C_{3-6}$ cycloalkyl, aryl, heteroaryl and benzyl, said $C_{1-6}$ alkyl, $(F)_pC_{1-6}$ alkyl, $C_{3-6}$ cycloalkyl, aryl, heteroaryl and benzyl unsubstituted or substituted with halogen, hydroxy or $C_1$-$C_6$ alkoxy, and where $R^{10}$ and $R^{11}$ are attached to the same nitrogen atom they may optionally join to form a ring selected from: azetidinyl, pyrrolidinyl, piperidinyl, piperazinyl and morpholinyl, which ring is unsubstituted or substituted with 1-5 substituents each independently selected from $R^4$;

$R^4$ is independently selected from: H, $C_{1-6}$ alkyl, $(F)_pC_{1-6}$ alkyl, $C_{3-6}$ cycloalkyl, aryl and heteroaryl, said $C_{1-6}$ alkyl, $(F)_pC_{1-6}$ alkyl, $C_{3-6}$ cycloalkyl, aryl and heteroaryl unsubstituted or substituted with hydroxy or $C_1$-$C_6$ alkoxy;

W is $NR^4$ or $C(R^4)_2$;

$R^6$ is independently selected from H and:
   a) $C_{1-6}$ alkyl,
   b) $C_{3-6}$ cycloalkyl,
   c) $(F)_pC_{1-3}$ alkyl,
   d) halogen,
   e) $OR^4$,
   f) $CO_2R^4$,
   g) $(CO)NR^{10}R^{11}$,
   h) $SO_2NR^{10}R^{11}$,
   i) $N(R^{10})SO_2R^{11}$,
   j) $S(O)_mR^{10}$,
   k) CN,
   l) $NR^{10}R^{11}$, and
   m) $O(CO)R^4$;

Z is Z1 and:
   J is a bond, V is a bond, Q is $-N(R^{7a})-$, and T is $-C(=O)-$, or
   J is a bond, V is a bond, Q is $-C(R^{7a})_2-$, and T is $-C(=O)-$, or
   J is a bond, V is a bond, Q is $=N-$, and T is $=C(R^{7b})-$, or
   J is a bond, V is a bond, Q is $-C(R^{7a})_2-$, and T is $-C(R^{7b})_2-$, or
   J is a bond, V is a bond, Q is $=C(R^7a)-$, T is $=C(R^{7b})-$, and the atoms to which $R^{7a}$ and $R^{7b}$ are attached join to form a benzene, pyridine, or diazine ring, or
   J is a bond, V is $C(R^6)_2$, Q is $=C(R^7a)-$, T is $=C(R^{7b})-$, and the atoms to which $R^{7a}$ and $R^{7b}$ are attached join to form a benzene, or pyridine ring, or
   J is O, V is a bond, Q is $=C(R^{7a})-$, T is $=C(R^{7b})-$, and the atoms to which $R^{7a}$ and $R^{7b}$ are attached are joined together to form a benzene, or pyridine ring, or Z is Z2 and:
   G-L is N, Q is $-C(R^{7a})_2-$, and T is $-C(R^{7b})_2-$, or
   G-L is N, Q is $=C(R^{7a})-$ and T is $=C(R^{7b})-$, or
   G-L is N, Q is $=N-$, and T is $=C(R^{7b})-$, or
   G-L is N, Q is $-C(R^{7a})_2-$, and T is $-C(O)-$, or
   G-L is $C=C(R^6)$, Q is $=C(R^{7a})-$ and T is $=C(R^{7b})-$, or
   G-L is $C=C(R^6)$, Q is $=C(R^{7a})-$ and T is $=N-$, or
   G-L is $C=C(R^6)$, Q is $=N-$ and T is $=C(R^{7b})-$, or
   G-L is $C=N$, Q is $=C(R^{7a})-$ and T is $=C(R^{7b})-$, or
   G-L is N, Q is $=C(R^{7a})-$, and T is $=C(R^{7b})-$, and the atoms to which $R^{7a}$ and $R^{7b}$ are attached join to form a benzene, pyridine, or diazine ring, or
   G-L is $N-C(R^6)_2$, Q is $=C(R^{7a})-$, and T is $=C(R^{7b})-$, and the atoms to which $R^{7a}$ and $R^{7b}$ are attached join to form a benzene, or pyridine ring, or
   G-J is $C=N$, Q is $=C(R^{7a})-$, and T is $=C(R^{7b})-$, and the atoms to which $R^{7a}$ and $R^{7b}$ are attached are join to form a benzene ring, or
   G-L is $C=C(R^6)$, Q is $=C(R^{7a})-$, and T is $=C(R^{7b})-$, and the atoms to which $R^{7a}$ and $R^{7b}$ are attached join to form a benzene ring, or
   G-L is $N-C(R^6)_2-C(R^6)_2$, Q is $=C(R^{7a})-$, and T is $=C(R^{7b})-$, and the atoms to which $R^{7a}$ and $R^{7b}$ are attached join to form a benzene ring;

R³ is independently selected from H, substituted or unsubstituted $C_1$-$C_3$ alkyl, F, CN and $CO_2R^4$;

$R^{7a}$ and $R^{7b}$ are each independently selected from $R^2$, where $R^{7a}$ and $R^{7b}$ and the atom or atoms to which they are attached optionally join to form a ring selected from $C_{3-6}$cycloalkyl, aryl, heterocycle, and heteroaryl which is unsubstituted or substituted with 1-10 substituents each each independently selected from $R^6$;

p is selected from an integer in the range of 0 to 2 times q plus 1, for a substituent with q carbons;

m is 0, 1 or 2;

s is 1, 2 or 3;

and pharmaceutically acceptable salts and individual stereoisomers thereof.

8. A compound selected from:

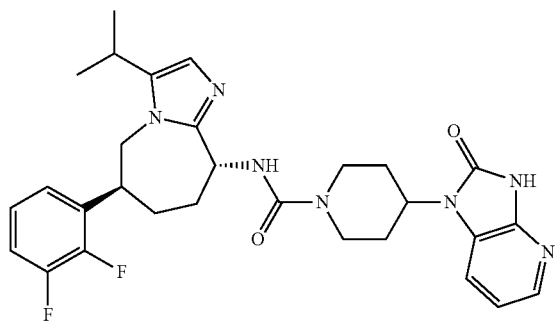

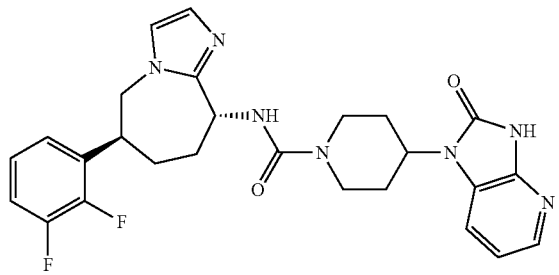

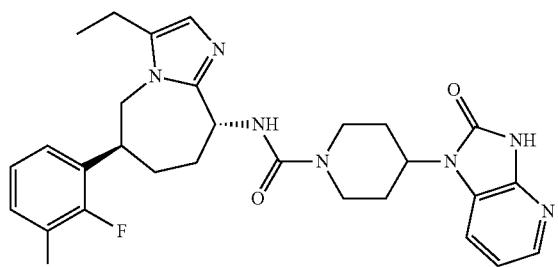

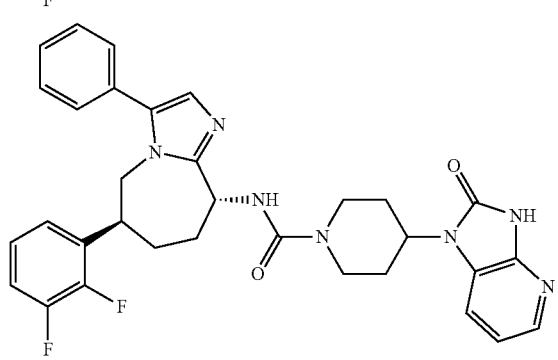

-continued

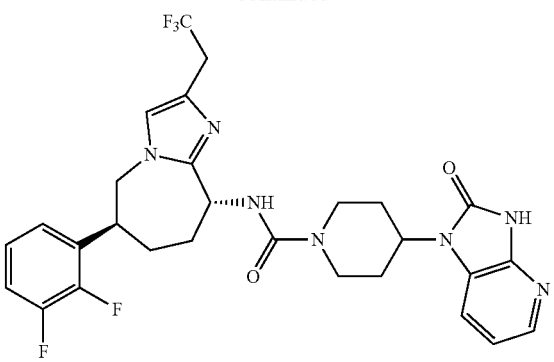

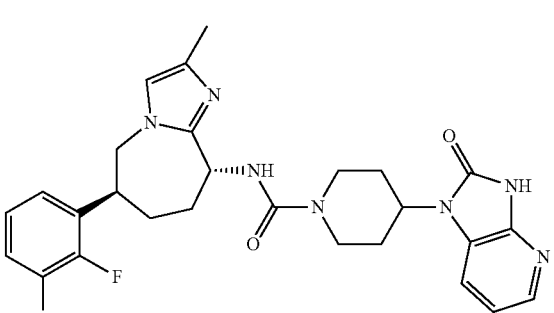

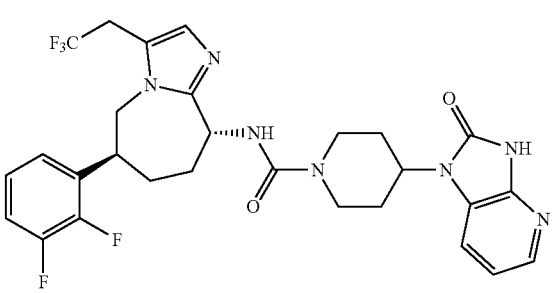

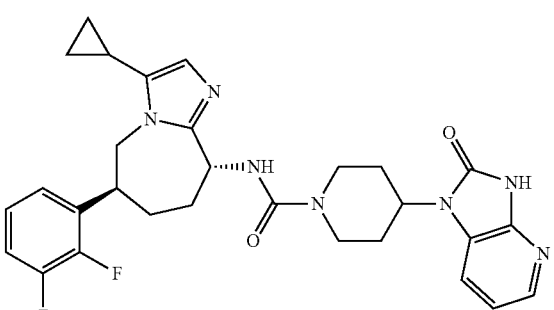

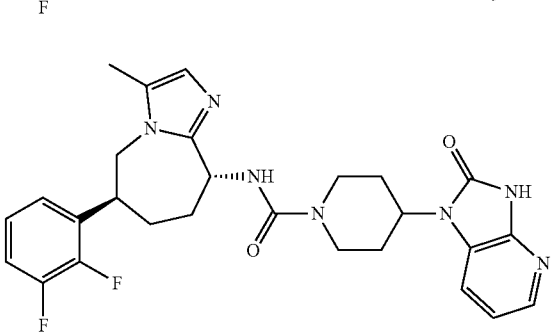

223
-continued
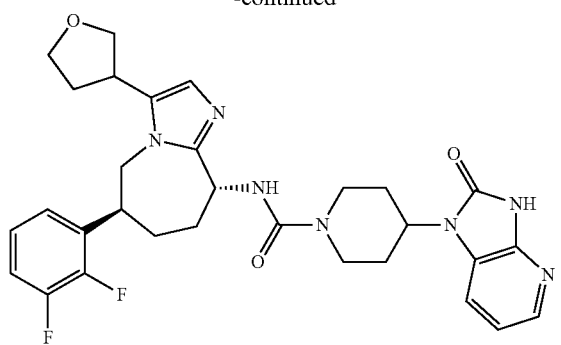
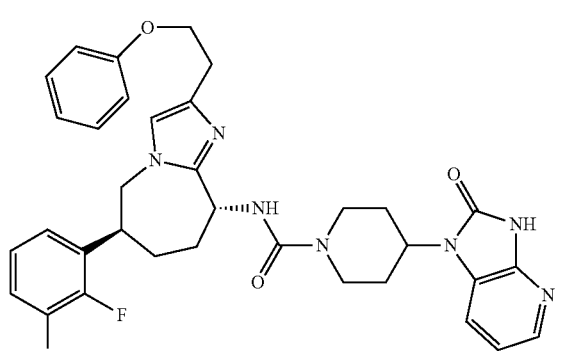
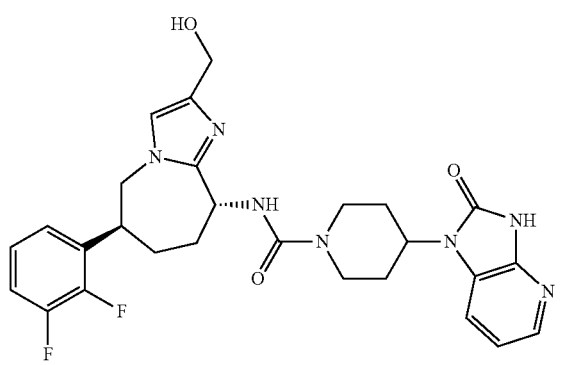
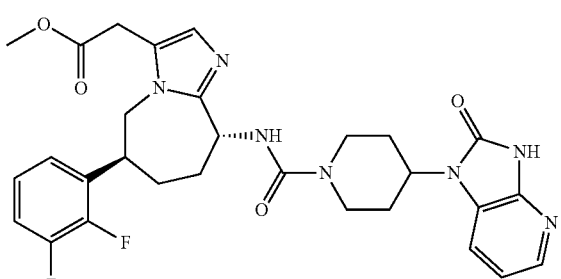
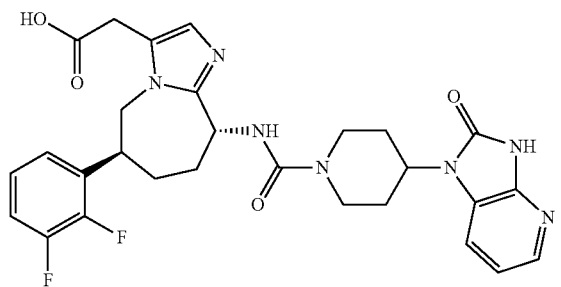
224
-continued
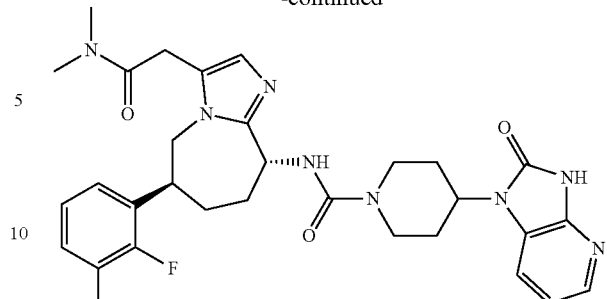
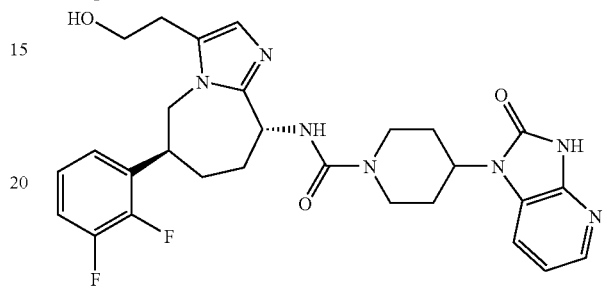
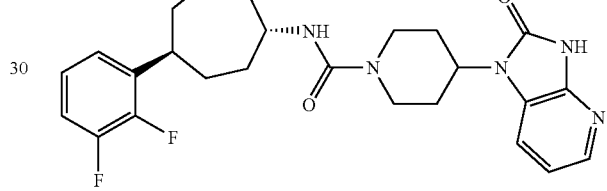
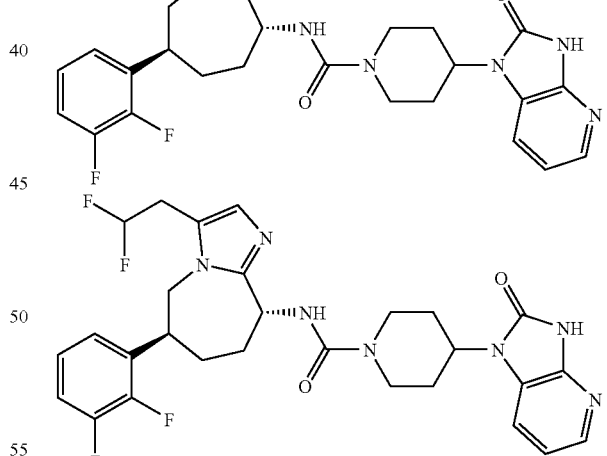
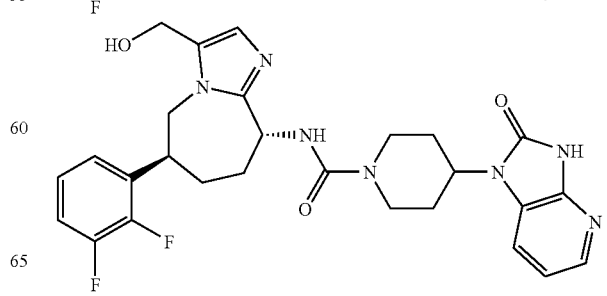

225
-continued
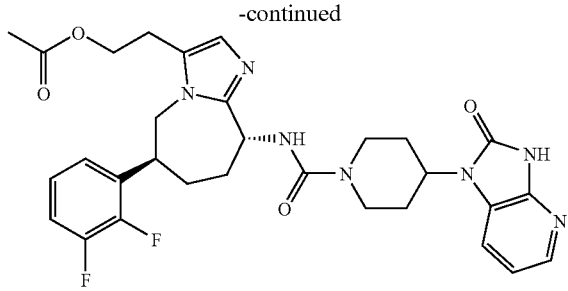
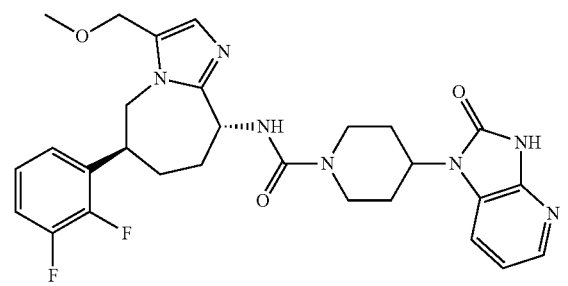
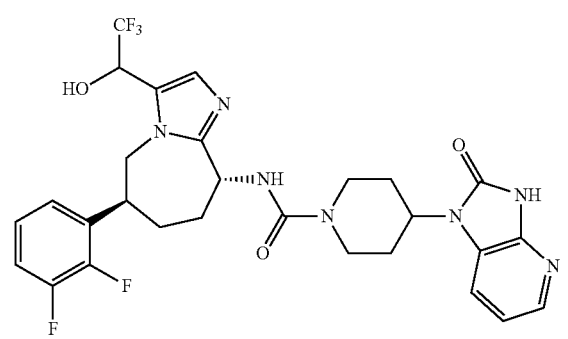
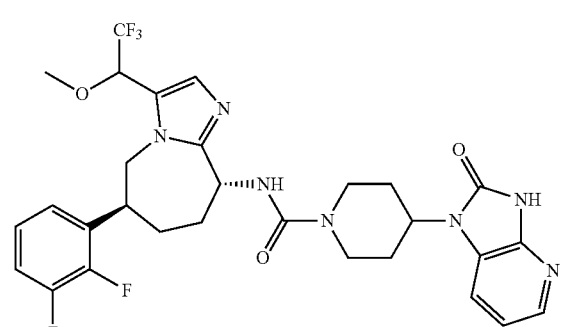
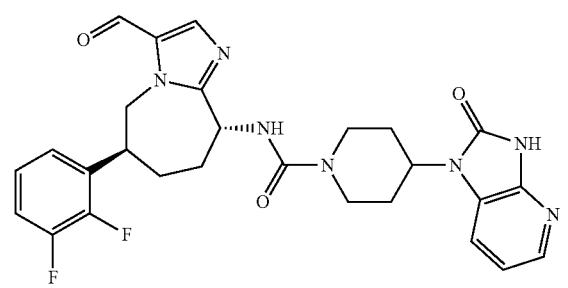
226
-continued
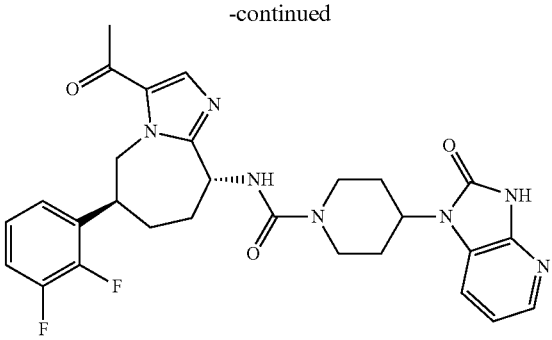
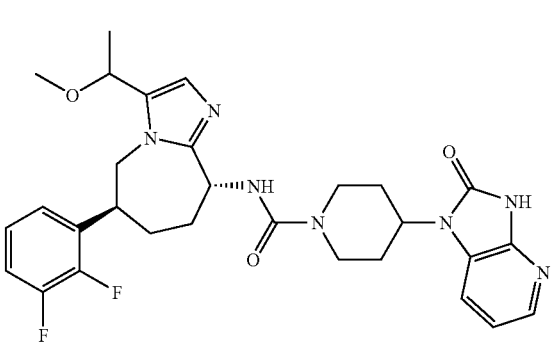
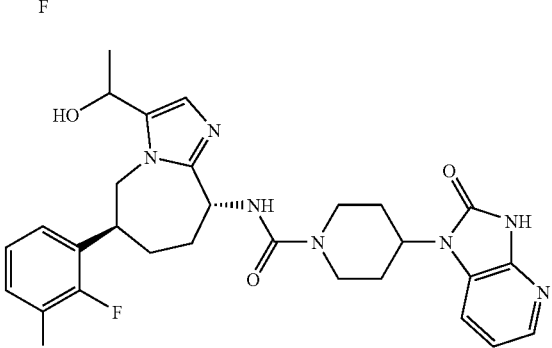
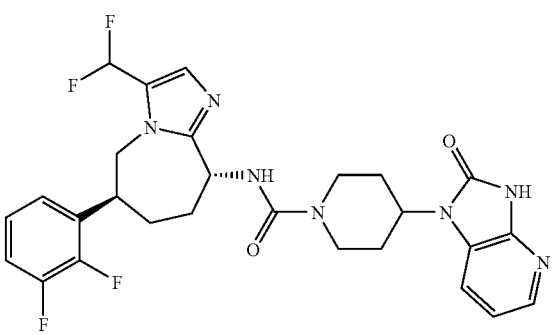
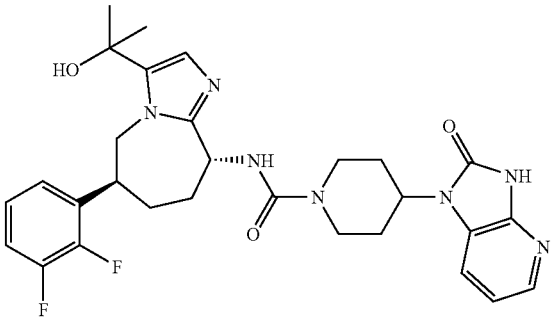

227
-continued
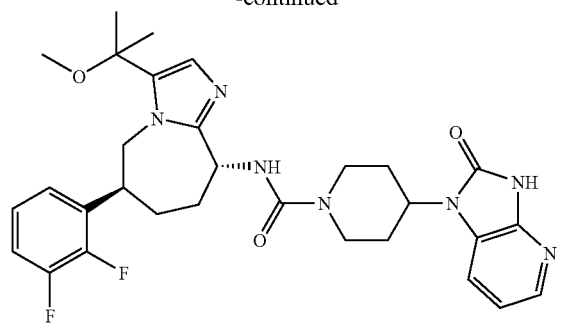
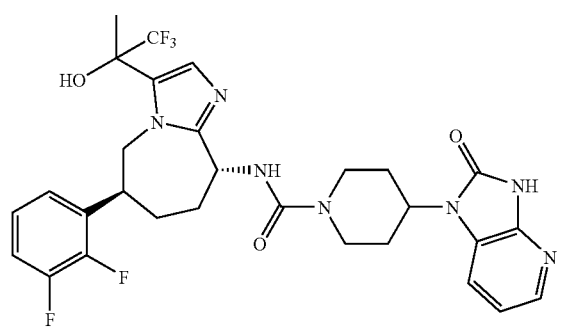
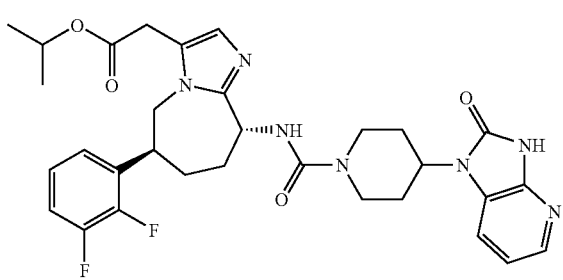
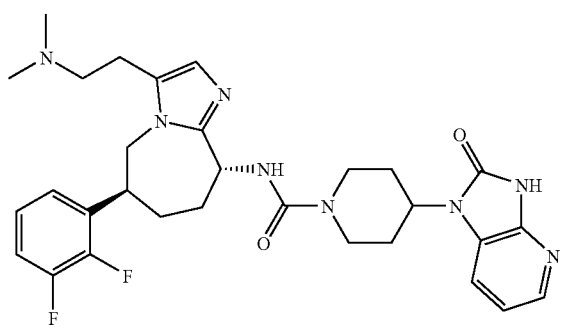
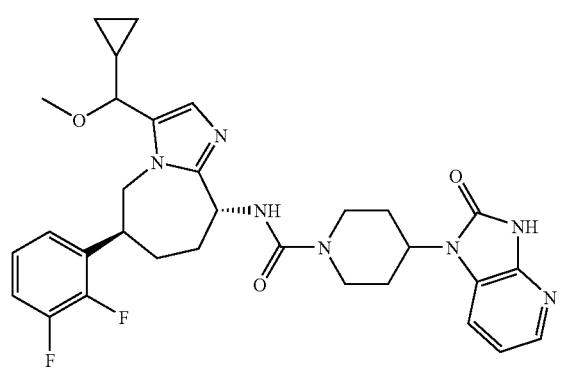
228
-continued
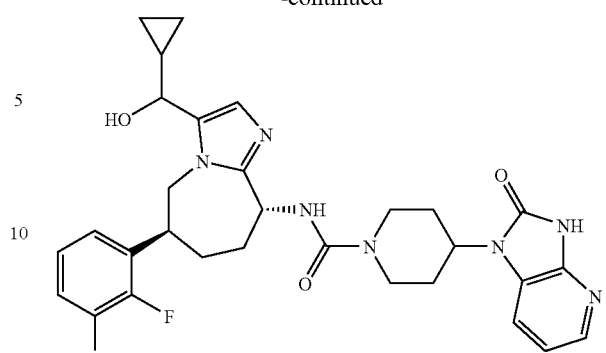
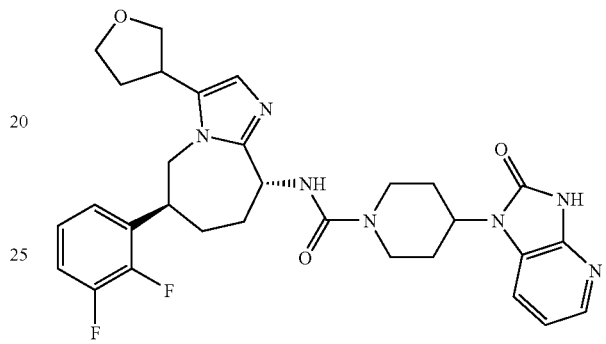
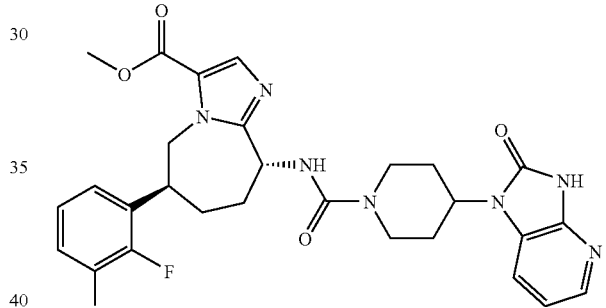
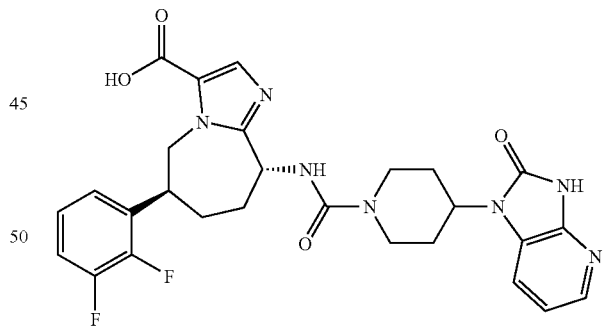
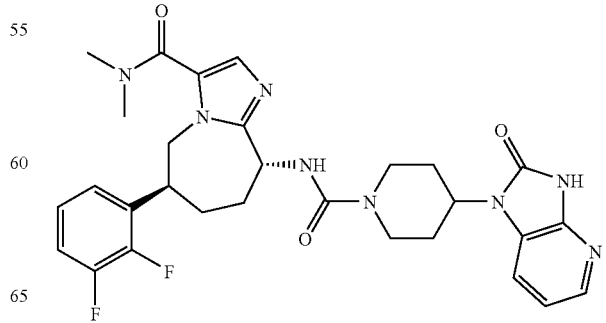

229
-continued
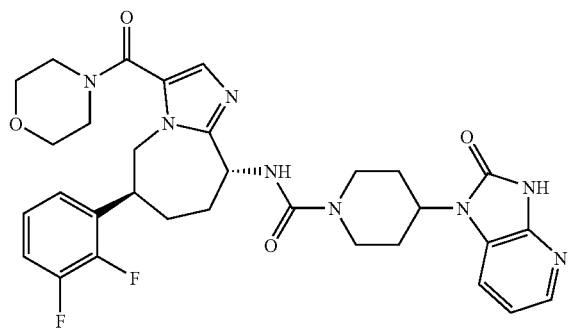
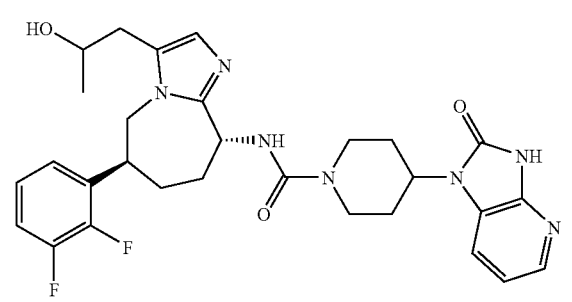
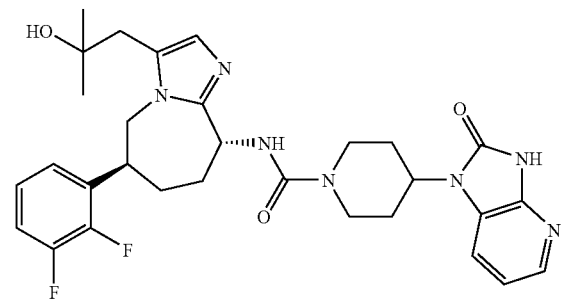
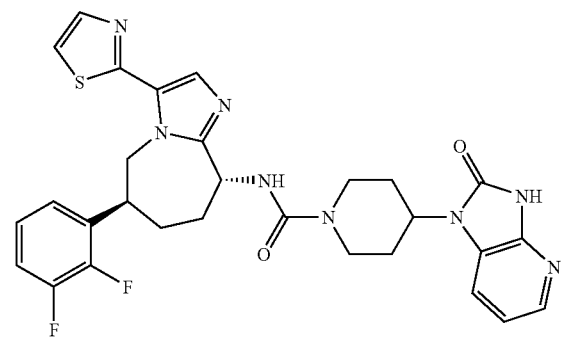
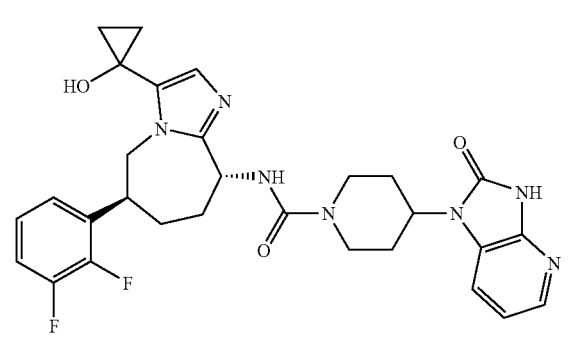
230
-continued
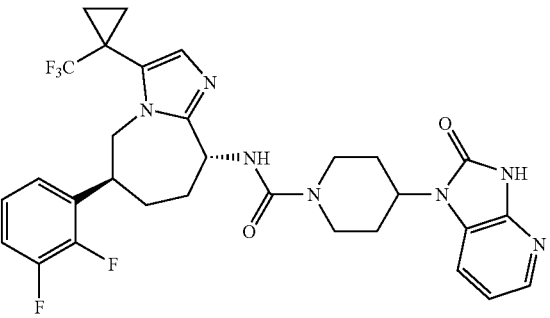
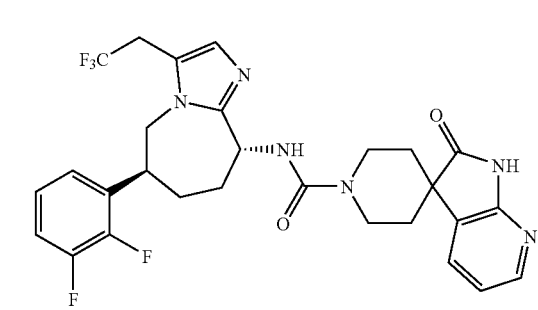
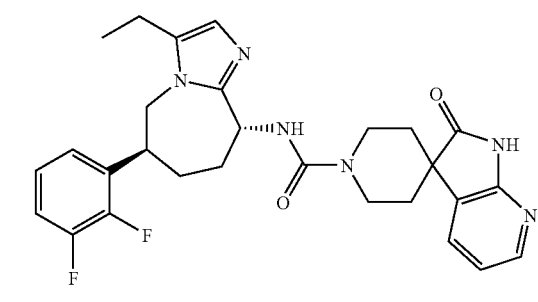
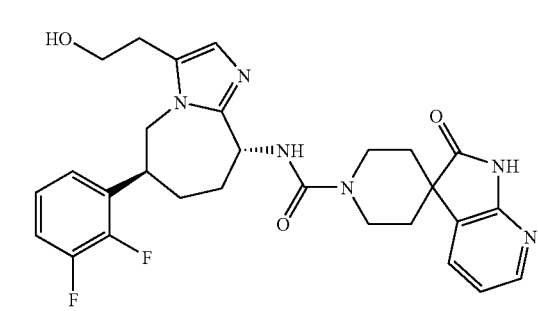
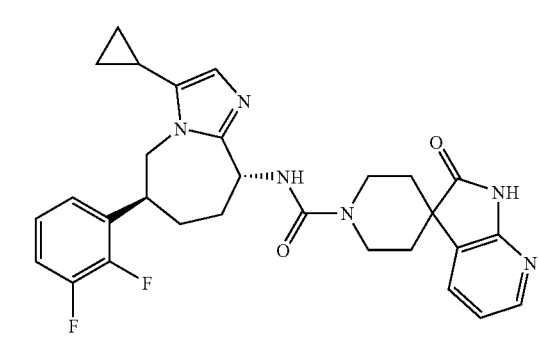

231
-continued
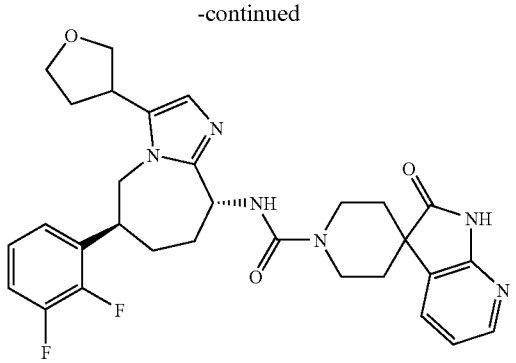
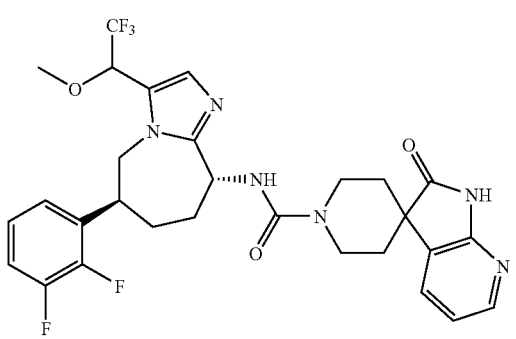
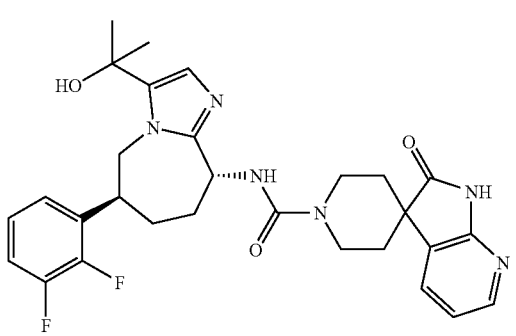
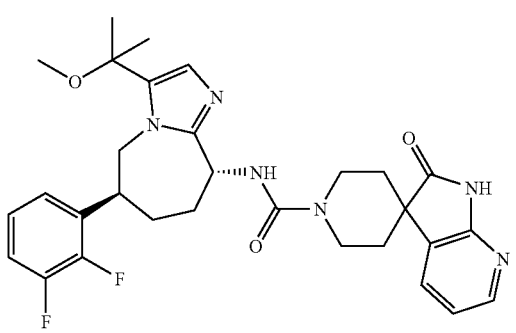
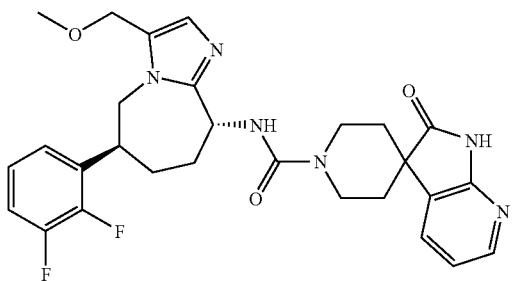
232
-continued
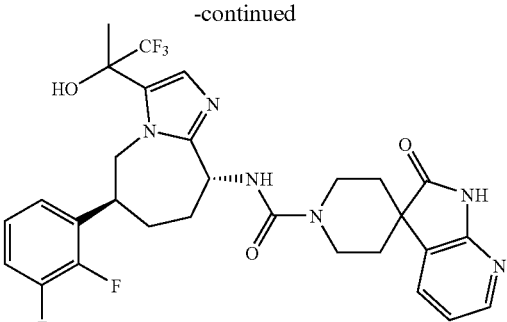
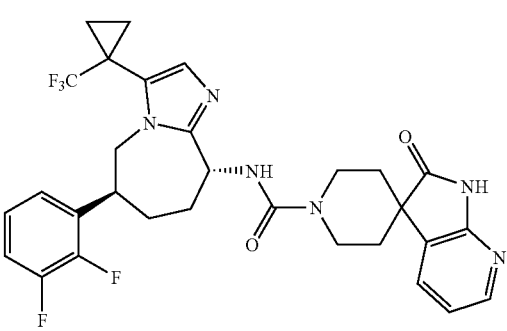
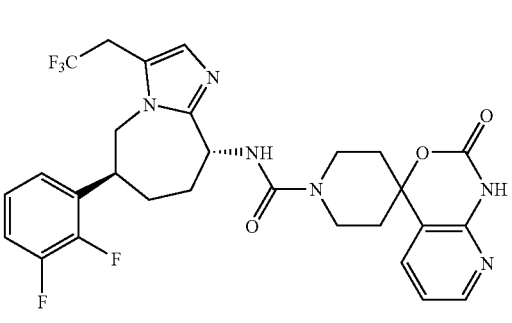
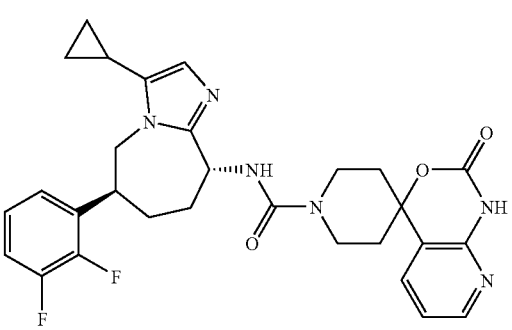
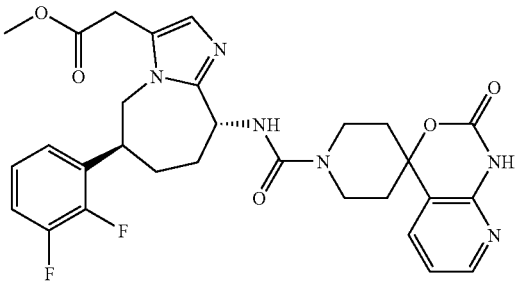

233
-continued
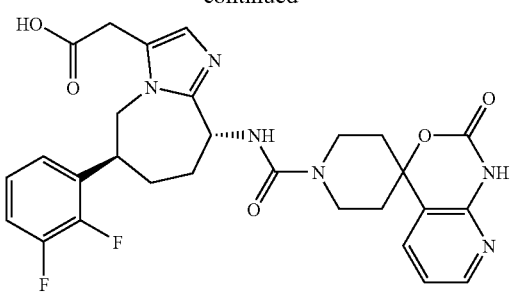
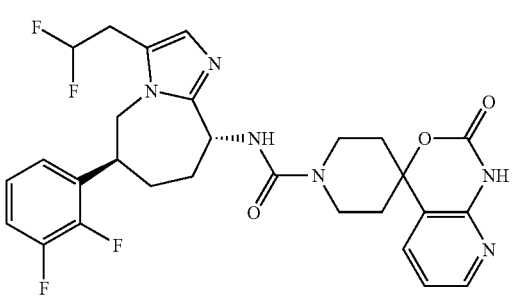
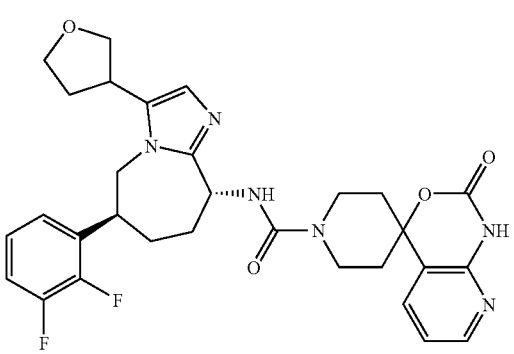
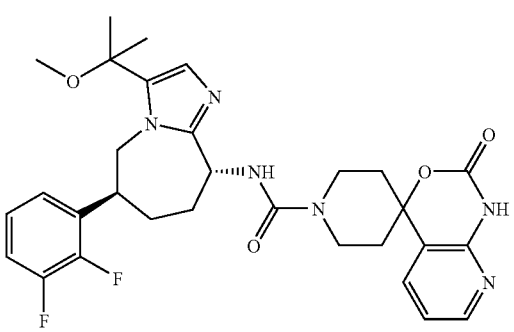
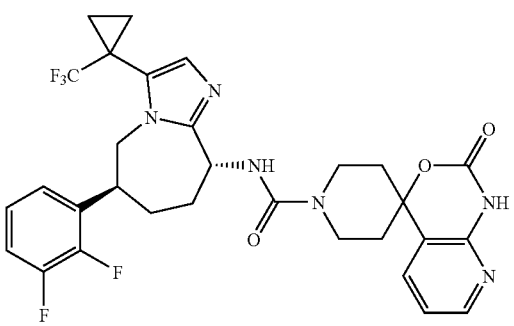
234
-continued
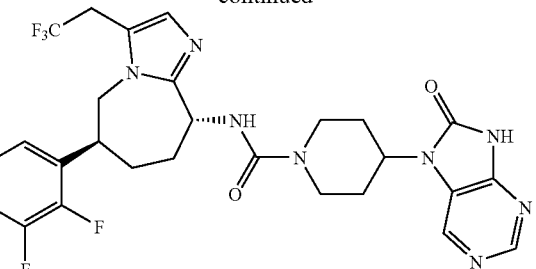
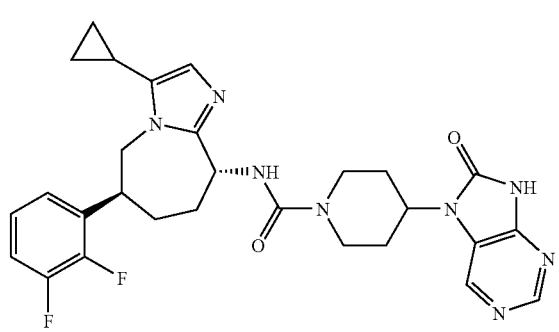
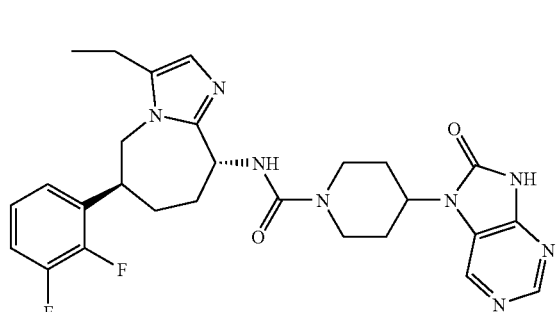
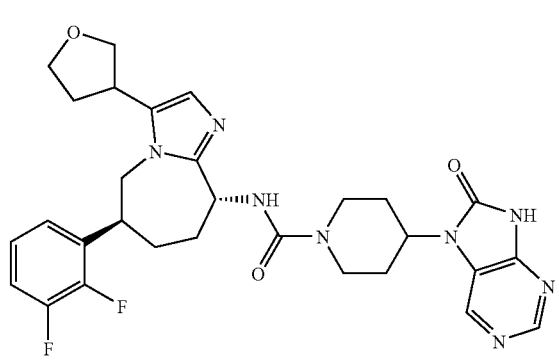
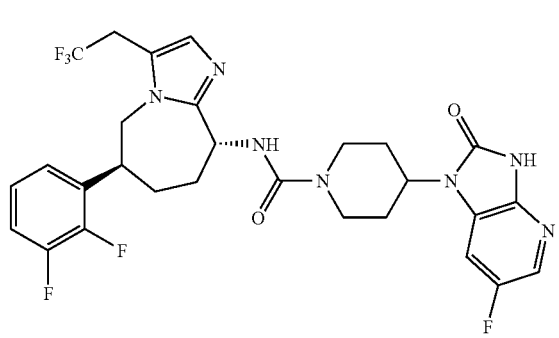

235
-continued
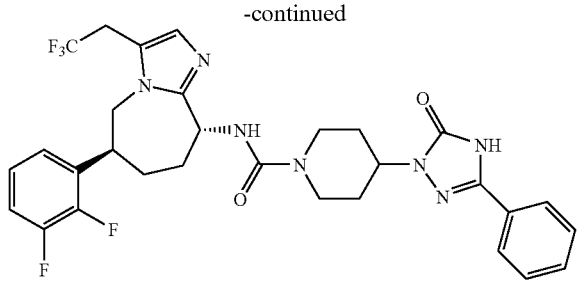
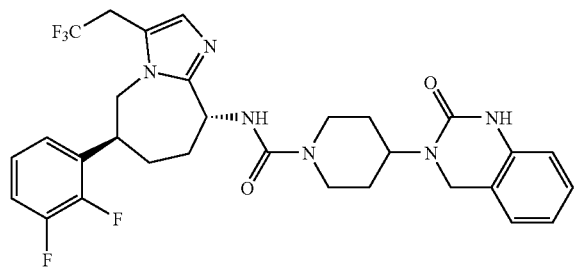
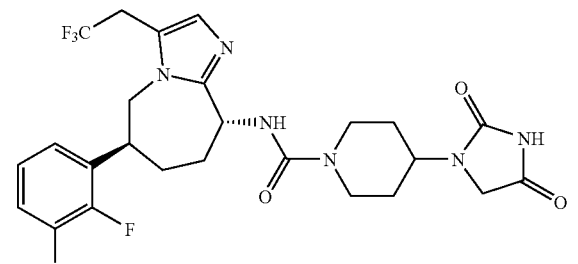
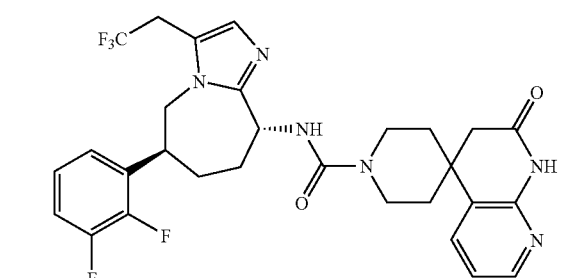
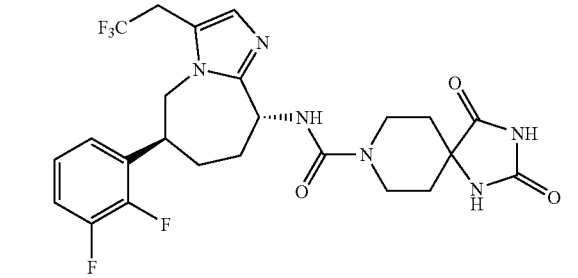
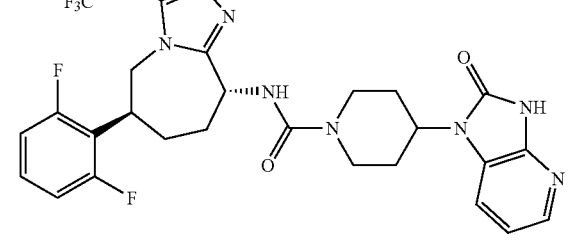
236
-continued
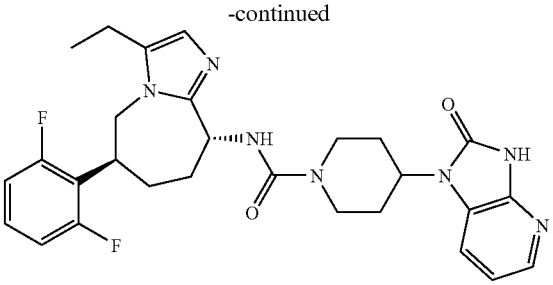
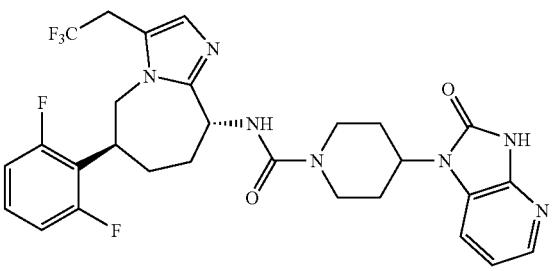
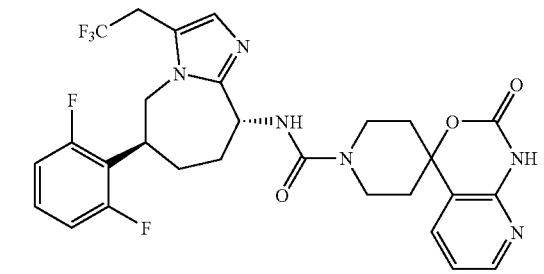
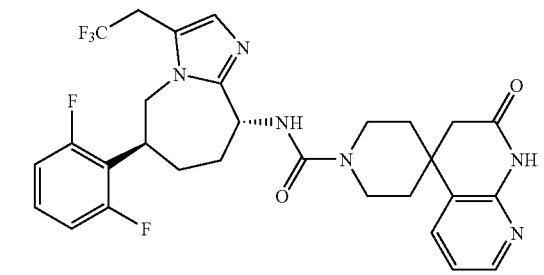
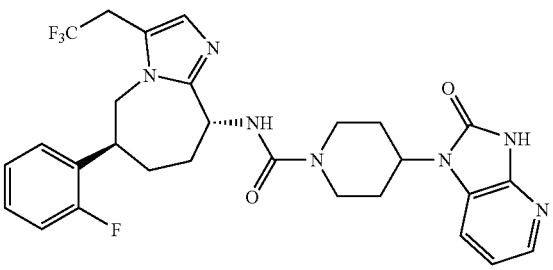
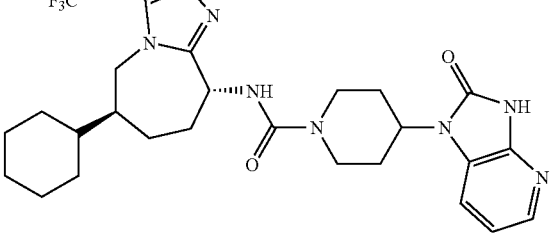

237
-continued
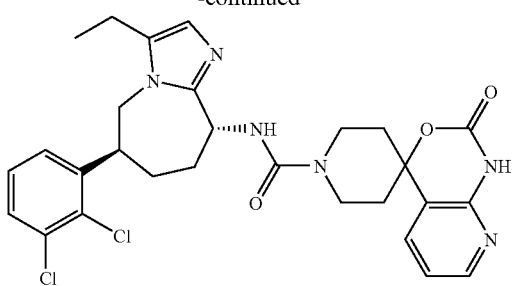
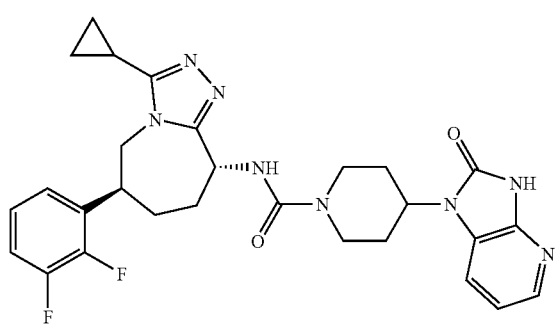
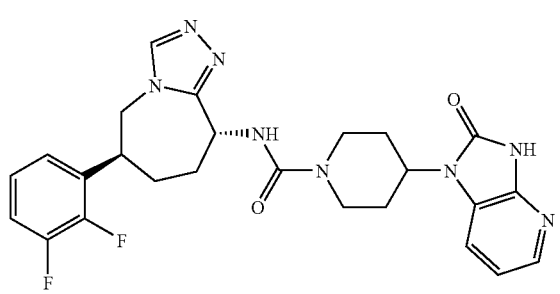
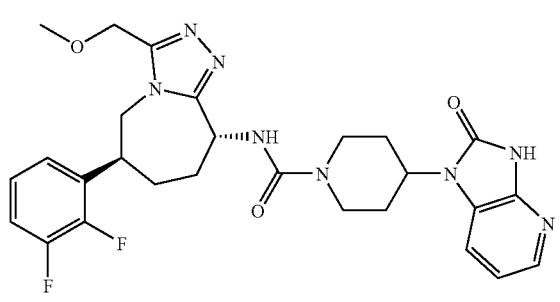
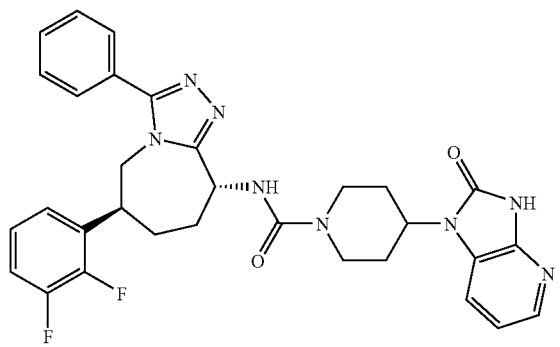
238
-continued
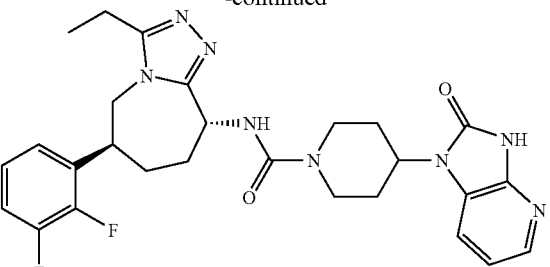
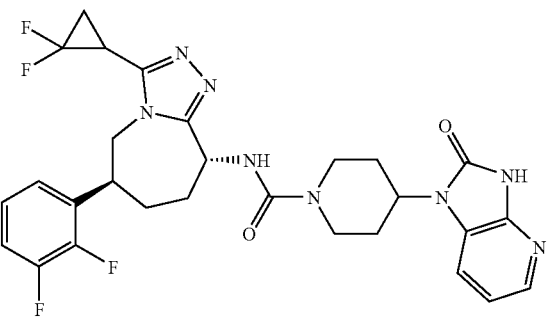
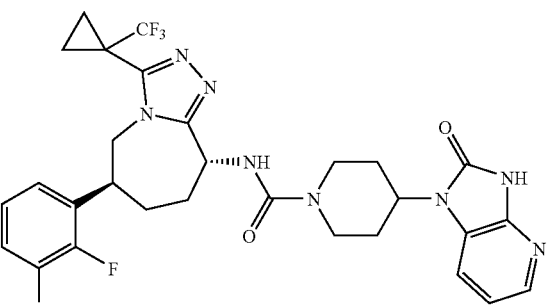
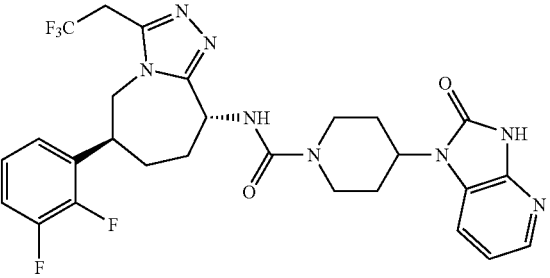
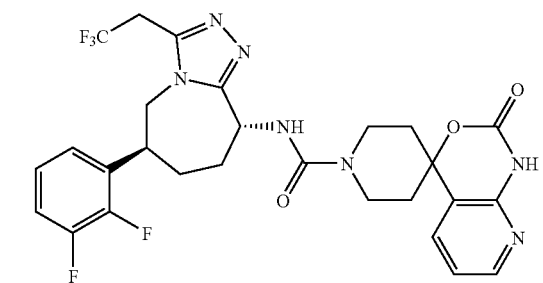

-continued
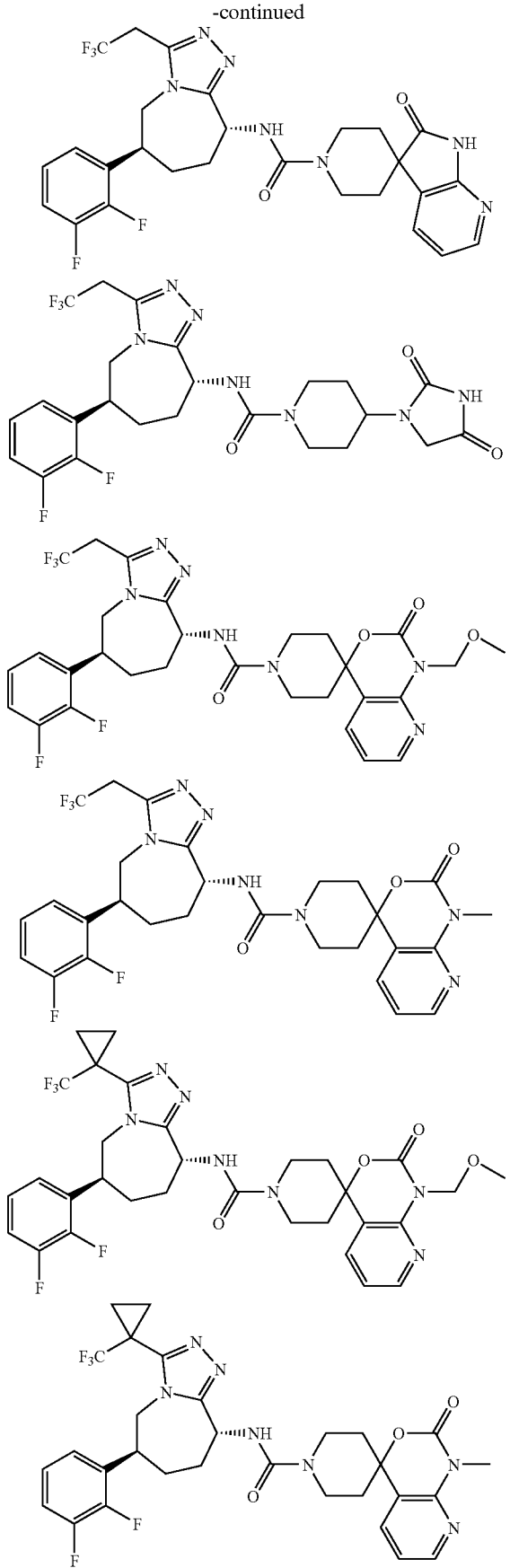
-continued
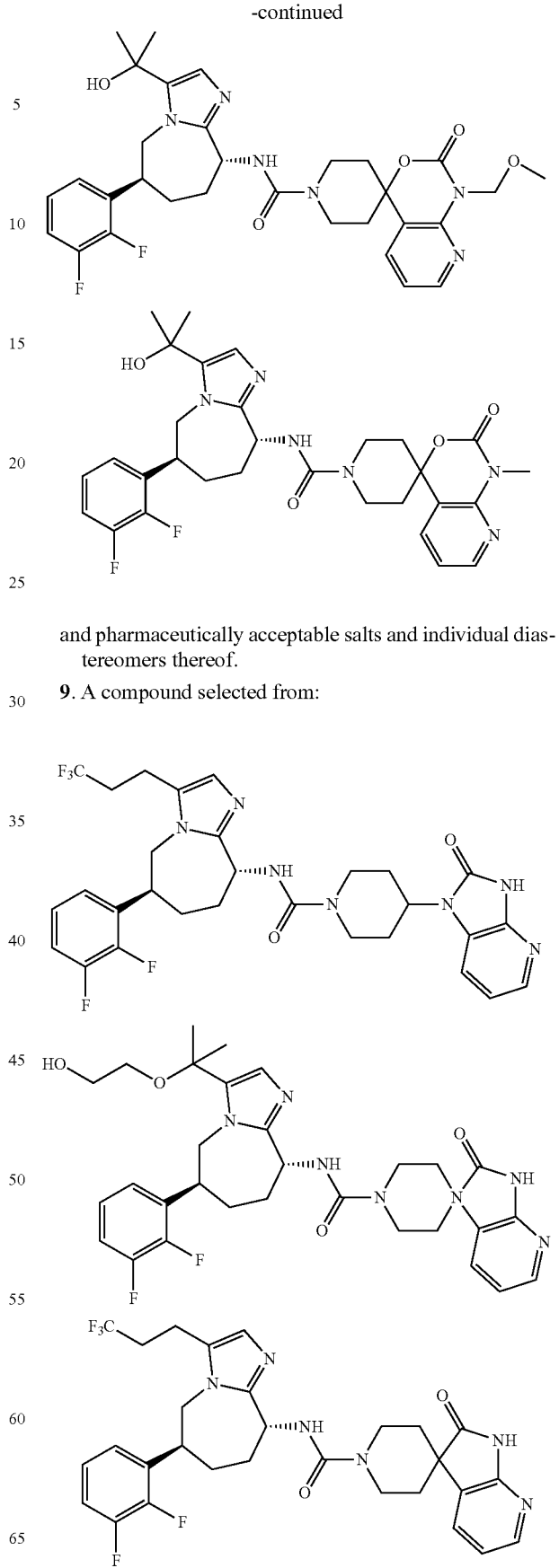
and pharmaceutically acceptable salts and individual diastereomers thereof.
9. A compound selected from:

241
-continued
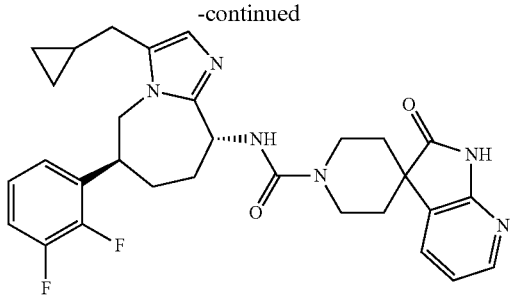
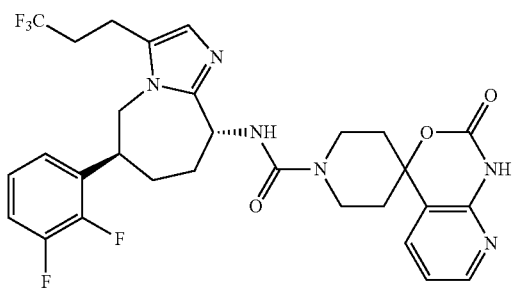
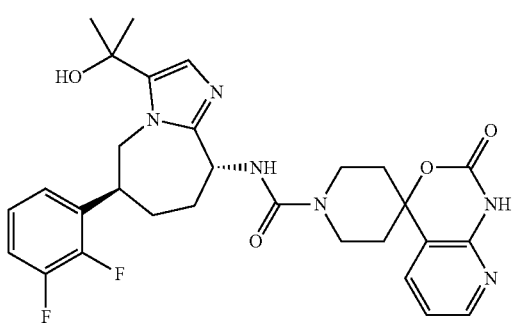
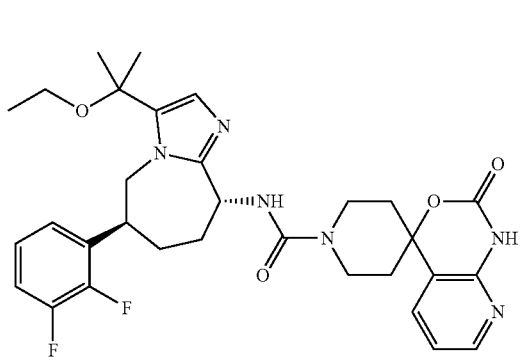
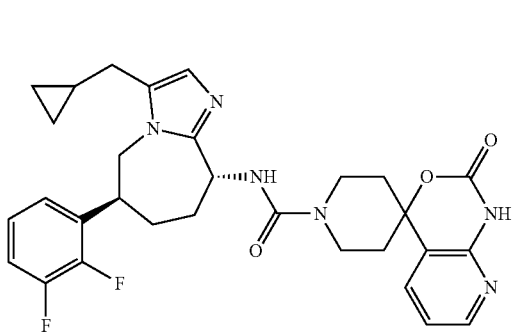
242
-continued
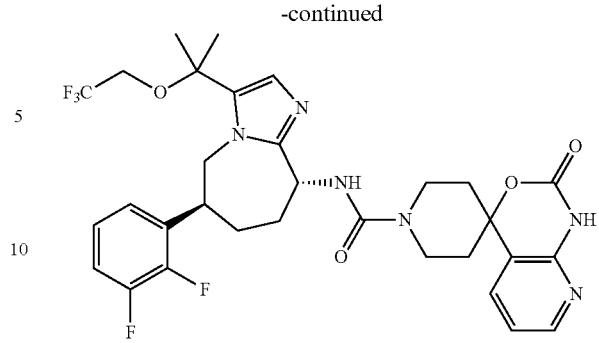
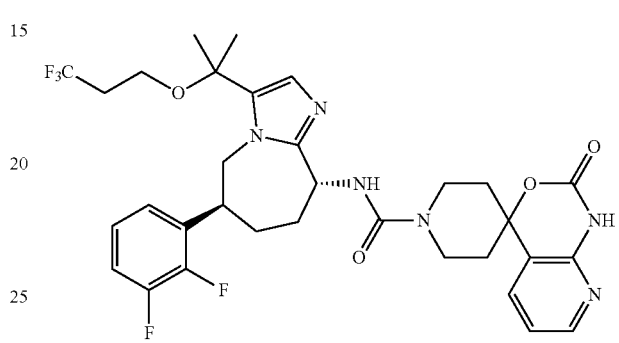
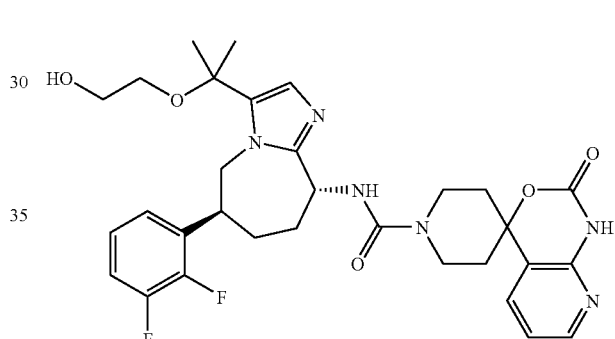
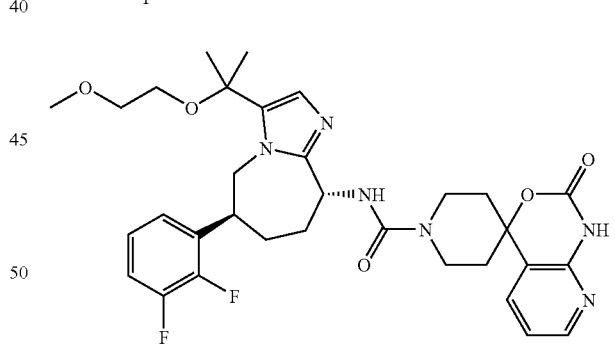
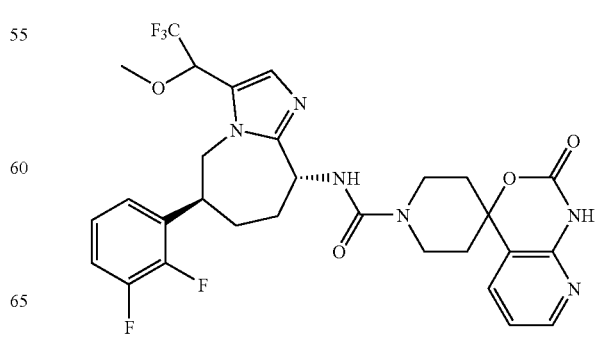

243
-continued
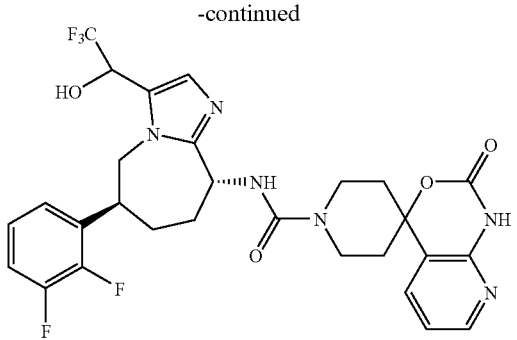
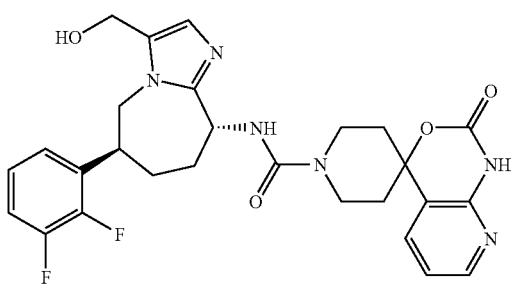
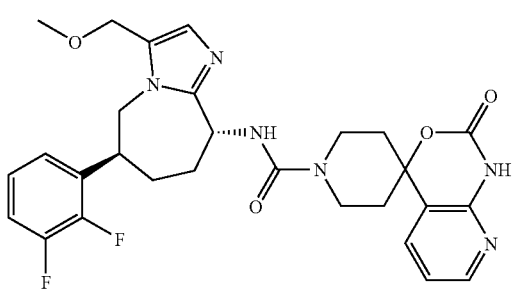
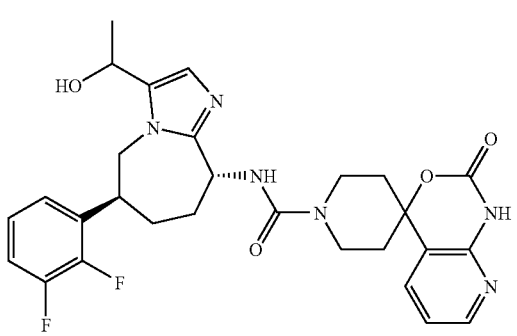
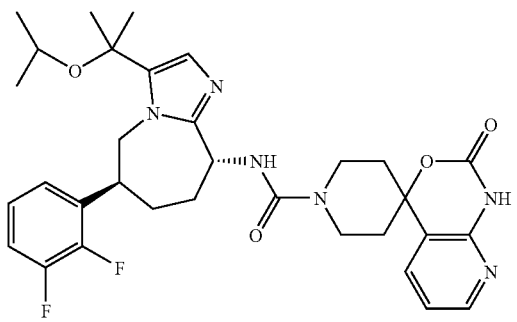
244
-continued
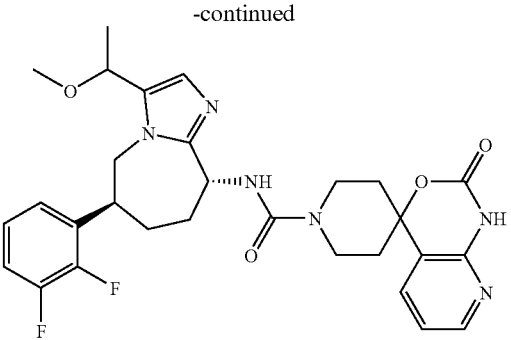
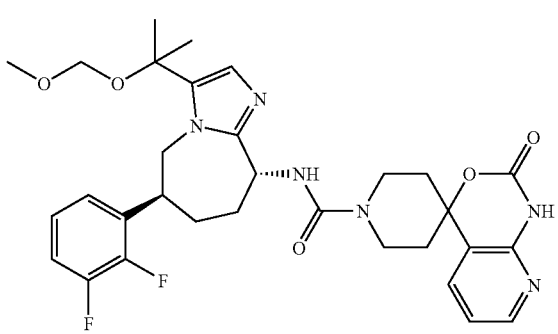
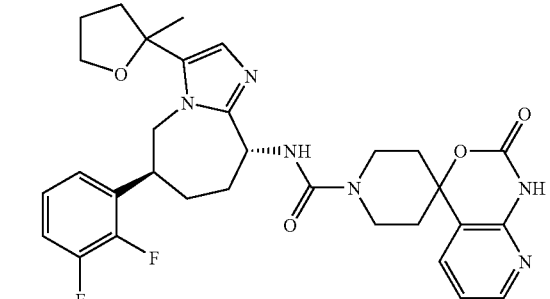
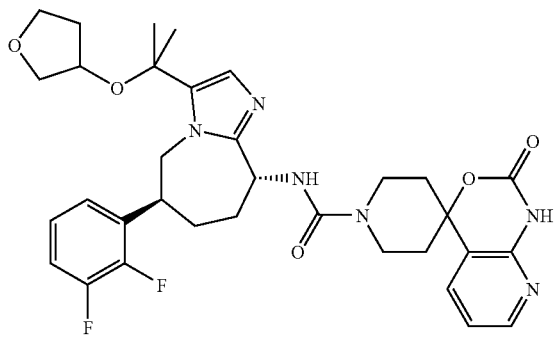
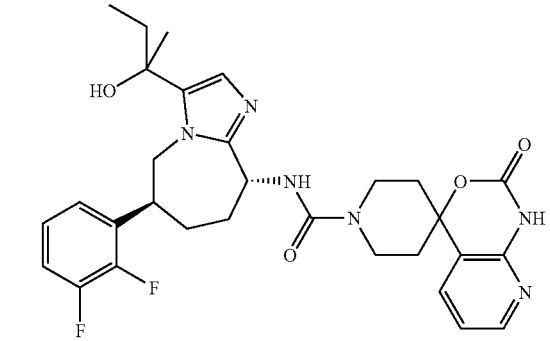

245
-continued
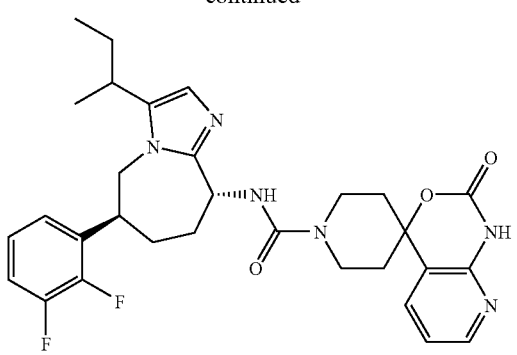
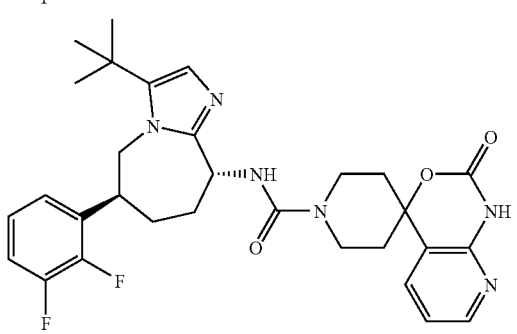
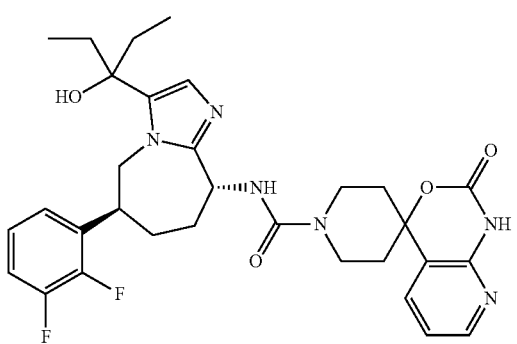
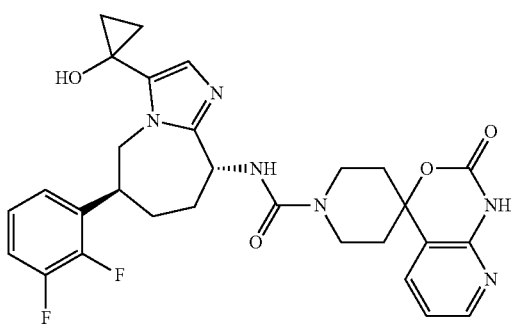
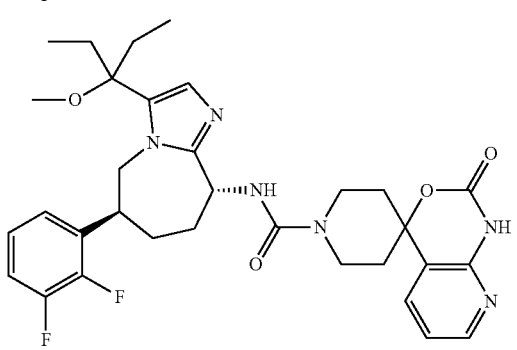
246
-continued
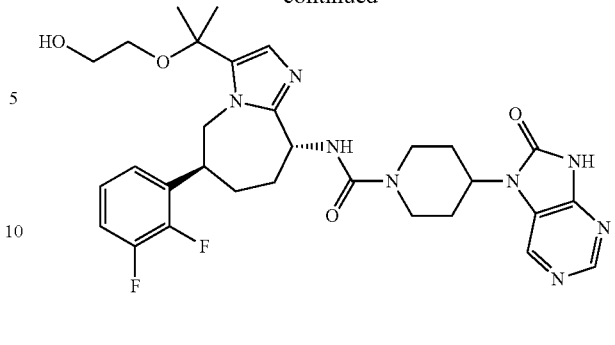
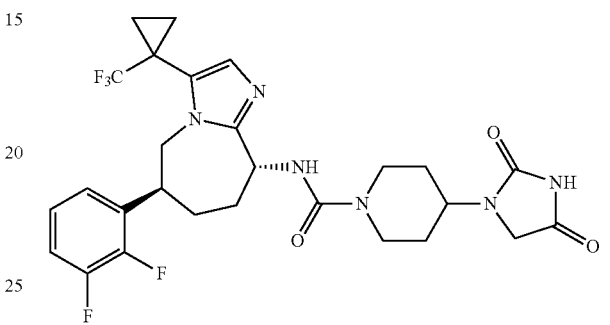
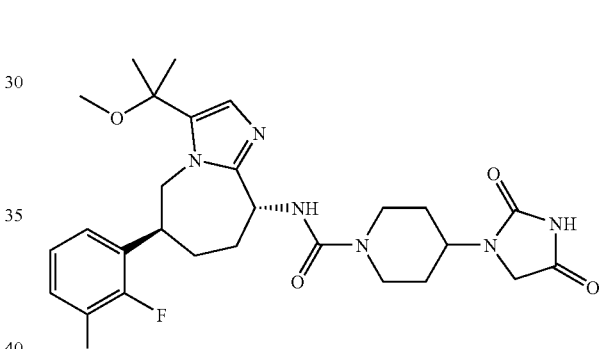
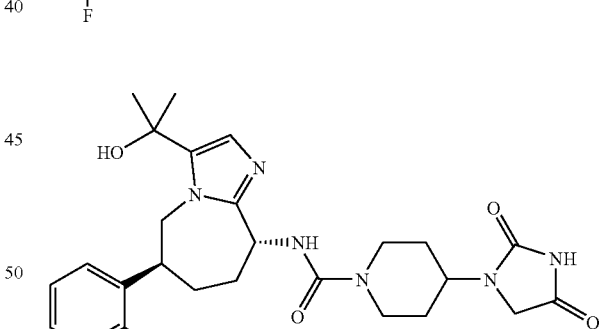
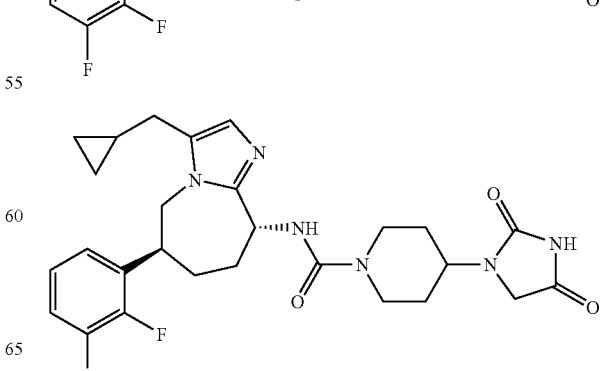

247
-continued
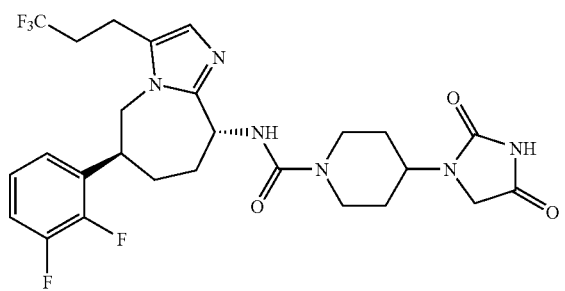
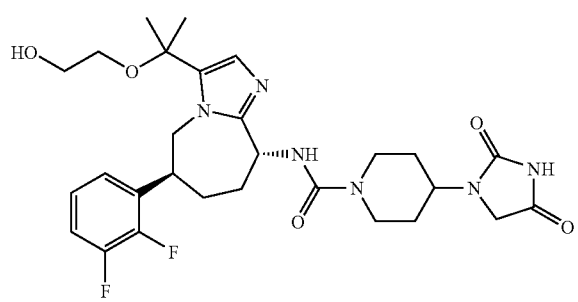
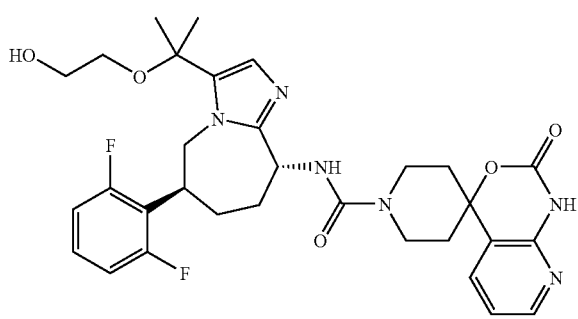
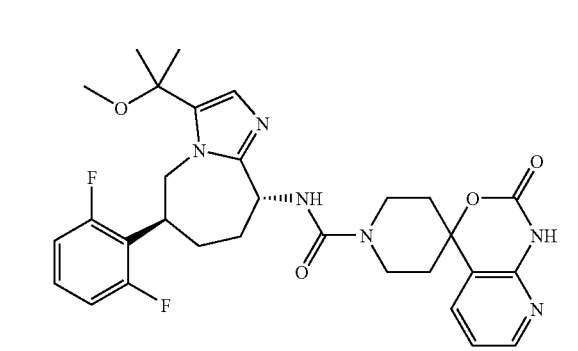
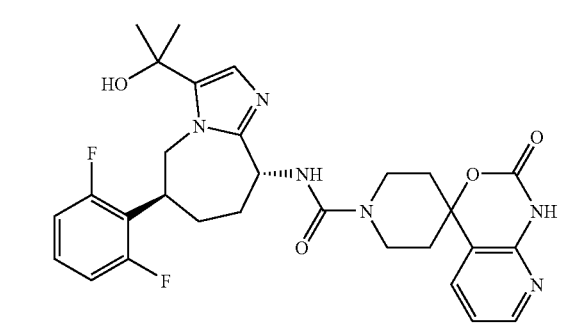
248
-continued
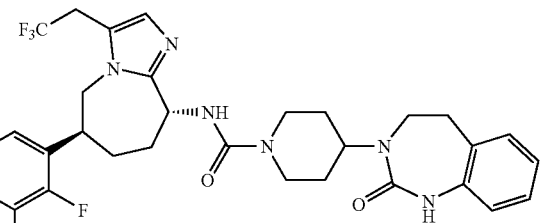
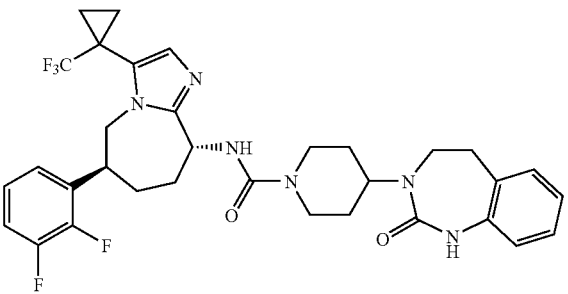
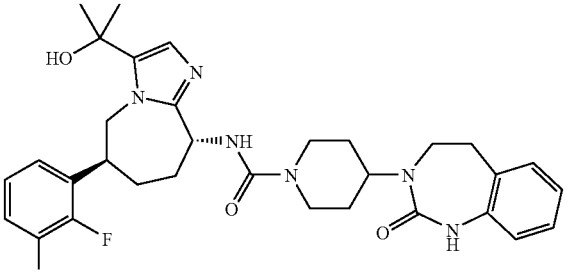
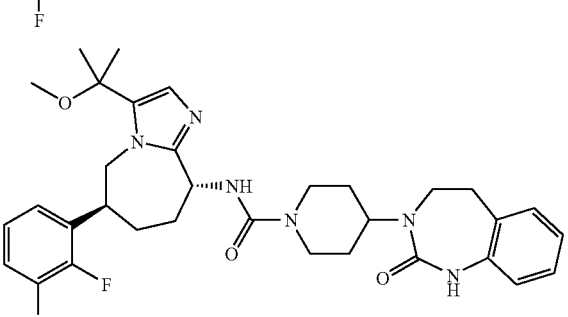
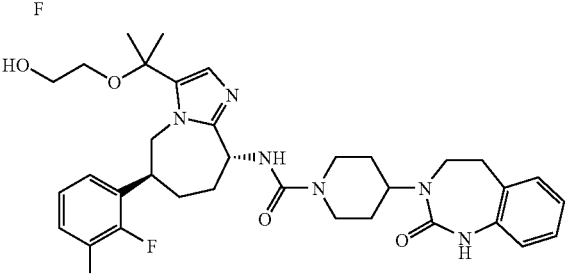
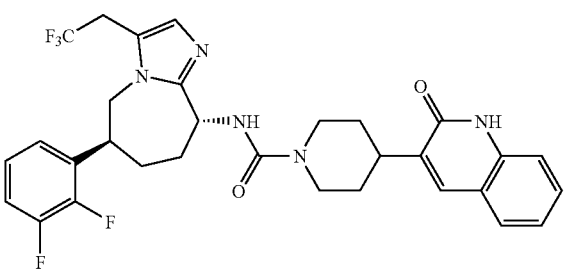

249
-continued
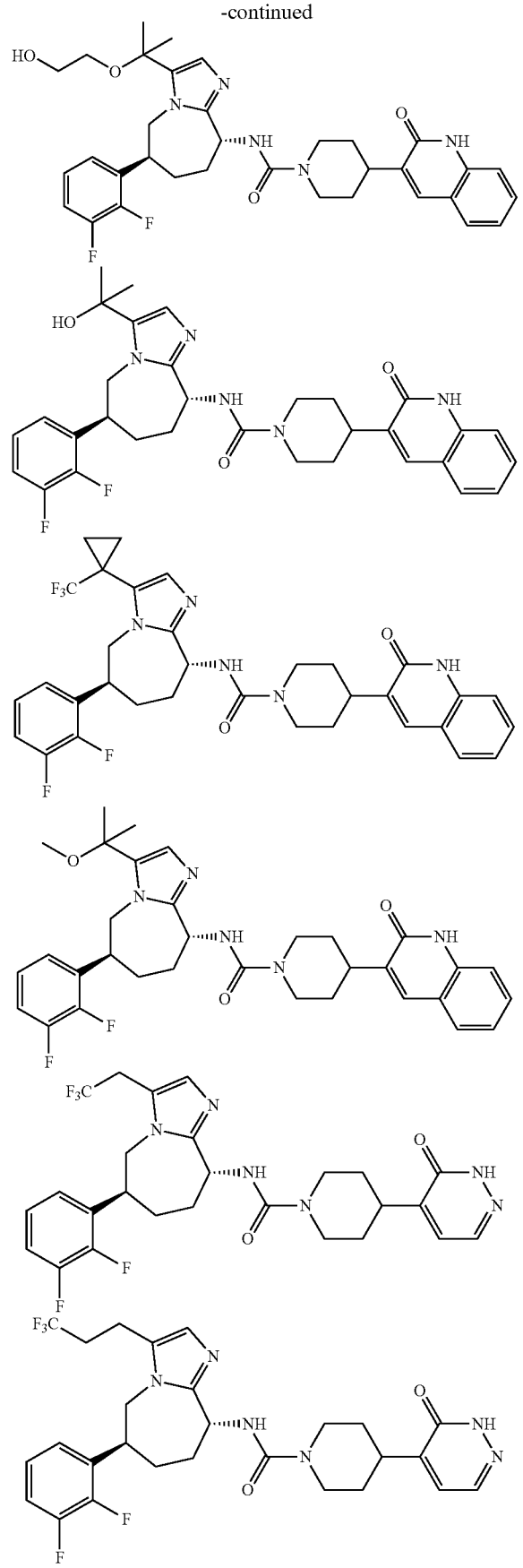
250
-continued
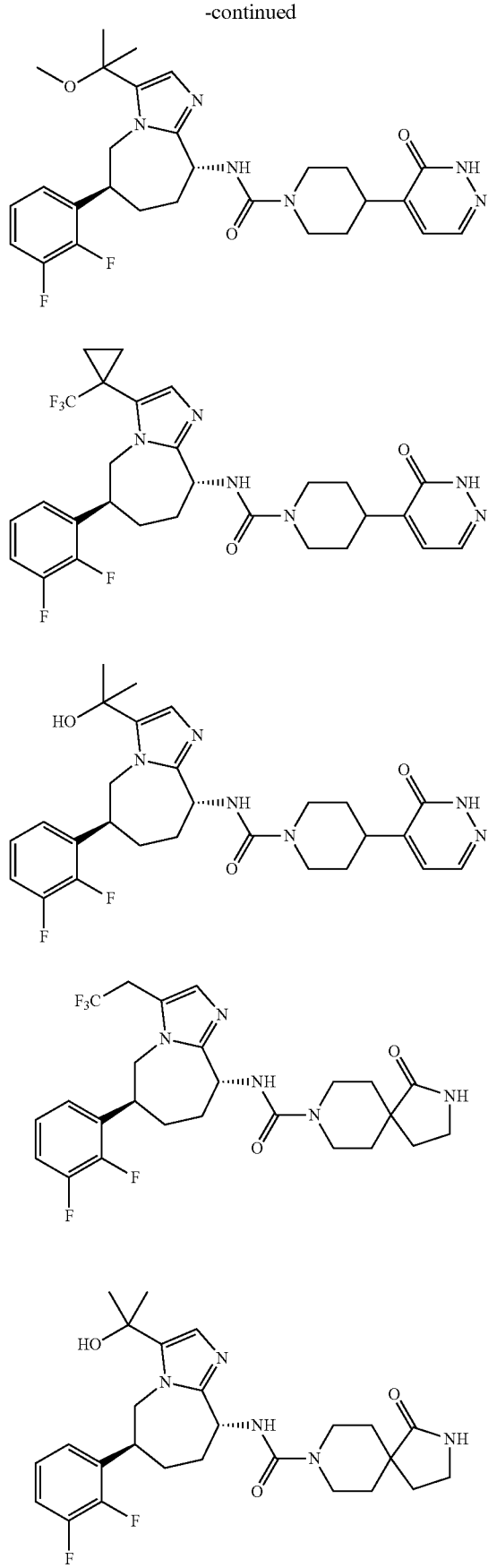

251
-continued
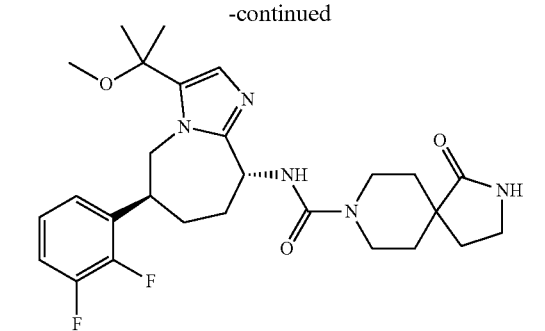
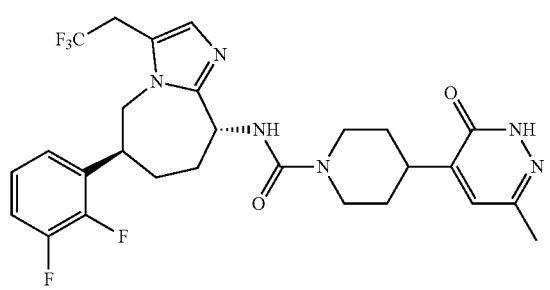
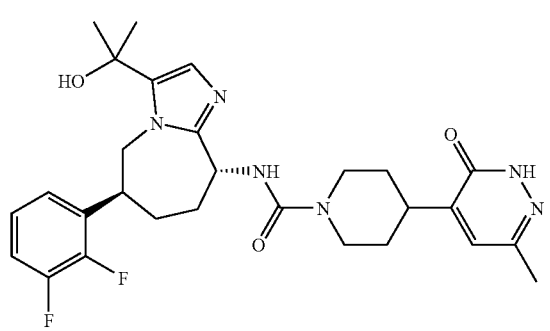
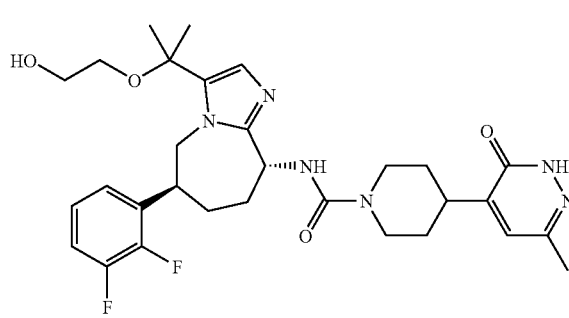
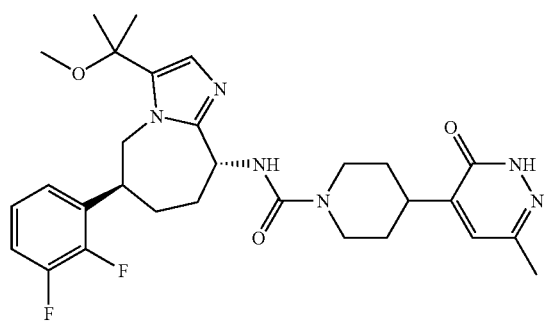
252
-continued
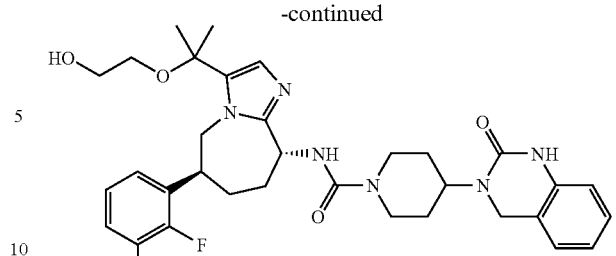
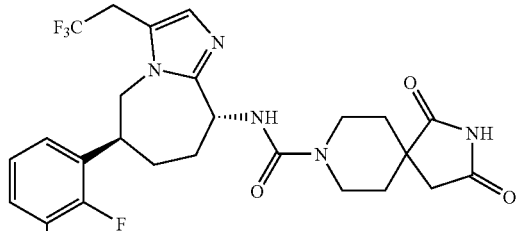
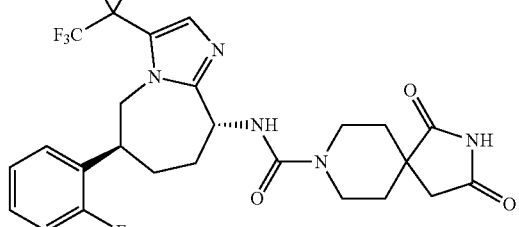
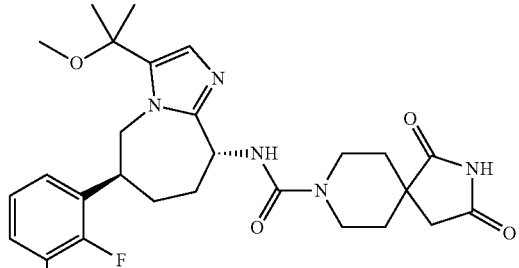
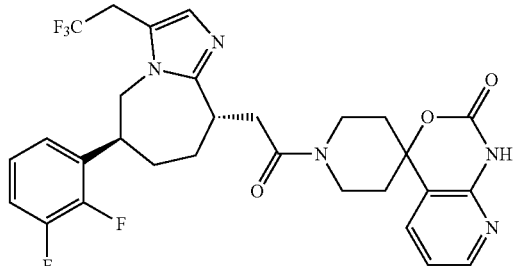
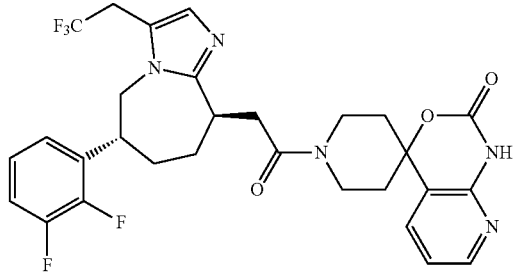

253
-continued
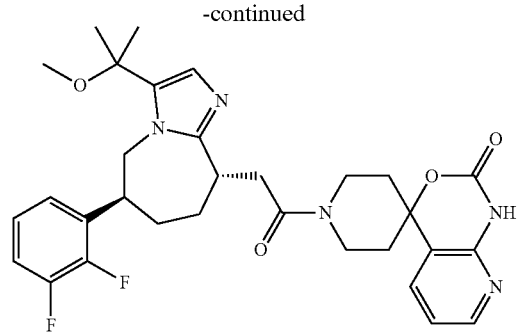
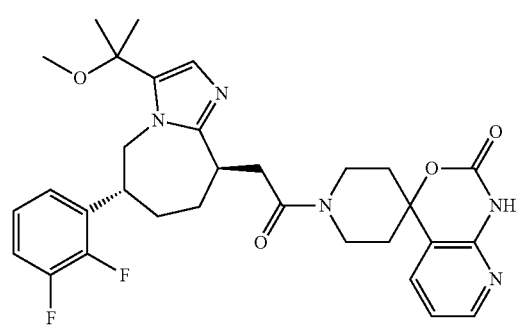
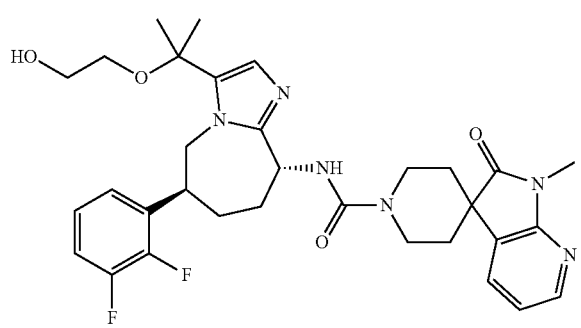
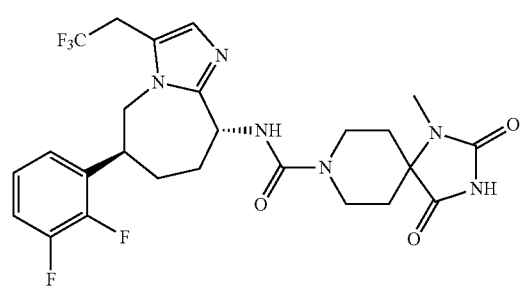
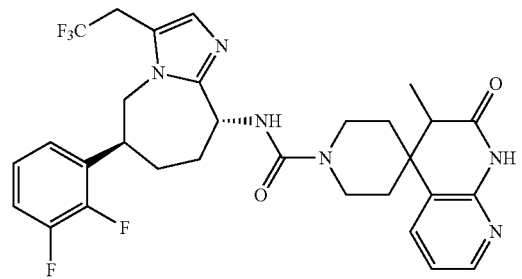
254
-continued
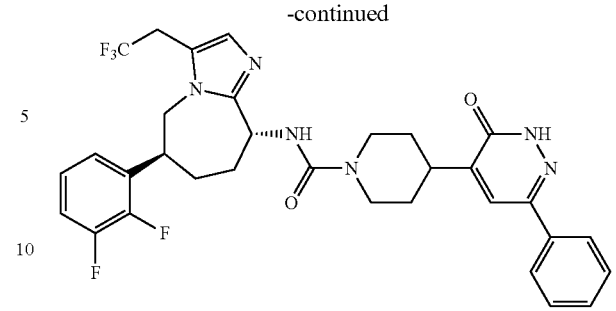
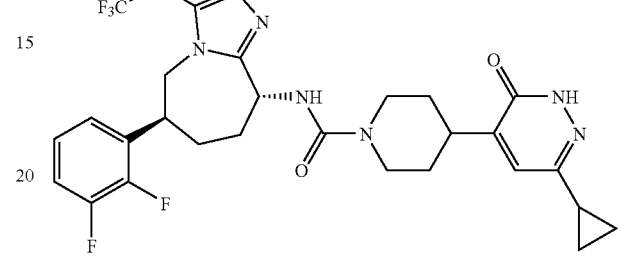
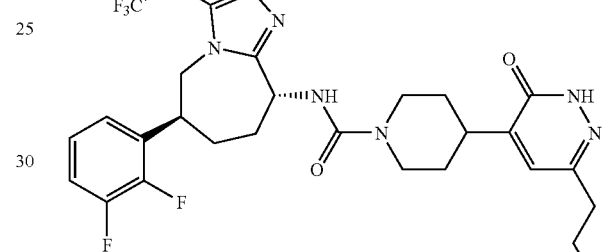
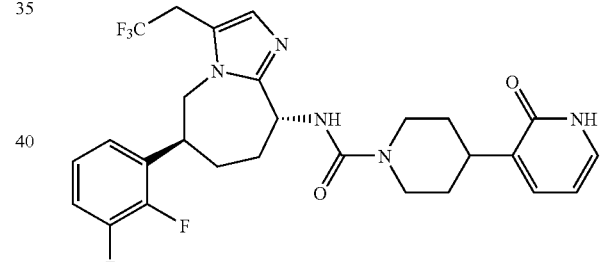
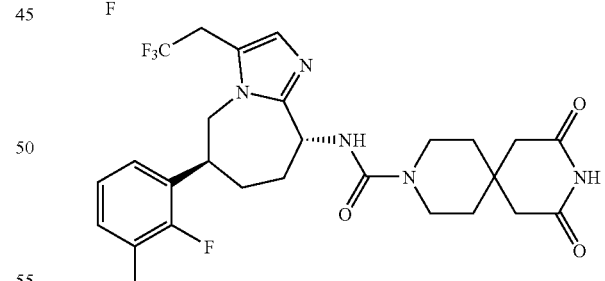
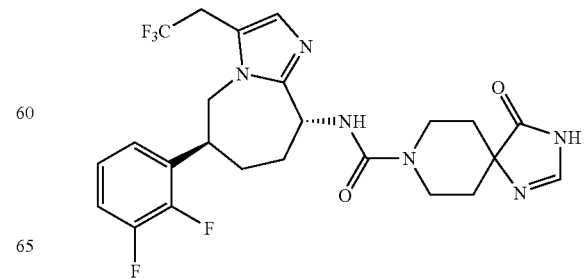

255
-continued
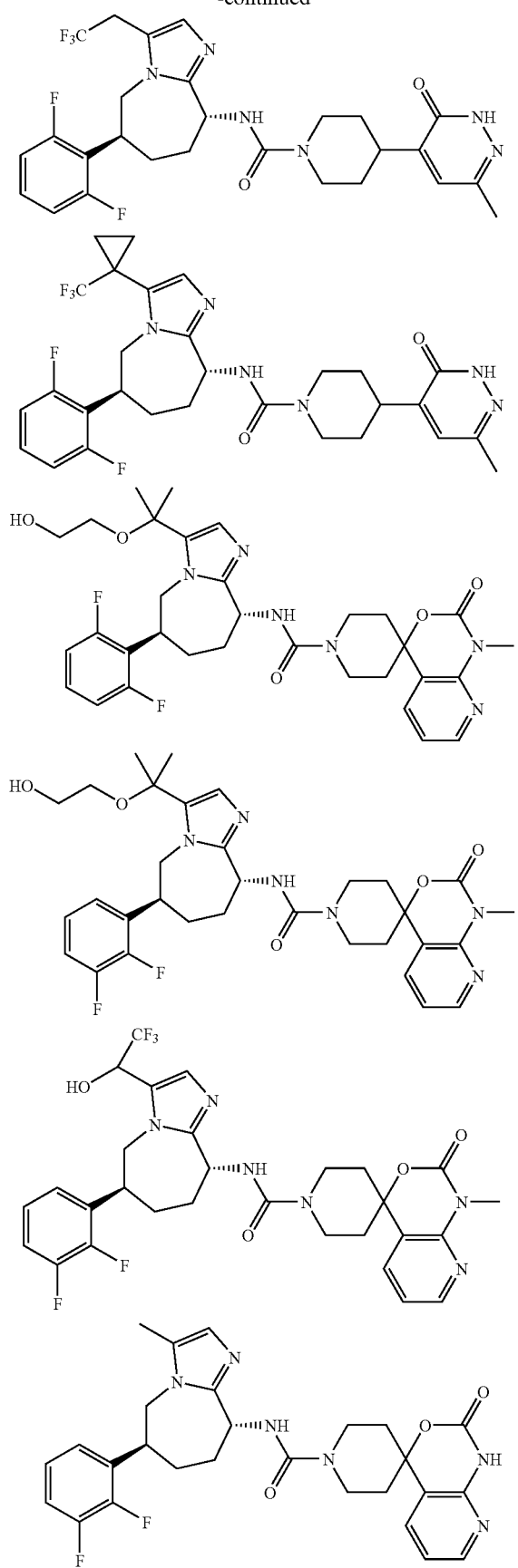
256
-continued
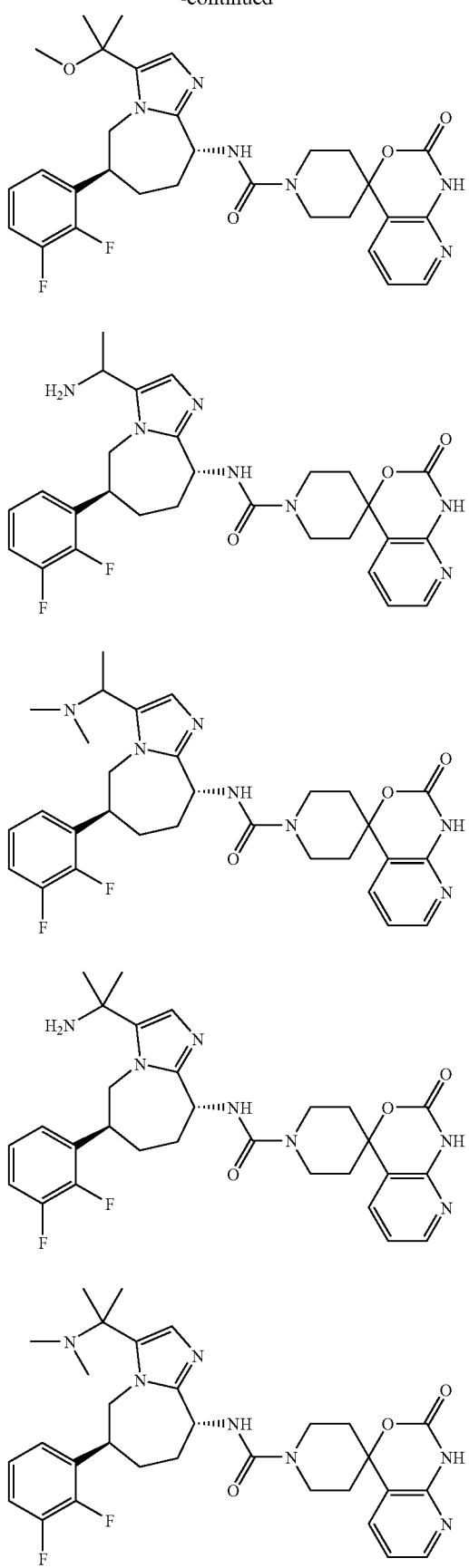

257
-continued
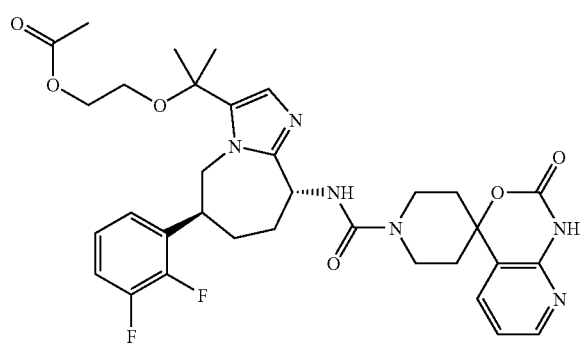
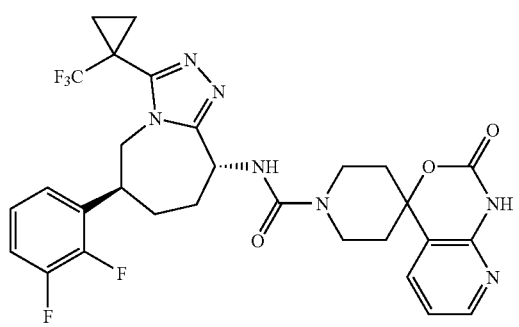
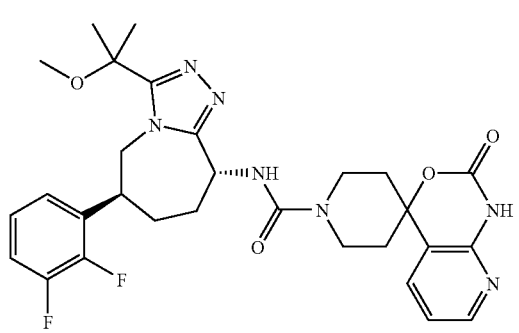
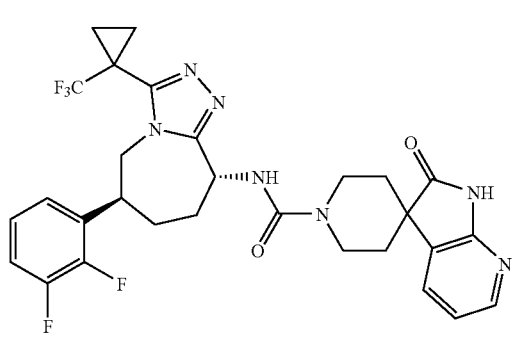
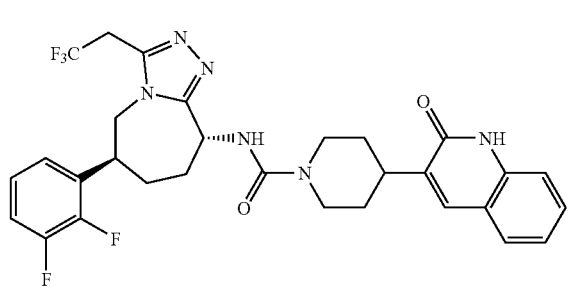
258
-continued
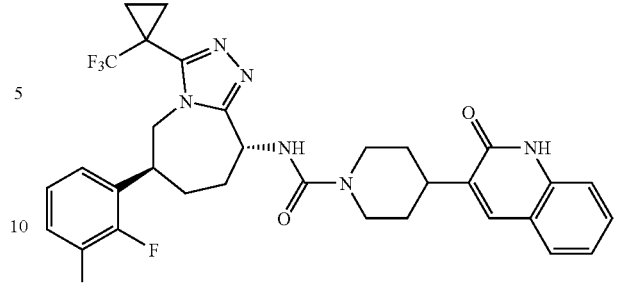
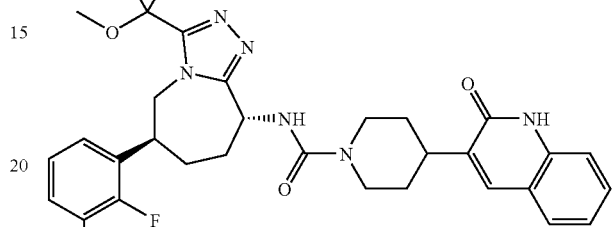
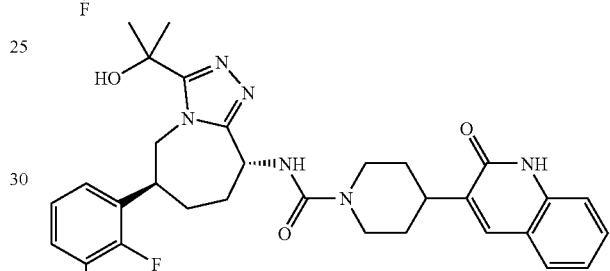
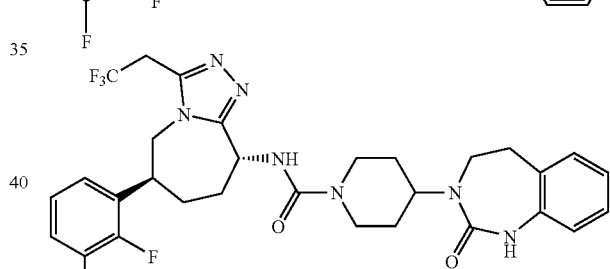
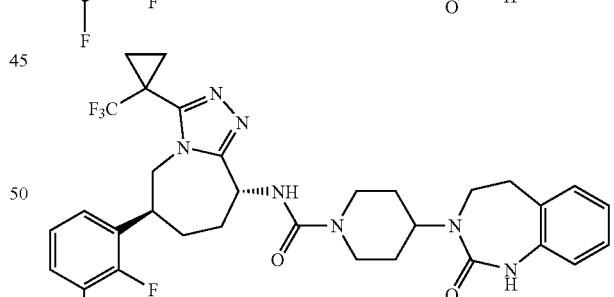
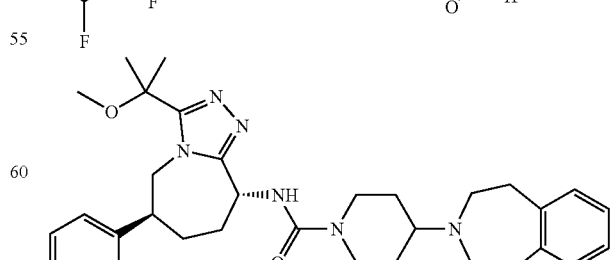
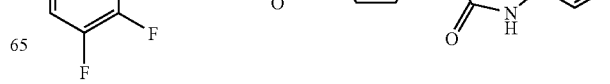

259
-continued
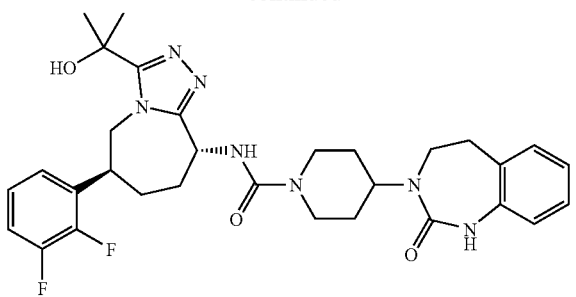
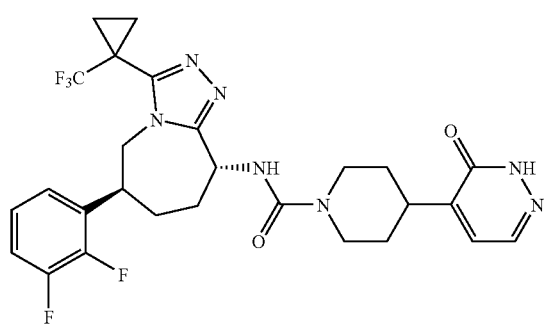
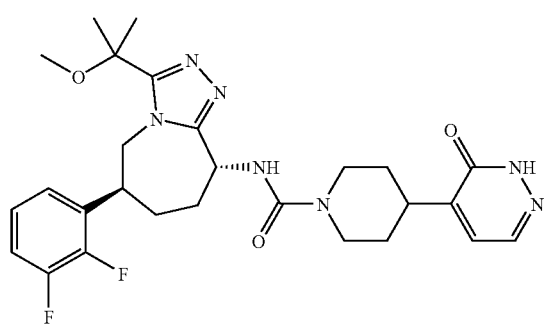
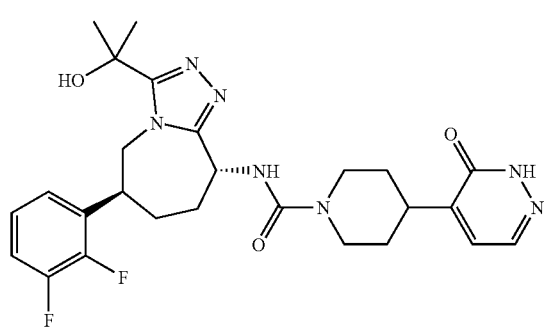
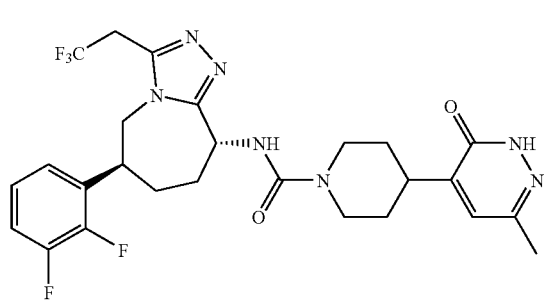
260
-continued
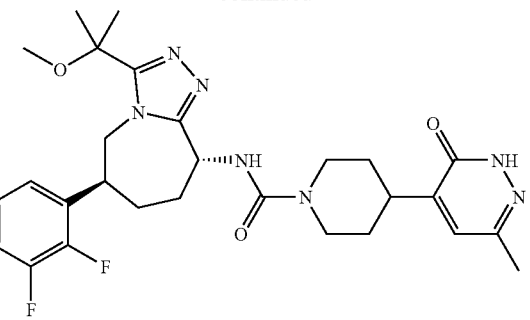
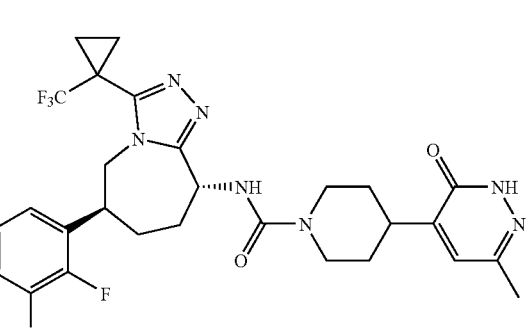
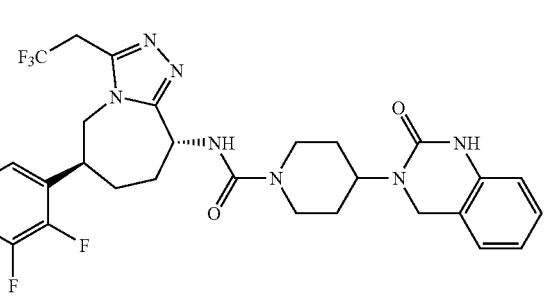
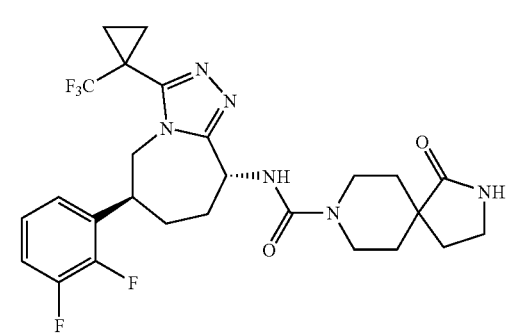
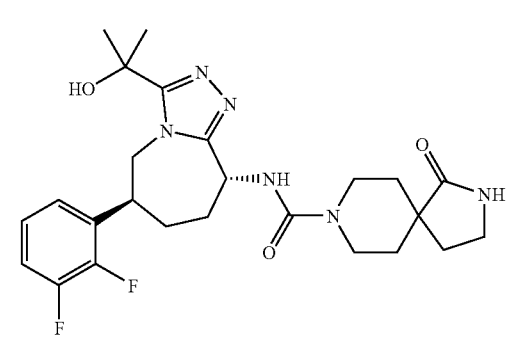

261
-continued
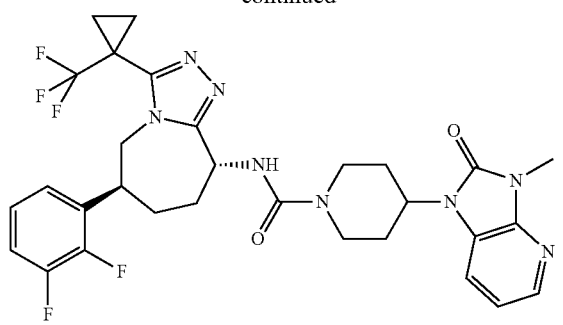
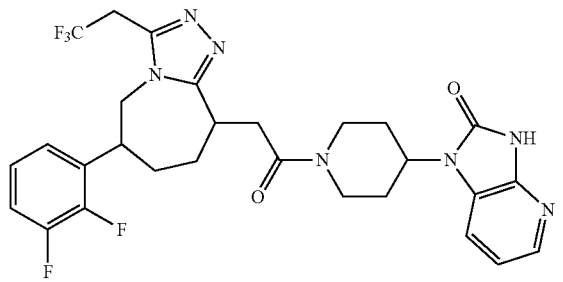
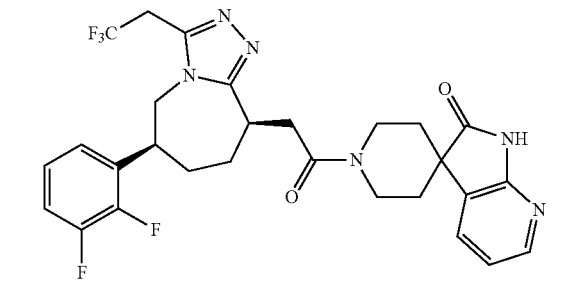
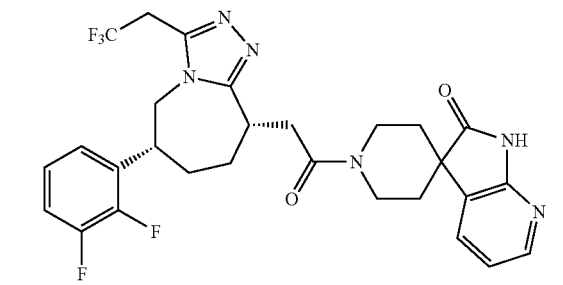
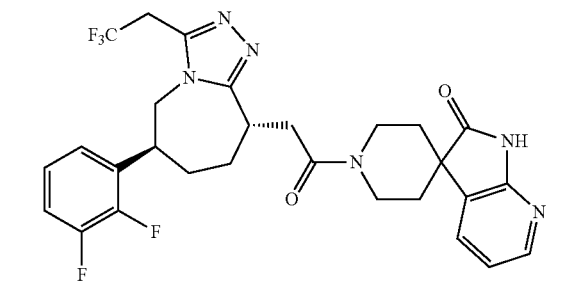
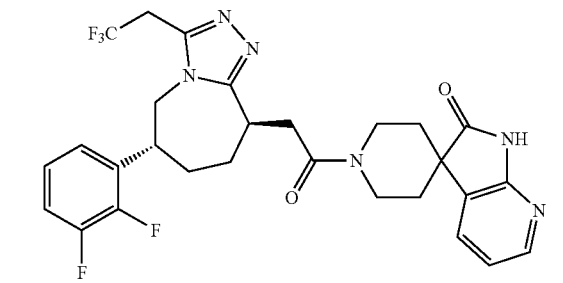
262
-continued
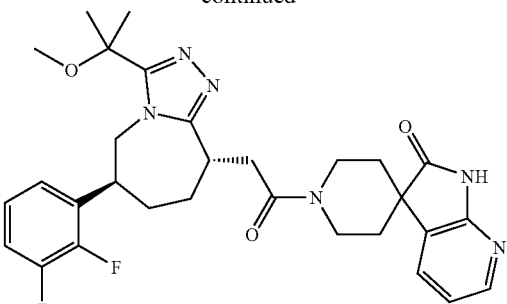
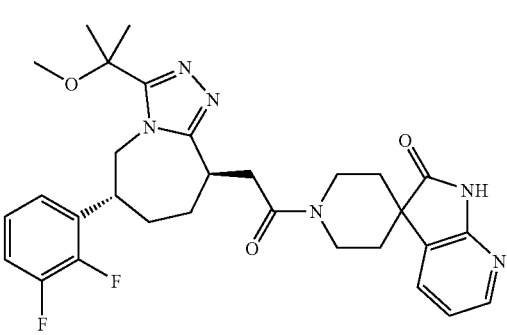
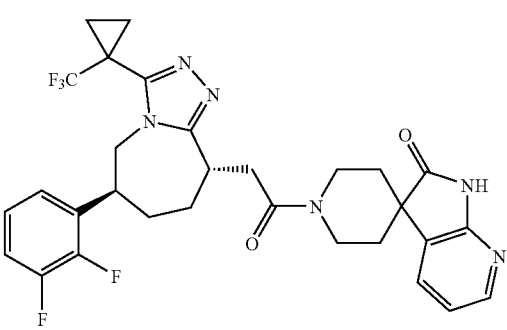
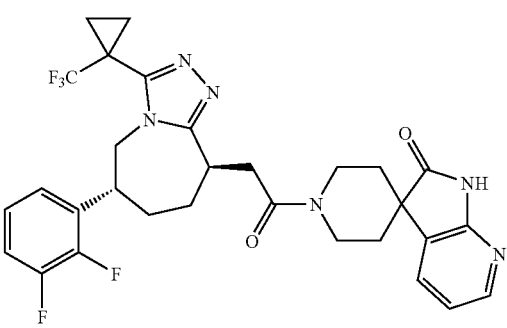
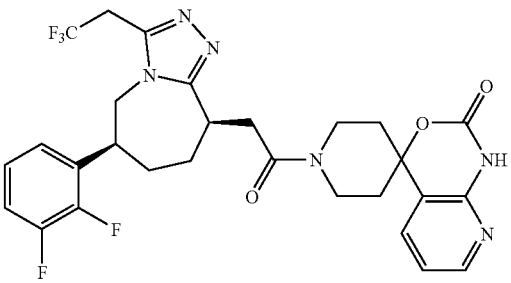

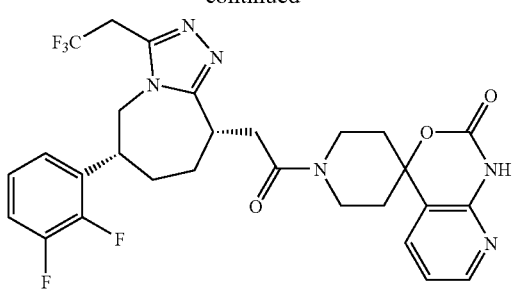
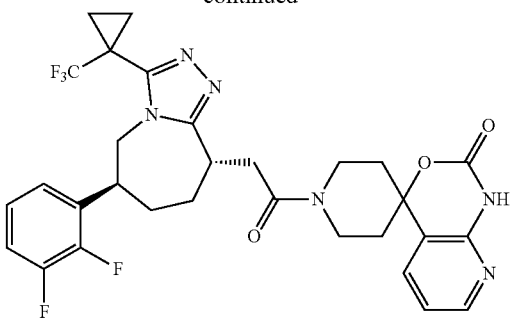

265
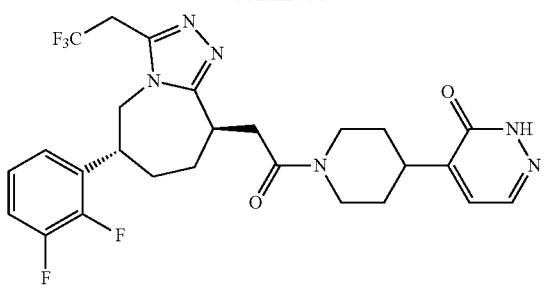
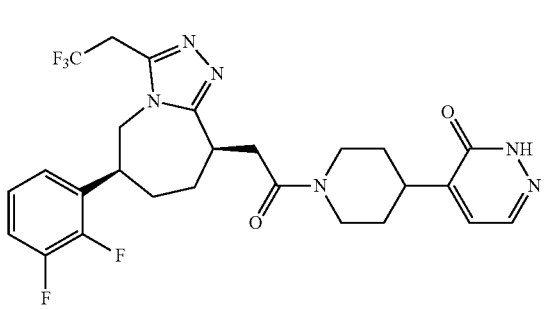
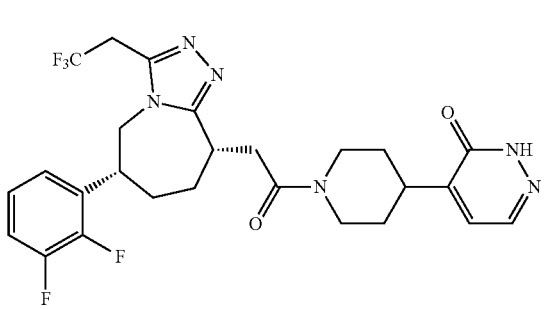
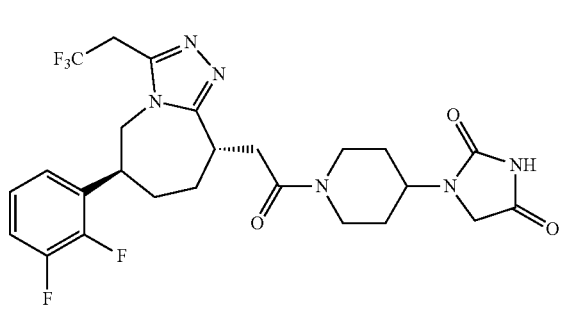
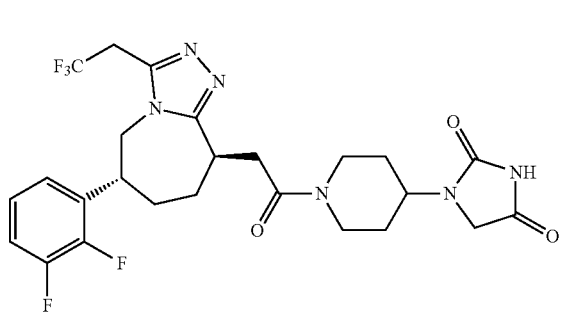
266
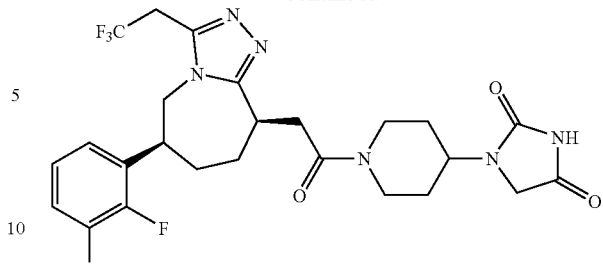
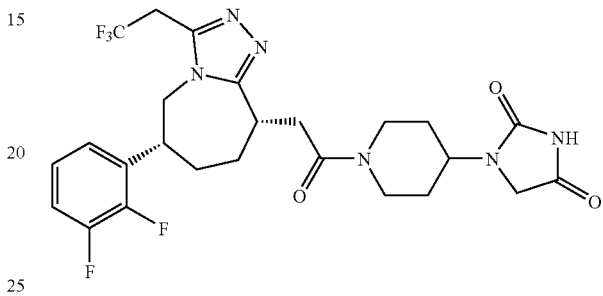
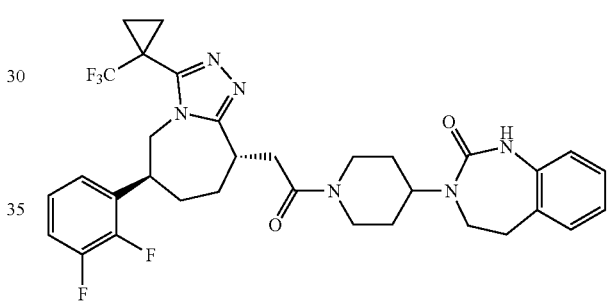
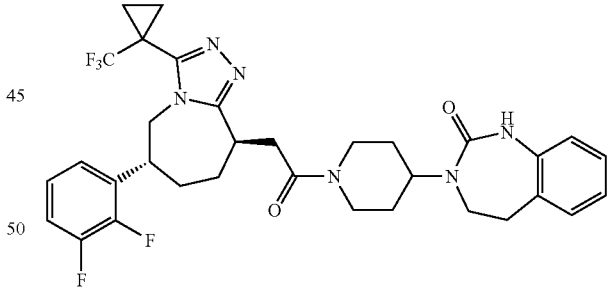
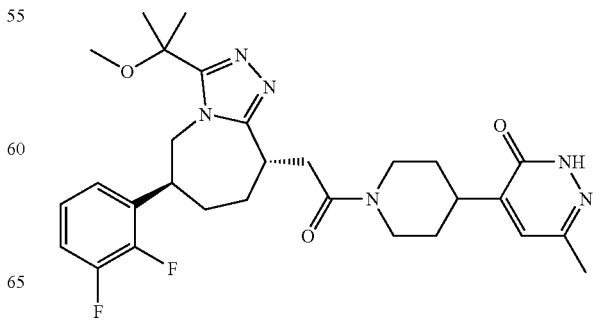

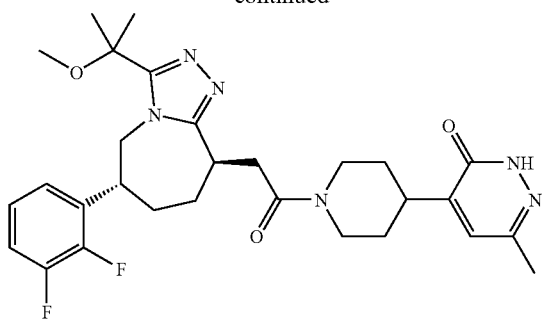

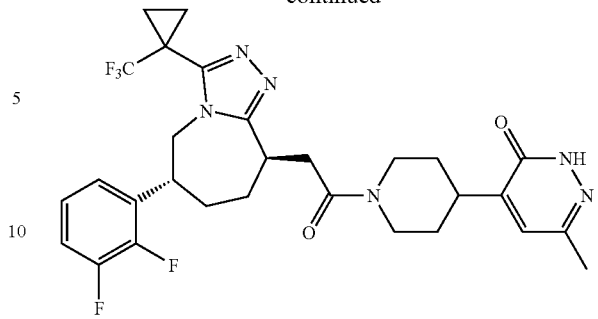

and pharmaceutically acceptable salts and individual diastereomers thereof.

10. A pharmaceutical composition which comprises an inert carrier and the compound of claim 1, or a pharmaceutically acceptable salt thereof.

11. A method for treating, controlling, ameliorating or reducing the risk of headache, migraine or cluster headache in a mammalian patient in need of such which comprises administering to the patient a therapeutically effective amount of the compound of claim 1, or a pharmaceutically acceptable salt thereof.

* * * * *